United States Patent
Bosanac et al.

(10) Patent No.: US 12,043,613 B2
(45) Date of Patent: Jul. 23, 2024

(54) INHIBITORS OF SARM1

(71) Applicant: Disarm Therapeutics, Inc., Indianapolis, IN (US)

(72) Inventors: Todd Bosanac, New Milford, CT (US); Andrew Simon Brearley, Chilton (GB); Rajesh Devraj, Chesterfield, MO (US); Robert Owen Hughes, Newtown, CT (US); Richard Andrew Jarjes-Pike, Newbury (GB); Shelley Anne Parrott, Abingdon (GB)

(73) Assignee: Disarm Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/408,956

(22) Filed: Aug. 23, 2021

(65) Prior Publication Data
US 2022/0056013 A1    Feb. 24, 2022

Related U.S. Application Data

(60) Provisional application No. 63/142,398, filed on Jan. 27, 2021, provisional application No. 63/069,408, filed on Aug. 24, 2020.

(51) Int. Cl.
*C07D 401/14*     (2006.01)
*A61P 25/28*      (2006.01)
*C07D 413/14*     (2006.01)

(52) U.S. Cl.
CPC ............ *C07D 401/14* (2013.01); *A61P 25/28* (2018.01); *C07D 413/14* (2013.01); *C07B 2200/05* (2013.01)

(58) Field of Classification Search
CPC .............................. A61P 25/28; C07D 401/14
See application file for complete search history.

(56) References Cited

U.S. PATENT DOCUMENTS

| | | |
|---|---|---|
| 9,284,310 B2 | 3/2016 | Fader et al. |
| 9,486,521 B2 | 11/2016 | Freeman et al. |
| 2004/0122016 A1 | 6/2004 | Cao et al. |
| 2004/0157861 A1 | 8/2004 | Scarborough et al. |
| 2005/0272779 A1 | 12/2005 | Edwards et al. |
| 2006/0019956 A1 | 1/2006 | Green |
| 2009/0163469 A1 | 7/2009 | Caravatti et al. |
| 2012/0328629 A1 | 12/2012 | Freeman et al. |
| 2016/0304466 A1 | 10/2016 | Feng et al. |
| 2019/0330192 A1 | 10/2019 | Frackenpohl et al. |
| 2022/0289691 A1 | 9/2022 | Heil et al. |

FOREIGN PATENT DOCUMENTS

| | | |
|---|---|---|
| CN | 110392680 A | 10/2019 |
| EP | 2036905 A1 | 3/2009 |
| RU | 2570907 C2 | 12/2015 |
| WO | 99/21555 A2 | 5/1999 |
| WO | 02/088113 A1 | 11/2002 |
| WO | 2004/041813 A1 | 5/2004 |
| WO | 2004/60362 A2 | 7/2004 |
| WO | 2004/096797 A1 | 11/2004 |
| WO | 2005/105780 A2 | 11/2005 |
| WO | 2006/065946 A1 | 6/2006 |
| WO | 2008/034600 A1 | 3/2008 |
| WO | 2009/080694 A1 | 7/2009 |
| WO | 2009/080705 A2 | 7/2009 |
| WO | 2010/009290 A1 | 1/2010 |
| WO | 2010/093849 A2 | 8/2010 |
| WO | 2012/178022 A2 | 12/2012 |
| WO | 2014/099694 A1 | 6/2014 |
| WO | 2018/035204 A1 | 2/2018 |
| WO | 2018/057989 A1 | 3/2018 |
| WO | 2018/107056 A1 | 6/2018 |
| WO | 2018/114662 A1 | 6/2018 |
| WO | 2018/114663 A1 | 6/2018 |
| WO | 2019/236879 A1 | 12/2019 |
| WO | 2019/236884 A1 | 12/2019 |
| WO | 2019/236890 A1 | 12/2019 |
| WO | 2021/050913 A1 | 3/2020 |
| WO | 2020/158762 A1 | 8/2020 |
| WO | 2020/247701 A2 | 12/2020 |
| WO | 2020/252229 A2 | 12/2020 |
| WO | 2021/092240 A1 | 5/2021 |
| WO | 2021/142006 A1 | 7/2021 |
| WO | 2021/207302 A1 | 10/2021 |
| WO | 2021/207308 A1 | 10/2021 |
| WO | 2022/031736 A1 | 2/2022 |
| WO | WO-2022031736 A1 * | 2/2022 |

OTHER PUBLICATIONS

Bosanac, et al., "Pharmacological SARM1 inhibition protects axon structure and function in paclitaxel-induced peripheral neuropathy", Brain 2021, vol. 144, pp. 3226-3238.

Geisler, et al., Prevention of vincristine-induced peripheral neuropathy by genetic deletion of SARM1 in mice, Brain, 2016, vol. 139, pp. 3092-3108.

Green, Jeremy, et al., "Design, Synthesis, and Structure-Activity Relationships of Pyridine-Based Rho Kinase (ROCK) Inhibitors" J Med Chem, vol. 58, No. 12, pp. 5028-5037 (2015).

\* cited by examiner

*Primary Examiner* — Jeffrey S Lundgren
*Assistant Examiner* — Eric Tran
(74) *Attorney, Agent, or Firm* — Nicholas M. Kunz; Robert D. Shereda

(57) ABSTRACT

The present disclosure provides compounds and methods useful for inhibiting SARM1 and/or treating and/or preventing axonal degeneration.

19 Claims, 1 Drawing Sheet
Specification includes a Sequence Listing.

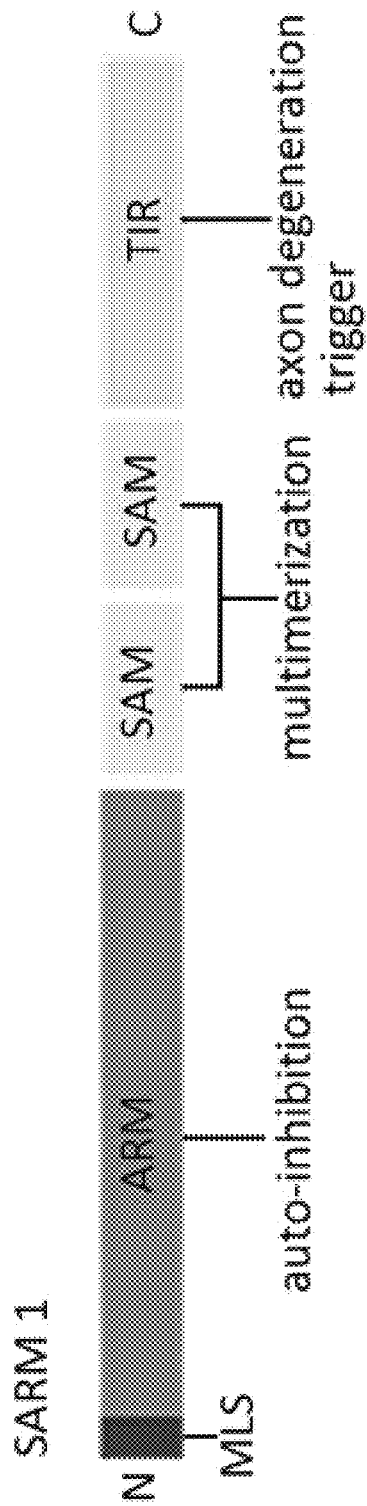

```
                        SEQUENCE LISTING

<160> NUMBER OF SEQ ID NOS: 1

<210> SEQ ID NO 1
<211> LENGTH: 6514
<212> TYPE: DNA
<213> ORGANISM: Artificial Sequence
<220> FEATURE:
<223> OTHER INFORMATION: Chemically synthesized nucleotide

<400> SEQUENCE: 1
gcgatcgcgg ctcccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctagt     240
aatcaattac ggggtcatta gttcatagcc catatatgga gttccgcgtt acataactta     300
cggtaaatgg cccgcctggc tgaccgccca acgaccccg cccattgacg tcaataatga     360
cgtatgttcc catagtaacg ccaataggga ctttccattg acgtcaatgg gtggagtatt     420
tacggtaaac tgcccacttg gcagtacatc aagtgtatca tatgccaagt acgcccccta     480
ttgacgtcaa tgacggtaaa tggcccgcct ggcattatgc ccagtacatg accttatggg     540
actttcctac ttggcagtac atctacgtat tagtcatcgc tattaccatg ctgatgcggt     600
tttggcagta catcaatggg cgtggatagc ggtttgactc acggggattt ccaagtctcc     660
accccattga cgtcaatggg agtttgtttt ggcaccaaaa tcaacgggac tttccaaaat     720
gtcgtaacaa ctccgcccca ttgacgcaaa tgggcggtag cgtgtacgg tgggaggtct     780 atataagcag agctggttta gtgaaccgtc agatcagatc tttgtcgatc ctaccatcca     840
ctcgacacac ccgccagcgg ccgctgccaa gcttccgagc tctcgaattc aaaggaggta     900
cccaccatgg ccatgcatca ccaccaccat catagctccg gcgtcgacct cggcaccgag     960
aatttatatt tccaaagcgg cctcaatgat atcttcgagg cccagaagat cgagtggcac    1020
gagggcagct ccgacctcgc cgtgcccggt cccgatggag gcggaggcac tggtccttgg    1080
tgggctgctg gcggcagagg ccctagagaa gtgagcccg gtgctggcac cgaggtcaa     1140 gacgctctgg agagggctct gcccgaactg cagcaagctc tgtccgcttt aaagcaagct    1200
ggaggagcta gagccgtcgg cgccggactg gccgaagtgt tccagctcgt ggaggaagct    1260
tggttattac ccgctgtggg aagagaggtc gcccaaggtc tgtgtgacgc cattcgtctg    1320
gacggaggtt tagacttatt actgaggctg ctgcaagctc ccgaactgga gacaagggtc    1380
```

```
caagctgctc gtctgctgga gcagatcctc gtggccgaga atcgtgacag agtggctaga    1440
atcggtttag gcgtcatcct caatttagcc aaagagaggg agcccgttga gctgccaga     1500 agcgtcgctg gcatcctcga gcacatgttc aagcattccg aggagacttg tcagagactg    1560
gtcgccgccg gaggactcga tgctgtttta tactggtgca aaggacaga ccccgcttta     1620 ctgaggcatt gtgctctggc cctcggcaat gcgctttac atggaggcca agccgtccag     1680
agaaggatgg tggagaaaag agccgccgag tggctgttcc ctttagcctt ctccaaagaa    1740
gacgaactgt tacgtctgca tgcttgtctc gctgtcgctg ttttagccac caacaaggag    1800
gtggaaaggg aagtggaaag aagcggaaca ctggctttag tcgaacctct ggtggcttct    1860
ttagatcccg gaaggtttgc cagatgtctg gtcgacgcca gcgataccctc caaggaaga   1920 ggccccgacg atctccagag actggtgcct ctgctggaca gcaatcgtct ggaggcccaa    1980
tgtattggcg ccttctatct ctgcgccgaa gccgccatca agtctttaca aggtaagacc    2040
aaggtgttct ccgacattgg agccatccaa tctttaaaga ggctggtgag ctattccacc    2100
aacggcacaa aaagcgcttt agccaaaaga gctttaagac tgctgggcga agaggtgcct    2160
aggcccattt taccttccgt gcctagctgg aaggaggccg aggtgcagac ttggctgcag    2220
cagatcggct ttagcaaata ttgcgaatcc tttagggagc agcaagttga cggcgattta    2280
ttattaaggc tgaccgagga agagctccag acagatttag gcatgaaaag cggcatcact    2340
cgtaagaggt tctttcgtga gctcaccgaa ctgaagacct tcgccaacta ctccacttgt    2400
gatcgtagca atttagctga ttggctcgga tccctcgatc ccagatttcg tcagtacacc    2460
tatggactcg tctcttgtgg actggacaga tctttactgc atcgtgtgag cgagcaacag    2520
ctgctggaag attgcggcat ccatttagga gtgcacagag ccagaattct gaccgccgct    2580
agagagatgc tgcattcccc tctcccttgt accggaggca agcctagcgg agacacccc    2640 gacgtgttca tcagctatcg tagaaacagc ggaagccagc tggcctcttt actgaaggtc    2700
catttacagc tgcacggatt tagcgtcttc atcgacgtgg agaaactgga ggctggcaag    2760
ttcgaggaca agctgatcca gtccgtgatg ggcgctagga atttcgttttt agtgctcagc    2820 cccggcgctc tggataaatg catgcaagat catgactgta aggactgggt ccacaaggaa    2880
atcgtgaccg ctctgtcttg tggcaagaac atcgtcccca tcatcgacgg cttcgaatgg    2940
cccgagcctc aagttctccc cgaagatatg caagctgttt taaccttcaa tggaatcaag    3000
tggagccacg agtaccaaga agccacaatc gagaagatca ttcgtttttct gcaaggtaga    3060 tcctccagag attcctccgc tggcagcgac acatctttag agggcgccgc ccctatgggt    3120
cctacctaat aatctagaag ttgtctcctc ctgcactgac tgactgatac aatcgatttc    3180
tggatccgca ggcctctgct agcttgactg actgagatac agcgtacctt cagctcacag    3240
acatgataag atacattgat gagtttggac aaaccacaac tagaatgcag tgaaaaaaat    3300
gctttatttg tgaaatttgt gatgctattg ctttatttgt aaccattata agctgcaata    3360
aacaagttaa caacaacaat tgcattcatt ttatgtttca ggttcagggg gaggtgtggg    3420 aggttttta aagcaagtaa aacctctaca aatgtggtat tggcccatct ctatcggtat    3480
cgtagcataa cccccttgggg cctctaaacg ggtcttgagg ggttttttgt gcccctcggg    3540
ccggattgct atctaccggc attggcgcag aaaaaaatgc ctgatgcgac gctgcgcgtc    3600
ttatactccc acatatgcca gattcagcaa cggatacggc ttccccaact tgcccacttc    3660
catacgtgtc ctccttacca gaaatttatc cttaaggtcg tcagctatcc tgcaggcgat    3720
```

```
ctctcgattt cgatcaagac attcctttaa tggtcttttc tggacaccac tagggggtcag    3780 aagtagttca tcaaactttc ttccctccct aatctcattg gttaccttgg gctatcgaaa    3840
cttaattaac cagtcaagtc agctacttgg cgagatcgac ttgtctgggt ttcgactacg    3900
ctcagaattg cgtcagtcaa gttcgatctg gtccttgcta ttgcacccgt tctccgatta    3960
cgagtttcat ttaaatcatg tgagcaaaag gccagcaaaa ggccaggaac cgtaaaaagg    4020
ccgcgttgct ggcgtttttc cataggctcc gcccccctga cgagcatcac aaaaatcgac    4080
gctcaagtca gaggtggcga aacccgacag gactataaag ataccaggcg tttccccctg    4140
gaagctccct cgtgcgctct cctgttccga cctgccgct taccggatac ctgtccgcct    4200 ttctccctttc gggaagcgtg gcgctttctc atagctcacg ctgtaggtat ctcagttcgg    4260
tgtaggtcgt tcgctccaag ctgggctgtg tgcacgaacc ccccgttcag cccgaccgct    4320
gcgccttatc cggtaactat cgtcttgagt ccaacccggt aagacacgac ttatcgccac    4380
tggcagcagc cactggtaac aggattagca gagcgaggta tgtaggcggt gctacagagt    4440
tcttgaagtg gtggcctaac tacggctaca ctagaagaac agtatttggt atctgcgctc    4500
tgctgaagcc agttaccttc ggaaaaagag ttggtagctc ttgatccggc aaacaaacca    4560
ccgctggtag cggtggtttt tttgtttgca agcagcagat tacgcgcaga aaaaaaggat    4620
ctcaagaaga tcctttgatc ttttctacgg ggtctgacgc tcagtggaac gaaaactcac    4680
gttaagggat tttggtcatg agattatcaa aaaggatctt cacctagatc cttttaaatt    4740
aaaaatgaag ttttaaatca atctaaagta tatatgagta aacttggtct gacagttacc    4800
aatgcttaat cagtgaggca cctatctcag cgatctgtct atttcgttca tccatagttg    4860
catttaaatt tccgaactct ccaaggccct cgtcggaaaa tcttcaaacc tttcgtccga    4920
tccatcttgc aggctacctc tcgaacgaac tatcgcaagt ctcttggccg gccttgcgcc    4980
ttggctattg cttggcagcg cctatcgcca ggtattactc caatcccgaa tatccgagat    5040
cgggatcacc cgagagaagt tcaacctaca tcctcaatcc cgatctatcc gagatccgag    5100
gaatatcgaa atcggggcgc gcctggtgta ccgagaacga tcctctcagt gcgagtctcg    5160
acgatccata tcgttgcttg gcagtcagcc agtcggaatc cagcttggga cccaggaagt    5220
ccaatcgtca gatattgtac tcaagcctgg tcacggcagc gtaccgatct gtttaaacct    5280
agatattgat agtctgatcg gtcaacgtat aatcgagtcc tagcttttgc aaacatctat    5340
caagagacag gatcagcagg aggctttcgc atgagtattc aacatttccg tgtcgccctt    5400 attcccttttt ttgcggcatt ttgccttcct gttttttgctc acccagaaac gctggtgaaa    5460
gtaaaagatg ctgaagatca gttgggtgcg cgagtgggtt acatcgaact ggatctcaac    5520
agcggtaaga tccttgagag ttttcgcccc gaagaacgct ttccaatgat gagcactttt    5580
aaagttctgc tatgtggcgc ggtattatcc cgtattgacg ccgggcaaga gcaactcggt    5640
cgccgcatac actattctca gaatgacttg gttgagtatt caccagtcac agaaaagcat    5700
cttacggatg gcatgacagt aagagaatta tgcagtgctg ccataaccat gagtgataac    5760
actgcggcca acttacttct gacaacgatt ggaggaccga aggagctaac cgcttttttg    5820
cacaacatgg gggatcatgt aactcgcctt gatcgttggg aaccggagct gaatgaagcc    5880
ataccaaacg acgagcgtga caccacgatg cctgtagcaa tggcaacaac cttgcgtaaa    5940
ctattaactg gcgaactact tactctagct tcccggcaac agttgataga ctggatggag    6000
gcggataaag ttgcaggacc acttctgcgc tcggcccttc cggctggctg gtttattgct    6060
gataaatctg gagccggtga gcgtgggtct cgcggtatca ttgcagcact ggggccagat    6120
```

```
ggtaagccct cccgtatcgt agttatctac acgacgggga gtcaggcaac tatggatgaa    6180
cgaaatagac agatcgctga gataggtgcc tcactgatta agcattggta accgattcta    6240
ggtgcattgg cgcagaaaaa aatgcctgat gcgacgctgc gcgtcttata ctcccacata    6300
tgccagattc agcaacggat acggcttccc caacttgccc acttccatac gtgtcctcct    6360
taccagaaat ttatccttaa gatcccgaat cgtttaaact cgactctggc tctatcgaat    6420
ctccgtcgtt tcgagcttac gcgaacagcc gtggcgctca tttgctcgtc gggcatcgaa    6480
tctcgtcagc tatcgtcagc ttaccttttt ggca                                6514
```

INHIBITORS OF SARM1

BACKGROUND

Axonal degeneration is a hallmark of several neurological disorders including peripheral neuropathy, traumatic brain injury, and neurodegenerative diseases (See, for example, Gerdts et al., SARM1 activation triggers axon degeneration locally via NAD(+) destruction. Science 348 2016, pp. 453-457 and Krauss et al., (2020) Trends Pharmacol. Sci. 41, 281, each of which is hereby incorporated by reference in its entirety). Neurodegenerative diseases and injuries are devastating to both patients and caregivers. Costs associated with these diseases currently exceed several hundred billion dollars annually in the Unites States alone. Since the incidence of many of these diseases and disorders increases with age, their incidence is rapidly increasing as demographics change.

SUMMARY

The present disclosure provides technologies useful, among other things, for treating and/or preventing neurodegeneration (e.g., for reducing axonal degeneration). In some embodiments, provided technologies inhibit SARM1.

In some embodiments, the present disclosure provides certain compounds and/or compositions that are useful in medicine, and particularly for treating neurodegeneration (e.g., for reducing axonal degeneration).

All references to Formula I, should also be read as a reference to Formula II.

In some embodiments, the present disclosure provides compounds having a structure as set forth in Formula I:

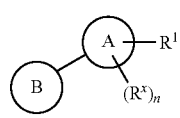

I or a pharmaceutically acceptable salt thereof, wherein:
Ring A is a 5- to 6-membered heteroaryl ring having 1-3 heteroatoms independently selected from oxygen, nitrogen, and sulfur;
$R^1$ is an optionally substituted group selected from a 3- to 7-membered saturated or partially unsaturated heterocyclic ring having 1-3 heteroatoms independently selected from oxygen, nitrogen, and sulfur or a 5- to 6-membered heteroaryl ring having 1-3 heteroatoms independently selected from oxygen, nitrogen, and sulfur;
each $R^x$ is independently selected from halogen, cyano, OR, SR, $N(R)_2$, or an optionally substituted group selected from $C_{1-4}$ aliphatic, a 3- to 7-membered saturated or partially unsaturated carbocyclic ring, a 3- to 7-membered saturated or partially unsaturated heterocyclic ring having 1-3 heteroatoms independently selected from oxygen, nitrogen, and sulfur, phenyl, and a 5- to 6-membered heteroaryl ring having 1-3 heteroatoms independently selected from oxygen, nitrogen, and sulfur;
Ring B is a saturated 5- to 7-membered heterocyclic ring having the structure

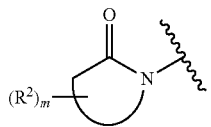

and optionally comprising one additional group selected from —NH—, —O—, and —$NR^2$—;
each R is independently hydrogen or an optionally substituted group selected from $C_{1-6}$ aliphatic, a 3- to 7-membered saturated or partially unsaturated heterocyclic ring having 1-3 heteroatoms independently selected from oxygen, nitrogen, and sulfur, phenyl, and a 5- to 6-membered heteroaryl ring having 1-3 heteroatoms independently selected from oxygen, nitrogen, and sulfur; or:
two R groups, together with the nitrogen atom to which they are attached, form an optionally substituted 3- to 7-membered monocyclic heterocyclic ring having 0-2 additional heteroatoms independently selected from oxygen, nitrogen, and sulfur;
each $R^2$ is independently halogen, $N(R)_2$, OR, $C_{1-3}$ aliphatic or —($C_{1-3}$ aliphatic)$R^3$;
each $R^3$ is independently an optionally substituted group selected from $C_{1-6}$ aliphatic, a 3- to 7-membered saturated or partially unsaturated heterocyclic ring having 1-3 heteroatoms independently selected from oxygen, nitrogen, and sulfur, phenyl, a 5- to 6-membered heteroaryl ring having 1-3 heteroatoms independently selected from oxygen, nitrogen, and sulfur, a 8- to 10-membered bicyclic saturated, partially unsaturated or aryl carbocyclic ring, a 8- to 10-membered bicyclic saturated or partially unsaturated heterocyclic ring having 1-3 heteroatoms independently selected from oxygen, nitrogen, and sulfur, or a 8- to 10-membered bicyclic heteroaryl ring having 1-3 heteroatoms independently selected from oxygen, nitrogen, and sulfur;
m is 0, 1, or 2; and
n is 0, 1, or 2.

In some embodiments, provided compounds have structures of Formulae I-a, I-a-i, I-b, I-b-i, I-b-ii, I-c, I-c-i, I-d, I-d-i, I-e, I-e-i, I-f, I-f-i, I-g, I-g-i, I-h, I-h-i, I-i, I-i-i, I-j, I-j-i, and I-j-ii, as set forth below.

In an embodiment, the present disclosure provides a compound of Formula II:

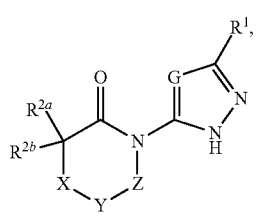

II or a pharmaceutically acceptable salt thereof, wherein:
$R^1$ is a 5- to 6-membered heteroaryl ring having 1-3 heteroatoms selected from oxygen, nitrogen and sulfur;
G is CH, $CR^x$ or N;
$R^x$ is $C_1$-$C_3$ alkyl, halogen or cyano;
X is $CH_2$, NH, N($C_1$-$C_3$ alkyl) or O;
Y is $C(R^P)_2$ or NH;
Z is bond, $CH_2$ or —$CH_2CH_2$—;

$R^{2a}$ is —($C_1$-$C_3$ alkyl)$R^3$;

$R^{2b}$ is hydrogen, halogen, $C_1$-$C_3$ alkyl or —($C_1$-$C_3$ alkyl)$R^3$;

$R^p$ is independently hydrogen, halogen or $NH_2$;

$R^3$ is a phenyl ring or a 5- to 6-membered heteroaryl ring having 1-3 heteroatoms selected from oxygen, nitrogen and sulfur, wherein the aryl ring or 5- to 6-membered heteroaryl ring are optionally substituted with 1 to 2 $R^q$;

$R^q$ is halogen, cyano or —$CF_3$.

In another embodiment, the present disclosure provides a compound, which is

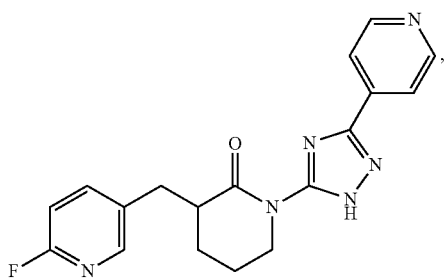 [SMILES: O=C1C(Cc2ccc(F)nc2)CCCN1c1nc(-c2ccncc2)n[nH]1]

or a pharmaceutically acceptable salt thereof.

In another embodiment, the present disclosure provides a compound, which is

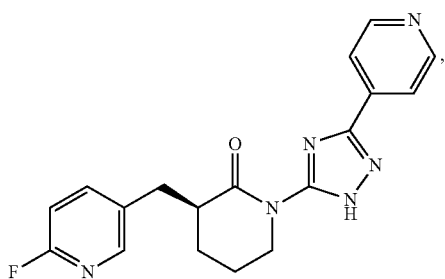 [SMILES: O=C1[C@H](Cc2ccc(F)nc2)CCCN1c1nc(-c2ccncc2)n[nH]1]

or a pharmaceutically acceptable salt thereof.

In another embodiment, the present disclosure provides a compound, which is

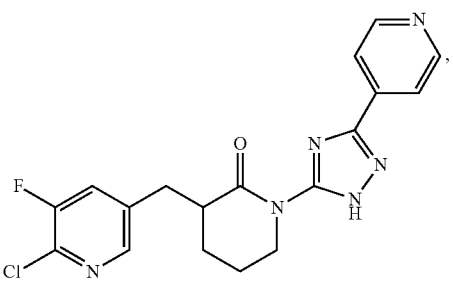 [SMILES: O=C1C(Cc2cnc(Cl)c(F)c2)CCCN1c1nc(-c2ccncc2)n[nH]1]

or a pharmaceutically acceptable salt thereof.

In another embodiment, the present disclosure provides a compound, which is

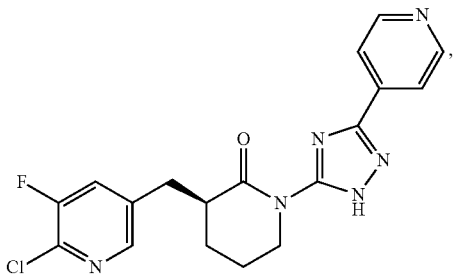 [SMILES: O=C1[C@H](Cc2cnc(Cl)c(F)c2)CCCN1c1nc(-c2ccncc2)n[nH]1]

or a pharmaceutically acceptable salt thereof.

In some embodiments, one or more compounds of Formula I is provided and/or utilized in a solid form (e.g., a crystal form or an amorphous form).

In some embodiments, the present disclosure provides compositions that comprise and/or deliver a compound of Formula I (e.g., in a form as described herein), a prodrug or active metabolite thereof.

In some embodiments, the present disclosure provides compositions that comprise and/or deliver a compound of Formula I. In some embodiments, such compositions are pharmaceutical compositions that include at least one pharmaceutically acceptable carrier, diluent or excipient.

In some embodiments, provided compounds reduce or inhibit binding of NAD+ by SARM1. In some embodiments, provided compounds bind to SARM1 within a pocket comprising one or more catalytic residues (e.g., a catalytic cleft of SARM1).

In some embodiments, provided compounds and/or compositions inhibit activity of SARM1. Alternatively or additionally, in some embodiments, provided compounds alleviate one or more attributes of neurodegeneration. In some embodiments, the present disclosure provides methods of treating a neurodegenerative disease or disorder associated with axonal degeneration.

In some embodiments, one or more compounds and/or compositions as described herein are useful, for example, in the practice of medicine. In some embodiments, one or more compounds and/or compositions as described herein are useful, for example, to treat, prevent, or ameliorate axonal degeneration (e.g., one or more features or characteristics thereof). In some embodiments, one or more compounds and/or compositions as described herein are useful, for example, to inhibit axonal degeneration, including axonal degeneration that results from reduction or depletion of NAD+. In some embodiments, one or more compounds and/or compositions as described herein are useful, for example, to prevent the axon distal to an axonal injury from degenerating.

In some embodiments, one or more compounds and/or compositions as described herein are useful, for example, to treat one or more neurodegenerative diseases, disorders or conditions selected from the group consisting of neuropathies or axonopathies. In some embodiments, one or more compounds and/or compositions as described herein are useful, for example, to treat a neuropathy or axonopathy associated with axonal degeneration. In some embodiments, a neuropathy associated with axonal degeneration is a hereditary or congenital neuropathy or axonopathy. In some embodiments, a neuropathy associated with axonal degeneration results from a de novo or somatic mutation. In some embodiments, a neuropathy associated with axonal degeneration is selected from a list contained herein. In some embodiments, a neuropathy or axonopathy is associated with axonal degeneration, including, but not limited to, Parkinson's disease, Parkinsonian syndromes or Parkinson's plus syndromes such as, for example, Multiple System Atrophy (MSA), Progressive Supranuclear Palsy (PSP), and corticobasal degeneration, Alzheimer's disease, Herpes infection, diabetes, amyotrophic lateral sclerosis (ALS), a demyelinating disease such as, for example, multiple sclerosis, ischemia or stroke, chemical injury, thermal injury, and AIDS.

In some embodiments, subjects to which a compound or composition as described herein is administered may be or comprise subjects suffering from or susceptible to a neurodegenerative disease, disorder or condition. In some embodiments, a neurodegenerative disease, disorder or condition may be or comprise a traumatic neuronal injury. In some embodiments, a traumatic neuronal injury is blunt force trauma, a closed-head injury, an open head injury, exposure to a concussive and/or explosive force, a penetrating injury in or to the brain cavity or innervated region of the body. In some embodiments, a traumatic neuronal injury is a force which causes axons to deform, stretch, crush or sheer.

In some embodiments, provided methods comprise administering a compound described herein to a patient in need thereof. In some such embodiments, the patient is at risk of developing a condition characterized by axonal degeneration. In some embodiments, the patient has a condition characterized by axonal degeneration. In some embodiments, the patient has been diagnosed with a condition characterized by axonal degeneration.

In some embodiments, provided methods comprise administering a composition as described herein to a patient population in need thereof. In some embodiments, the population is drawn from individuals who engage in activities where the potential for traumatic neuronal injury is high. In some embodiments, the population is drawn from athletes who engage in contact sports or other high-risk activities In some embodiments, the patient is at risk of developing a neurodegenerative disorder. In some embodiments the patient is elderly. In some embodiments, the patient is known to have a genetic risk factor for neurodegeneration.

In certain embodiments, the present disclosure provides compounds that are useful, for example, as analytical tools, as probes in biological assays, or as therapeutic agents in accordance with the present disclosure. Compounds provided by this disclosure are also useful for the study of SARM1 function in biological and pathological phenomena and the comparative evaluation of new SARM1 activity inhibitors in vitro or in vivo.

In some embodiments, one or more compounds and/or compositions as described herein are useful, for example, as a method for inhibiting the degradation of neurons derived from a subject. In some embodiments, one or more compounds and/or compositions as described herein are useful for inhibiting the degeneration of a neuron, or a portion thereof, cultured in vitro. In some embodiments, one or more compounds and/or compositions as described herein are useful as stabilizing agents to promote in vitro neuronal survival.

In an embodiment, the present disclosure provides a method comprising a step of administering a compound as described above, or a pharmaceutically acceptable salt thereof to a subject who (i) has a condition characterized by axonal degeneration or (ii) is at risk of developing a condition characterized by axonal degeneration.

In an embodiment, the present disclosure provides a method of treating or preventing axonal degeneration comprising administering to a subject in need thereof a compound as described above, or a pharmaceutically acceptable salt thereof.

In an embodiment, the present disclosure provides a method of inhibiting SARM1 comprising contacting a biological sample with a compound as described above, or a pharmaceutically acceptable salt thereof.

In an embodiment, the present disclosure provides a method of treating amyotrophic lateral sclerosis in a patient, comprising administering to a patient in need of such treatment and effective amount of a compound as described above, or a pharmaceutically acceptable salt thereof.

In an embodiment, the present disclosure provides a method of treating multiple sclerosis in a patient, comprising administering to a patient in need of such treatment and effective amount of a compound as described above, or a pharmaceutically acceptable salt thereof.

In an embodiment, the present disclosure provides a method of treating progressive supranuclear palsy in a patient, comprising administering to a patient in need of such treatment and effective amount of a compound as described above, or a pharmaceutically acceptable salt thereof.

In an embodiment, the present disclosure provides a compound as described above, or a pharmaceutically acceptable salt thereof, for use in therapy.

In an embodiment, the present disclosure provides a compound as described above, or a pharmaceutically acceptable salt thereof, for use in the treatment of amyotrophic lateral sclerosis.

In an embodiment, the present disclosure provides a compound as described above, or a pharmaceutically acceptable salt thereof, for use in the treatment of multiple sclerosis.

In an embodiment, the present disclosure provides a compound as described above, or a pharmaceutically acceptable salt thereof, for use in the treatment of progressive supranuclear palsy.

BRIEF DESCRIPTION OF THE DRAWING

FIG. 1 illustrates the structure of the SARM1 protein.

DEFINITIONS

Aliphatic: The term "aliphatic" refers to a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" or "cycloaliphatic") Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle") refers to a monocyclic $C_3$-$C_8$ hydrocarbon or a bicyclic $C_7$-$C_{10}$ hydrocarbon that is completely saturated or that contains one or more units of unsaturation, but which is not aromatic. Suitable aliphatic groups include, but are not limited to, linear or branched, substituted or unsubstituted alkyl, alkenyl, alkynyl, alkylene, alkenylene, alkynylene groups and hybrids thereof.

Alkyl: The term "alkyl", used alone or as part of a larger moiety, refers to a saturated, optionally substituted straight or branched chain or cyclic hydrocarbon group having 1-12, 1-10, 1-8, 1-6, 1-4, 1-3, or 1-2 carbon atoms. The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

Alkylene: The term "alkylene" refers to a bivalent alkyl group. In some embodiments, "alkylene" is a bivalent straight or branched alkyl group. In some embodiments, an "alkylene chain" is a polymethylene group, i.e., $-(CH_2)_n-$, wherein n is a positive integer, e.g., from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3- to 7-membered ring. The substituents can be on the same or different atoms.

Alkenyl: The term "alkenyl", used alone or as part of a larger moiety, refers to an optionally substituted straight or branched chain or cyclic hydrocarbon group having at least one double bond and having 2-12, 2-10, 2-8, 2-6, 2-4, or 2-3 carbon atoms. The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

Alkynyl: The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

Aryl: The term "aryl" refers to monocyclic and bicyclic ring systems having a total of five to fourteen ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic carbocyclic or heterocyclic rings, such as indanyl, phthalimidyl, naphthimidyl, phenanthridinyl, tetrahydronaphthyl, imidazolidinyl, imidazolidin-2-one, and the like.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

BiologicalSample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example, nucleic acids or proteins extracted from a sample or obtained by subjecting a primary sample to techniques such as amplification or reverse transcription of mRNA, isolation and/or purification of certain components, etc.

Biomarker: The term "biomarker" is used herein to refer to a to an entity, event, or characteristic whose presence, level, degree, type, and/or form, correlates with a particular biological event or state of interest, so that it is considered to be a "marker" of that event or state. To give but a few examples, in some embodiments, a biomarker may be or comprise a marker for a particular disease state, or for likelihood that a particular disease, disorder or condition may develop, occur, or reoccur. In some embodiments, a biomarker may be or comprise a marker for a particular disease or therapeutic outcome, or likelihood thereof. Thus, in some embodiments, a biomarker is predictive, in some embodiments, a biomarker is prognostic, in some embodiments, a biomarker is diagnostic, of the relevant biological event or state of interest. A biomarker may be or comprise an entity of any chemical class and may be or comprise a combination of entities. For example, in some embodiments, a biomarker may be or comprise a nucleic acid, a polypeptide, a lipid, a carbohydrate, a small molecule, an inorganic agent (e.g., a metal or ion), or a combination thereof. In some embodiments, a biomarker is a cell surface marker. In some embodiments, a biomarker is intracellular. In some embodiments, a biomarker is detected outside of cells (e.g., is secreted or is otherwise generated or present outside of cells, e.g., in a body fluid such as blood, urine, tears, saliva, cerebrospinal fluid, etc. In some embodiments, a biomarker may be or comprise a genetic or epigenetic signature. In some embodiments, a biomarker may be or comprise a gene expression signature.

In some embodiments, a biomarker may be or comprise a marker for neurodegeneration, or for likelihood that a neurodegenerative disease, disorder or condition may develop, occur, or reoccur. In some embodiments, a biomarker may be or comprise a marker of neurodegeneration a therapeutic outcome, or likelihood thereof. Thus, in some embodiments, a biomarker is predictive, in some embodiments, a biomarker is prognostic, in some embodiments, a biomarker is diagnostic, of a neurodegenerative disease, disorder or condition. In some embodiments changes in biomarker levels can be detected via cerebral spinal fluid (CSF), plasma and/or serum.

In some embodiments, neurodegeneration may be assessed, for example, by detecting an increase and/or decrease in the concentration of neurofilament protein light (NF-L) and/or neurofilament protein heavy (NF-H) (or its phosphorylated form (pNF-H)) contained in the CSF or in the blood/plasma of a subject. In some embodiments, the incidence and/or progression of neurodegeneration can be assessed via positron emission tomography (PET) with a synaptic vesicle glycoprotein 2a (SV2A) ligand. In some embodiments, a detectable change in constitutive NAD and/or cADPR levels in neurons can be used to assess neurodegeneration.

In some embodiments, a detectable change in one or more neurodegeneration associated proteins in a subject, relative to a healthy reference population can be used as a biomarker of neurodegeneration. Such proteins include, but are not limited to, albumin, amyloid-β (Aβ)38, Aβ40, Aβ42, glial fibrillary acid protein (GFAβ), heart-type fatty acid binding protein (hFABP), monocyte chemoattractin protein (MCP)-1, neurogranin, neuron specific enolayse (NSE), soluble amyloid precursor protein (sAPP)α, sAPPβ, soluble triggering receptor expressed on myeloid cells (sTREM) 2, phospho-tau, and/or total-tau. In some embodiments, an increase in cytokines and/or chemokines, including, but not limited to, Ccl2, Ccl7, Ccl12, Csf1, and/or I16, can be used as a biomarker of neurodegeneration.

Carrier: As used herein, the term "carrier" refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Combination therapy: As used herein, the term "combination therapy" refers to those situations in which a subject is simultaneously exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Composition: Those skilled in the art will appreciate that the term "composition" may be used to refer to a discrete physical entity that comprises one or more specified components. In general, unless otherwise specified, a composition may be of any form—e.g., gas, gel, liquid, solid, etc.

Domain: The term "domain" as used herein refers to a section or portion of an entity. In some embodiments, a "domain" is associated with a particular structural and/or functional feature of the entity so that, when the domain is physically separated from the rest of its parent entity, it substantially or entirely retains the particular structural and/or functional feature. Alternatively or additionally, a domain may be or include a portion of an entity that, when separated from that (parent) entity and linked with a different (recipient) entity, substantially retains and/or imparts on the recipient entity one or more structural and/or functional features that characterized it in the parent entity. In some embodiments, a domain is a section or portion of a molecule (e.g., a small molecule, carbohydrate, lipid, nucleic acid, or polypeptide). In some embodiments, a domain is a section of a polypeptide; in some such embodiments, a domain is characterized by a particular structural element (e.g., a particular amino acid sequence or sequence motif, α-helix character, β-sheet character, coiled-coil character, random coil character, etc.), and/or by a particular functional feature (e.g., binding activity, enzymatic activity, folding activity, signaling activity, etc.).

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen or therapeutic regimen: Those skilled in the art will appreciate that the terms "dosing regimen" and "therapeutic regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Excipient: as used herein, refers to a non-therapeutic agent that may be included in a pharmaceutical composition, for example, to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Heteroaryl: The terms "heteroaryl" and "heteroar-", used alone or as part of a larger moiety, e.g., "heteroaralkyl", or "heteroaralkoxy", refer to groups having 5 to 10 ring atoms, preferably 5, 6, 9, or 10 ring atoms; having 6, 10, or 14 π-electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

Heterocycle: As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, such as one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or NR$^+$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings (e.g., 2,3-dihydrobenzofuran, 2,3-dihydrobenzo[b][1,4]dioxine, etc.).

Hydrogen: As used herein, the term "hydrogen" is used to refer to all three isotopes of hydrogen, namely protium (H), deuterium ($^2$H) and tritium (3H).

Inhibitory agent: As used herein, the term "inhibitory agent" refers to an entity, condition, or event whose presence, level, or degree correlates with decreased level or activity of a target. In some embodiments, an inhibitory agent may act directly (in which case it exerts its influence directly upon its target, for example, by binding to the target); in some embodiments, an inhibitory agent may act indirectly (in which case it exerts its influence by interacting with and/or otherwise altering a regulator of the target, so that level and/or activity of the target is reduced). In some embodiments, an inhibitory agent is one whose presence or level correlates with a target level or activity that is reduced relative to a particular reference level or activity (e.g., that observed under appropriate reference conditions, such as presence of a known inhibitory agent, or absence of the inhibitory agent in question, etc.).

Neurodegeneration: As used herein, the term "neurodegeneration" refers to a reduction in one or more features, structures, function, or characteristics of a neuron or neuronal tissue. In some embodiments, neurodegeneration is observed as a pathological reduction in an organism. Those skilled in the art will appreciate that neurodegeneration is associated with certain diseases, disorders and conditions, including those that affect humans. In some embodiments, neurodegeneration may be transient (e.g., as sometimes occurs in association with certain infections and/or chemical or mechanical disruptions); in some embodiments, neurodegeneration may be chronic and/or progressive (e.g., as is often associated with certain diseases, disorders or conditions such as, but not limited to, Parkinson's disease, amyotrophic lateral sclerosis, multiple sclerosis, Huntington disease, or Alzheimer's disease). In some embodiments, neurodegeneration may be assessed, for example, by detecting in a subject an increase in a biomarker associated with neurodegeneration. In some embodiments, neurodegeneration may be assessed, for example, by detecting in a subject a decrease in a biomarker associated with neurodegeneration. Alternatively, or additionally, in some embodiments, neurodegeneration may be assessed by magnetic resonance imaging (MRI), biomarkers contained in CSF or blood/plasma, or other biomarkers observed in patients. In some embodiments, neurodegeneration is defined as a score of below 24 on the mini-mental state examination. In some embodiments, neurodegeneration refers to loss of synapses. In some embodiments, neurodegeneration refers to a reduction in neural tissue relating to a traumatic injury (e.g., exposure to an external force which disrupts the integrity of the neural tissue). In some embodiments, neurodegeneration refers to a reduction in peripheral neural tissue. In some embodiments, neurodegeneration refers to a reduction in central nervous tissue.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intra-arterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Partially Unsaturated: As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the patient is receiving or has received certain therapy to diagnose and/or to treat a disease, disorder, or condition.

Pharmaceutical composition: As used herein, the term "pharmaceutical composition" refers to an active agent, formulated together with one or more pharmaceutically acceptable carriers. In some embodiments, the active agent is present in unit dose amount appropriate for administration in a therapeutic or dosing regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Prevent or prevention: As used herein, the terms "prevent" or "prevention", when used in connection with the occurrence of a disease, disorder, and/or condition, refer to reducing the risk of developing the disease, disorder and/or condition and/or to delaying onset of one or more characteristics or symptoms of the disease, disorder or condition.

Prevention may be considered complete when onset of a disease, disorder or condition has been delayed for a predefined period of time.

Specific: The term "specific", when used herein with reference to an agent having an activity, is understood by those skilled in the art to mean that the agent discriminates between potential target entities or states. For example, in some embodiments, an agent is said to bind "specifically" to its target if it binds preferentially with that target in the presence of one or more competing alternative targets. In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of the binding agent for one or more other potential target entities (e.g., competitors). In some embodiments, specificity is evaluated relative to that of a reference specific binding agent. In some embodiments, specificity is evaluated relative to that of a reference non-specific binding agent. In some embodiments, the agent or entity does not detectably bind to the competing alternative target under conditions of binding to its target entity. In some embodiments, a binding agent binds with higher on-rate, lower off-rate, increased affinity, decreased dissociation, and/or increased stability to its target entity as compared with the competing alternative target(s).

Subject: As used herein, the term "subject" refers to an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Substituted or optionally substituted: As described herein, compounds of the invention may contain "optionally substituted" moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure (e.g.,

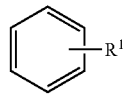

refers to at least

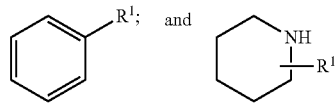

refers to at least

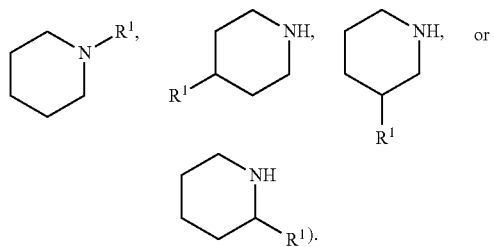

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}R^\circ$; —$O(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)(NH)R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)$O$—$N(R^\circ)_2$; or —$(C_{1-4}$ straight or branched alkylene)$C(O)O$—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5- to 6-membered heteroaryl ring), a 5- to 6-membered saturated, partially unsaturated, or aryl ring having 0-4 heteroatoms independently selected from nitrogen, oxygen, or sulfur, or an 8- to 10-membered bicyclic aryl ring having 0-4 heteroatoms independently selected from nitrogen, oxygen, or sulfur, or, notwithstanding the definition above, two independent occurrences of $R^\circ$, taken together with their intervening atom(s), form a 3- to 12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_1$-4 straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 3- to 6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O ("oxo"), =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5- to 6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5- to 6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3- to 12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Treat: As used herein, the terms "treat," "treatment," or "treating" refer to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example, for the purpose of decreasing the risk of developing pathology associated with the disease, disorder, and/or condition.

DETAILED DESCRIPTION OF CERTAIN EMBODIMENTS

Programmed Axonal Degeneration and SARM1

Axonal degeneration is a major pathological feature of neurological diseases such as, but not limited to, Alzheimer's disease, Parkinson's disease, ALS, multiple sclerosis, diabetic peripheral neuropathy, chemotherapy-induced peripheral neuropathy, inherited neuropathy, traumatic brain injury, and/or glaucoma. Damaged or unhealthy axons are eliminated via an intrinsic self-destruction program that is distinct from traditional cellular death pathways like apoptosis known as Wallerian degeneration. (Gerdts, J., et al., Neuron, 2016, 89, 449-460; Whitmore, A. V. et al., Cell Death Differ., 2003, 10, 260-261). In Wallerian degeneration, a peripheral nerve undergoes selective breakdown of the axon segment distal to an injury, whereas the proximal axon segment and cell body remain intact. This degeneration is characterized, first, by a depletion of nicotinamide mononucleotide adenyltransferase (NMNAT), followed by nicotinamide adenine dinucleotide (NAD+) loss, adenosine triphosphate (ATP) loss, neurofilament proteolysis, and finally axonal degradation approximately 8 to 24 hours following injury. (Gerdts, J., et al., Neuron, 2016, 89, 449-460).

NAD+ is a ubiquitous metabolite with critical roles in energy metabolism and cell signaling (Belenkey et al., Trends Biochem., 2007, 32, 12-19; Chiarugi et al., Nat. Rev. Cancer, 2012, 12, 741-752). The homeostatic regulation of NAD+ levels is also responsible for maintaining axonal stability and integrity. Accordingly, manipulations that increase axonal localization of NMNAT1 confer axonal protection (Babetto et al., Cell Rep., 2010, 3, 1422-1429; Sasaki et al., J. Neurosci., 2009).

In a genome-wide RNAi screen in primary mouse neurons, Sterile Alpha and TIR motif-containing 1 (SARM1)

was identified, in which knockdown of SARM1 led to long-lasting protection of sensory neurons against injury-induced axon degeneration (Gerdts et al., *J Neurosci*, 2013, 33, 13569-13580). SARM1 belongs to the family of cytosolic adaptor proteins but is unique among its members because it is the most evolutionary ancient adaptor, paradoxically inhibits TLR signaling, and has been identified as the central executioner of the injury-induced axon death pathway (O'Neill, L. A. & Bowie, A. G., *Nat. Rev. Immunol.*, 2007, 7, 353-364; Osterloh, J. M., et al., *Science*, 2012, 337, 481-484; Gerdts, J., et al., *J. Neurosci*. 33, 2013, 13569-13580). Activation of SARM1 via axonal injury or forced dimerization of SARM1-TIR domains promotes rapid and catastrophic depletion of Nicotinamide Adenine Dinucleotide (NAD+), followed soon after by axonal degradation, thus highlighting the central role of NAD+ homeostasis in axonal integrity. (Gerdts, J., et al., *Science*, 2015, 348, 453-457). SARM1 is required for this injury-induced NAD+ depletion both in vitro and in vivo and SARM1 activation triggers axon degeneration locally via NAD(+) destruction (Gerdts et al., et al., *Science*, 2015 348, 452-457; Sasaki et al., *J. Biol. Chem*. 2015, 290, 17228-17238; both of which are hereby incorporated by reference in their entireties).

From genetic loss-of-function studies it is clear that SARM1 serves as the central executioner of the axonal degeneration pathway following an injury. Genetic knockout of SARM1 allows for preservation of axons for 14 or more days after nerve transection (Osterloh, J. M., et al., *Science*, 2012, 337, 481-484; Gerdts, J., et al. *J. Neurosci.*, 2013, 33, 13569-13580) and also improves functional outcomes in mice after traumatic brain injury (Henninger, N. et al., *Brain* 139, 2016, 1094-1105). In addition to the role of SARM1 in direct axonal injury, SARM1 is also required for axonal degeneration observed in chemotherapy-induced peripheral neuropathy. Loss of SARM1 blocks chemotherapy-induced peripheral neuropathy, both inhibiting axonal degeneration and heightened pain sensitivity that develops after chemotherapeutic vincristine treatment (Geisler et al, *Brain*, 2016, 139, 3092-3108).

SARM1 contains multiple conserved motifs including SAM domains, ARM/HEAT motifs and a TIR domain (FIG. 1) that mediate oligomerization and protein-protein interactions (O'Neill, L. A. & Bowie, A. G., *Nat. Rev. Immunol.*, 2007, 7, 353-364; Tewari, R., et al., *Trends Cell Biol.*, 2010, 20, 470-481; Qiao, F. & Bowie, J. U., *Sci. STKE* 2005, re7, 2005). TIR domains are commonly found in signaling proteins functioning in innate immunity pathways where they serve as scaffolds for protein complexes (O'Neill, L. A. & Bowie, A. G., *Nat. Rev. Immunol.*, 2007, 7, 353-364). Interestingly, dimerization of SARM1-TIR domains is sufficient to induce axonal degeneration and to rapidly trigger degradation of NAD+ by acting as the NAD+ cleaving enzyme (Milbrandt et al., WO 2018/057989; Gerdts, J., et al., *Science*, 2015, 348, 453-457). Given the central role of SARM1 in the axonal-degeneration pathway and its identified NADase activity, efforts have been undertaken to identify agents that can regulate SARM1, and potentially act as useful therapeutic agents, for example, to protect against neurodegenerative diseases including peripheral neuropathy, traumatic brain injury, and/or neurodegenerative diseases.

Among other things, the present disclosure provides certain compounds and/or compositions that act as SARM1 inhibitory agents (e.g., as SARM1 inhibitory agents), and technologies relating thereto.

Compounds

In some embodiments, the present disclosure provides a compound of Formula I:

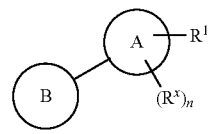

I or a pharmaceutically acceptable salt thereof, wherein:
Ring A is a 5- to 6-membered heteroaryl ring having 1-3 heteroatoms independently selected from oxygen, nitrogen, and sulfur;
$R^1$ is an optionally substituted group selected from a 3- to 7-membered saturated or partially unsaturated heterocyclic ring having 1-3 heteroatoms independently selected from oxygen, nitrogen, and sulfur or a 5- to 6-membered heteroaryl ring having 1-3 heteroatoms independently selected from oxygen, nitrogen, and sulfur;
each $R^x$ is selected from halogen, cyano, OR, SR, $N(R)_2$, or an optionally substituted group selected from $C_{1-4}$ aliphatic, a 3- to 7-membered saturated or partially unsaturated carbocyclic ring, a 3- to 7-membered saturated or partially unsaturated heterocyclic ring having 1-3 heteroatoms independently selected from oxygen, nitrogen, and sulfur, phenyl, and a 5- to 6-membered heteroaryl ring having 1-3 heteroatoms independently selected from oxygen, nitrogen, and sulfur;
Ring B is a saturated 5- to 7-membered heterocyclic ring having the structure

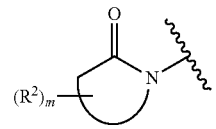

and optionally comprising one additional group selected from —NH—, —O—, and —$NR^2$—;
each R is independently hydrogen, or an optionally substituted group selected from $C_{1-6}$ aliphatic, a 3- to 7-membered saturated or partially unsaturated heterocyclic ring having 1-3 heteroatoms independently selected from oxygen, nitrogen, and sulfur, phenyl, and a 5- to 6-membered heteroaryl ring having 1-3 heteroatoms independently selected from oxygen, nitrogen, and sulfur; or:
two R groups, together with the nitrogen atom to which they are attached, form an optionally substituted 3- to 7-membered monocyclic heterocyclic ring having 0-2 additional heteroatoms independently selected from oxygen, nitrogen, and sulfur;
each $R^2$ is independently halogen, $N(R)_2$, OR, $C_{1-3}$ aliphatic or —($C_{1-3}$ aliphatic)$R^3$;
each $R^3$ is independently an optionally substituted group selected from $C_{1-6}$ aliphatic, a 3- to 7-membered saturated or partially unsaturated heterocyclic ring having 1-3 heteroatoms independently selected from oxygen, nitrogen, and sulfur, phenyl, a 5- to 6-membered heteroaryl ring having 1-3 heteroatoms independently selected from oxygen, nitrogen, and sulfur, a 8- to 10-membered bicyclic saturated, partially unsaturated or aryl carbocyclic ring, a 8- to 10-membered bicyclic saturated or partially unsaturated heterocyclic ring having 1-3 heteroatoms independently selected from oxygen, nitrogen, and sulfur, or a 8- to 10-membered bicyclic heteroaryl ring having 1-3 heteroatoms independently selected from oxygen, nitrogen, and sulfur;

m is 0, 1, or 2; and n is 0, 1, or 2.

As defined generally above, Ring A is a 5- to 6-membered heteroaryl ring having 1-3 heteroatoms independently selected from oxygen, nitrogen, and sulfur. In some embodiments, Ring A is a 5-membered heteroaryl ring having 1-3 heteroatoms independently selected from oxygen, nitrogen, and sulfur. In some embodiments, Ring A is pyrrolyl, furanyl, or thiophenyl. In some embodiments, Ring A is a 5-membered heteroaryl ring having 2-3 heteroatoms independently selected from oxygen, nitrogen, and sulfur. In some embodiments, Ring A is a 5-membered heteroaryl ring having 2 heteroatoms independently selected from oxygen, nitrogen, and sulfur. In some embodiments, Ring A is a group selected from pyrazolyl, imidazolyl, isothiazolyl, and thiazolyl.

In some embodiments, Ring A is a 5-membered heteroaryl ring having 3 heteroatoms independently selected from oxygen, nitrogen, and sulfur. In some such embodiments, Ring A is a group selected from triazolyl and thiadiazolyl.

In some embodiments, Ring A is a 6-membered heteroaryl ring having 1-2 nitrogen atoms. In some embodiments, Ring A is pyridinyl. In some embodiments, Ring A is pyridin-2(1H)-onyl.

In some embodiments, Ring A is selected from

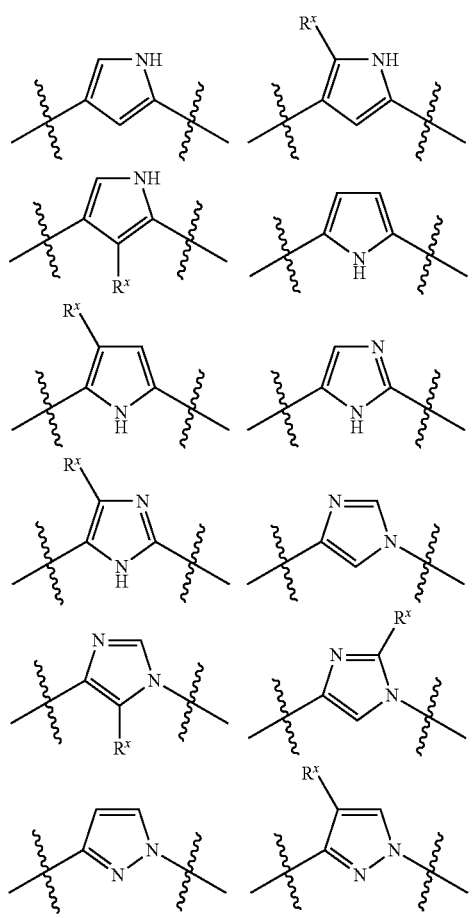

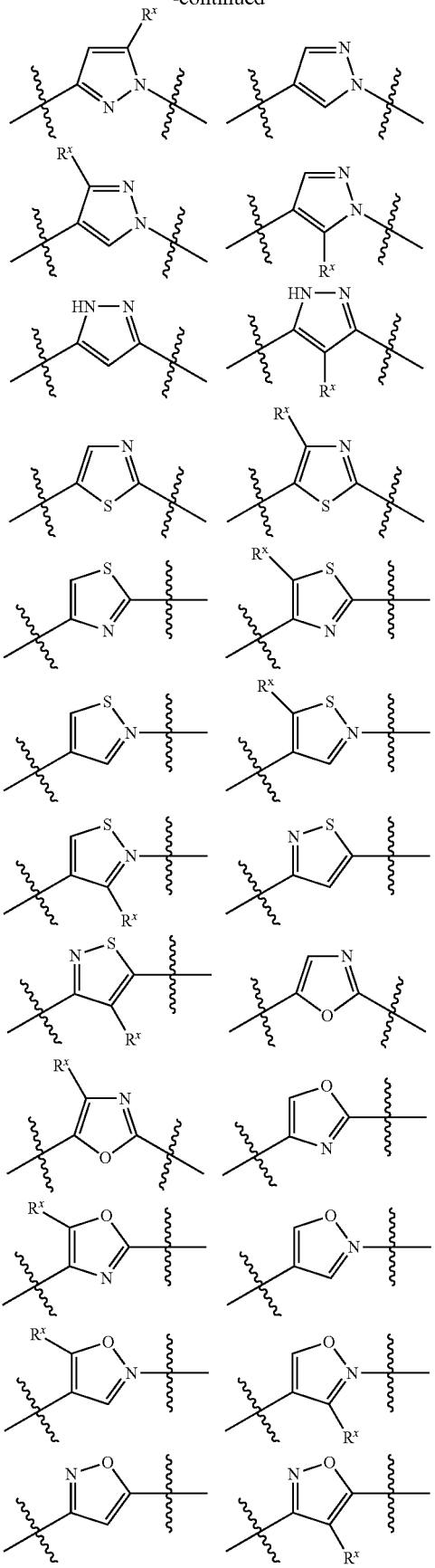

-continued

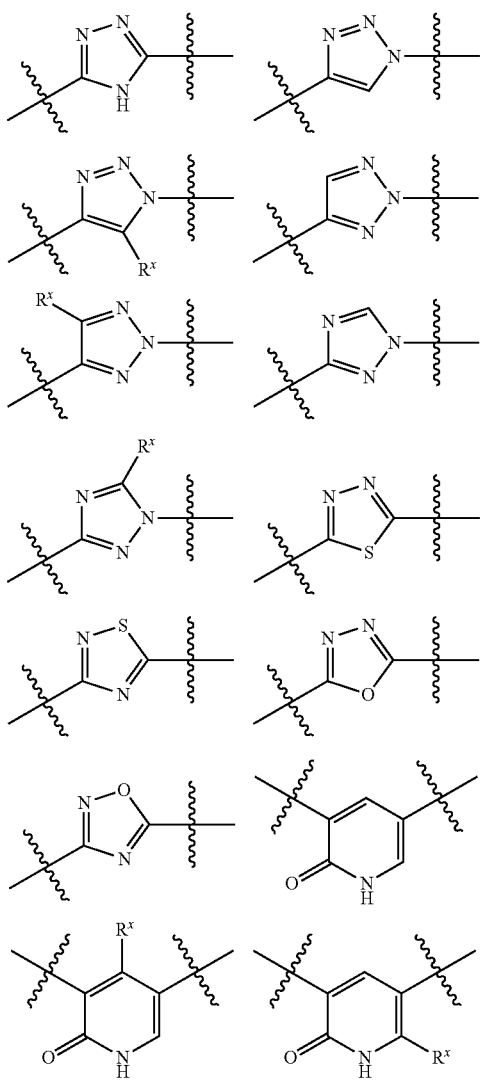

In some embodiments, Ring A is selected from

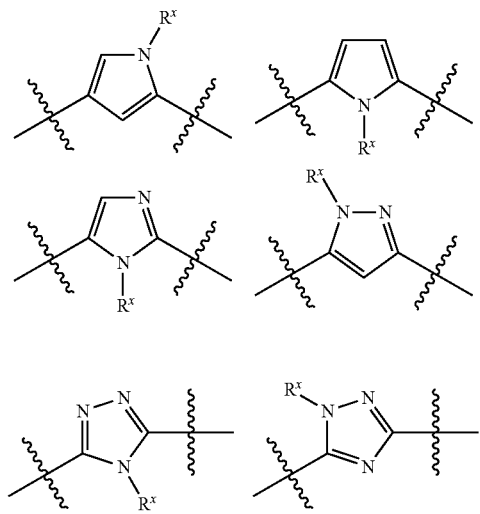

-continued

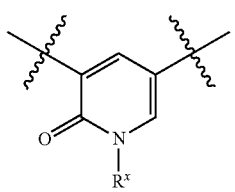

wherein each $R^x$ is independently an optionally substituted group selected from $C_{1-4}$ aliphatic, a 3- to 7-membered saturated or partially unsaturated carbocyclic ring, a 3- to 7-membered saturated or partially unsaturated heterocyclic ring having 1-3 heteroatoms independently selected from oxygen, nitrogen, and sulfur, phenyl, and a 5- to 6-membered heteroaryl ring having 1-3 heteroatoms independently selected from oxygen, nitrogen, and sulfur.

In some embodiments, Ring A is selected from

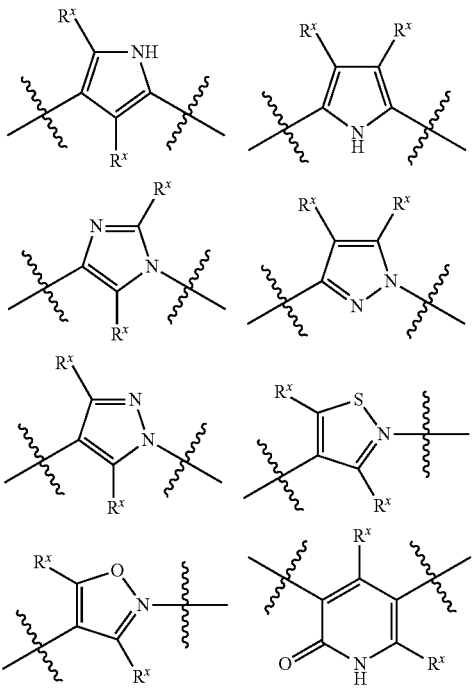

In some embodiments, Ring A is selected from

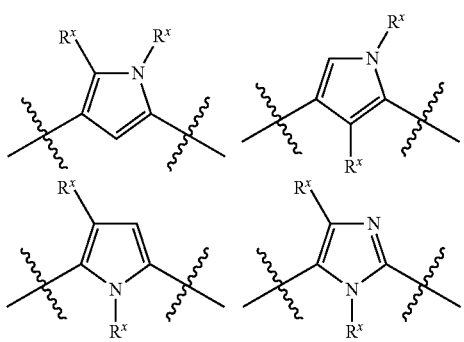

-continued

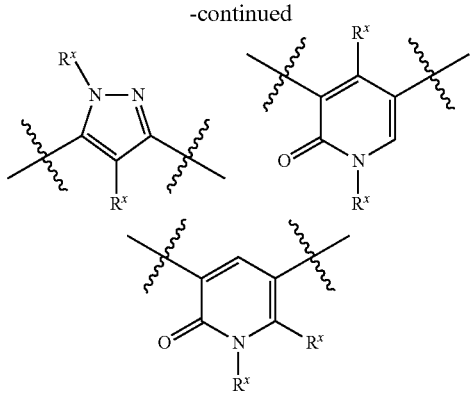

wherein:
  each $R^x$ on a nitrogen atom is independently selected from an optionally substituted group selected from $C_{1-4}$ aliphatic, a 3- to 7-membered saturated or partially unsaturated carbocyclic ring, a 3- to 7-membered saturated or partially unsaturated heterocyclic ring having 1-3 heteroatoms independently selected from oxygen, nitrogen, and sulfur, phenyl, and a 5- to 6-membered heteroaryl ring having 1-3 heteroatoms independently selected from oxygen, nitrogen, and sulfur; and
  each $R^x$ on a carbon atom is independently selected from halogen, cyano, OR, SR, $N(R)_2$, or an optionally substituted group selected from $C_{1-4}$ aliphatic, a 3- to 7-membered saturated or partially unsaturated carbocyclic ring, a 3- to 7-membered saturated or partially unsaturated heterocyclic ring having 1-3 heteroatoms independently selected from oxygen, nitrogen, and sulfur, phenyl, and a 5- to 6-membered heteroaryl ring having 1-3 heteroatoms independently selected from oxygen, nitrogen, and sulfur.

In some embodiments, Ring A is selected from

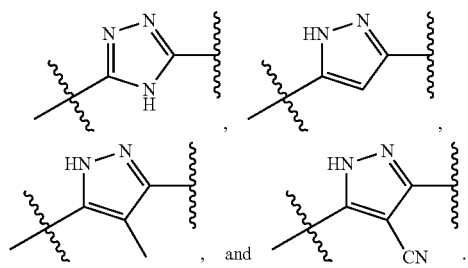

In certain particularly preferred embodiments, Ring A is selected from

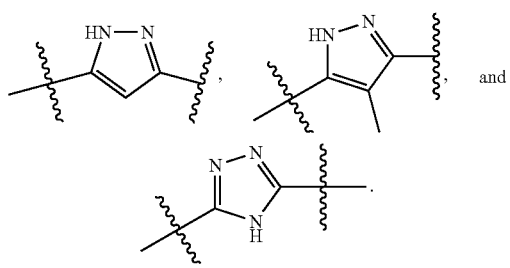

As defined generally above, $R^1$ is an optionally substituted group selected from a 3- to 7-membered saturated or partially unsaturated heterocyclic ring having 1-3 heteroatoms independently selected from oxygen, nitrogen, and sulfur or a 5- to 6-membered heteroaryl ring having 1-3 heteroatoms independently selected from oxygen, nitrogen, and sulfur.

In some embodiments, $R^1$ is an optionally substituted 3- to 7-membered saturated or partially unsaturated heterocyclic ring having 1-3 heteroatoms independently selected from oxygen, nitrogen, and sulfur. In some embodiments, $R^1$ is an optionally substituted 5- to 6-membered saturated or partially unsaturated heterocyclic ring having 1-3 heteroatoms independently selected from oxygen, nitrogen, and sulfur. In some embodiments, $R^1$ is an optionally substituted group selected from pyrrolidinyl, piperidinyl, morpholinyl, and piperazinyl.

In some embodiments, $R^1$ is an optionally substituted 5- to 6-membered heteroaryl ring having 1-3 heteroatoms independently selected from oxygen, nitrogen, and sulfur.

In some embodiments, $R^1$ is an optionally substituted 5-membered heteroaryl ring having 1-3 heteroatoms independently selected from oxygen, nitrogen, and sulfur. In some embodiments, $R^1$ is an optionally substituted 5-membered heteroaryl ring having 1-2 heteroatoms independently selected from oxygen, nitrogen, and sulfur. In some embodiments, $R^1$ is an optionally substituted group selected from pyrazolyl, thiazolyl, and thiophenyl ring.

In some embodiments, $R^1$ is an optionally substituted 6-membered heteroaryl ring having 1-3 nitrogen atoms. In some embodiments, $R^1$ is an optionally substituted 6-membered heteroaryl ring having 1-2 nitrogen atoms. In some embodiments, $R^1$ is an optionally substituted group selected from pyridinyl, pyrimidinyl and pyridazinyl.

In some embodiments, $R^1$ is selected from

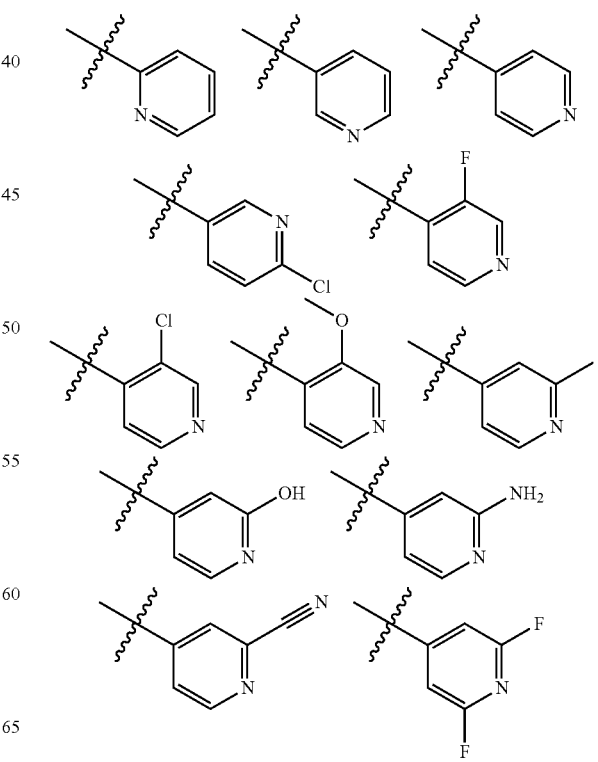

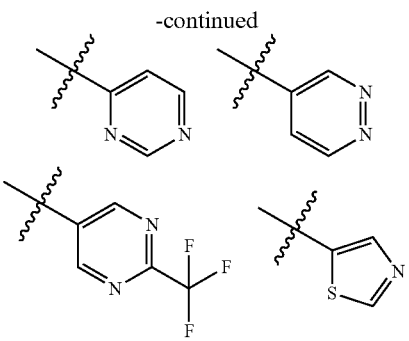

In certain particularly preferred embodiments, $R^1$ is selected from

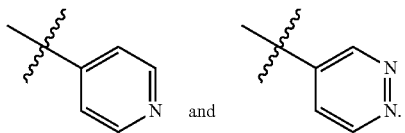 [SMILES: *c1ccncc1 ; *c1ccnnc1]

As defined generally above, each $R^x$ is independently selected from halogen, cyano, OR, SR, N(R)₂, or an optionally substituted group selected from $C_{1-4}$ aliphatic, a 3- to 7-membered saturated or partially unsaturated carbocyclic ring, a 3- to 7-membered saturated or partially unsaturated heterocyclic ring having 1-3 heteroatoms independently selected from oxygen, nitrogen, and sulfur, phenyl, and a 5- to 6-membered heteroaryl ring having 1-3 heteroatoms independently selected from oxygen, nitrogen, and sulfur. In some embodiments, $R^x$ is halogen. In some such embodiments, $R^x$ is chloro or bromo.

In some embodiments, $R^x$ is cyano.

In some embodiments, $R^x$ is OR. In some embodiments, $R^x$ is OR, wherein R is selected from hydrogen and optionally substituted $C_{1-6}$ aliphatic. In some embodiments, $R^x$ is OR, wherein R is selected from hydrogen and optionally substituted $C_{1-4}$ aliphatic. In some embodiments, $R^x$ is selected from OH, OCH₃, and OCH₂CH₃.

In some embodiments, $R^x$ is SR. In some embodiments, $R^x$ is SR, wherein R is selected from hydrogen and optionally substituted $C_{1-6}$ aliphatic. In some embodiments, $R^x$ is SR, wherein R is selected from hydrogen and optionally substituted $C_{1-4}$ aliphatic. In some embodiments, $R^x$ is selected from SH, SCH₃, and SCH₂CH₃.

In some embodiments, $R^x$ is N(R)₂. In some embodiments, $R^x$ is N(R)₂, wherein R is selected from hydrogen and optionally substituted $C_{1-6}$ aliphatic. In some embodiments, $R^x$ is N(R)₂, wherein R is selected from hydrogen and optionally substituted $C_{1-4}$ aliphatic. In some embodiments, $R^x$ is selected from NH₂, NHCH₃, NHCH₂CH₃, N(CH₃)₂, and N(CH₂CH₃)₂.

In some embodiments, $R^x$ is optionally substituted $C_{1-4}$ aliphatic. In some embodiments, $R^x$ is optionally substituted $C_{3-4}$ aliphatic. In some such embodiments, $R^x$ is selected from tert-butyl,

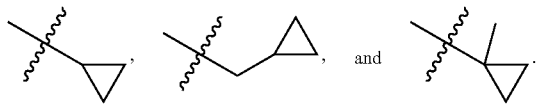

In some embodiments, $R^x$ is $C_{1-4}$ aliphatic optionally substituted with a group selected from halogen, —(CH₂)₀₋₄R°, —(CH₂)₀₋₄OR°, —(CH₂)₀₋₄N(R°)₂, —(CH₂)₀₋₄C(O)OR°, and —(CH₂)₀₋₄C(O)NR°₂. In some such embodiments, R° is selected from hydrogen, $C_{1-6}$ aliphatic, —CH₂Ph, —O(CH₂)₀₋₁Ph, —CH₂-(5- to 6-membered heteroaryl ring), a 5- to 6-membered saturated, partially unsaturated, or aryl ring having 0-4 heteroatoms independently selected from nitrogen, oxygen, or sulfur, or an 8- to 10-membered bicyclic aryl ring having 0-4 heteroatoms independently selected from nitrogen, oxygen, or sulfur, or: two independent occurrences of R°, taken together with their intervening atom(s), form a 3- to 12-membered saturated, partially unsaturated, or aryl mono- or bicyclic ring having 0-4 heteroatoms independently selected from nitrogen, oxygen, or sulfur.

In some embodiments, $R^x$ is $C_{1-4}$ aliphatic optionally substituted with a group selected from halogen, —R°, —OR°, —N(R°)₂, —C(O)OR°, and —C(O)NR°₂. In some embodiments, $R^x$ is $C_{1-4}$ aliphatic optionally substituted with halogen. In some such embodiments, $R^x$ is selected from —CH₃, —CF₃, —CHF₂, and CH₂F.

In some embodiments, $R^x$ is selected from —CH₂R°, —CH₂OR°, —CH₂N(R°)₂, —CH₂C(O)OR°, and —CH₂C(O)N(R°)₂. In some such embodiments, $R^x$ is selected from —CH₂OH, —CH₂OCH₃, —CH₂C(O)NH₂, —CH₂C(O)NHCH₃, and —CH₂C(O)N(CH₃)₂.

In some embodiments, $R^x$ is an optionally substituted 3- to 7-membered saturated or partially unsaturated carbocyclic ring. In some embodiments, $R^x$ is an optionally substituted 5- to 7-membered saturated or partially unsaturated carbocyclic ring. In some embodiments, $R^x$ is an optionally substituted 5- to 7-membered saturated carbocyclic ring. In some such embodiments, $R^x$ is selected from optionally substituted cyclopentyl or cyclohexyl.

In some embodiments, $R^x$ is an optionally substituted 3- to 7-membered saturated or partially unsaturated heterocyclic ring having 1-3 heteroatoms independently selected from oxygen, nitrogen, and sulfur. In some embodiments, $R^x$ is an optionally substituted 3- to 4-membered saturated heterocyclic ring having 1 heteroatom selected from oxygen, nitrogen, and sulfur. In some embodiments, $R^x$ is an optionally substituted 5- to 7-membered saturated or partially unsaturated heterocyclic ring having 1-3 heteroatoms independently selected from oxygen, nitrogen, and sulfur. In some embodiments, $R^x$ is an optionally substituted 5- to 7-membered saturated heterocyclic ring having 1-3 heteroatoms independently selected from oxygen, nitrogen, and sulfur. In some such embodiments, $R^x$ is selected from optionally substituted pyrrolidinyl, piperidinyl, piperazinyl, and morpholinyl.

In some embodiments, $R^x$ is optionally substituted phenyl.

In some embodiments, $R^x$ is an optionally substituted 5- to 6-membered heteroaryl ring having 1-3 heteroatoms independently selected from oxygen, nitrogen, and sulfur. In some embodiments, $R^x$ is an optionally substituted 5-membered heteroaryl ring having 1-3 heteroatoms independently selected from oxygen, nitrogen, and sulfur. In some embodiments, $R^x$ is an optionally substituted 5-membered heteroaryl ring having 1-2 heteroatoms independently selected from oxygen, nitrogen, and sulfur. In some such embodiments, $R^x$ is selected from optionally substituted pyrrolyl, pyrazolyl, imidazolyl, oxazolyl, and thiazolyl.

In some embodiments, $R^x$ is an optionally substituted 6-membered heteroaryl ring having 1-3 nitrogen atoms. In some embodiments, $R^x$ is an optionally substituted 6-membered heteroaryl ring having 1-2 nitrogen atoms. In some such embodiments, $R^x$ is selected from optionally substituted pyridinyl, pyridazinyl, pyrimidinyl, and pyrazinyl.

As defined generally above, Ring B is a saturated 5- to 7-membered heterocyclic ring having the structure

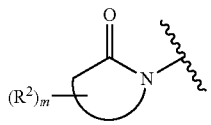

and optionally comprising one additional group selected from —NH—, —O—, and —NR²—. In some embodiments, Ring B is a saturated 5- to 7-membered heterocyclic ring having the structure

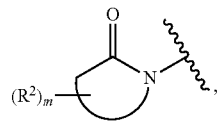

wherein Ring B further comprises one additional group selected from —NH—, —O—, and —NR²—.

In some embodiments, Ring B is a saturated 5-membered heterocyclic ring having the structure

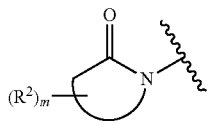

and optionally comprising one additional group selected from —NH—, —O—, and —NR²—.

In some embodiments Ring B is a saturated 6-membered heterocyclic ring having the structure

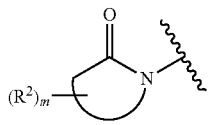

and optionally comprising one additional group selected from —NH—, —O—, and —NR²—. In some embodiments, Ring B is a saturated 6-membered heterocyclic ring having the structure,

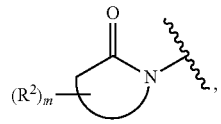

wherein Ring B further comprises one additional group selected from —NH—, —O—, and —NR²—.

In some embodiments, Ring B is a saturated 7-membered heterocyclic having the structure

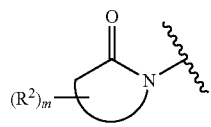

and optionally comprising one additional group selected from —NH—, —O—, and —NR²—. In some embodiments, Ring B is a saturated 7-membered heterocyclic having the structure

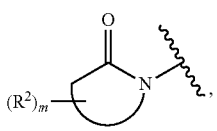

wherein Ring B further comprises one additional group selected from —NH—, —O—, and —NR²—.

In some embodiments, Ring B is selected from

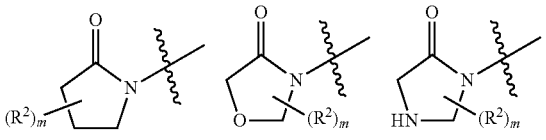
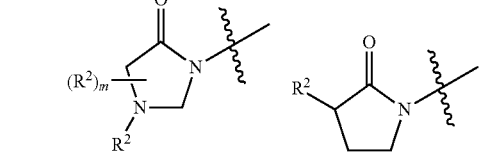
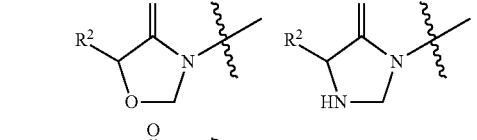
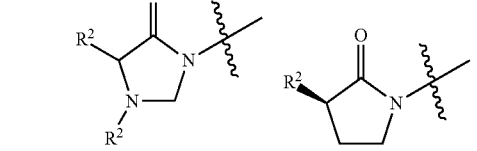
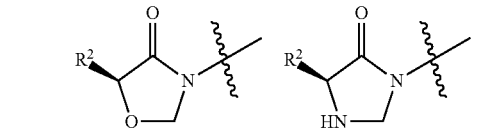
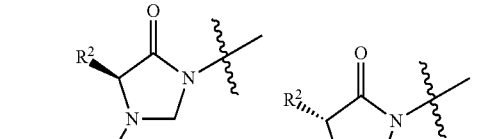
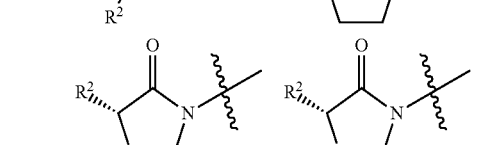

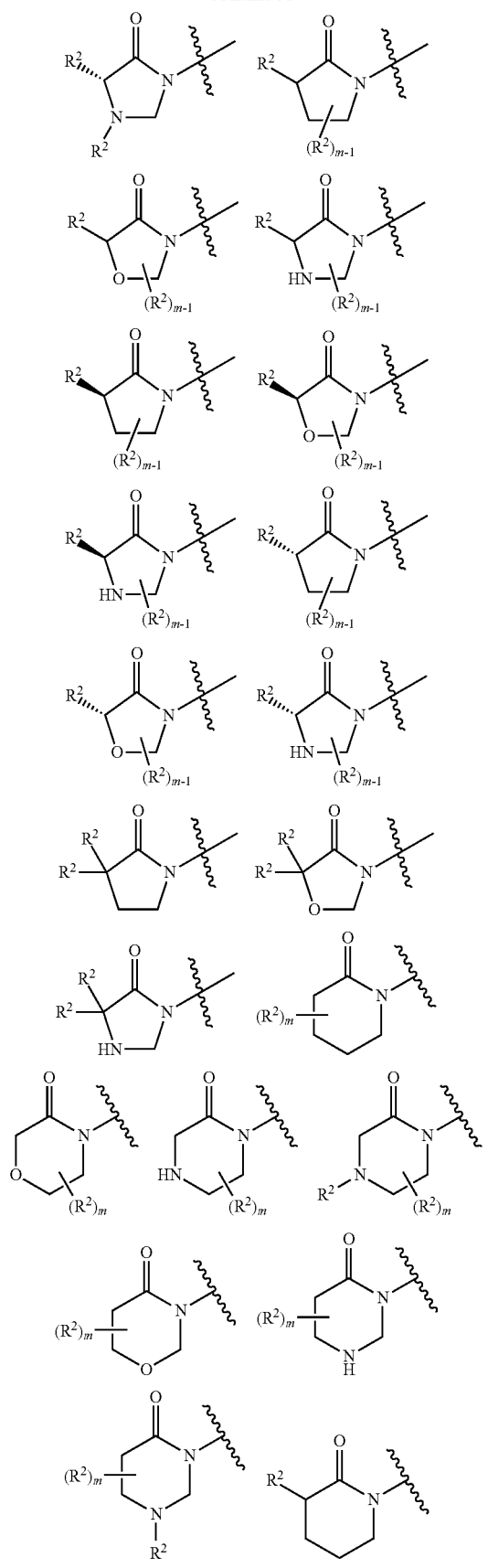
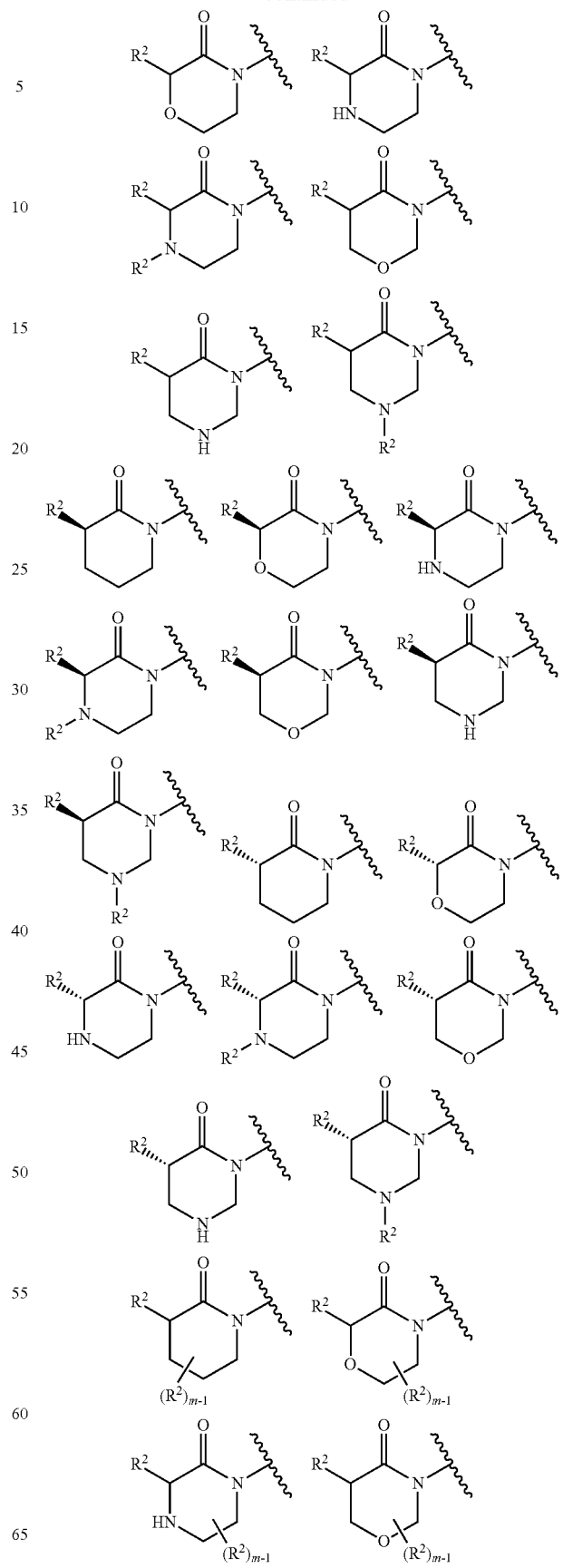

-continued
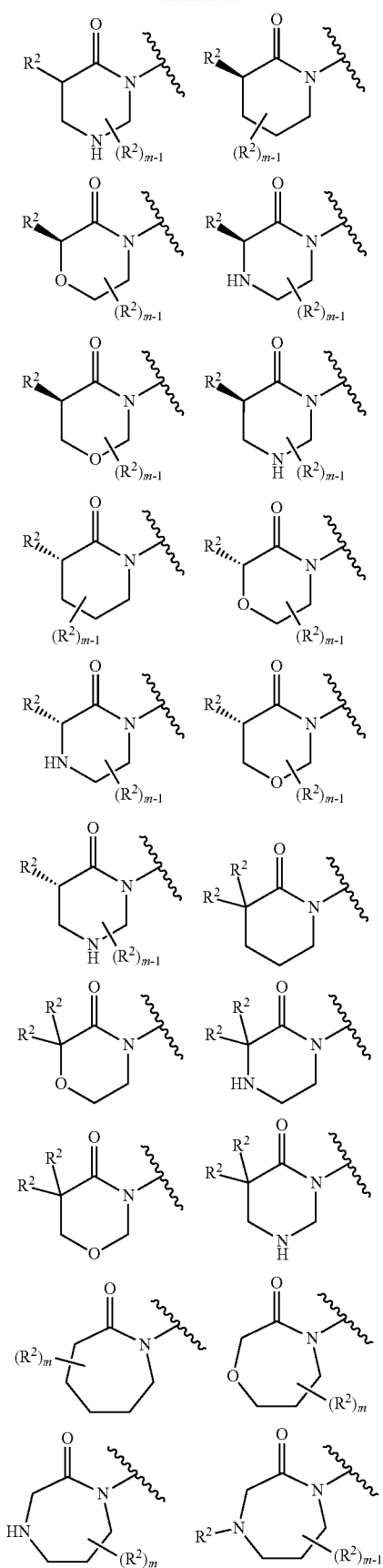
-continued
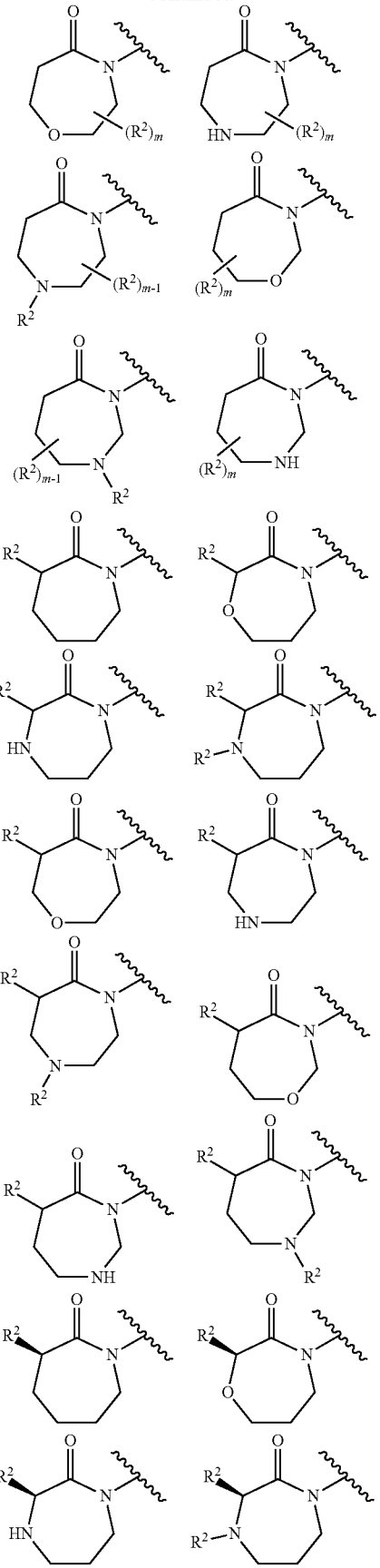

-continued
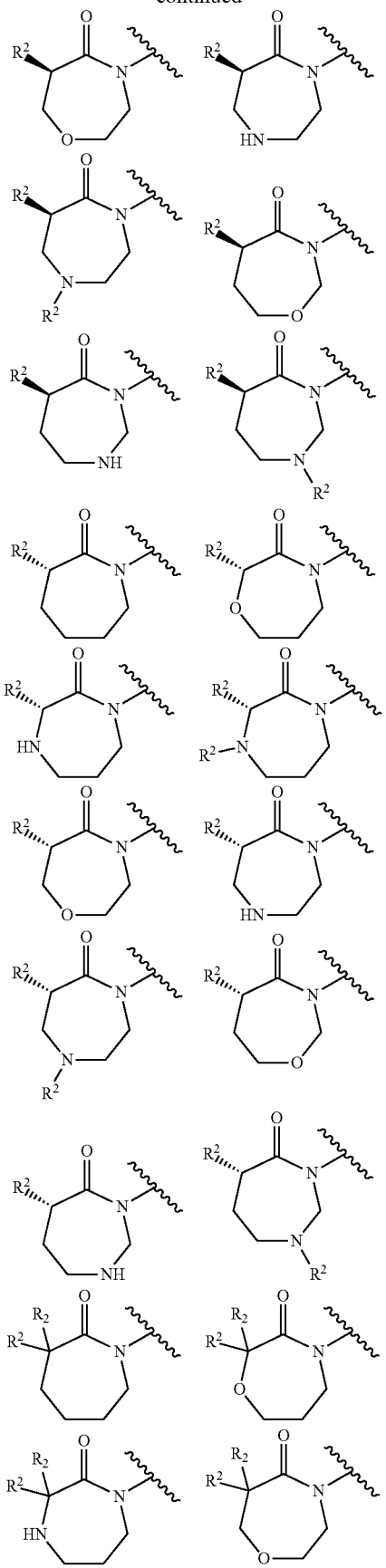
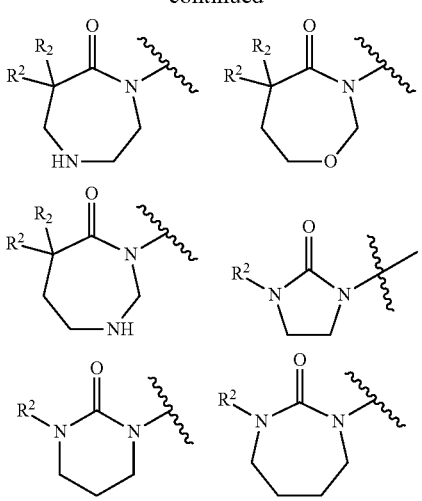
wherein:
each R² on a nitrogen atom is —(C₁₋₃ aliphatic)R³; and
each R² on a carbon atom is independently selected from halogen, N(R)₂, OR, or —(C₁₋₃ aliphatic)R³.
In some embodiments, Ring B is selected from
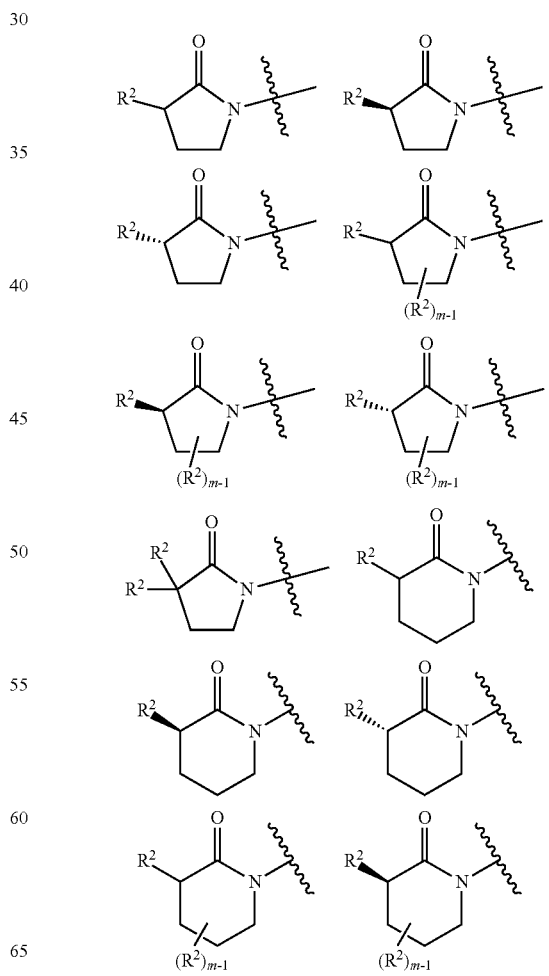

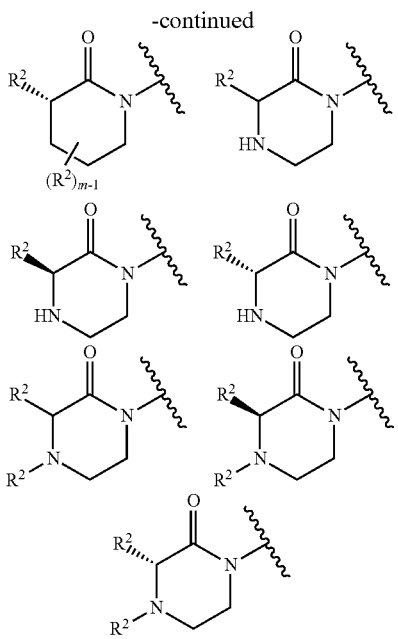

As defined generally above, each R is independently hydrogen or an optionally substituted group selected from $C_{1-6}$ aliphatic, a 3- to 7-membered saturated or partially unsaturated heterocyclic ring having 1-3 heteroatoms independently selected from oxygen, nitrogen, and sulfur, phenyl, and a 5- to 6-membered heteroaryl ring having 1-3 heteroatoms independently selected from oxygen, nitrogen, and sulfur; or two R groups, together with the nitrogen atom to which they are attached, form an optionally substituted 3- to 7-membered monocyclic heterocyclic ring having 0-2 additional heteroatoms independently selected from oxygen, nitrogen, and sulfur. In some embodiments, R is hydrogen. In some embodiments, R is an optionally substituted group selected from $C_{1-6}$ aliphatic, a 3- to 7-membered saturated or partially unsaturated heterocyclic ring having 1-3 heteroatoms independently selected from oxygen, nitrogen, and sulfur, phenyl, and a 5- to 6-membered heteroaryl ring having 1-3 heteroatoms independently selected from oxygen, nitrogen, and sulfur; or two R groups, together with the nitrogen atom to which they are attached, form an optionally substituted 3- to 7-membered monocyclic heterocyclic ring having 0-2 additional heteroatoms independently selected from oxygen, nitrogen, and sulfur.

In some embodiments, R is optionally substituted $C_{1-6}$ aliphatic. In some embodiments, R is $C_{1-6}$ aliphatic optionally substituted with oxo and $OR°$, wherein $R°$ is $C_{1-6}$ aliphatic. In some such embodiments, R is —C(O)OtBu.

In some embodiments, R is $C_{1-6}$ aliphatic. In some such embodiments, R is methyl or ethyl.

In some embodiments, R is selected from hydrogen and optionally substituted $C_{1-6}$ aliphatic. In some such embodiments, R is selected from hydrogen, methyl or ethyl.

As defined generally above, each $R^2$ is independently halogen, $N(R)_2$, OR, or —($C_{1-3}$ aliphatic)$R^3$. In some embodiments, $R^2$ is halogen. In some embodiments, $R^2$ is $N(R)_2$. In some such embodiments, $R^2$ is $NH_2$. In some embodiments, $R^2$ is OR. In some such embodiments, $R^2$ is OH.

In some embodiments, $R^2$ is —($C_{1-3}$ aliphatic)$R^3$. In some embodiments, $R^2$ is —$CH_2R^3$. In some embodiments, $R^2$ is —$CH(CH_3)R^3$. In some embodiments, $R^2$ is —$CH_2CH_2R^3$.

As defined generally above, each $R^3$ is independently an optionally substituted group selected from $C_{1-6}$ aliphatic, a 3- to 7-membered saturated or partially unsaturated heterocyclic ring having 1-3 heteroatoms independently selected from oxygen, nitrogen, and sulfur, phenyl, a 5- to 6-membered heteroaryl ring having 1-3 heteroatoms independently selected from oxygen, nitrogen, and sulfur, a 8- to 10-membered bicyclic saturated, partially unsaturated or aryl carbocyclic ring, a 8- to 10-membered bicyclic saturated or partially unsaturated heterocyclic ring having 1-3 heteroatoms independently selected from oxygen, nitrogen, and sulfur, or a 8- to 10-membered bicyclic heteroaryl ring having 1-3 heteroatoms independently selected from oxygen, nitrogen, and sulfur.

In some embodiments, $R^3$ is optionally substituted $C_{1-6}$ aliphatic. In some such embodiments, $R^3$ is an optionally substituted group selected from cyclopentyl or cyclohexyl. In some embodiments, $R^3$ is $C_{1-6}$ aliphatic. In some embodiments, $R^3$ is methyl. In some embodiments, $R^3$ is ethyl. In some embodiments, $R^3$ is cyclohexyl.

In some embodiments, $R^3$ is optionally substituted phenyl.

In some embodiments, $R^3$ is an optionally substituted 3- to 7-membered saturated or partially unsaturated heterocyclic ring having 1-3 heteroatoms independently selected from oxygen, nitrogen, and sulfur. In some embodiments, $R^3$ is an optionally substituted 3-membered saturated heterocyclic ring having 1 heteroatom selected from oxygen, nitrogen, and sulfur. In some embodiments, $R^3$ is an optionally substituted 4-membered saturated heterocyclic ring having 1 heteroatom selected from oxygen, nitrogen, and sulfur. In some embodiments, $R^3$ is an optionally substituted 5-membered saturated or partially unsaturated heterocyclic ring having 1-2 heteroatoms independently selected from oxygen, nitrogen, and sulfur. In some embodiments, $R^3$ is an optionally substituted 6-membered saturated or partially unsaturated heterocyclic ring having 1-3 heteroatoms independently selected from oxygen, nitrogen, and sulfur. In some embodiments, $R^3$ is an optionally substituted group selected from pyrrolidinyl, piperidinyl, morpholinyl, and piperazinyl.

In some embodiments, $R^3$ is an optionally substituted 5- to 6-membered heteroaryl ring having 1-3 heteroatoms independently selected from oxygen, nitrogen, and sulfur. In some embodiments, $R^3$ is an optionally substituted 5-membered heteroaryl ring having 1-3 heteroatoms independently selected from oxygen, nitrogen, and sulfur. In some embodiments, $R^3$ is an optionally substituted 5-membered heteroaryl ring having 1-2 heteroatoms independently selected from oxygen, nitrogen, and sulfur. In some such embodiments, $R^3$ is an optionally substituted group selected from thiophenyl, pyrazolyl, and imidazolyl.

In some embodiments, $R^3$ is an optionally substituted 6-membered heteroaryl ring having 1-3 nitrogen atoms. In some embodiments, $R^3$ is an optionally substituted 6-membered heteroaryl ring having 1-2 nitrogen atoms. In some such embodiments, $R^3$ is an optionally substituted group selected from pyridinyl or pyrimidinyl.

In some embodiments, $R^3$ is an optionally substituted 8- to 10-membered bicyclic saturated, partially unsaturated or aryl carbocyclic ring. In some embodiments, $R^3$ is an optionally substituted 9-membered bicyclic saturated, partially unsaturated or aryl carbocyclic ring. In some such embodiments, $R^3$ is optionally substituted 2,3-dihydro-1H-indenyl. In some embodiments, $R^3$ is an optionally substituted 10-membered bicyclic saturated, partially unsaturated or aryl carbocyclic ring. In some such embodiments, $R^3$ is an optionally substituted group selected from 1,2,3,4-tetrahydronaphthalenyl and naphthalenyl.

In some embodiments, R³ is an optionally substituted 8- to 10-membered bicyclic saturated or partially unsaturated heterocyclic ring having 1-3 heteroatoms independently selected from oxygen, nitrogen, and sulfur. In some embodiments, R³ is an optionally substituted 9-membered bicyclic saturated or partially unsaturated heterocyclic ring having 1-3 heteroatoms independently selected from oxygen, nitrogen, and sulfur. In some embodiments, R³ is an optionally substituted 10-membered bicyclic saturated or partially unsaturated heterocyclic ring having 1-3 heteroatoms independently selected from oxygen, nitrogen, and sulfur. In some such embodiments, R³ is an optionally substituted group selected from chromanyl, isochromanyl, 1,2,3,4-tetrahydroquinolinyl, 3,4-dihydro-2H-benzo[b][1,4]oxazinyl, and 2H-benzo[b][1,4]oxazin-3(4H)-onyl.

In some embodiments, R³ is an optionally substituted 8- to 10-membered bicyclic heteroaryl ring having 1-3 heteroatoms independently selected from oxygen, nitrogen, and sulfur. In some embodiments, R³ is an optionally substituted 9-membered bicyclic heteroaryl ring having 1-3 heteroatoms independently selected from oxygen, nitrogen, and sulfur. In some such embodiments, R³ is an optionally substituted group selected from indolyl, benzopyrazolyl, benzimidazolyl, and imidazo[1,2-a]pyridinyl.

In some embodiments, R³ is selected from the group consisting of

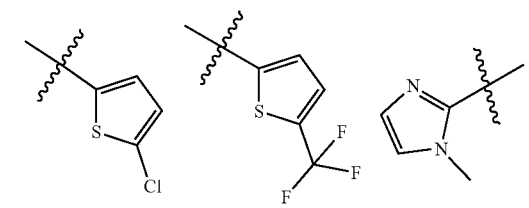

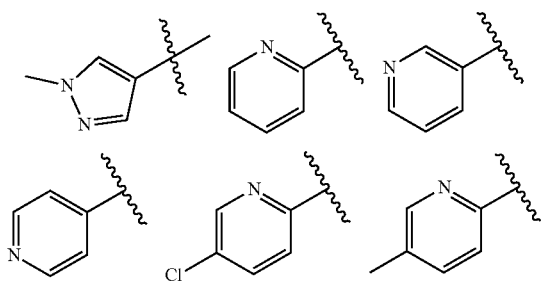

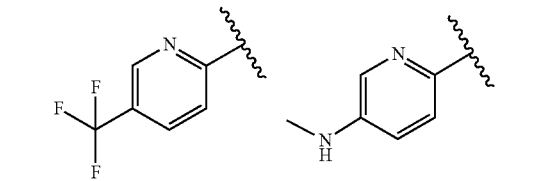

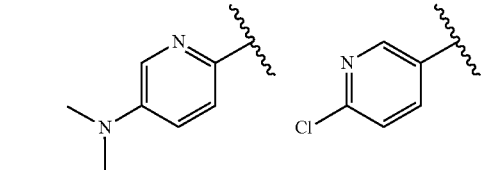

-continued

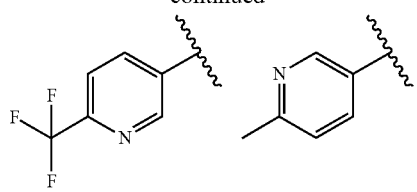

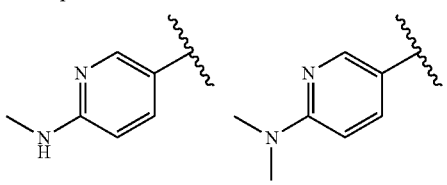

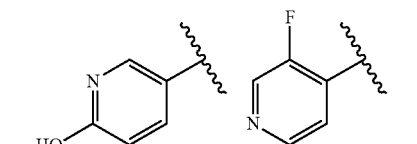

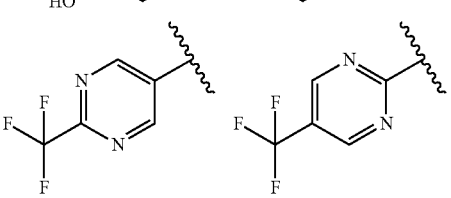

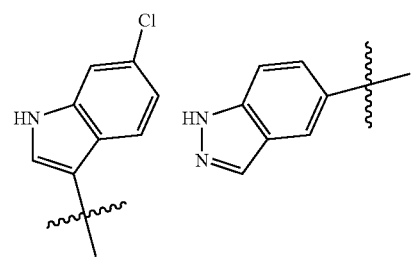

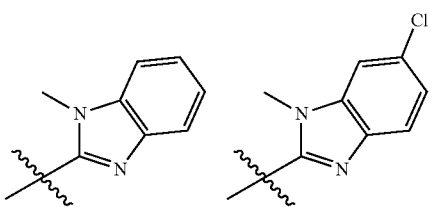

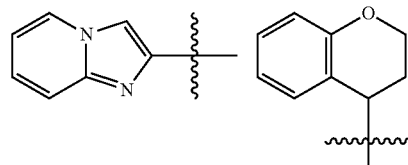

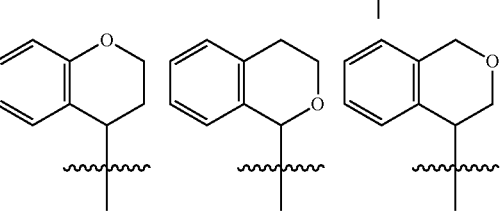

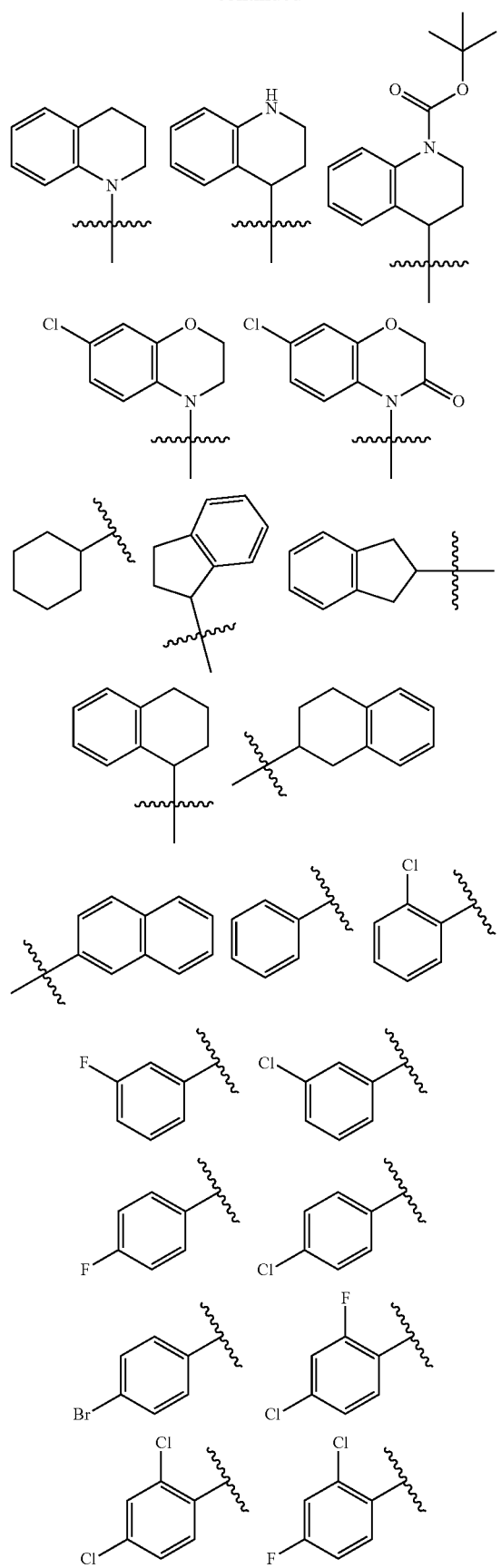
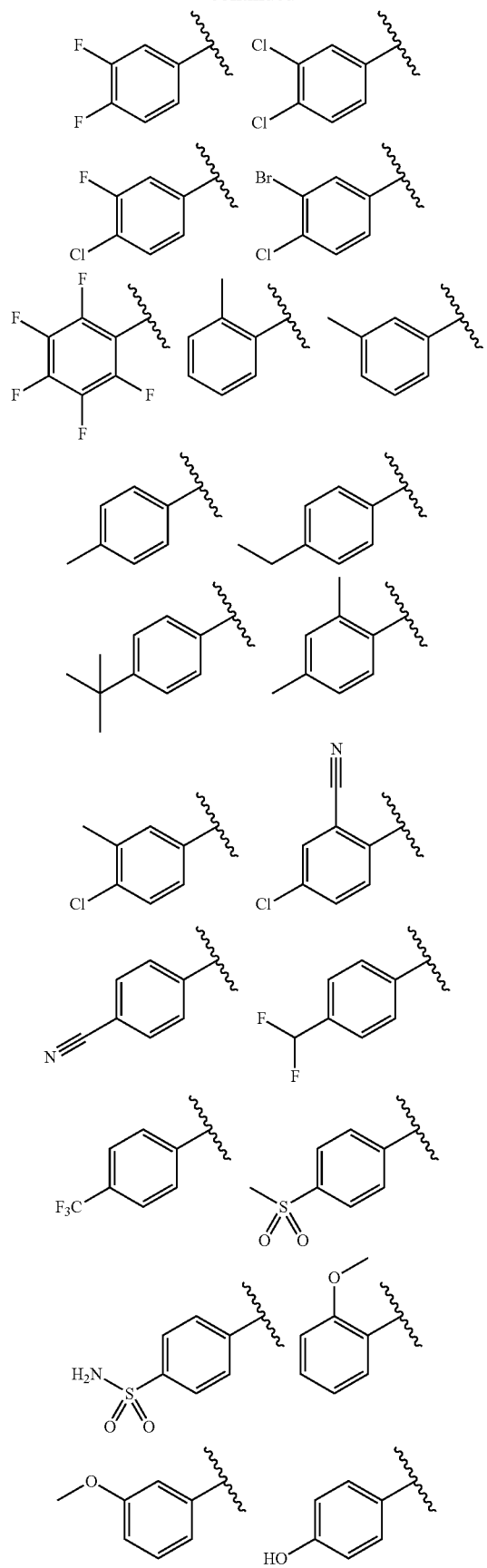

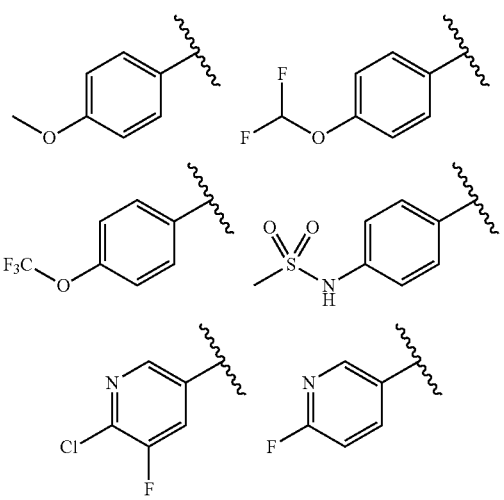

In certain particularly preferred embodiments, $R^3$ is selected from

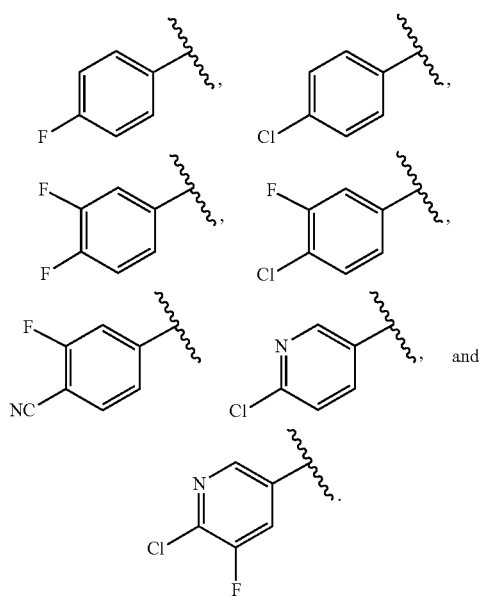

Accordingly, in some embodiments, $R^2$ is selected from

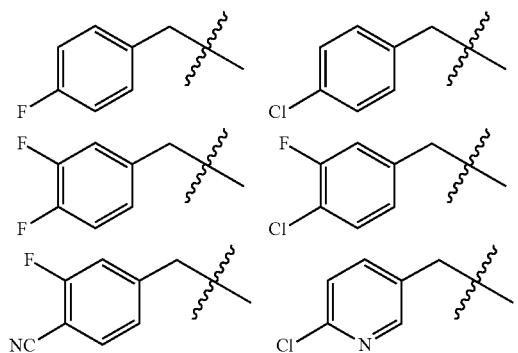

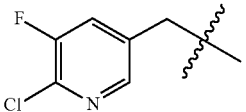

In certain particularly preferred embodiments, $R^3$ is selected from

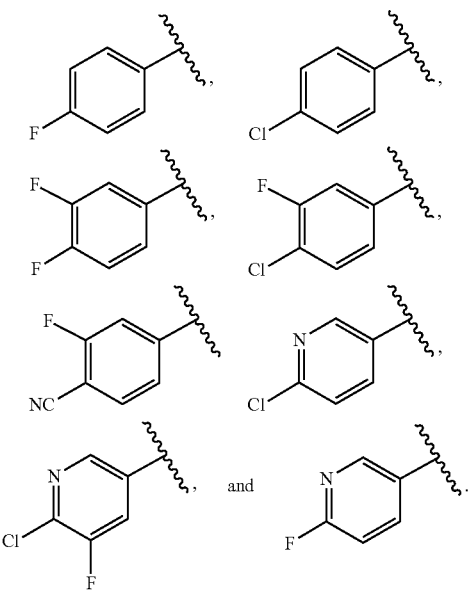

Accordingly, in some embodiments, $R^2$ is selected from

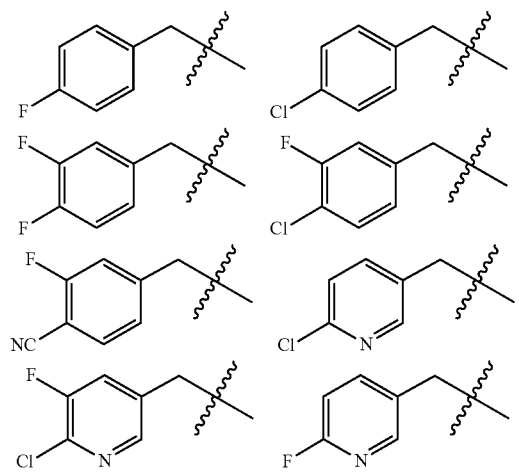

In some embodiments of Formula I, Ring B is

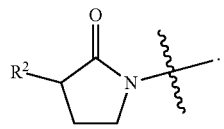

Accordingly, in some embodiments, the present disclosure provides a compound of Formula I-a:

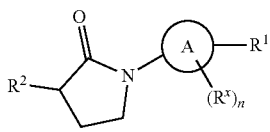

I-a or a pharmaceutically acceptable salt thereof, wherein each of Ring A, $R^x$, $R^1$, $R^2$, and n is as defined above and described herein.

In some embodiments of Formula I, Ring B is

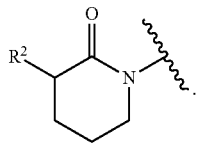

Accordingly, in some embodiments, the present disclosure provides a compound of Formula I-b:

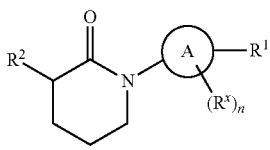

I-b or a pharmaceutically acceptable salt thereof, wherein each of Ring A, $R^x$, $R^1$, $R^2$, and n is as defined above and described herein.

In some embodiments of Formula I, Ring B is

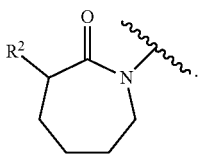

Accordingly, in some embodiments, the present disclosure provides a compound of Formula I-c:

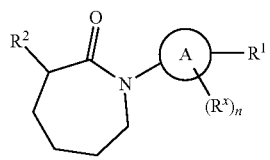

I-c or a pharmaceutically acceptable salt thereof, wherein each of Ring A, $R^x$, $R^1$, $R^2$, and n is as defined above and described herein.

In some embodiments of Formula I, Ring B is

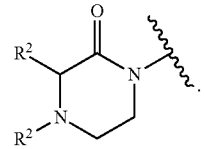

Accordingly, in some embodiments, the present disclosure provides a compound of Formula I-d:

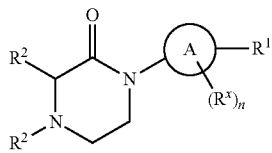

I-d or a pharmaceutically acceptable salt thereof, wherein each of Ring A, $R^x$, $R^1$, $R^2$, and n is as defined above and described herein.

In some embodiments of Formula I, Ring B is

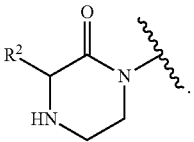

Accordingly, in some embodiments, the present disclosure provides a compound of Formula I-e:

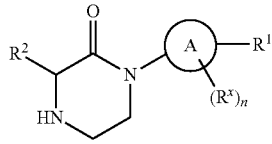

I-e or a pharmaceutically acceptable salt thereof, wherein each of Ring A, $R^x$, $R^1$, $R^2$, and n is as defined above and described herein.

In some embodiments of Formula I, Ring A is a 5-membered heteroaryl ring having 2-3 nitrogen atoms. Accordingly, in some embodiments, the present disclosure provides a compound of Formulae I-f, I-g, I-h, or I-i:

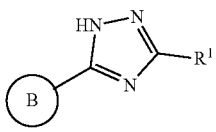

I-f

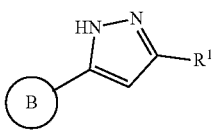

I-g

-continued

I-h
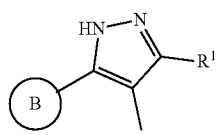

I-i
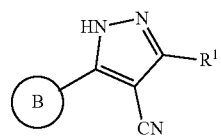

or a pharmaceutically acceptable salt thereof, wherein each of Ring B and $R^1$ is as defined above and described herein.

In some embodiments, $R^1$ is

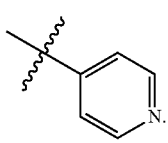 [SMILES: *c1ccncc1]

Accordingly, in some embodiments, the present disclosure provides a compound of Formulae I-a-i, I-b-i, I-c-i, I-d-i, I-e-i, I-f-i, and I-g-i:

I-a-i
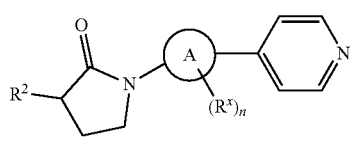

I-b-i
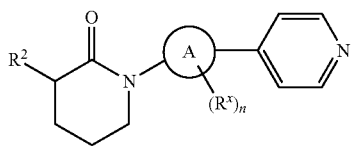

I-c-i
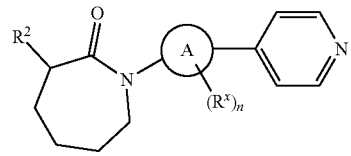

I-d-i
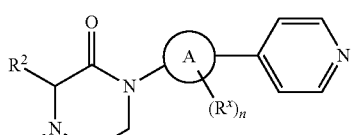

I-e-i
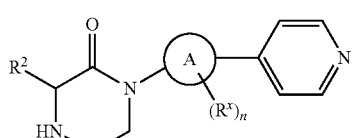

-continued

I-f-i
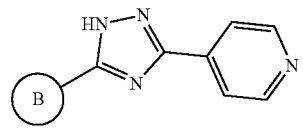

I-g-i
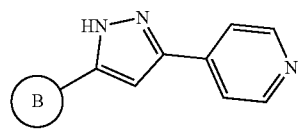

I-h-i
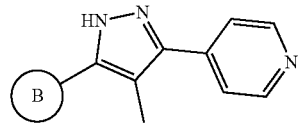

I-i-i
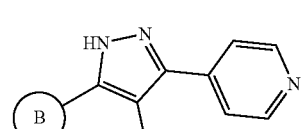

or a pharmaceutically acceptable salt thereof, wherein each of Ring A, Ring B, $R^x$, $R^2$, and n is as defined above and described herein.

In some embodiments of Formula I-b, Ring A is

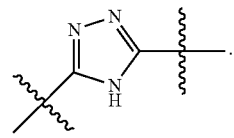 [SMILES: *c1nnc(*)[nH]1]

Accordingly, in some embodiments, the present disclosure provides a compound of Formula I-b-ii:

I-b-ii
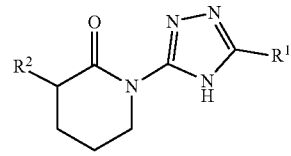

or a pharmaceutically acceptable salt thereof, wherein each of $R^1$ and $R^2$ is as defined above and described herein.

In some embodiments of Formula I-b-ii, $R^2$ is —$CH_2R^3$. Accordingly, in some embodiments, the present disclosure provides a compound of Formula I-j, I-j-i, and I-j-ii:

I-j
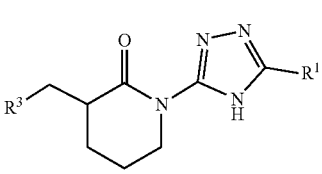

-continued

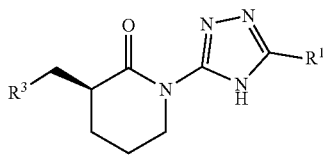

I-j-i

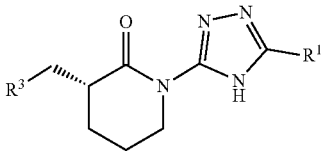

I-j-ii or a pharmaceutically acceptable salt thereof, wherein each of $R^1$ and $R^3$ is as defined above and described herein.

In an embodiment, the present disclosure provides a compound of Formula II:

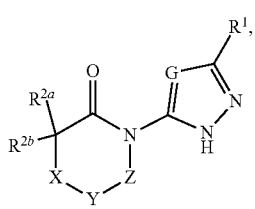

II or a pharmaceutically acceptable salt thereof, wherein:
  $R^2$ is a 5- to 6-membered heteroaryl ring having 1-3 heteroatoms selected from oxygen, nitrogen and sulfur;
  G is CH, $CR^x$ or N;
  $R^x$ is $C_1$-$C_3$ alkyl, halogen or cyano;
  X is $CH_2$, NH, N($C_1$-$C_3$ alkyl) or O;
  Y is $C(R^p)_2$ or NH;
  Z is bond, $CH_2$ or —$CH_2CH_2$—;
  $R^{2a}$ is —($C_1$-$C_3$ alkyl)$R^3$;
  $R^{2b}$ is hydrogen, halogen, $C_1$-$C_3$ alkyl or —($C_1$-$C_3$ alkyl)$R^3$;
  $R^p$ is independently hydrogen, halogen or $NH_2$;
  $R^3$ is a phenyl ring or a 5- to 6-membered heteroaryl ring having 1-3 heteroatoms selected from oxygen, nitrogen and sulfur, wherein the aryl ring or 5- to 6-membered heteroaryl ring are optionally substituted with 1 to 2 $R^q$;
  $R^q$ is halogen, cyano or —$CF_3$.

In another embodiment, the present disclosure provides a compound of Formula II as described above, wherein $R^{2b}$ is hydrogen.

In another embodiment, the present disclosure provides a compound of Formula II as described above, wherein $R^1$ is selected from

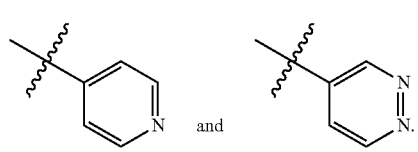 [SMILES: *c1ccncc1 ; *c1ccnnc1]

and

In another embodiment, the present disclosure provides a compound of Formula II as described above, wherein X is $CH_2$, Y is $CH_2$, and Z is $CH_2$.

In another embodiment, the present disclosure provides a compound of Formula II as described above, wherein $R^{2a}$ is —$CH_2$—$R^3$.

In another embodiment, the present disclosure provides a compound of Formula II as described above, wherein $R^3$ is selected from

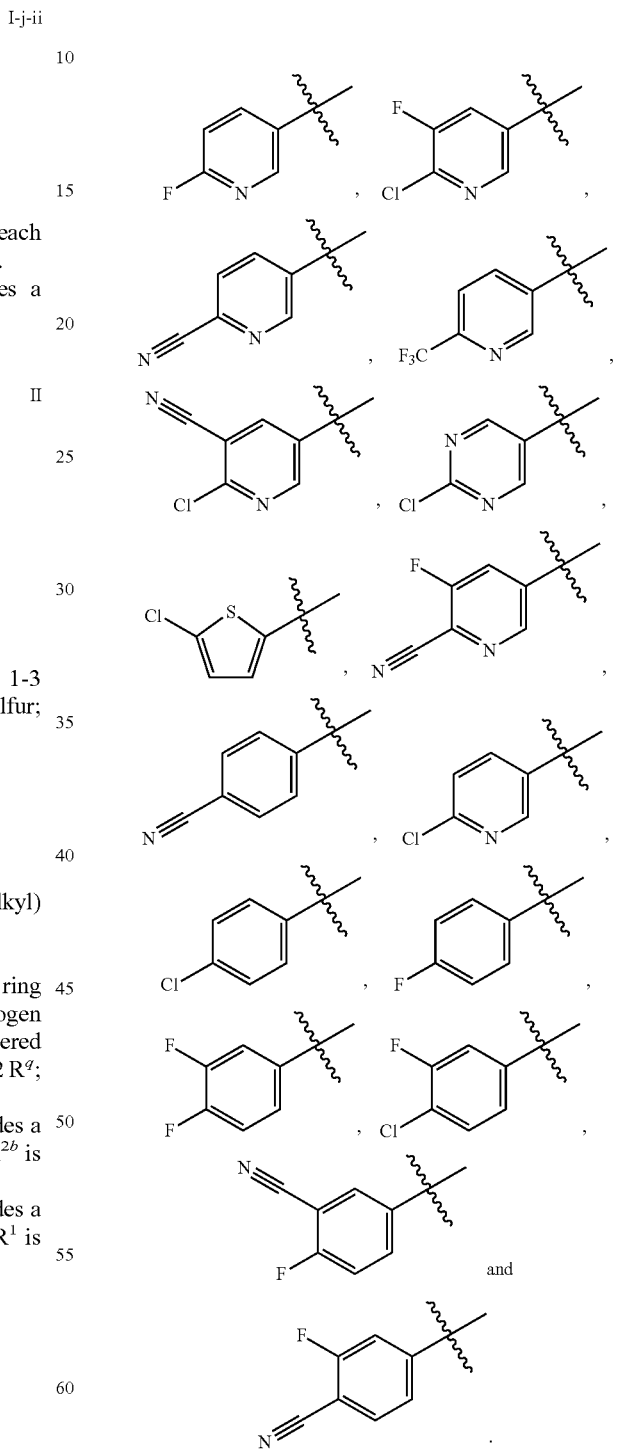

In another embodiment, the present disclosure provides a compound of Formula II as described above, wherein $R^3$ is selected from

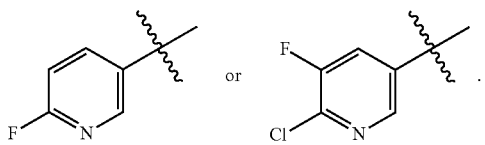 [SMILES: *c1ccc(F)nc1 ; *c1cnc(Cl)c(F)c1]

In another embodiment, the present disclosure provides a compound of Formula II as described above, which is

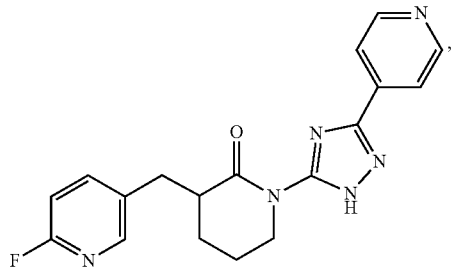 [SMILES: O=C1C(Cc2ccc(F)nc2)CCCN1c1nc(-c2ccncc2)n[nH]1]

or a pharmaceutically acceptable salt thereof.

In another embodiment, the present disclosure provides a compound of Formula II as described above, which is

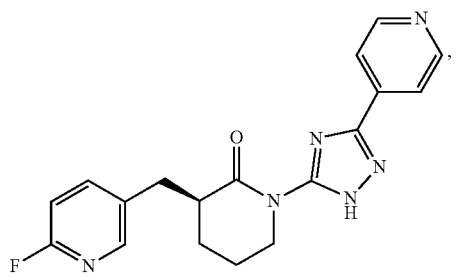 [SMILES: O=C1[C@H](Cc2ccc(F)nc2)CCCN1c1nc(-c2ccncc2)n[nH]1]

or a pharmaceutically acceptable salt thereof.

In another embodiment, the present disclosure provides a compound of Formula II as described above, which is

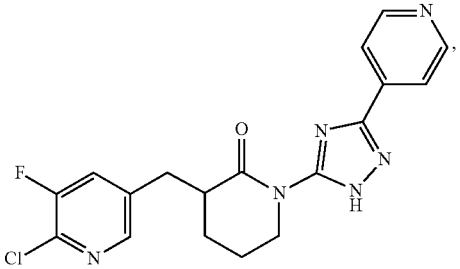 [SMILES: O=C1C(Cc2cnc(Cl)c(F)c2)CCCN1c1nc(-c2ccncc2)n[nH]1]

or a pharmaceutically acceptable salt thereof.

In another embodiment, the present disclosure provides a compound of Formula II as described above, which is

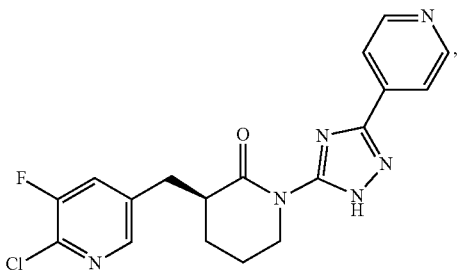 [SMILES: O=C1[C@H](Cc2cnc(Cl)c(F)c2)CCCN1c1nc(-c2ccncc2)n[nH]1]

or a pharmaceutically acceptable salt thereof.

In some embodiments, the present disclosure provides a compound selected from:

| Structure | |
|---|---|
| 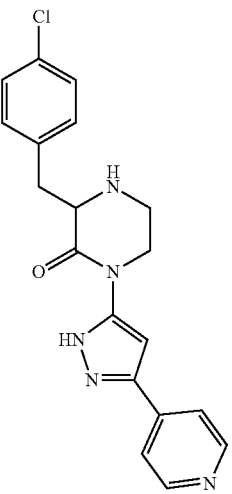 [SMILES: O=C1C(Cc2ccc(Cl)cc2)NCCN1c1cc(-c2ccncc2)n[nH]1] | I-1 |
| 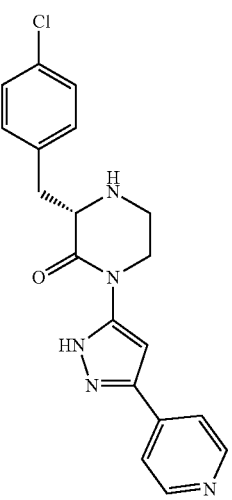 [SMILES: O=C1[C@H](Cc2ccc(Cl)cc2)NCCN1c1cc(-c2ccncc2)n[nH]1] | I-1-a |

| Structure | |
|---|---|
| 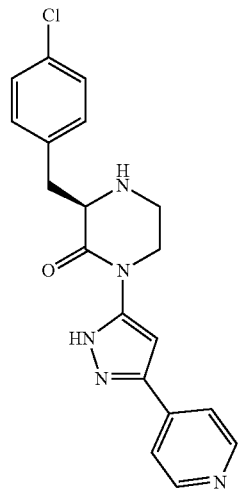 [SMILES: O=C1[C@@H](Cc2ccc(Cl)cc2)NCCN1c1cc(-c2ccncc2)n[nH]1] | I-1-b |
| 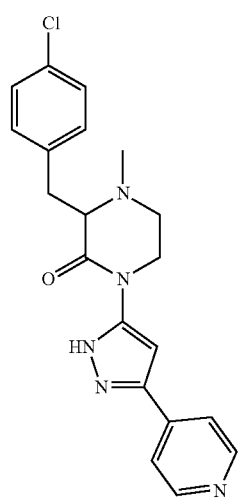 [SMILES: CN1CCN(c2cc(-c3ccncc3)n[nH]2)C(=O)C1Cc1ccc(Cl)cc1] | I-2 |
| 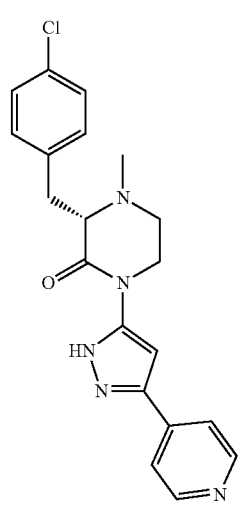 [SMILES: CN1CCN(c2cc(-c3ccncc3)n[nH]2)C(=O)[C@@H]1Cc1ccc(Cl)cc1] | I-2-a |
| 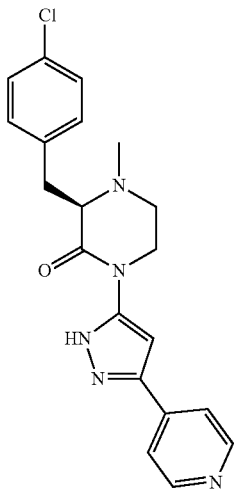 [SMILES: CN1CCN(c2cc(-c3ccncc3)n[nH]2)C(=O)[C@H]1Cc1ccc(Cl)cc1] | I-2-b |
| 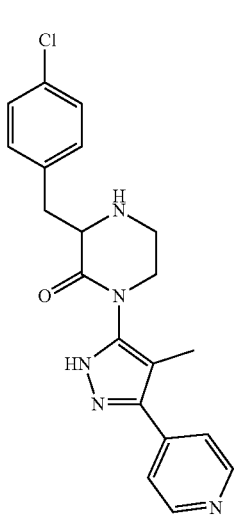 [SMILES: Cc1c(-c2ccncc2)n[nH]c1N1CCNC(Cc2ccc(Cl)cc2)C1=O] | I-3 |
| 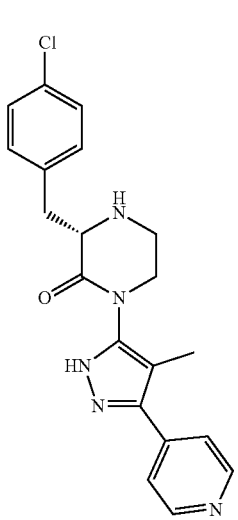 [SMILES: Cc1c(-c2ccncc2)n[nH]c1N1CCN[C@@H](Cc2ccc(Cl)cc2)C1=O] | I-3-a |

| 55 -continued | | 56 -continued | |
|---|---|---|---|
| Structure | | Structure | |
| 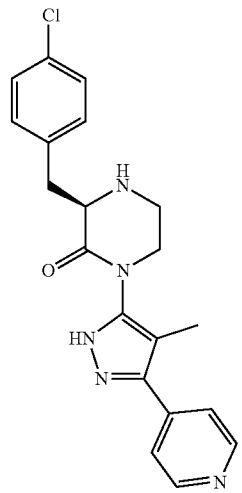 [SMILES: Cc1c(-c2ccncc2)n[nH]c1N1CCN[C@H](Cc2ccc(Cl)cc2)C1=O] | I-3-b | 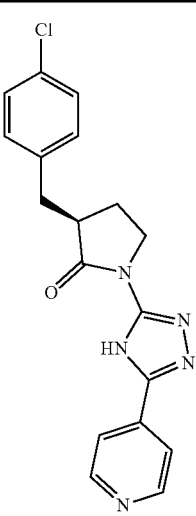 | I-4-b |
| 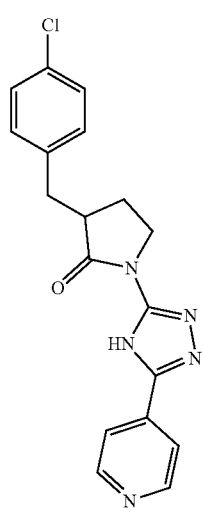 [SMILES: O=C1C(Cc2ccc(Cl)cc2)CCN1c1nnc(-c2ccncc2)[nH]1] | I-4 | 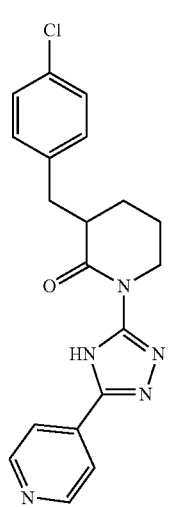 | I-5 |
| 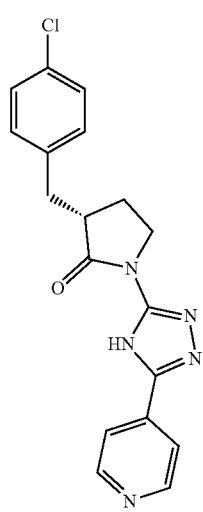 [SMILES: O=C1[C@H](Cc2ccc(Cl)cc2)CCN1c1nnc(-c2ccncc2)[nH]1] | I-4-a | 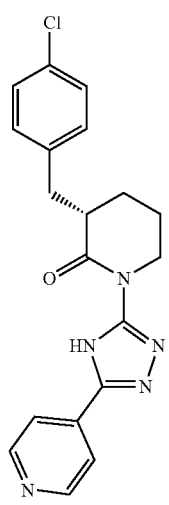 [SMILES: O=C1[C@H](Cc2ccc(Cl)cc2)CCCN1c1nnc(-c2ccncc2)[nH]1] | I-5-a |

| Structure | |
|---|---|
| 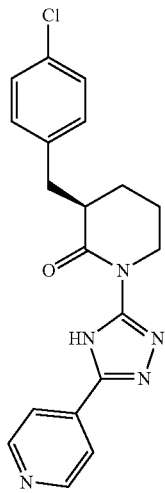 [SMILES: O=C1[C@@H](Cc2ccc(Cl)cc2)CCCN1c1nnc(-c2ccncc2)[nH]1] | I-5-b |
| 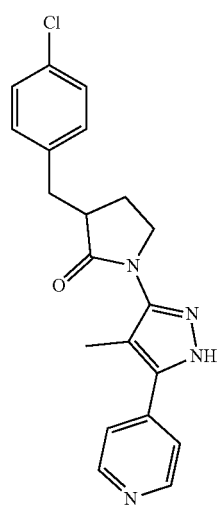 | I-6 |
| 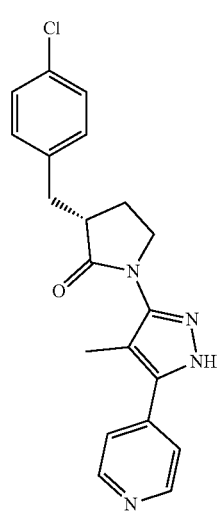 [SMILES: Cc1c(N2CC[C@@H](Cc3ccc(Cl)cc3)C2=O)n[nH]c1-c1ccncc1] | I-6-a |
| Structure | |
|---|---|
| 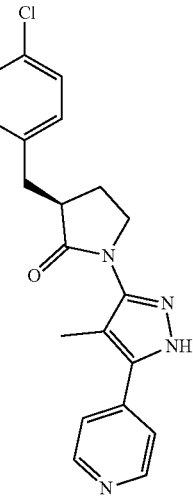 | I-6-b |
| 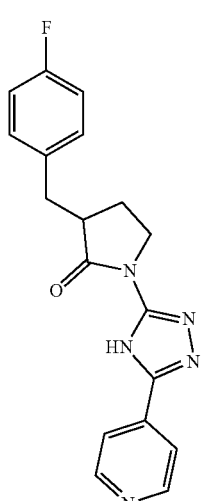 | I-7 |
| 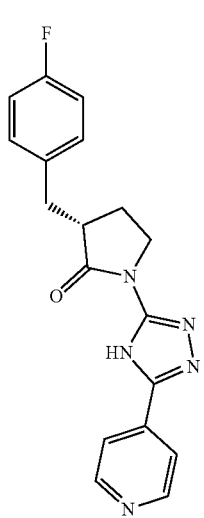 [SMILES: O=C1[C@H](Cc2ccc(F)cc2)CCN1c1nnc(-c2ccncc2)[nH]1] | I-7-a |

| Structure | | Structure | |
|---|---|---|---|
| 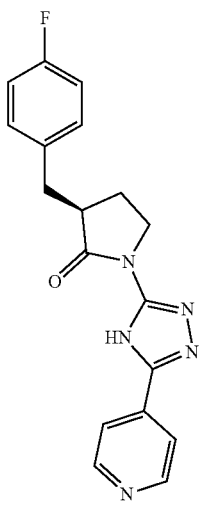 [SMILES: O=C1[C@@H](Cc2ccc(F)cc2)CCN1c1nnc(-c2ccncc2)[nH]1] | I-7-b | 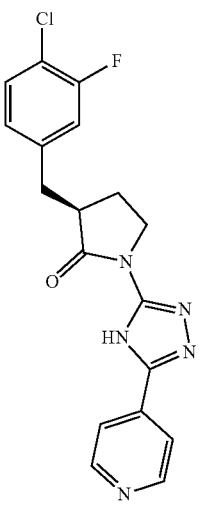 | I-8-b |
| 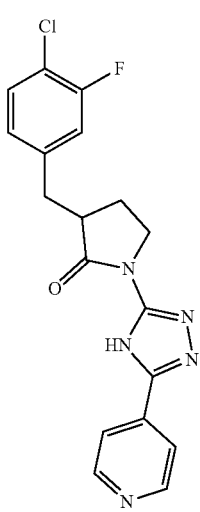 [SMILES: O=C1C(Cc2ccc(Cl)c(F)c2)CCN1c1nnc(-c2ccncc2)[nH]1] | I-8 | 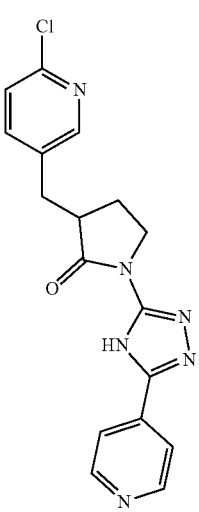 | I-9 |
| 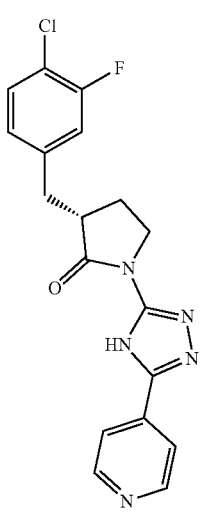 [SMILES: O=C1[C@H](Cc2ccc(Cl)c(F)c2)CCN1c1nnc(-c2ccncc2)[nH]1] | I-8-a | 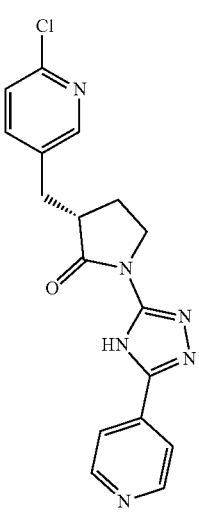 [SMILES: O=C1[C@H](Cc2ccc(Cl)nc2)CCN1c1nnc(-c2ccncc2)[nH]1] | I-9-a |

-continued
| Structure | |
|---|---|
| 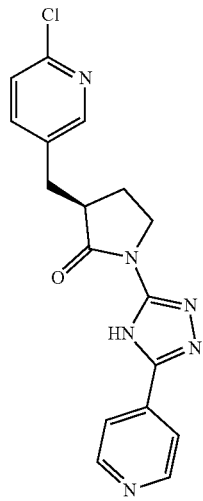 [SMILES: O=C1[C@@H](Cc2ccc(Cl)nc2)CCN1c1nnc(-c2ccncc2)[nH]1] | I-9-b |
| 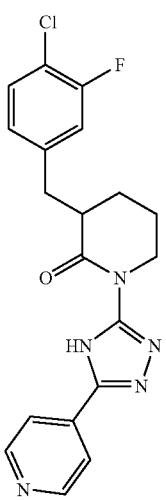 [SMILES: O=C1C(Cc2ccc(Cl)c(F)c2)CCCN1c1nnc(-c2ccncc2)[nH]1] | I-10 |
| 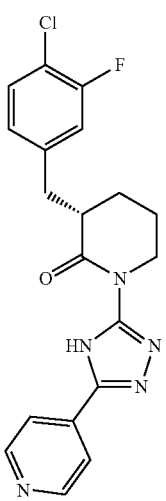 [SMILES: O=C1[C@H](Cc2ccc(Cl)c(F)c2)CCCN1c1nnc(-c2ccncc2)[nH]1] | I-10-a |
-continued
| Structure | |
|---|---|
| 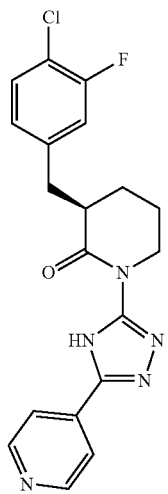 [SMILES: O=C1[C@@H](Cc2ccc(Cl)c(F)c2)CCCN1c1nnc(-c2ccncc2)[nH]1] | I-10-b |
| 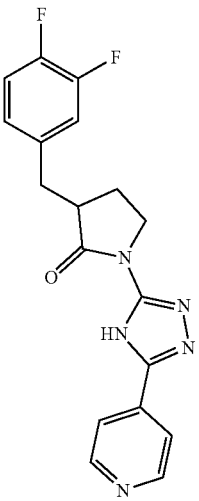 [SMILES: O=C1C(Cc2ccc(F)c(F)c2)CCN1c1nnc(-c2ccncc2)[nH]1] | I-11 |
| 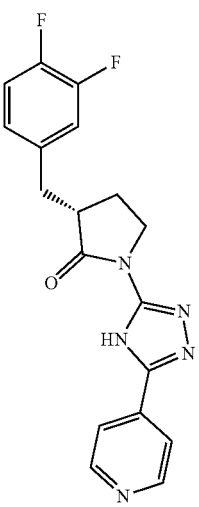 [SMILES: O=C1[C@H](Cc2ccc(F)c(F)c2)CCN1c1nnc(-c2ccncc2)[nH]1] | I-11-a |

| Structure | | Structure | |
|---|---|---|---|
| 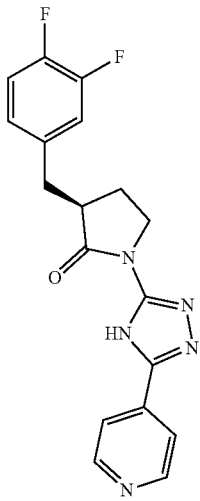 [SMILES: O=C1[C@@H](Cc2ccc(F)c(F)c2)CCN1c1nnc(-c2ccncc2)[nH]1] | I-11-b | 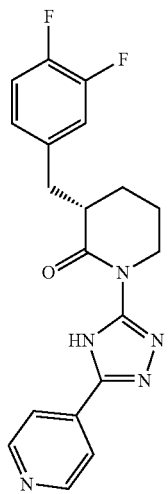 | I-13-a |
| 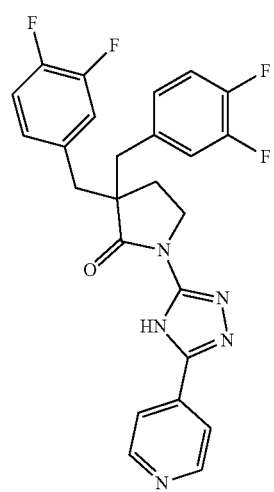 [SMILES: O=C1N(c2nnc(-c3ccncc3)[nH]2)CCC1(Cc1ccc(F)c(F)c1)Cc1ccc(F)c(F)c1] | I-12 | 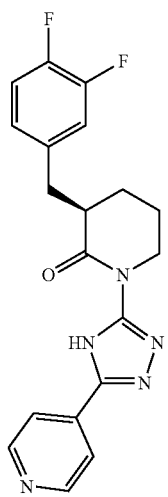 | I-13-b |
| 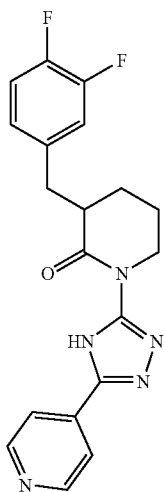 [SMILES: O=C1C(Cc2ccc(F)c(F)c2)CCCN1c1nnc(-c2ccncc2)[nH]1] | I-13 | 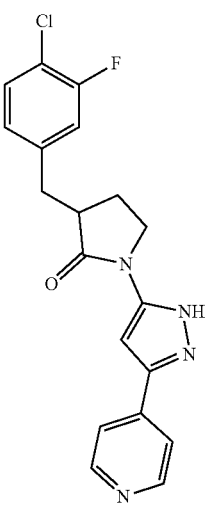 [SMILES: O=C1C(Cc2ccc(Cl)c(F)c2)CCN1c1cc(-c2ccncc2)n[nH]1] | I-14 |

| Structure | | Structure | |
|---|---|---|---|
| 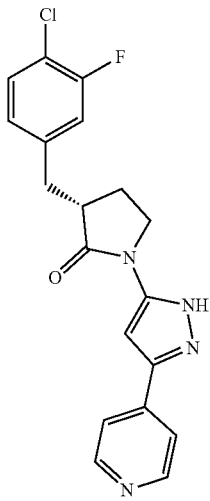 [SMILES: O=C1[C@H](Cc2ccc(Cl)c(F)c2)CCN1c1cc(-c2ccncc2)n[nH]1] | I-14-a | 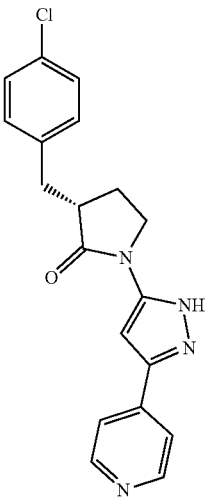 [SMILES: O=C1[C@H](Cc2ccc(Cl)cc2)CCN1c1cc(-c2ccncc2)n[nH]1] | I-15-a |
| 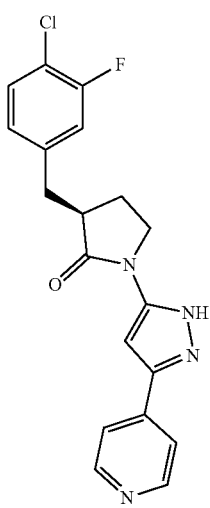 | I-14-b | 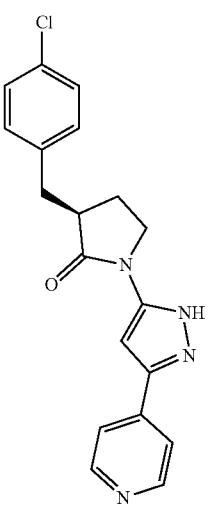 [SMILES: O=C1[C@@H](Cc2ccc(Cl)cc2)CCN1c1cc(-c2ccncc2)n[nH]1] | I-15-b |
| 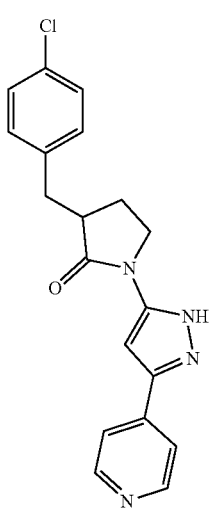 | I-15 | 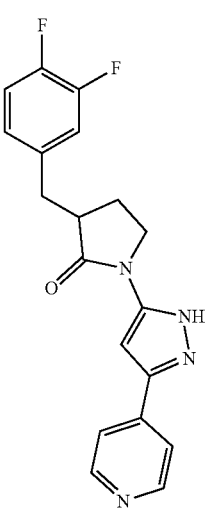 [SMILES: O=C1C(Cc2ccc(F)c(F)c2)CCN1c1cc(-c2ccncc2)n[nH]1] | I-16 |

| Structure | | Structure | |
|---|---|---|---|
| 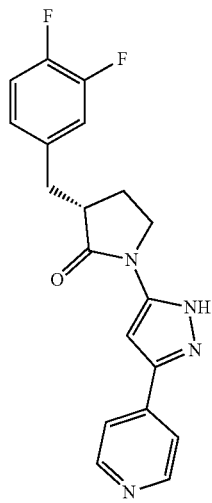 [SMILES: O=C1[C@H](Cc2ccc(F)c(F)c2)CCN1c1cc(-c2ccncc2)n[nH]1] | I-16-a | 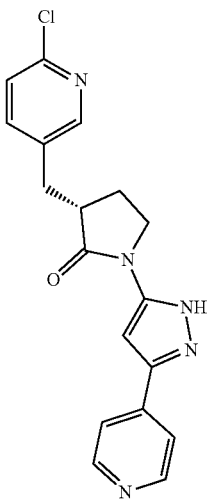 | I-17-a |
| 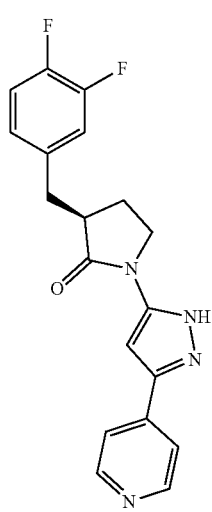 [SMILES: O=C1[C@@H](Cc2ccc(F)c(F)c2)CCN1c1cc(-c2ccncc2)n[nH]1] | I-16-b | 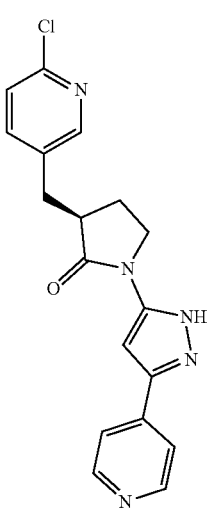 [SMILES: O=C1[C@@H](Cc2ccc(Cl)nc2)CCN1c1cc(-c2ccncc2)n[nH]1] | I-17-b |
| 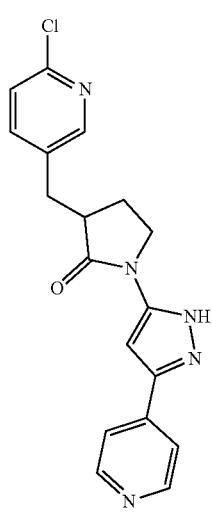 | I-17 | 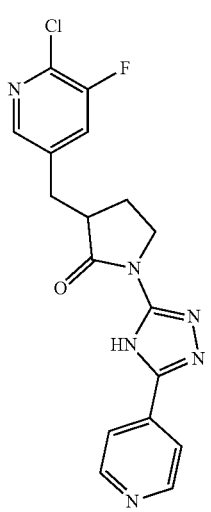 [SMILES: O=C1C(Cc2cnc(Cl)c(F)c2)CCN1c1nnc(-c2ccncc2)[nH]1] | I-18 |

| Structure | | Structure | |
|---|---|---|---|
| 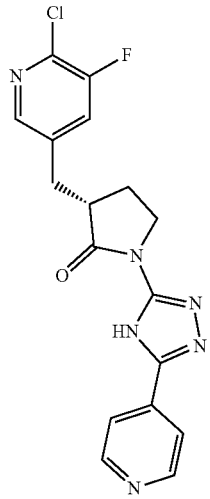 [SMILES: O=C1[C@H](Cc2cnc(Cl)c(F)c2)CCN1c1nnc(-c2ccncc2)[nH]1] | I-18-a | 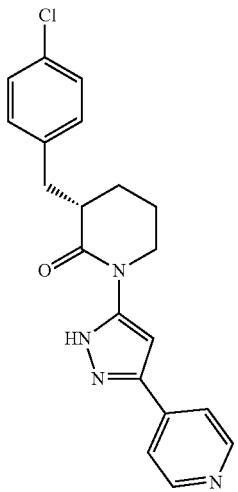 | I-19-a |
| 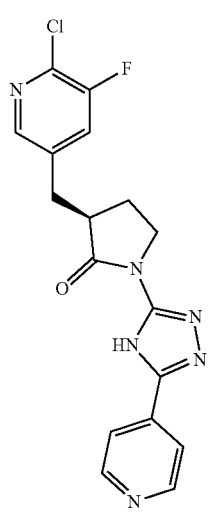 [SMILES: O=C1[C@@H](Cc2cnc(Cl)c(F)c2)CCN1c1nnc(-c2ccncc2)[nH]1] | I-18-b | 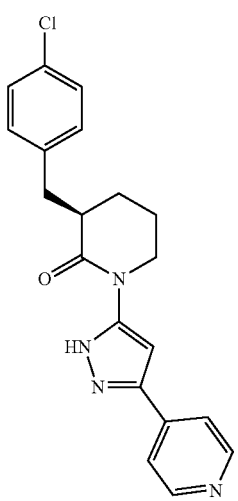 | I-19-b |
| 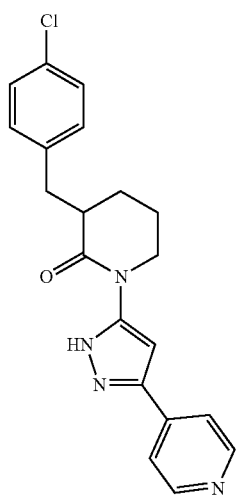 [SMILES: O=C1C(Cc2ccc(Cl)cc2)CCCN1c1cc(-c2ccncc2)n[nH]1] | I-19 | 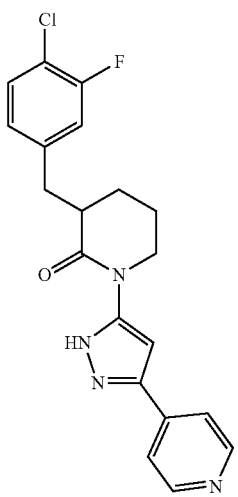 [SMILES: O=C1C(Cc2ccc(Cl)c(F)c2)CCCN1c1cc(-c2ccncc2)n[nH]1] | I-20 |

| 71 -continued Structure | | 72 -continued Structure | |
|---|---|---|---|
| 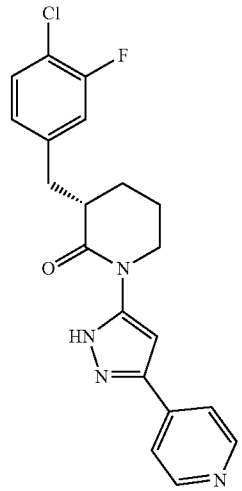 [SMILES: O=C1[C@H](Cc2ccc(Cl)c(F)c2)CCCN1c1cc(-c2ccncc2)n[nH]1] | I-20-a | 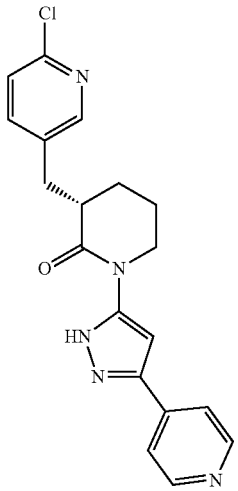 | I-21-a |
| 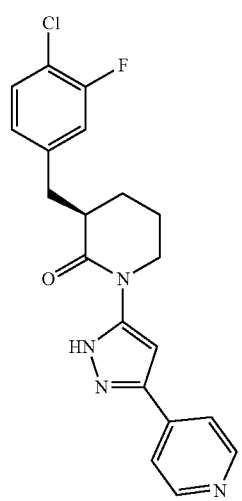 [SMILES: O=C1[C@@H](Cc2ccc(Cl)c(F)c2)CCCN1c1cc(-c2ccncc2)n[nH]1] | I-20-b | 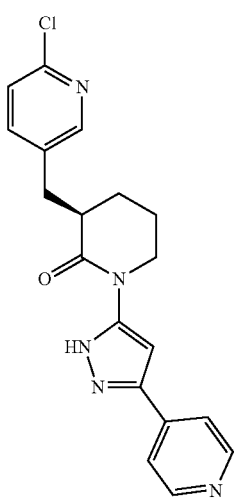 | I-21-b |
| 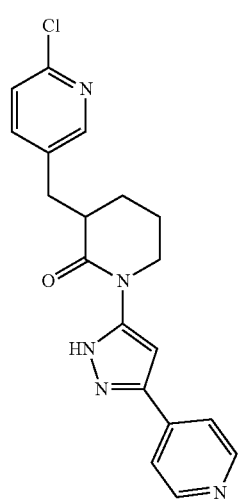 [SMILES: O=C1C(Cc2ccc(Cl)nc2)CCCN1c1cc(-c2ccncc2)n[nH]1] | I-21 | 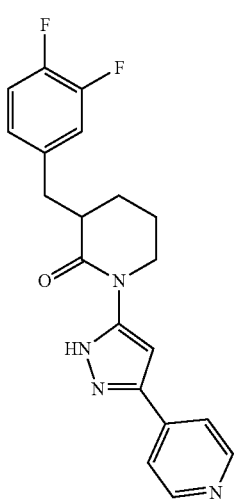 [SMILES: O=C1C(Cc2ccc(F)c(F)c2)CCCN1c1cc(-c2ccncc2)n[nH]1] | I-22 |

| Structure | | Structure | |
|---|---|---|---|
| 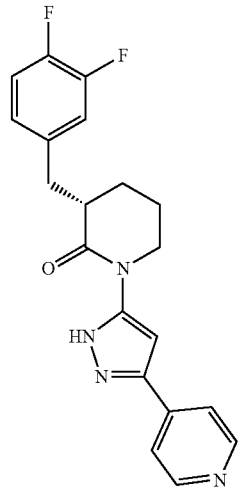 [SMILES: O=C1[C@H](Cc2ccc(F)c(F)c2)CCCN1c1cc(-c2ccncc2)n[nH]1] | I-22-a | 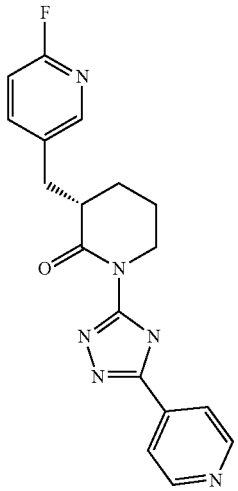 | I-23-a |
| 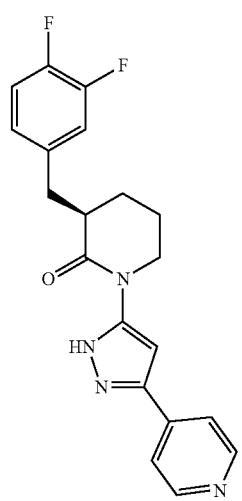 [SMILES: O=C1[C@@H](Cc2ccc(F)c(F)c2)CCCN1c1cc(-c2ccncc2)n[nH]1] | I-22-b | 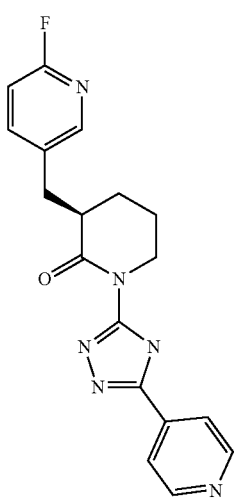 | I-23-b |
| 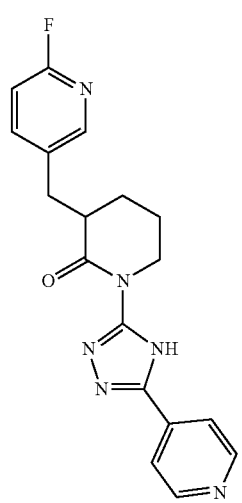 [SMILES: O=C1C(Cc2ccc(F)nc2)CCCN1c1nnc(-c2ccncc2)[nH]1] | I-23 | 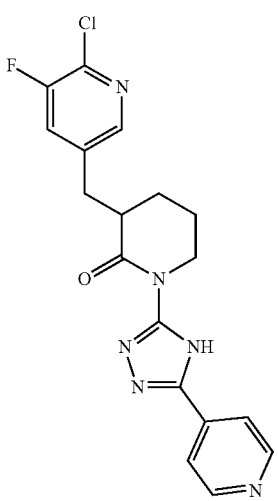 [SMILES: O=C1C(Cc2cnc(Cl)c(F)c2)CCCN1c1nnc(-c2ccncc2)[nH]1] | I-24 |

| Structure | | Structure | |
|---|---|---|---|
| 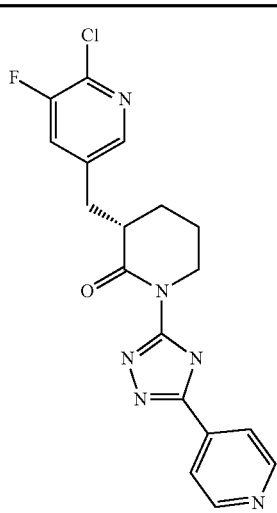 | I-24-a | 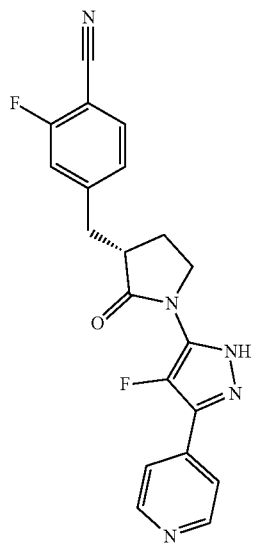 | I-25-a |
| 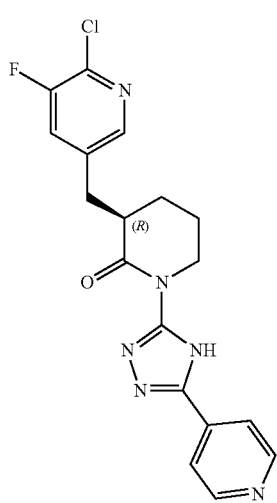 | I-24-b | | I-25-b |
| 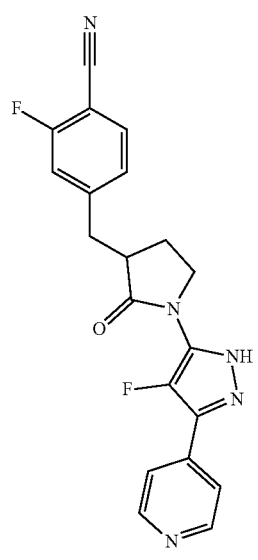 [SMILES: N#Cc1ccc(CC2CCN(c3[nH]nc(-c4ccncc4)c3F)C2=O)cc1F] | I-25 | | I-26 |

| Structure | | Structure | |
|---|---|---|---|
| 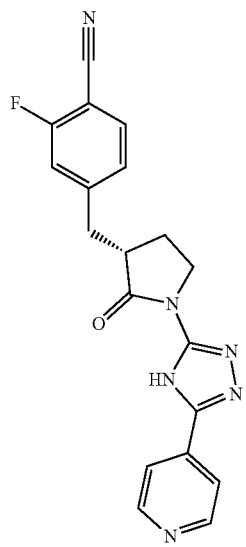 [SMILES: N#Cc1ccc(C[C@@H]2CCN(c3nnc(-c4ccncc4)[nH]3)C2=O)cc1F] | I-26-a | 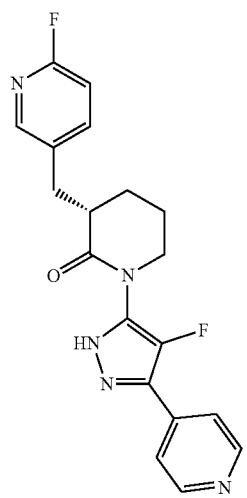 | I-27-a |
| 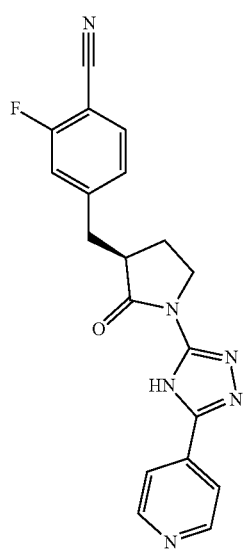 [SMILES: N#Cc1ccc(C[C@H]2CCN(c3nnc(-c4ccncc4)[nH]3)C2=O)cc1F] | I-26-b | 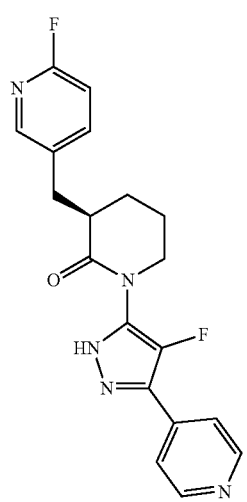 | I-27-b |
| 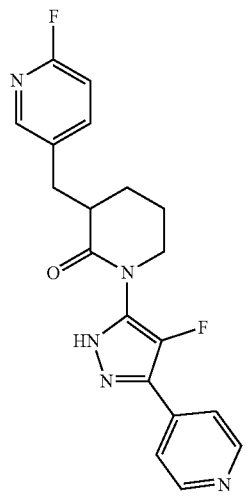 [SMILES: O=C1C(Cc2ccc(F)nc2)CCCN1c1[nH]nc(-c2ccncc2)c1F] | I-27 | 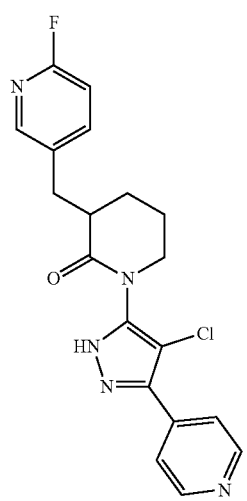 [SMILES: O=C1C(Cc2ccc(F)nc2)CCCN1c1[nH]nc(-c2ccncc2)c1Cl] | I-28 |

-continued
| Structure | |
|---|---|
| 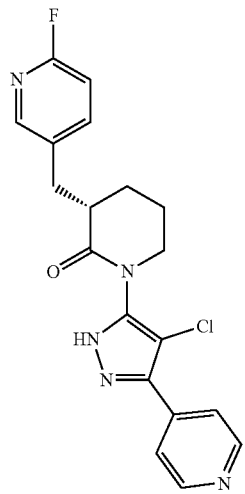 [SMILES: O=C1[C@H](Cc2ccc(F)nc2)CCCN1c1[nH]nc(-c2ccncc2)c1Cl] | I-28-a |
| 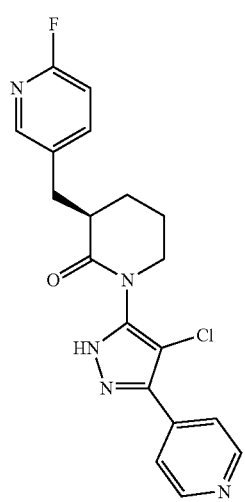 [SMILES: O=C1[C@@H](Cc2ccc(F)nc2)CCCN1c1[nH]nc(-c2ccncc2)c1Cl] | I-28-b |
| 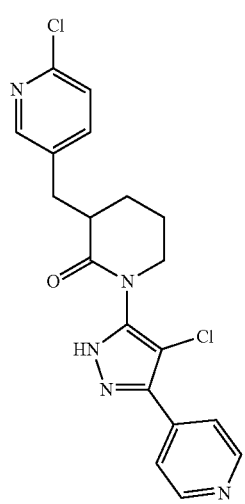 [SMILES: O=C1C(Cc2ccc(Cl)nc2)CCCN1c1[nH]nc(-c2ccncc2)c1Cl] | I-29 |
-continued
| Structure | |
|---|---|
| 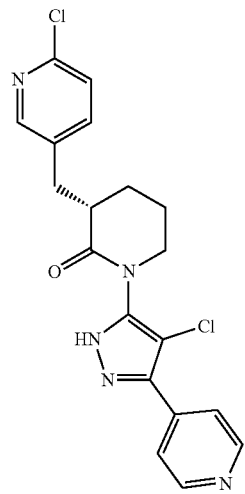 | I-29-a |
| 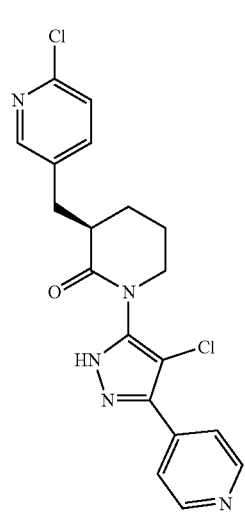 | I-29-b |

| Structure | | Structure | |
|---|---|---|---|
| 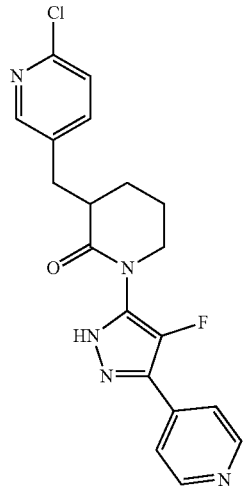 [SMILES: O=C1C(Cc2ccc(Cl)nc2)CCCN1c1[nH]nc(-c2ccncc2)c1F] | I-31 | 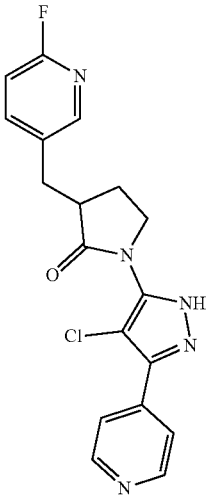 | I-32 |
| 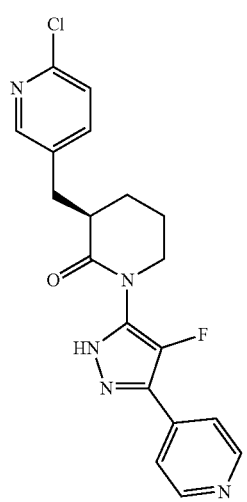 [SMILES: O=C1[C@@H](Cc2ccc(Cl)nc2)CCCN1c1[nH]nc(-c2ccncc2)c1F] | I-31-a | 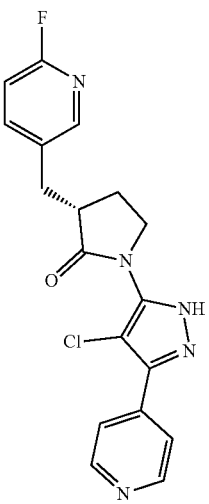 [SMILES: O=C1[C@H](Cc2ccc(F)nc2)CCN1c1[nH]nc(-c2ccncc2)c1Cl] | I-32-a |
| | I-31-b | | I-32-b |

| Structure | | Structure | |
|---|---|---|---|
| 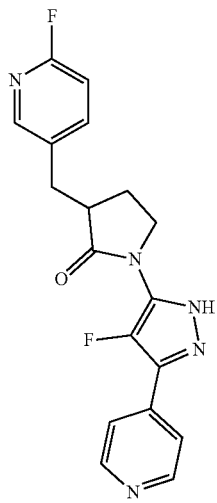 [SMILES: O=C1C(Cc2ccc(F)nc2)CCN1c1[nH]nc(-c2ccncc2)c1F] | I-33 | 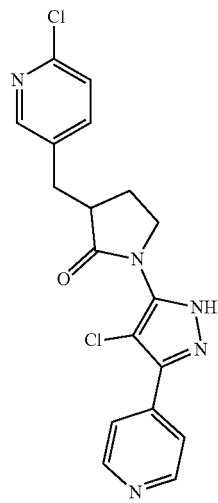 [SMILES: O=C1C(Cc2ccc(Cl)nc2)CCN1c1[nH]nc(-c2ccncc2)c1Cl] | I-34 |
| 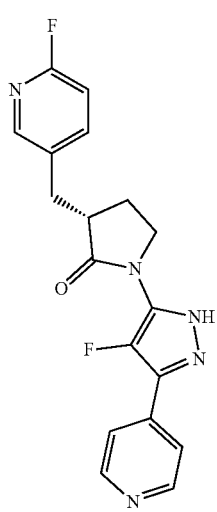 | I-33-a | 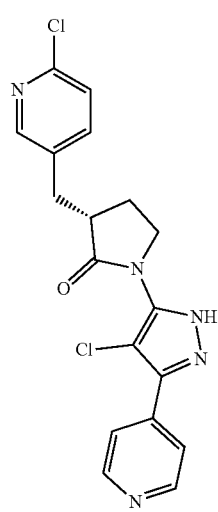 [SMILES: O=C1[C@H](Cc2ccc(Cl)nc2)CCN1c1[nH]nc(-c2ccncc2)c1Cl] | I-34-a |
| 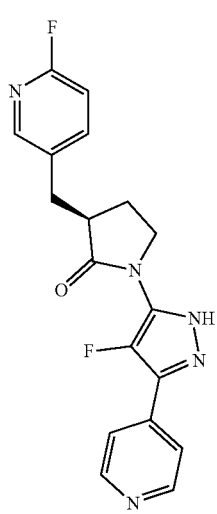 | I-33-b | 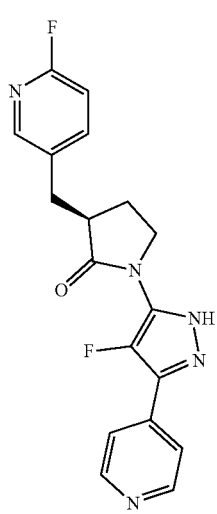 | I-34-b |

| Structure | |
|---|---|
| 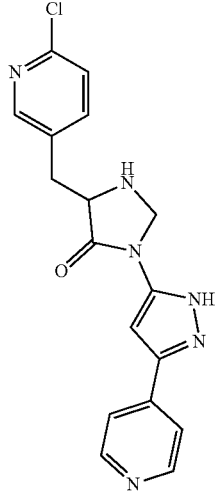 [SMILES: O=C1C(Cc2ccc(Cl)nc2)NCN1c1cc(-c2ccncc2)n[nH]1] | I-35 |
| 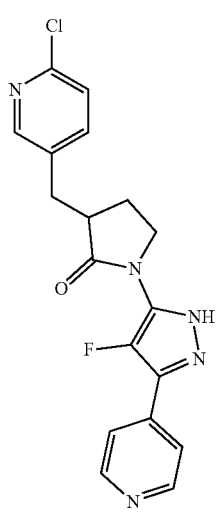 | I-36 |
| 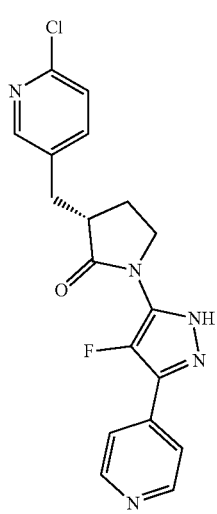 | I-36-a |
| Structure | |
|---|---|
| 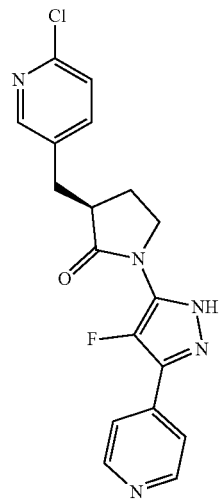 [SMILES: O=C1[C@@H](Cc2ccc(Cl)nc2)CCN1c1[nH]nc(-c2ccncc2)c1F] | I-36-b |
| 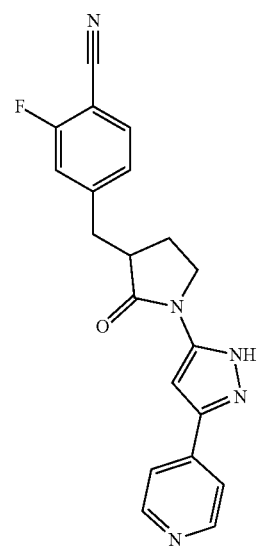 [SMILES: N#Cc1ccc(CC2CCN(c3cc(-c4ccncc4)n[nH]3)C2=O)cc1F] | I-37 |
| 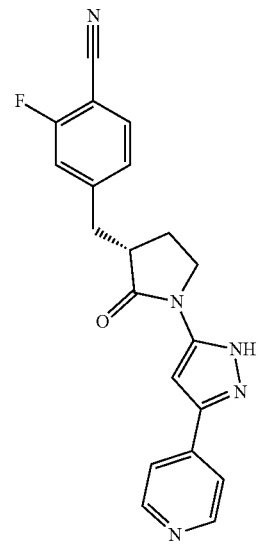 [SMILES: N#Cc1ccc(C[C@@H]2CCN(c3cc(-c4ccncc4)n[nH]3)C2=O)cc1F] | I-37-a |

| Structure | |
|---|---|
| 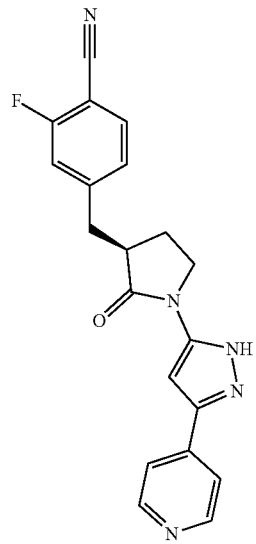 [SMILES: N#Cc1ccc(C[C@H]2CCN(c3cc(-c4ccncc4)n[nH]3)C2=O)cc1F] | I-37-b |
| 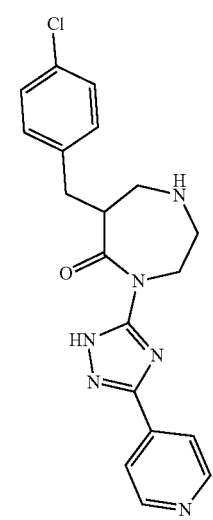 [SMILES: O=C1C(Cc2ccc(Cl)cc2)CNCCN1c1nc(-c2ccncc2)n[nH]1] | I-38 |
| 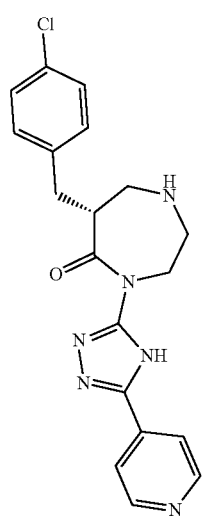 [SMILES: O=C1[C@H](Cc2ccc(Cl)cc2)CNCCN1c1nnc(-c2ccncc2)[nH]1] | I-38-a |
| Structure | |
|---|---|
|  | I-38-b |
| 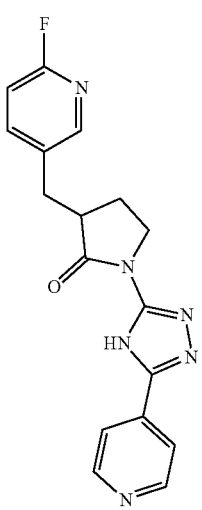 [SMILES: O=C1C(Cc2ccc(F)nc2)CCN1c1nnc(-c2ccncc2)[nH]1] | I-39 |

| 89 -continued | 90 -continued |
|---|---|
| Structure | Structure |
| 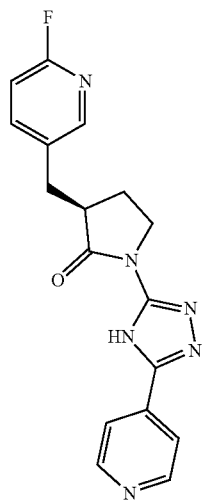 [SMILES: O=C1[C@@H](Cc2ccc(F)nc2)CCN1c1nnc(-c2ccncc2)[nH]1] I-39-b | 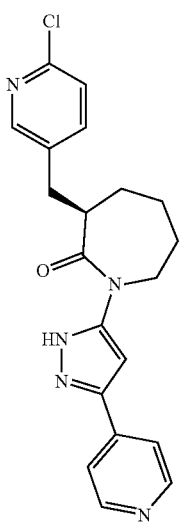 I-40-b |
| 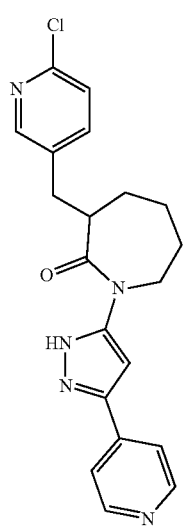 [SMILES: O=C1C(Cc2ccc(Cl)nc2)CCCCN1c1cc(-c2ccncc2)n[nH]1] I-40 | 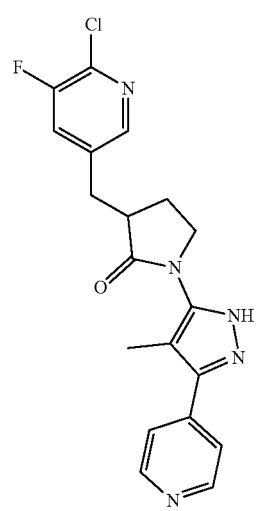 I-41 |
| 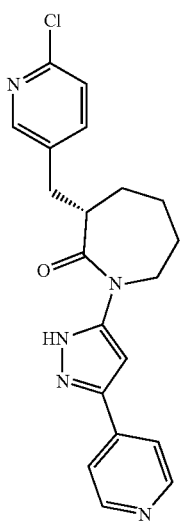 [SMILES: O=C1[C@H](Cc2ccc(Cl)nc2)CCCCN1c1cc(-c2ccncc2)n[nH]1] I-40-a | 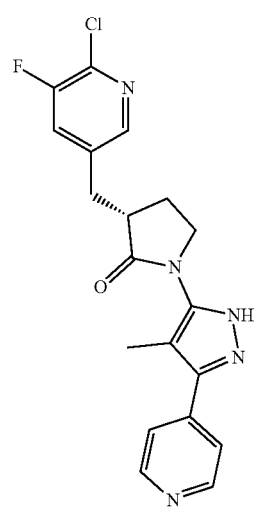 I-41-a |

| Structure | | Structure | |
|---|---|---|---|
| 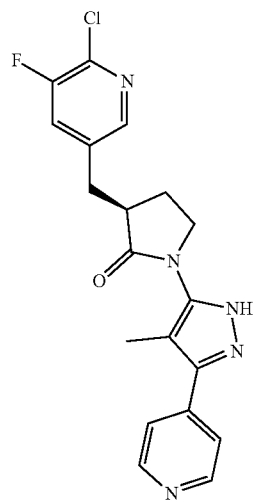 [SMILES: Cc1c(-c2ccncc2)n[nH]c1N1CC[C@H](Cc2cnc(Cl)c(F)c2)C1=O] | I-41-b | 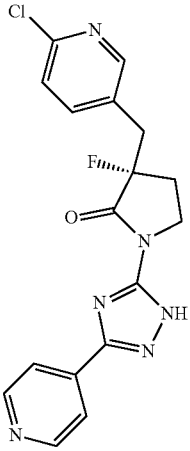 | I-42-b |
| 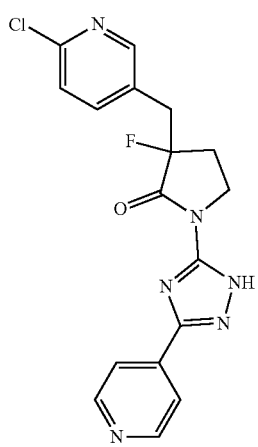 [SMILES: O=C1N(c2nc(-c3ccncc3)n[nH]2)CCC1(F)Cc1ccc(Cl)nc1] | I-42 | 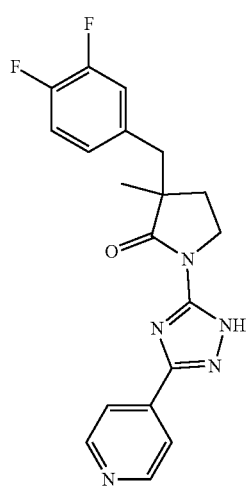 | I-43 |
| 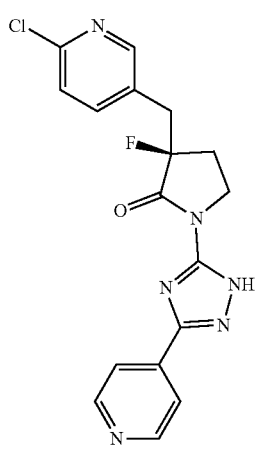 [SMILES: O=C1N(c2nc(-c3ccncc3)n[nH]2)CC[C@@]1(F)Cc1ccc(Cl)nc1] | I-42-a | 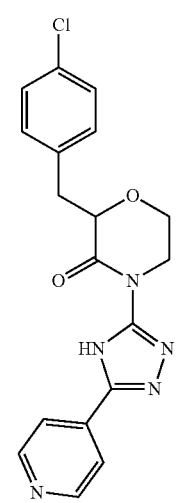 [SMILES: O=C1C(Cc2ccc(Cl)cc2)OCCN1c1nnc(-c2ccncc2)[nH]1] | I-44 |

| Structure | |
|---|---|
| 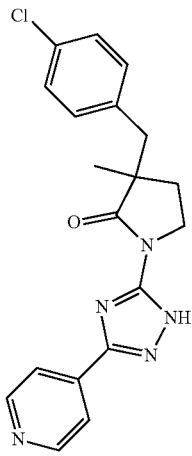 | I-45 |
| 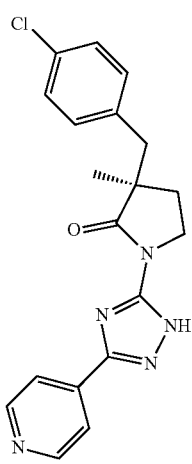 | I-46-a |
| | I-46-b |
| Structure | |
|---|---|
| 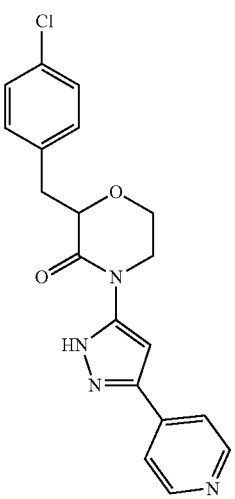 [SMILES: O=C1C(Cc2ccc(Cl)cc2)OCCN1c1cc(-c2ccncc2)n[nH]1] | I-47 |
| 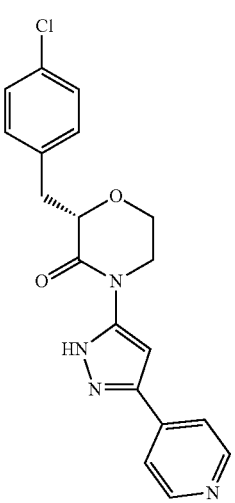 [SMILES: O=C1[C@H](Cc2ccc(Cl)cc2)OCCN1c1cc(-c2ccncc2)n[nH]1] | I-47-a |
| 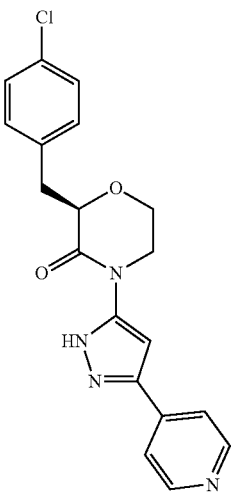 [SMILES: O=C1[C@@H](Cc2ccc(Cl)cc2)OCCN1c1cc(-c2ccncc2)n[nH]1] | I-47-b |

| Structure | | Structure | |
|---|---|---|---|
| 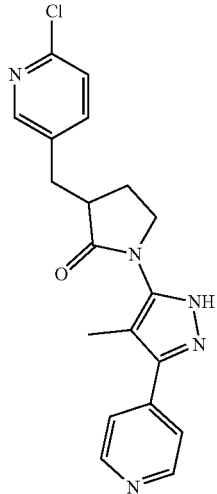 [SMILES: Cc1c(-c2ccncc2)n[nH]c1N1CCC(Cc2ccc(Cl)nc2)C1=O] | I-48 | 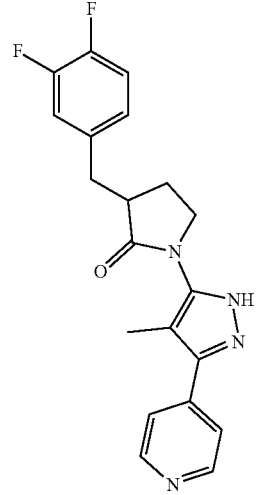 [SMILES: Cc1c(-c2ccncc2)n[nH]c1N1CCC(Cc2ccc(F)c(F)c2)C1=O] | I-49 |
| 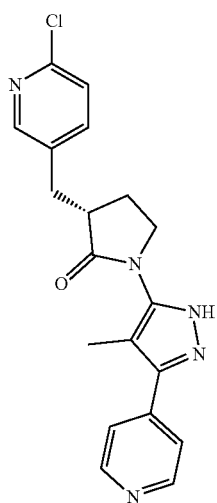 | I-48-a | 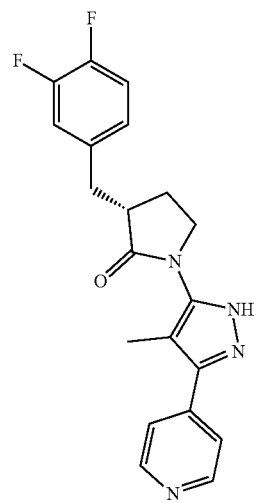 [SMILES: Cc1c(-c2ccncc2)n[nH]c1N1CC[C@@H](Cc2ccc(F)c(F)c2)C1=O] | I-49-a |
| 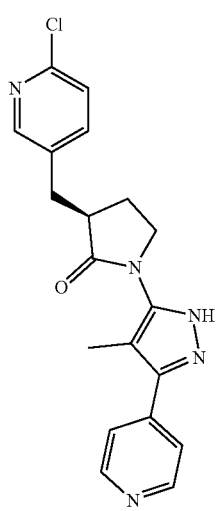 | I-48-b | 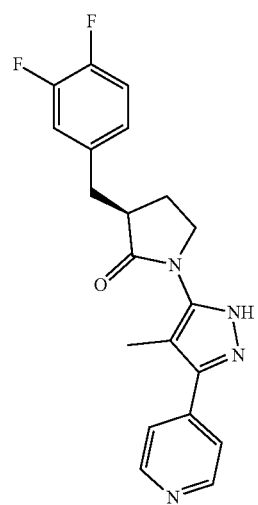 [SMILES: Cc1c(-c2ccncc2)n[nH]c1N1CC[C@H](Cc2ccc(F)c(F)c2)C1=O] | I-49-b |

-continued
| Structure | |
|---|---|
| 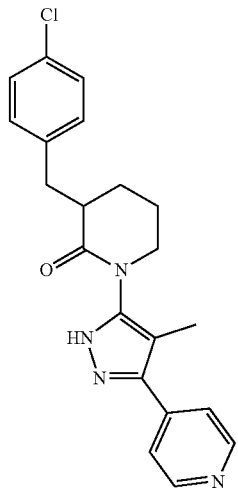 [SMILES: Cc1c(-c2ccncc2)n[nH]c1N1CCCC(Cc2ccc(Cl)cc2)C1=O] | I-50 |
| 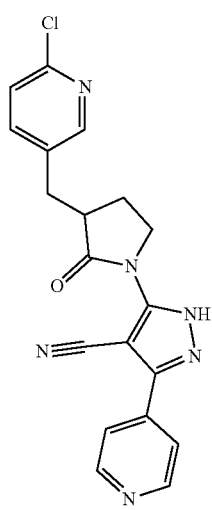 [SMILES: N#Cc1c(-c2ccncc2)n[nH]c1N1CCC(Cc2ccc(Cl)nc2)C1=O] | I-51 |
| 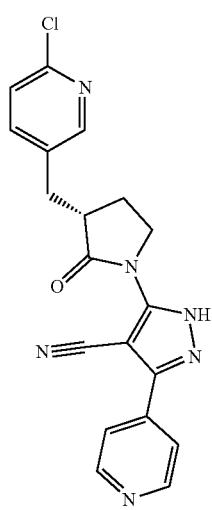 [SMILES: N#Cc1c(-c2ccncc2)n[nH]c1N1CC[C@@H](Cc2ccc(Cl)nc2)C1=O] | I-51-a |
-continued
| Structure | |
|---|---|
| 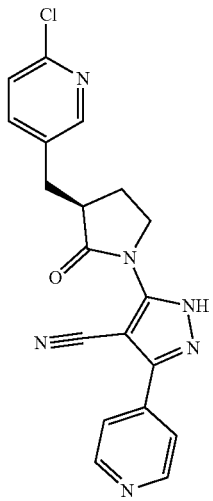 [SMILES: N#Cc1c(-c2ccncc2)n[nH]c1N1CC[C@H](Cc2ccc(Cl)nc2)C1=O] | I-51-b |
| 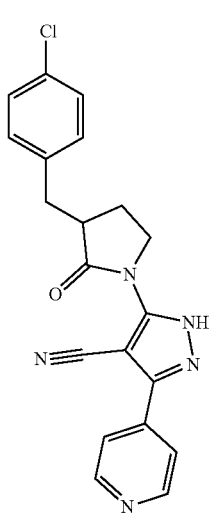 [SMILES: N#Cc1c(-c2ccncc2)n[nH]c1N1CCC(Cc2ccc(Cl)cc2)C1=O] | I-52 |
| 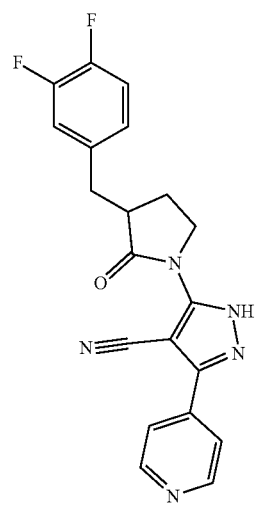 [SMILES: N#Cc1c(-c2ccncc2)n[nH]c1N1CCC(Cc2ccc(F)c(F)c2)C1=O] | I-53 |

| Structure | | Structure | |
|---|---|---|---|
| 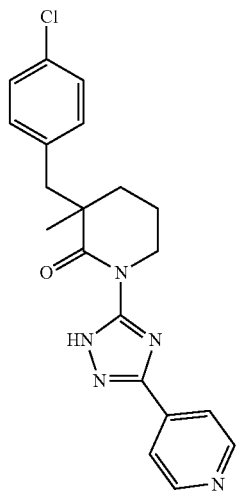 [SMILES: CC1(Cc2ccc(Cl)cc2)CCCN(c2nc(-c3ccncc3)n[nH]2)C1=O] | I-54 | 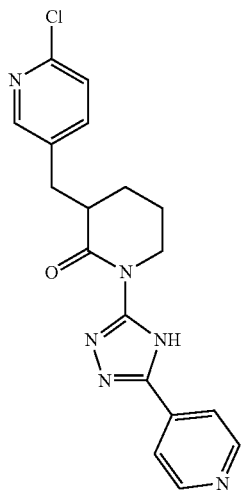 | I-55 |
| 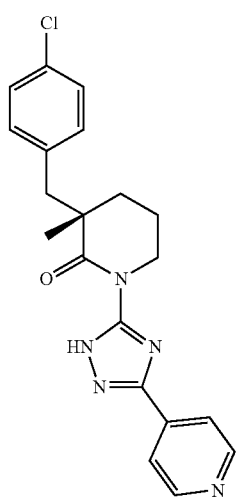 [SMILES: C[C@@]1(Cc2ccc(Cl)cc2)CCCN(c2nc(-c3ccncc3)n[nH]2)C1=O] | I-54-a | 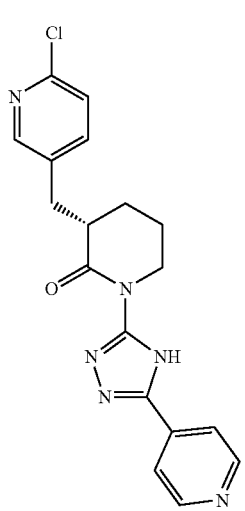 | I-55-a |
| 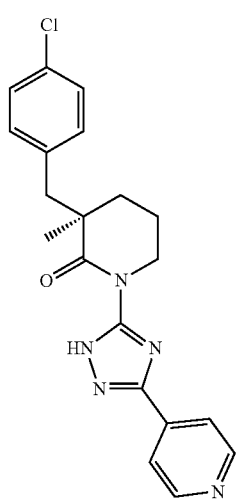 [SMILES: C[C@]1(Cc2ccc(Cl)cc2)CCCN(c2nc(-c3ccncc3)n[nH]2)C1=O] | I-54-b | 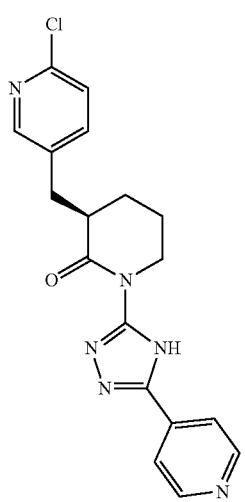 [SMILES: O=C1[C@@H](Cc2ccc(Cl)nc2)CCCN1c1nnc(-c2ccncc2)[nH]1] | I-55-b |

| 101 -continued | | 102 -continued | |
|---|---|---|---|
| Structure | | Structure | |
| 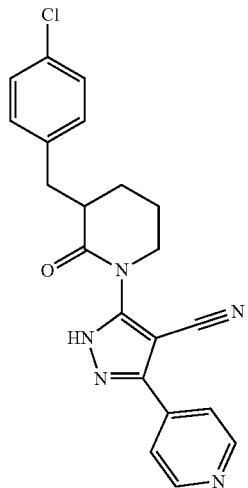 [SMILES: N#Cc1c(-c2ccncc2)n[nH]c1N1CCCC(Cc2ccc(Cl)cc2)C1=O] | I-56 | 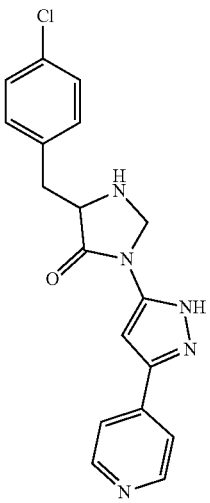 | I-59 |
| 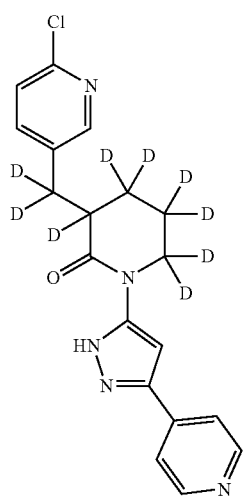 [SMILES: [2H]C([2H])(c1ccc(Cl)nc1)C1([2H])C(=O)N(c2cc(-c3ccncc3)n[nH]2)C([2H])([2H])C([2H])([2H])C1([2H])[2H]] | I-79 | 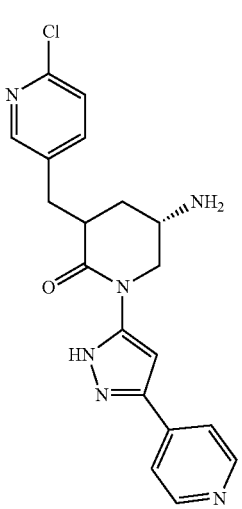 | I-60 |
| 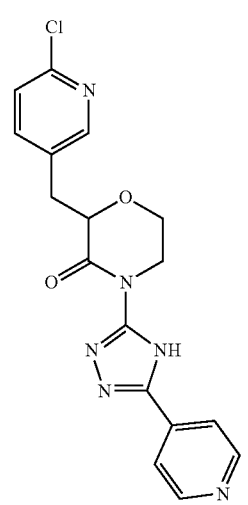 [SMILES: O=C1C(Cc2ccc(Cl)nc2)OCCN1c1nnc(-c2ccncc2)[nH]1] | I-58 | 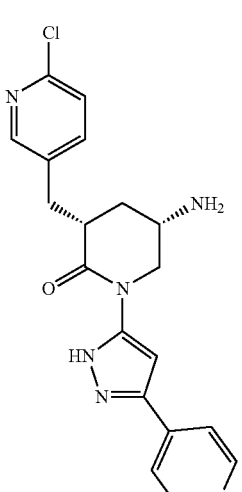 | I-60-a |

| Structure | |
|---|---|
| 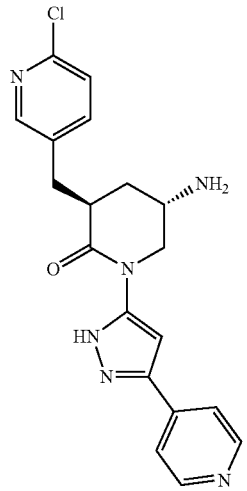 [SMILES: N[C@H]1C[C@H](Cc2ccc(Cl)nc2)C(=O)N(c2cc(-c3ccncc3)n[nH]2)C1] | I-60-b |
| 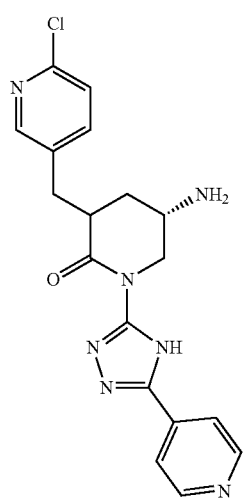 [SMILES: N[C@H]1CC(Cc2ccc(Cl)nc2)C(=O)N(c2nnc(-c3ccncc3)[nH]2)C1] | I-61 |
| 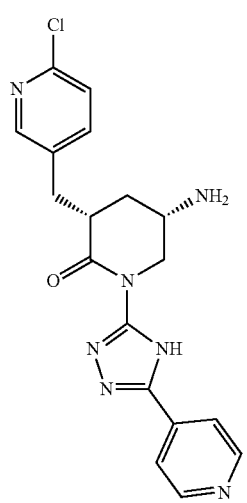 [SMILES: N[C@H]1C[C@@H](Cc2ccc(Cl)nc2)C(=O)N(c2nnc(-c3ccncc3)[nH]2)C1] | I-61-a |
| Structure | |
|---|---|
| 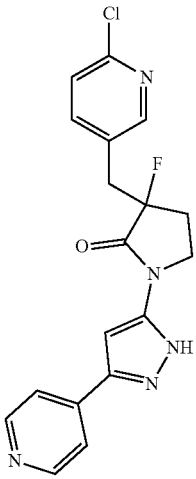 [SMILES: O=C1N(c2cc(-c3ccncc3)n[nH]2)CCC1(F)Cc1ccc(Cl)nc1] | I-62 |
| 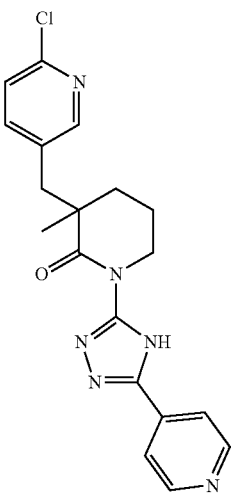 [SMILES: CC1(Cc2ccc(Cl)nc2)CCCN(c2nnc(-c3ccncc3)[nH]2)C1=O] | I-63 |
| 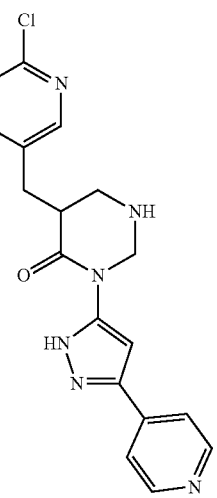 | I-64 |

| Structure | | Structure | |
|---|---|---|---|
| 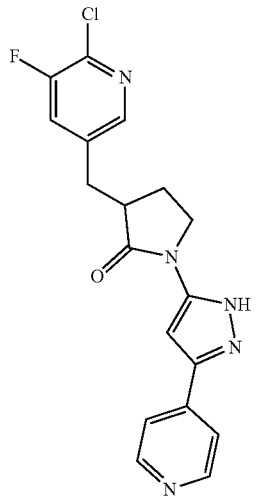 [SMILES: O=C1C(Cc2cnc(Cl)c(F)c2)CCN1c1cc(-c2ccncc2)n[nH]1] | I-65 | 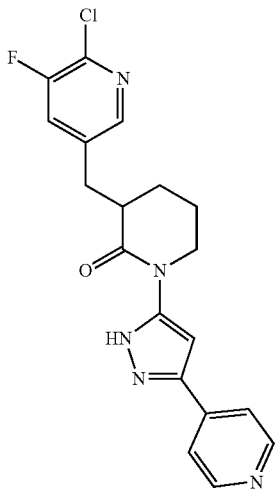 | I-66 |
| 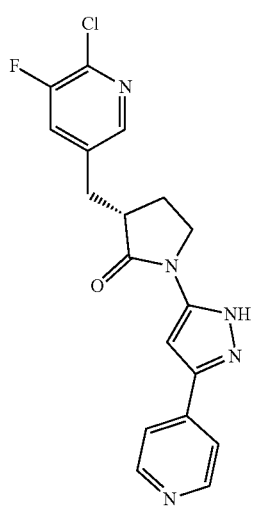 [SMILES: O=C1[C@H](Cc2cnc(Cl)c(F)c2)CCN1c1cc(-c2ccncc2)n[nH]1] | I-65-a | 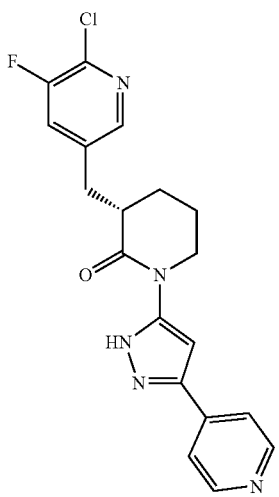 | I-66-a |
| 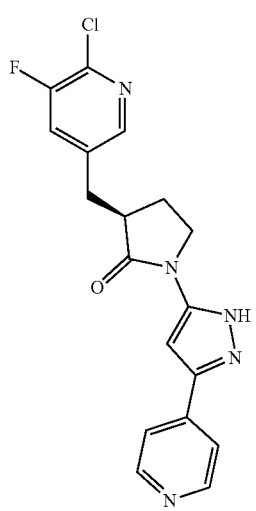 [SMILES: O=C1[C@@H](Cc2cnc(Cl)c(F)c2)CCN1c1cc(-c2ccncc2)n[nH]1] | I-65-b | 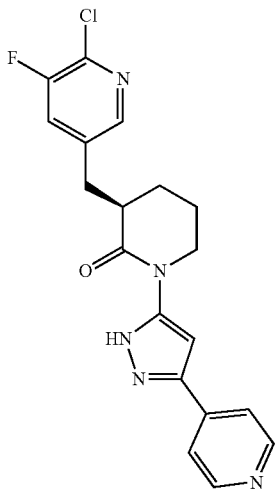 [SMILES: O=C1[C@@H](Cc2cnc(Cl)c(F)c2)CCCN1c1cc(-c2ccncc2)n[nH]1] | I-66-b |

| Structure | | Structure | |
|---|---|---|---|
| 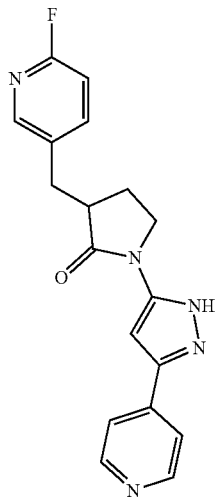 [SMILES: O=C1C(Cc2ccc(F)nc2)CCN1c1cc(-c2ccncc2)n[nH]1] | I-67 | 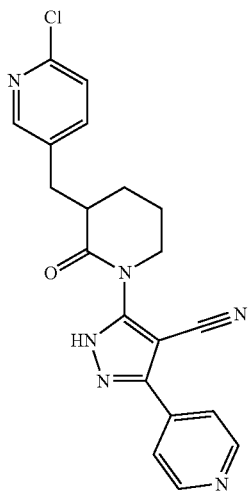 | I-68 |
| 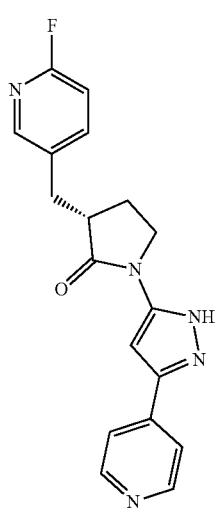 | I-67-a | 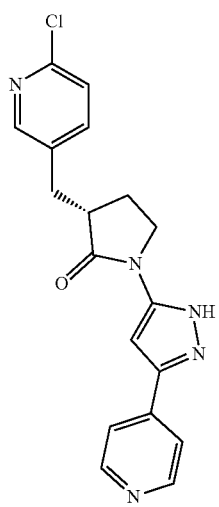 [SMILES: O=C1[C@H](Cc2ccc(F)nc2)CCN1c1cc(-c2ccncc2)n[nH]1] | I-69-a |
| 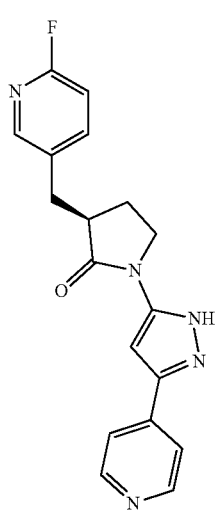 [SMILES: O=C1[C@@H](Cc2ccc(F)nc2)CCN1c1cc(-c2ccncc2)n[nH]1] | I-67-b | 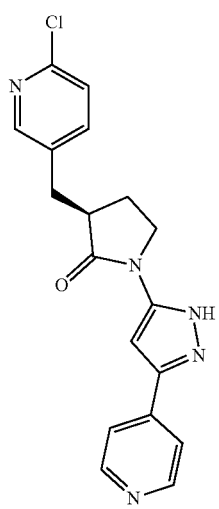 [SMILES: O=C1[C@@H](Cc2ccc(Cl)nc2)CCN1c1cc(-c2ccncc2)n[nH]1] | I-69-b |

| Structure | | Structure | |
|---|---|---|---|
| 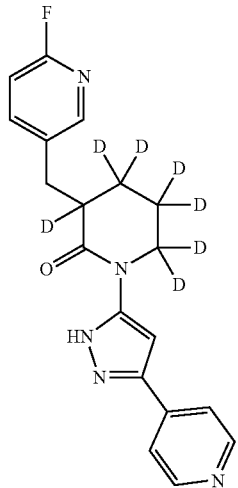 [SMILES: [2H]C1(Cc2ccc(F)nc2)C(=O)N(c2cc(-c3ccncc3)n[nH]2)C([2H])([2H])C([2H])([2H])C1([2H])[2H]] | I-70 | 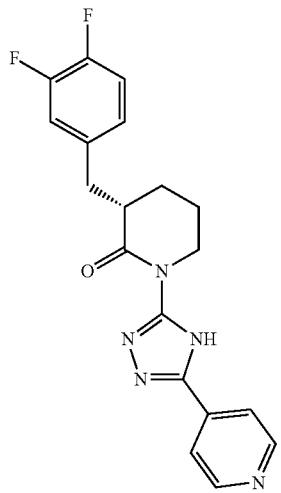 | I-72-a |
| 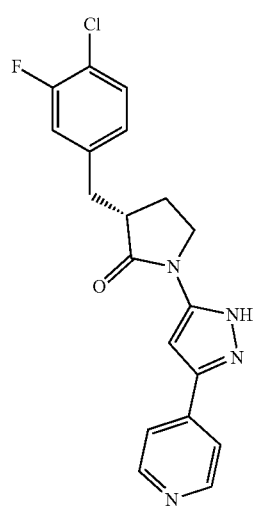 [SMILES: O=C1[C@H](Cc2ccc(Cl)c(F)c2)CCN1c1cc(-c2ccncc2)n[nH]1] | I-71-a | 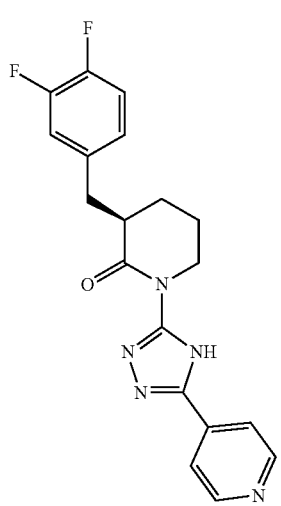 | I-72-b |
| 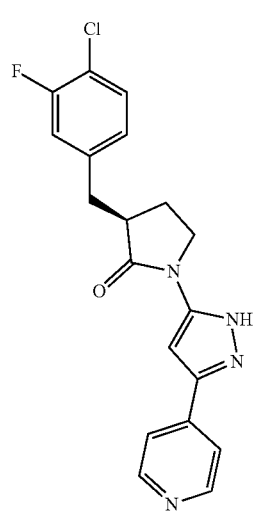 [SMILES: O=C1[C@@H](Cc2ccc(Cl)c(F)c2)CCN1c1cc(-c2ccncc2)n[nH]1] | I-71-b | 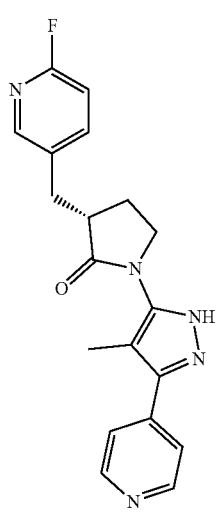 [SMILES: Cc1c(-c2ccncc2)n[nH]c1N1CC[C@@H](Cc2ccc(F)nc2)C1=O] | I-73-a |

111
-continued
| Structure | |
|---|---|
| 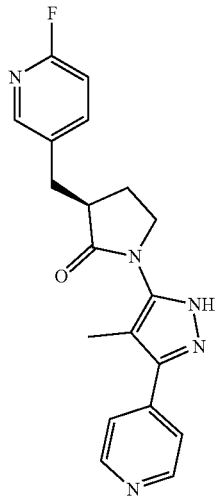 [SMILES: Cc1c(-c2ccncc2)n[nH]c1N1CC[C@H](Cc2ccc(F)nc2)C1=O] | I-73-b |
| 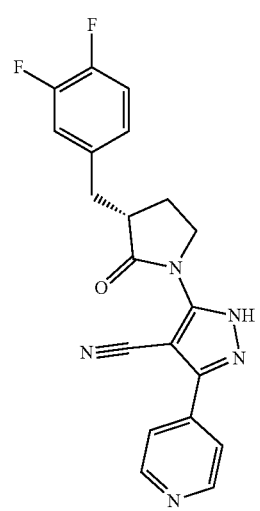 | I-74-a |
| 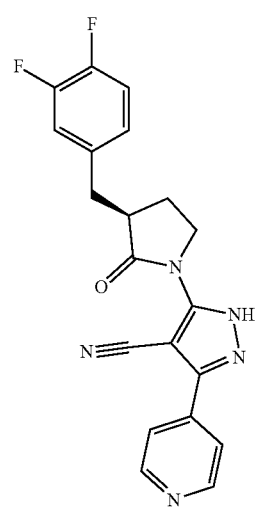 [SMILES: N#Cc1c(-c2ccncc2)n[nH]c1N1CC[C@H](Cc2ccc(F)c(F)c2)C1=O] | I-74-b |
112
-continued
| Structure | |
|---|---|
| 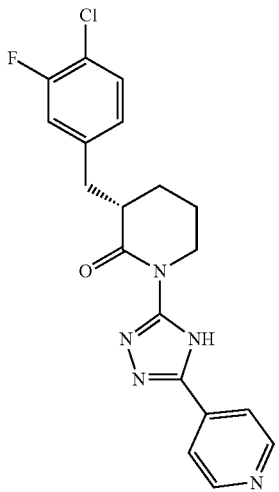 [SMILES: O=C1[C@H](Cc2ccc(Cl)c(F)c2)CCCN1c1nnc(-c2ccncc2)[nH]1] | I-75-a |
| 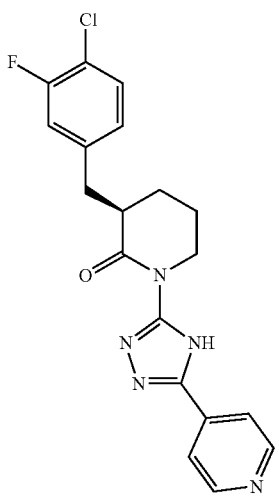 [SMILES: O=C1[C@@H](Cc2ccc(Cl)c(F)c2)CCCN1c1nnc(-c2ccncc2)[nH]1] | I-75-b |
| 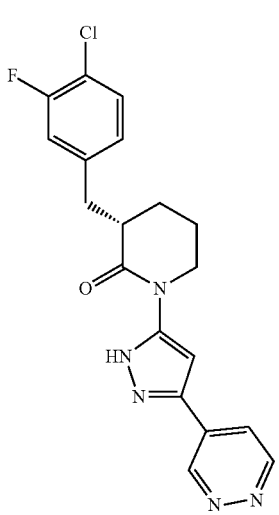 [SMILES: O=C1[C@H](Cc2ccc(Cl)c(F)c2)CCCN1c1cc(-c2ccnnc2)n[nH]1] | I-76-a |

| 113 -continued | | 114 -continued | |
|---|---|---|---|
| Structure | | Structure | |
| 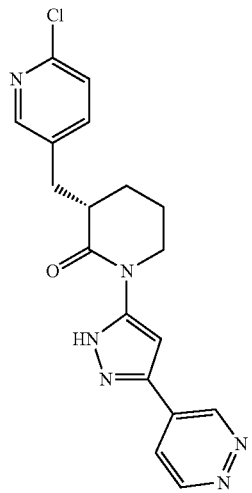 [SMILES: O=C1[C@H](Cc2ccc(Cl)nc2)CCCN1c1cc(-c2ccnnc2)n[nH]1] | I-77-a | 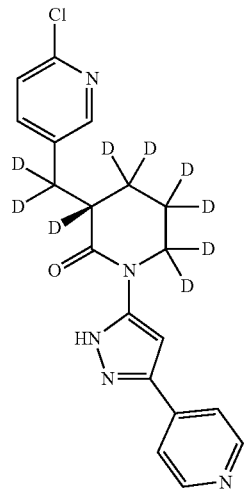 | I-79-a |
| 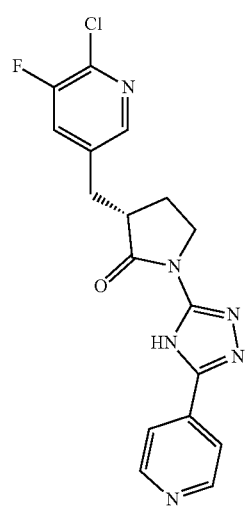 [SMILES: O=C1[C@H](Cc2cnc(Cl)c(F)c2)CCN1c1nnc(-c2ccncc2)[nH]1] | I-78-a | 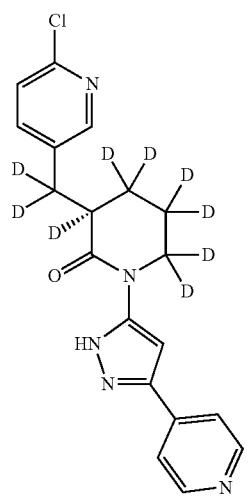 | I-79-b |
| 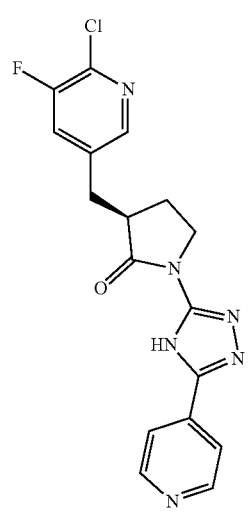 [SMILES: O=C1[C@@H](Cc2cnc(Cl)c(F)c2)CCN1c1nnc(-c2ccncc2)[nH]1] | I-78-b | 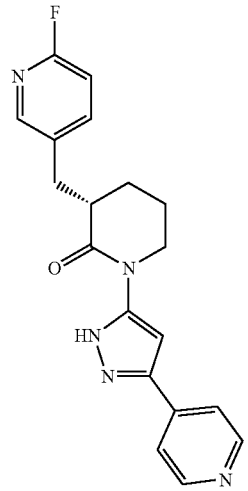 [SMILES: O=C1[C@H](Cc2ccc(F)nc2)CCCN1c1cc(-c2ccncc2)n[nH]1] | I-80-a |

| Structure | |
|---|---|
| 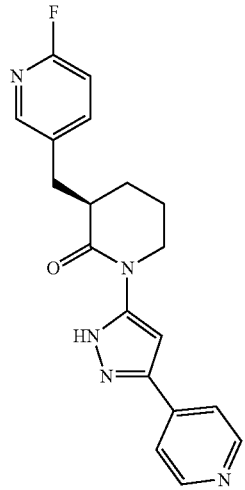 [SMILES: O=C1[C@@H](Cc2ccc(F)nc2)CCCN1c1cc(-c2ccncc2)n[nH]1] | I-80-b |
| 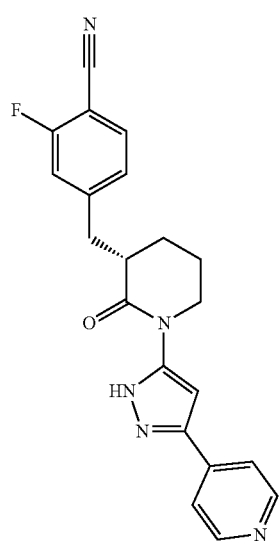 [SMILES: N#Cc1ccc(C[C@@H]2CCCN(c3cc(-c4ccncc4)n[nH]3)C2=O)cc1F] | I-81-a |
| 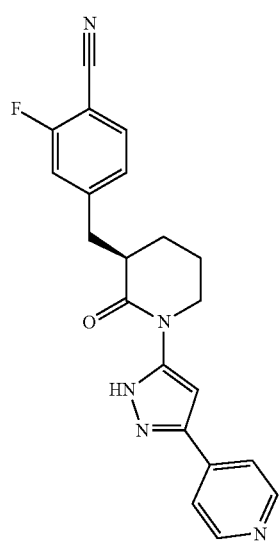 [SMILES: N#Cc1ccc(C[C@H]2CCCN(c3cc(-c4ccncc4)n[nH]3)C2=O)cc1F] | I-81-b |
| 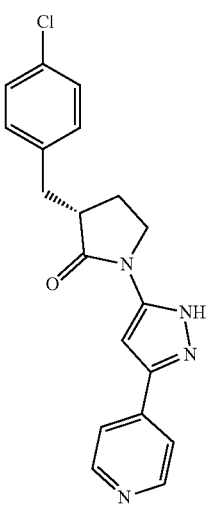 [SMILES: O=C1[C@H](Cc2ccc(Cl)cc2)CCN1c1cc(-c2ccncc2)n[nH]1] | I-82-a |
| 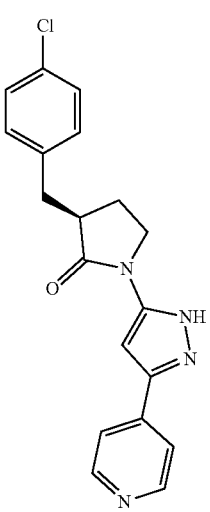 [SMILES: O=C1[C@@H](Cc2ccc(Cl)cc2)CCN1c1cc(-c2ccncc2)n[nH]1] | I-82-b |
| 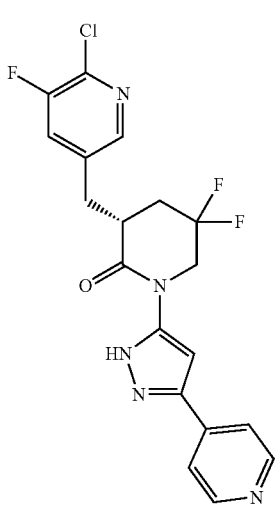 [SMILES: O=C1[C@H](Cc2cnc(Cl)c(F)c2)CC(F)(F)CN1c1cc(-c2ccncc2)n[nH]1] | I-83-a |

| Structure | | Structure | |
|---|---|---|---|
| 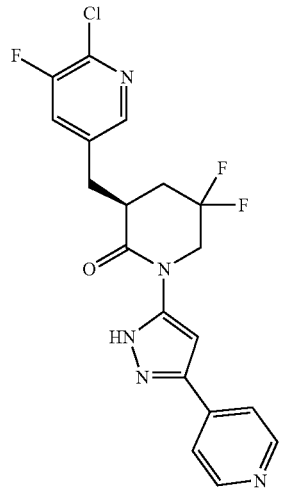 [SMILES: O=C1[C@@H](Cc2cnc(Cl)c(F)c2)CC(F)(F)CN1c1cc(-c2ccncc2)n[nH]1] | I-83-b | 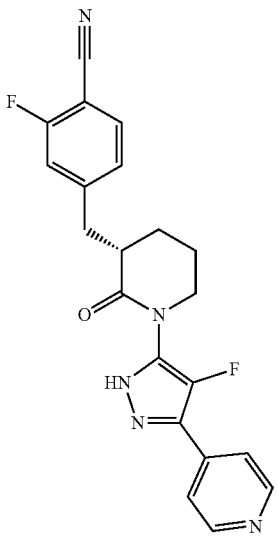 | I-86-a |
| 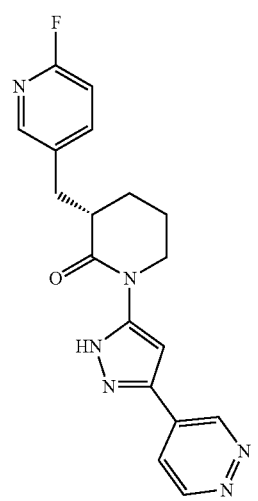 [SMILES: O=C1[C@H](Cc2ccc(F)nc2)CCCN1c1cc(-c2ccnnc2)n[nH]1] | I-84-a | | I-86-b |
| 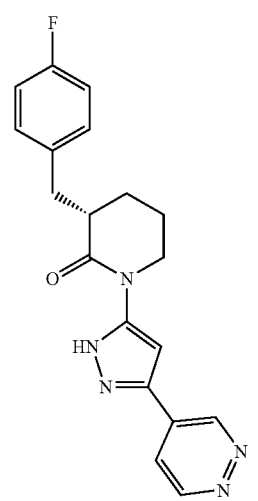 [SMILES: O=C1[C@H](Cc2ccc(F)cc2)CCCN1c1cc(-c2ccnnc2)n[nH]1] | I-85-a | | I-87-a |

| Structure | | Structure | |
|---|---|---|---|
| 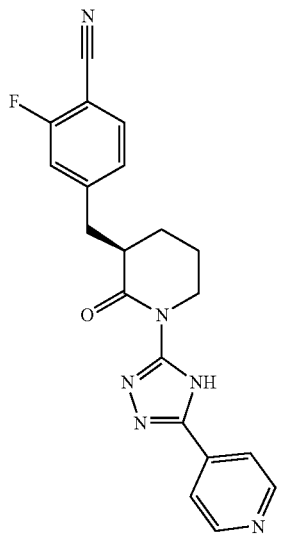 [SMILES: N#Cc1ccc(C[C@H]2CCCN(c3nnc(-c4ccncc4)[nH]3)C2=O)cc1F] | I-87-b | 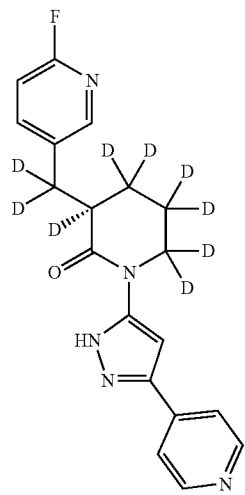 | I-90-a |
| 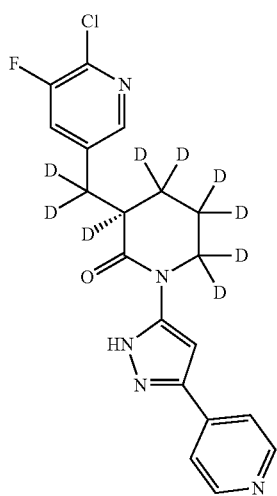 [SMILES: [2H]C1([2H])N(c2cc(-c3ccncc3)n[nH]2)C(=O)[C@@]([2H])(C([2H])([2H])c2cnc(Cl)c(F)c2)C([2H])([2H])C1([2H])[2H]] | I-88-a | 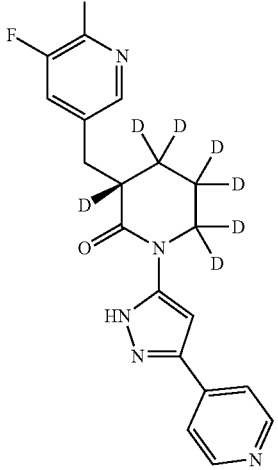 | I-91-a |
| 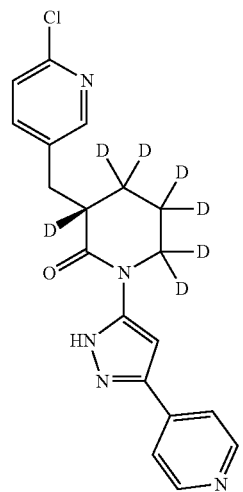 [SMILES: [2H]C1([2H])N(c2cc(-c3ccncc3)n[nH]2)C(=O)[C@]([2H])(Cc2ccc(Cl)nc2)C([2H])([2H])C1([2H])[2H]] | I-89-a | 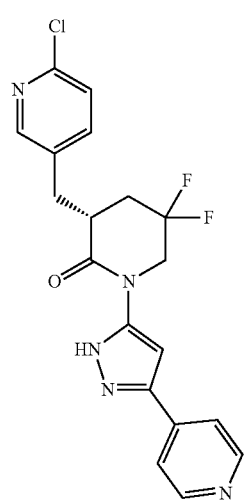 [SMILES: O=C1[C@H](Cc2ccc(Cl)nc2)CC(F)(F)CN1c1cc(-c2ccncc2)n[nH]1] | I-92-a |

| Structure | | Structure | |
|---|---|---|---|
| 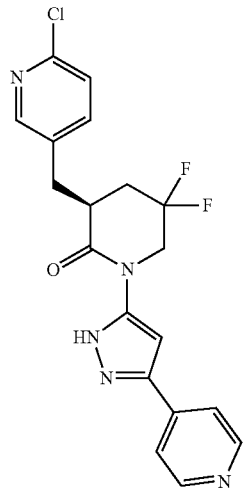 [SMILES: O=C1[C@@H](Cc2ccc(Cl)nc2)CC(F)(F)CN1c1cc(-c2ccncc2)n[nH]1] | I-92-b | 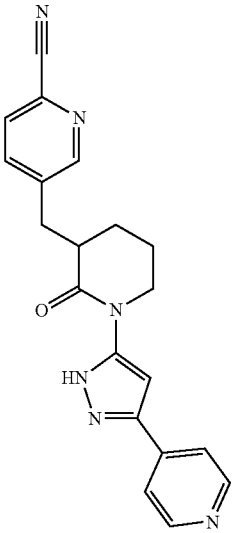 | I-94 |
| 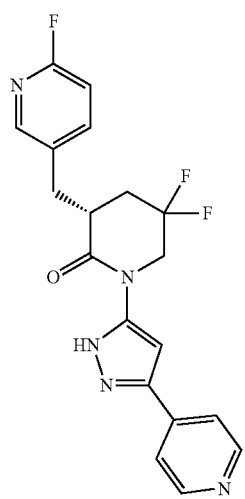 [SMILES: O=C1[C@H](Cc2ccc(F)nc2)CC(F)(F)CN1c1cc(-c2ccncc2)n[nH]1] | I-93-a | 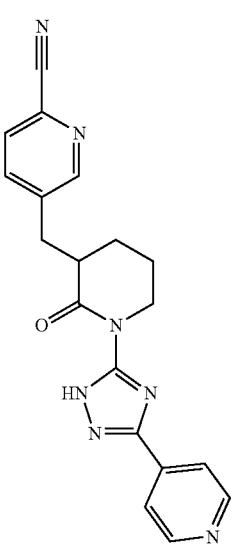 | I-95 |
| 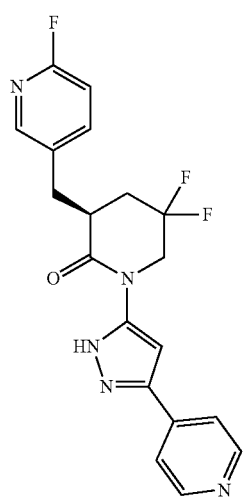 [SMILES: O=C1[C@@H](Cc2ccc(F)nc2)CC(F)(F)CN1c1cc(-c2ccncc2)n[nH]1] | I-93-b | 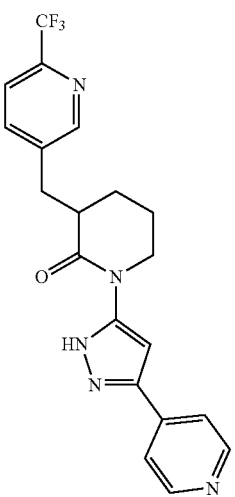 [SMILES: O=C1C(Cc2ccc(C(F)(F)F)nc2)CCCN1c1cc(-c2ccncc2)n[nH]1] | I-96 |

| Structure | | Structure | |
|---|---|---|---|
| 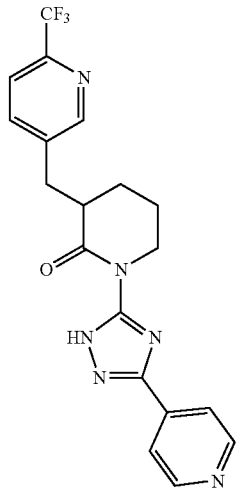 [SMILES: O=C1C(Cc2ccc(C(F)(F)F)nc2)CCCN1c1nc(-c2ccncc2)n[nH]1] | I-97 | 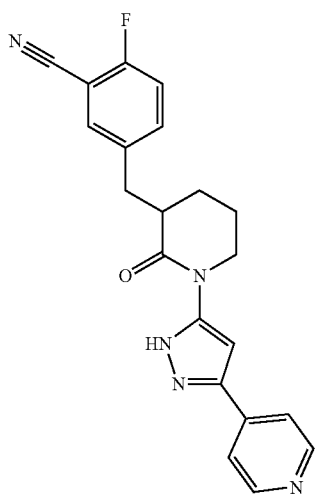 | I-100 |
| 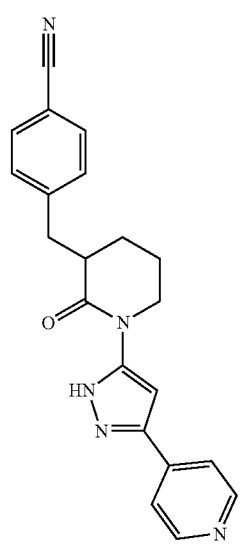 [SMILES: N#Cc1ccc(CC2CCCN(c3cc(-c4ccncc4)n[nH]3)C2=O)cc1] | I-98 | 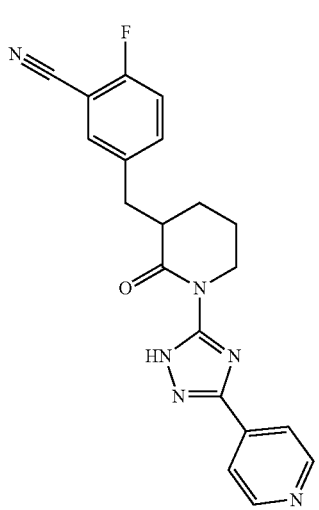 | I-101 |
| 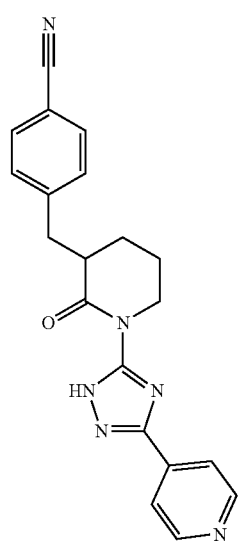 [SMILES: N#Cc1ccc(CC2CCCN(c3nc(-c4ccncc4)n[nH]3)C2=O)cc1] | I-99 | 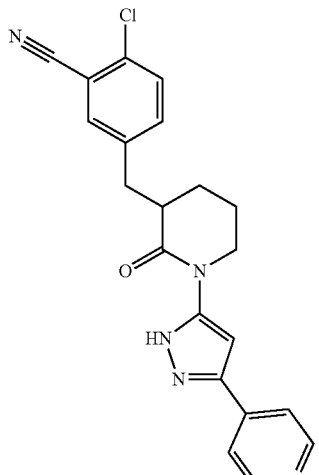 | I-102 |

| 125 -continued | 126 -continued |
|---|---|
| Structure | Structure |
| 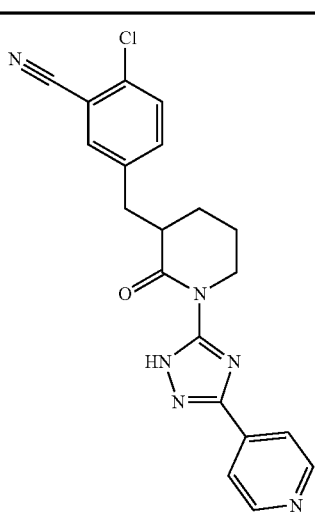 I-103 | 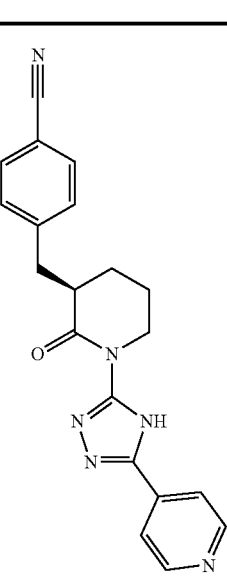 I-105-b |
| 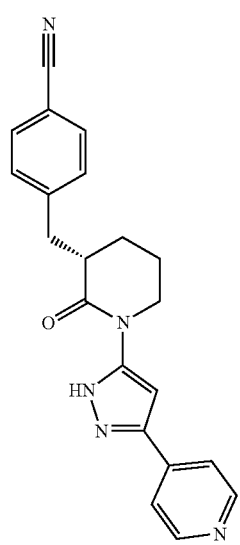 [SMILES: N#Cc1ccc(C[C@@H]2CCCN(c3cc(-c4ccncc4)n[nH]3)C2=O)cc1] I-104-a | 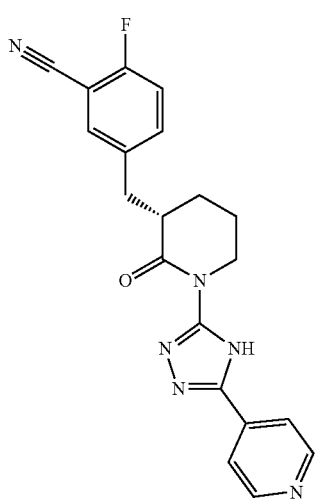 I-106-a |
| 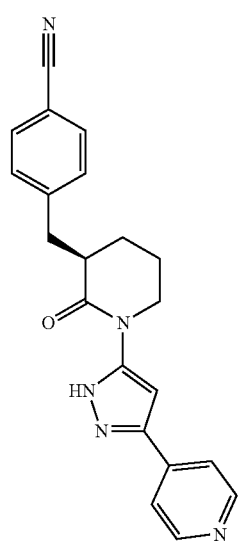 [SMILES: N#Cc1ccc(C[C@H]2CCCN(c3cc(-c4ccncc4)n[nH]3)C2=O)cc1] I-104-b | 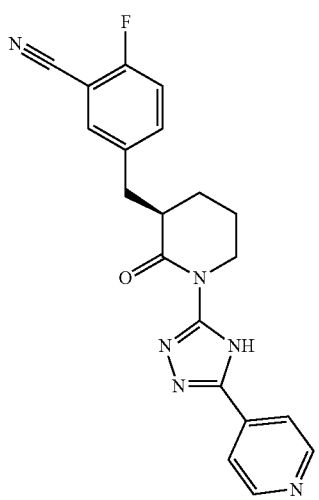 [SMILES: N#Cc1cc(C[C@H]2CCCN(c3nnc(-c4ccncc4)[nH]3)C2=O)ccc1F] I-106-b |

| Structure | | Structure | |
|---|---|---|---|
| 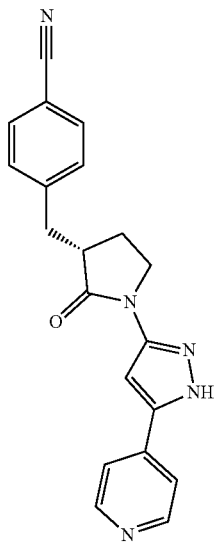 [SMILES: N#Cc1ccc(C[C@@H]2CCN(c3cc(-c4ccncc4)[nH]n3)C2=O)cc1] | I-107-a | 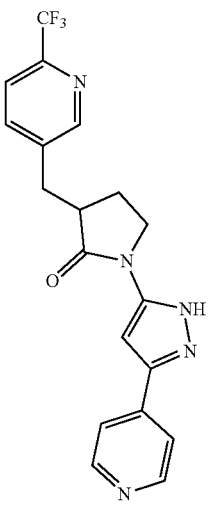 | I-112 |
| 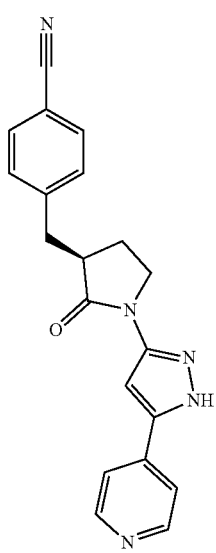 [SMILES: N#Cc1ccc(C[C@H]2CCN(c3cc(-c4ccncc4)[nH]n3)C2=O)cc1] | I-107-b | 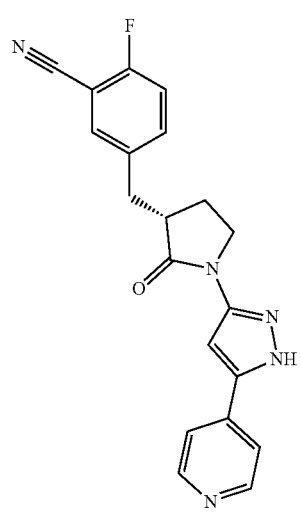 | I-113-a |
| 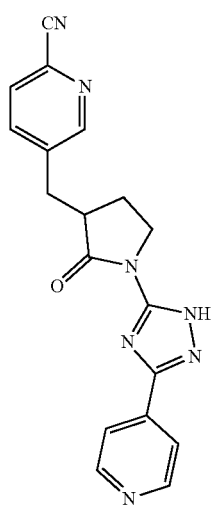 [SMILES: N#Cc1ccc(CC2CCN(c3nc(-c4ccncc4)n[nH]3)C2=O)cn1] | I-111 | 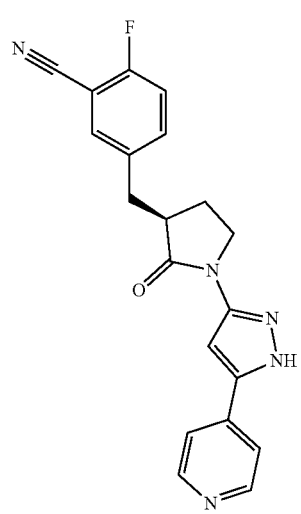 [SMILES: N#Cc1cc(C[C@H]2CCN(c3cc(-c4ccncc4)[nH]n3)C2=O)ccc1F] | I-113-b |

-continued
| Structure | |
|---|---|
| 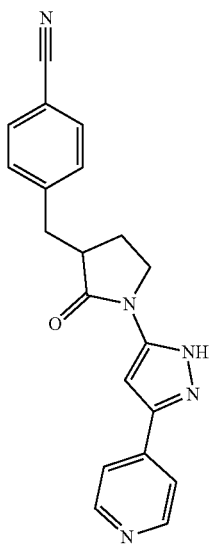 [SMILES: N#Cc1ccc(CC2CCN(c3cc(-c4ccncc4)n[nH]3)C2=O)cc1] | I-114 |
| 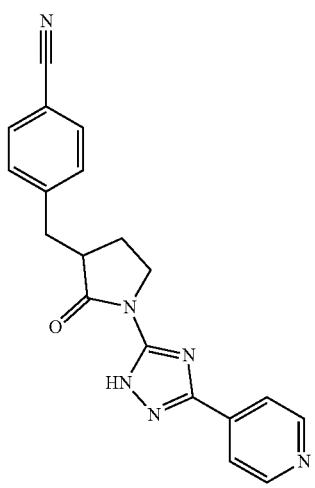 [SMILES: N#Cc1ccc(CC2CCN(c3nc(-c4ccncc4)n[nH]3)C2=O)cc1] | I-115 |
| 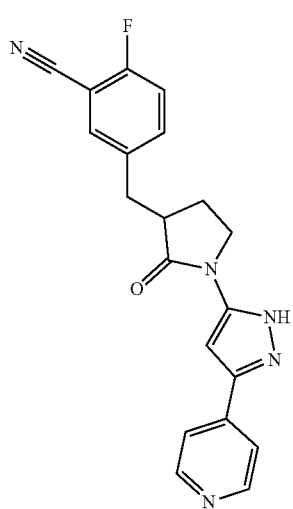 [SMILES: N#Cc1cc(CC2CCN(c3cc(-c4ccncc4)n[nH]3)C2=O)ccc1F] | I-116 |
-continued
| Structure | |
|---|---|
| 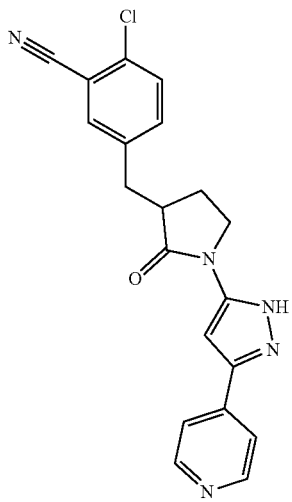 [SMILES: N#Cc1cc(CC2CCN(c3cc(-c4ccncc4)n[nH]3)C2=O)ccc1Cl] | I-118 |
| 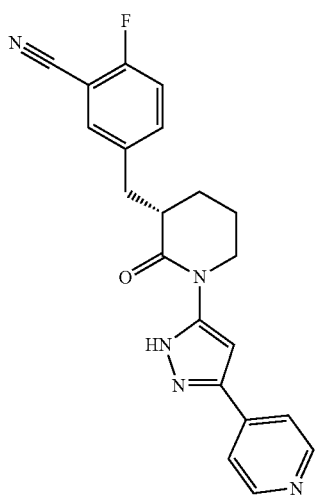 [SMILES: N#Cc1cc(C[C@@H]2CCCN(c3cc(-c4ccncc4)n[nH]3)C2=O)ccc1F] | I-119-a |
| 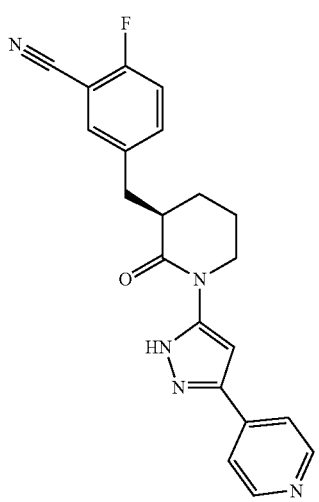 [SMILES: N#Cc1cc(C[C@H]2CCCN(c3cc(-c4ccncc4)n[nH]3)C2=O)ccc1F] | I-119-b |
or a pharmaceutically acceptable salt thereof.
In some aspects, the present disclosure provides a compound according to the following embodiments:

Embodiment 1. A compound of Formula I:

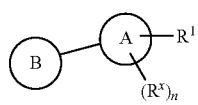

I or a pharmaceutically acceptable salt thereof, wherein:
Ring A is a 5- to 6-membered heteroaryl ring having 1-3 heteroatoms independently selected from oxygen, nitrogen, and sulfur;
$R^1$ is an optionally substituted group selected from a 3- to 7-membered saturated or partially unsaturated heterocyclic ring having 1-3 heteroatoms independently selected from oxygen, nitrogen, and sulfur or a 5- to 6-membered heteroaryl ring having 1-3 heteroatoms independently selected from oxygen, nitrogen, and sulfur;
each $R^x$ is independently selected from halogen, cyano, OR, SR, $N(R)_2$, or an optionally substituted group selected from $C_{1-4}$ aliphatic, a 3- to 7-membered saturated or partially unsaturated carbocyclic ring, a 3- to 7-membered saturated or partially unsaturated heterocyclic ring having 1-3 heteroatoms independently selected from oxygen, nitrogen, and sulfur, phenyl, and a 5- to 6-membered heteroaryl ring having 1-3 heteroatoms independently selected from oxygen, nitrogen, and sulfur;
Ring B is a saturated 5- to 7-membered heterocyclic ring having the structure

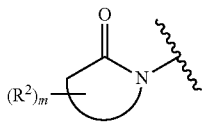

and optionally comprising one additional group selected from —NH—, —O—, and —NR²—;
each R is independently hydrogen or an optionally substituted group selected from $C_{1-6}$ aliphatic, a 3- to 7-membered saturated or partially unsaturated heterocyclic ring having 1-3 heteroatoms independently selected from oxygen, nitrogen, and sulfur, phenyl, and a 5- to 6-membered heteroaryl ring having 1-3 heteroatoms independently selected from oxygen, nitrogen, and sulfur; or:
two R groups, together with the nitrogen atom to which they are attached, form an optionally substituted 3- to 7-membered monocyclic heterocyclic ring having 0-2 additional heteroatoms independently selected from oxygen, nitrogen, and sulfur;
each $R^2$ is independently halogen, $N(R)_2$, OR, or —($C_{1-3}$ aliphatic)$R^3$;
each $R^3$ is independently an optionally substituted group selected from $C_{1-6}$ aliphatic, a 3- to 7-membered saturated or partially unsaturated heterocyclic ring having 1-3 heteroatoms independently selected from oxygen, nitrogen, and sulfur, phenyl, a 5- to 6-membered heteroaryl ring having 1-3 heteroatoms independently selected from oxygen, nitrogen, and sulfur, a 8- to 10-membered bicyclic saturated, partially unsaturated or aryl carbocyclic ring, a 8- to 10-membered bicyclic saturated or partially unsaturated heterocyclic ring having 1-3 heteroatoms independently selected from oxygen, nitrogen, and sulfur, or a 8- to 10-membered bicyclic heteroaryl ring having 1-3 heteroatoms independently selected from oxygen, nitrogen, and sulfur;
m is 0, 1, or 2; and
n is 0, 1, or 2.

Embodiment 2. The compound according to embodiment 1, wherein Ring A is a 6-membered heteroaryl ring having 1-2 nitrogen atoms.

Embodiment 3. The compound according to embodiment 1, wherein Ring A is a 5-membered heteroaryl ring having 1-3 heteroatoms independently selected from oxygen, nitrogen, and sulfur.

Embodiment 4. The compound according to embodiment 3, wherein Ring A is a 5-membered heteroaryl ring having 2 heteroatoms independently selected from oxygen, nitrogen, and sulfur.

Embodiment 5. The compound according to embodiment 3, wherein Ring A is a 5-membered heteroaryl ring having 3 heteroatoms independently selected from oxygen, nitrogen, and sulfur.

Embodiment 6. The compound according to embodiment 1, wherein Ring A is selected from

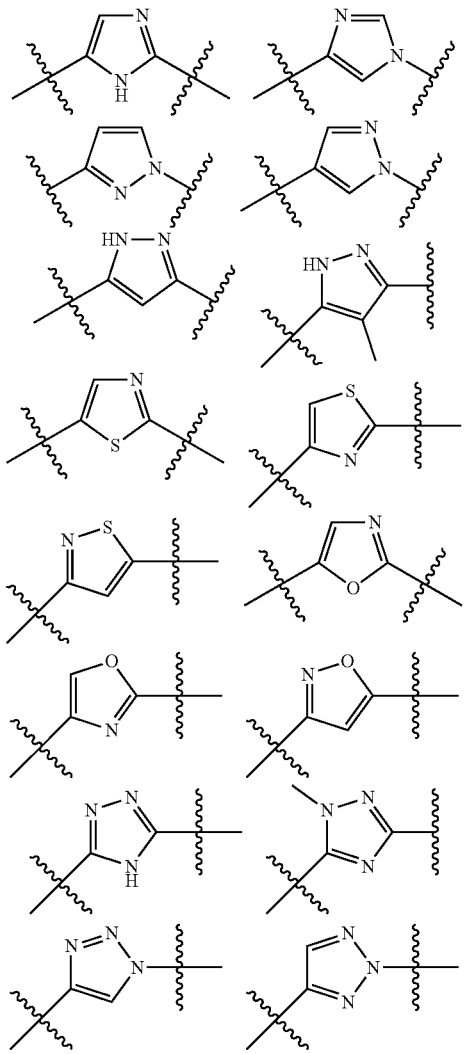

-continued
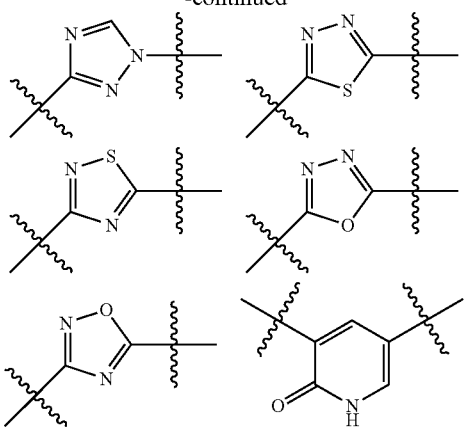
Embodiment 7. The compound according to embodiment 6, wherein Ring A is selected from
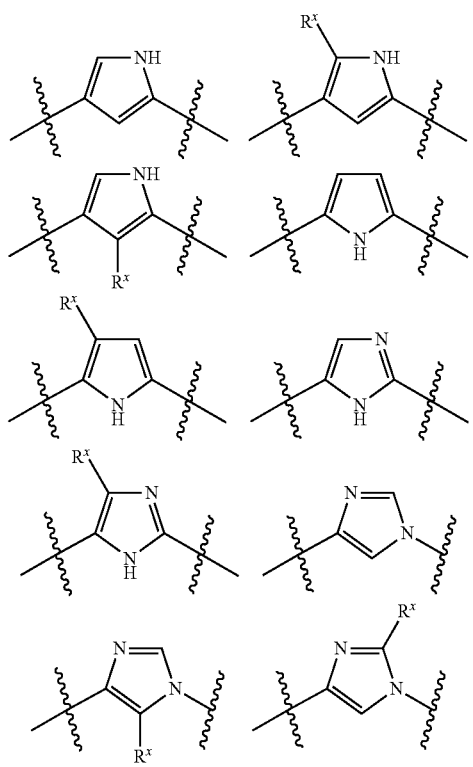
Embodiment 8. The compound according to embodiment 1, wherein Ring A is selected from
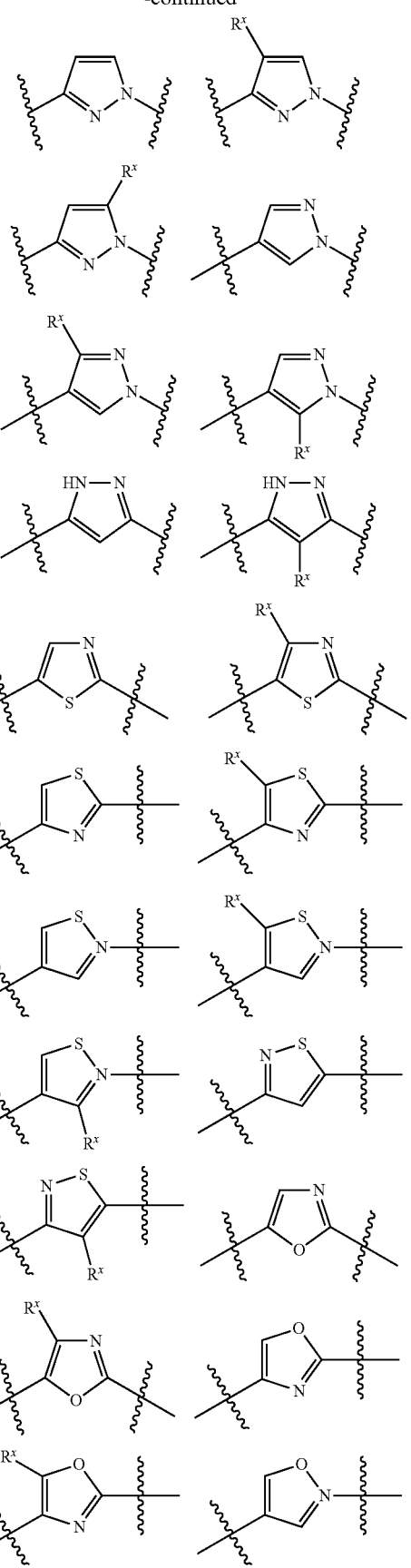
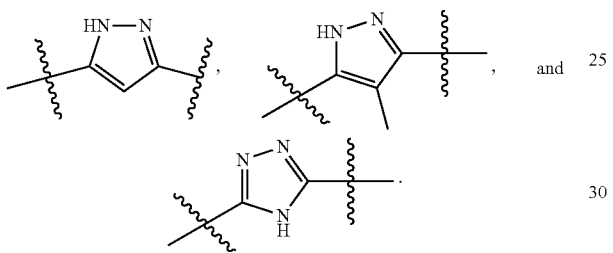

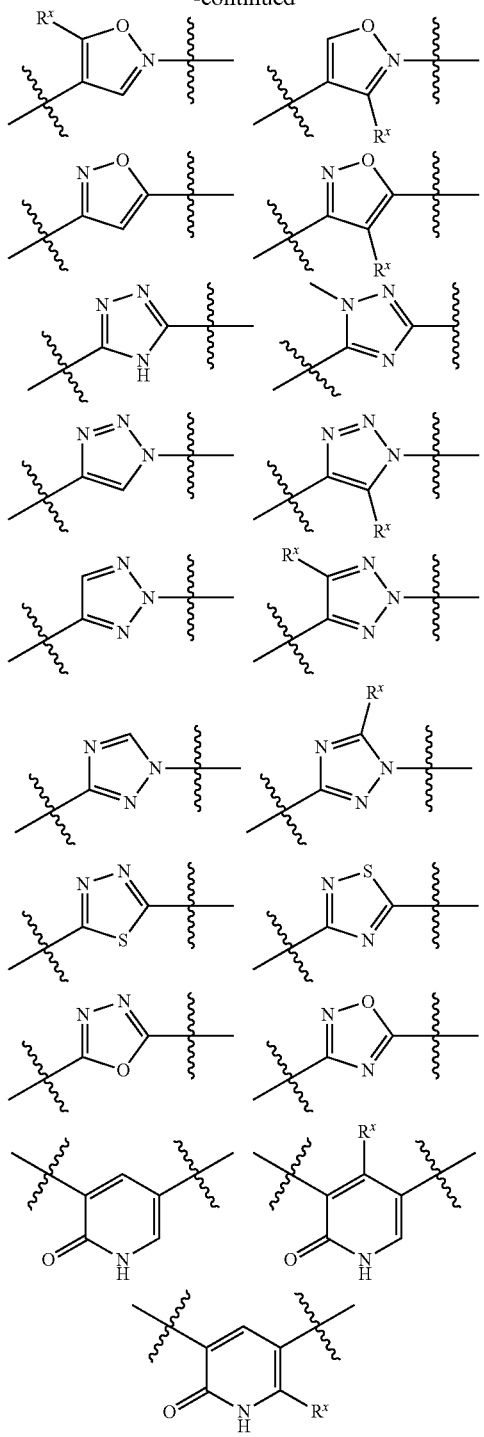

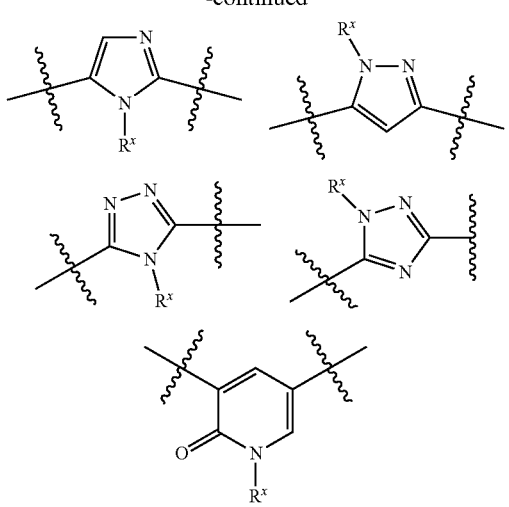

wherein $R^x$ is an optionally substituted group selected from $C_{1-4}$ aliphatic, a 3- to 7-membered saturated or partially unsaturated carbocyclic ring, a 3- to 7-membered saturated or partially unsaturated heterocyclic ring having 1-3 heteroatoms independently selected from oxygen, nitrogen, and sulfur, phenyl, and a 5- to 6-membered heteroaryl ring having 1-3 heteroatoms independently selected from oxygen, nitrogen, and sulfur.

Embodiment 10. The compound according to embodiment 1, wherein Ring A is selected from

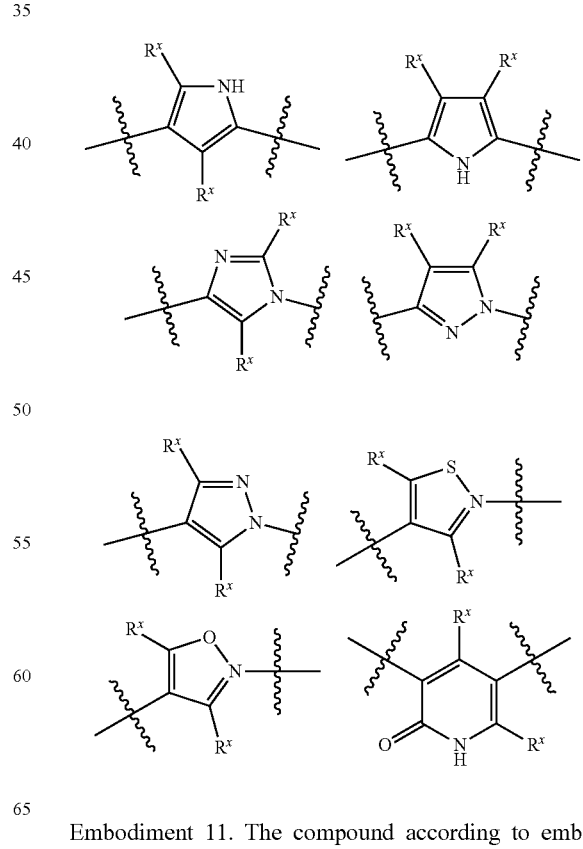

Embodiment 9. The compound according to embodiment 1, wherein Ring A is selected from

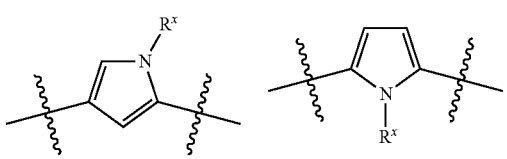

Embodiment 11. The compound according to embodiment 1, wherein Ring A is selected from

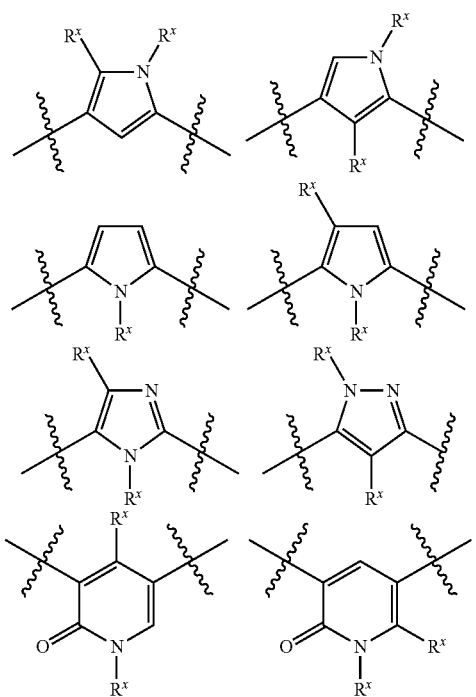

wherein:
R$^x$ on a nitrogen atom is selected from an optionally substituted group selected from C$_{1-4}$ aliphatic, a 3- to 7-membered saturated or partially unsaturated carbocyclic ring, a 3- to 7-membered saturated or partially unsaturated heterocyclic ring having 1-3 heteroatoms independently selected from oxygen, nitrogen, and sulfur, phenyl, and a 5- to 6-membered heteroaryl ring having 1-3 heteroatoms independently selected from oxygen, nitrogen, and sulfur; and R$^x$ on a carbon atom is selected from halogen, cyano, OR, SR, N(R)$_2$, or an optionally substituted group selected from C$_{1-4}$ aliphatic, a 3- to 7-membered saturated or partially unsaturated carbocyclic ring, a 3- to 7-membered saturated or partially unsaturated heterocyclic ring having 1-3 heteroatoms independently selected from oxygen, nitrogen, and sulfur, phenyl, and a 5- to 6-membered heteroaryl ring having 1-3 heteroatoms independently selected from oxygen, nitrogen, and sulfur.

Embodiment 12. The compound according to any one of embodiments 1-11, wherein R$^x$ is halogen.

Embodiment 13. The compound according to any one of embodiments 1-11, wherein R$^x$ is cyano.

Embodiment 14. The compound according to any one of embodiments 1-11, wherein R$^x$ is OR.

Embodiment 15. The compound according to any one of embodiments 1-11, wherein R$^x$ is SR.

Embodiment 16. The compound according to any one of embodiments 1-11, wherein R$^x$ is N(R)$_2$.

Embodiment 17. The compound according to any one of embodiments 14-16, wherein R is selected from hydrogen and optionally substituted C$_{1-6}$ aliphatic.

Embodiment 18. The compound according to embodiment 17, wherein R is selected from hydrogen and optionally substituted C$_{1-4}$ aliphatic.

Embodiment 19. The compound according to any one of embodiments 14, 17, and 18, wherein R$^x$ is OH, OCH$_3$, and OCH$_2$CH$_3$.

Embodiment 20. The compound according to any one of embodiments 15, 17, and 18, wherein R$^x$ is SH, SCH$_3$, and SCH$_2$CH$_3$.

Embodiment 21. The compound according to any one of embodiments 16-18, wherein R$^x$ is selected from NH$_2$, NHCH$_3$, NHCH$_2$CH$_3$, N(CH$_3$)$_2$, and N(CH$_2$CH$_3$)$_2$.

Embodiment 22. The compound according to any one of embodiments 1-11, wherein R$^x$ is optionally substituted C$_{1-4}$ aliphatic.

Embodiment 23. The compound according to embodiment 22, wherein R$^x$ is optionally substituted C$_{3-4}$ aliphatic.

Embodiment 24. The compound according to embodiment 23, wherein R$^x$ is selected from tert-butyl

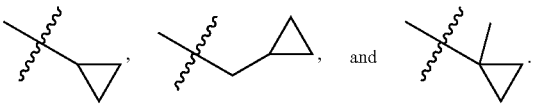

Embodiment 25. The compound according to embodiment 22, wherein R$^x$ is C$_{1-4}$ aliphatic optionally substituted with a group selected from halogen, —(CH$_2$)$_{0-4}$R°, —(CH$_2$)$_{0-4}$OR°, —(CH$_2$)$_{0-4}$N(R°)$_2$, —(CH$_2$)$_{0-4}$C(O)OR°, and —(CH$_2$)$_{0-4}$C(O)NR°$_2$.

Embodiment 26. The compound according to embodiment 25, wherein R° is selected from hydrogen, C$_{1-6}$ aliphatic, —CH$_2$Ph, —O(CH$_2$)$_{0-1}$Ph, —CH$_2$-(5- to 6-membered heteroaryl ring), a 5- to 6-membered saturated, partially unsaturated, or aryl ring having 0-4 heteroatoms independently selected from nitrogen, oxygen, or sulfur, or an 8- to 10-membered bicyclic aryl ring having 0-4 heteroatoms independently selected from nitrogen, oxygen, or sulfur, or: two independent occurrences of R°, taken together with their intervening atom(s), form a 3- to 12-membered saturated, partially unsaturated, or aryl mono- or bicyclic ring having 0-4 heteroatoms independently selected from nitrogen, oxygen, or sulfur.

Embodiment 27. The compound according to embodiment 22, wherein R$^x$ is C$_{1-4}$ aliphatic optionally substituted with a group selected from halogen, —R°, —OR°, —N(R°)$_2$, —C(O)OR°, and —C(O)NR°$_2$.

Embodiment 28. The compound according to embodiment 22, wherein R$^x$ is CuI aliphatic optionally substituted with halogen.

Embodiment 29. The compound according to embodiment 28, wherein R$^x$ is selected from —CH$_3$, —CF$_3$, —CHF$_2$, and CH$_2$F.

Embodiment 30. The compound according to embodiment 22, wherein R$^x$ is selected from —CH$_2$R°, —CH$_2$OR°, —CH$_2$N(R°)$_2$, —CH$_2$C(O)OR°, and —CH$_2$C(O)N(R°)$_2$.

Embodiment 31. The compound according to embodiment 30, wherein R$^x$ is selected from —CH$_2$OH, —CH$_2$OCH$_3$, —CH$_2$C(O)NH$_2$, —CH$_2$C(O)NHCH$_3$, and —CH$_2$C(O)N(CH$_3$)$_2$.

Embodiment 32. The compound according to any one of embodiments 1-31, wherein R$^1$ is an optionally substituted 5- to 6-membered heteroaryl ring having 1-3 heteroatoms independently selected from oxygen, nitrogen, and sulfur.

Embodiment 33. The compound according to embodiment 32, wherein R$^1$ is an optionally substituted 5-membered heteroaryl ring having 1-3 heteroatoms independently selected from oxygen, nitrogen, and sulfur.

Embodiment 34. The compound according to embodiment 33, wherein R¹ is an optionally substituted 5-membered heteroaryl ring having 1-2 heteroatoms independently selected from oxygen, nitrogen, and sulfur.

Embodiment 35. The compound according to embodiment 32, wherein R¹ is an optionally substituted 6-membered heteroaryl ring having 1-3 nitrogen atoms.

Embodiment 36. The compound according to embodiment 35, wherein R¹ is an optionally substituted 6-membered heteroaryl ring having 1-2 nitrogen atoms.

Embodiment 37. The compound according to embodiment 32, wherein R¹ is selected from

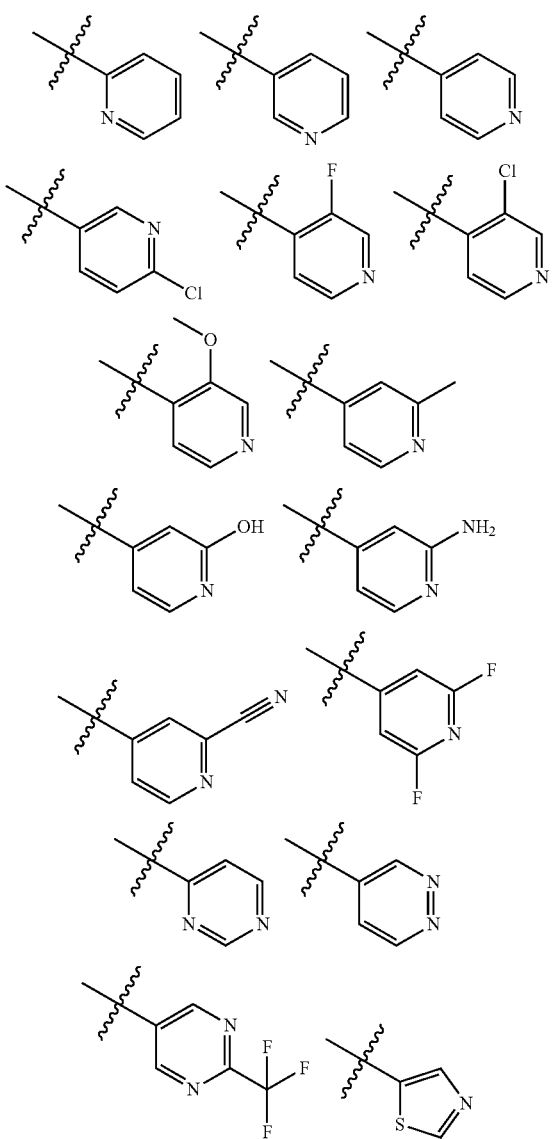

Embodiment 38. The compound according to embodiment 37, wherein R¹ is selected from

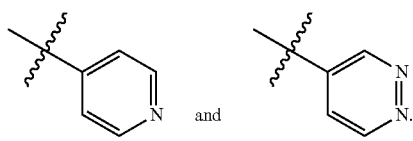 [SMILES: *c1ccncc1 ; *c1ccnnc1]

Embodiment 39. The compound according to any one of embodiments 1-38, wherein Ring B is a saturated 5-membered heterocyclic ring having the structure

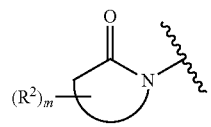

and optionally comprising one additional group selected from —NH—, —O— and —NR²—.

Embodiment 40. The compound according to any one of embodiments 1-38, wherein Ring B is a saturated 6-membered heterocyclic ring having the structure

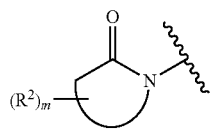

and optionally comprising one additional group selected from —NH—, —O—, and —NR²—.

Embodiment 41. The compound according to embodiment 40, wherein Ring B is a saturated 6-membered heterocyclic ring having the structure

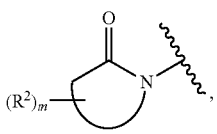

wherein Ring B further comprises one additional group selected from —NH—, —O—, and —NR²—.

Embodiment 42. The compound according to any one of embodiments 1-38, wherein Ring B is a saturated 7-membered heterocyclic having the structure

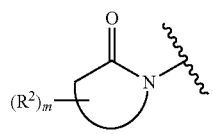

and optionally comprising one additional group selected from —NH—, —O— and —NR²—.

Embodiment 43. The compound according to embodiment 42, wherein Ring B is a saturated 7-membered heterocyclic ring having the structure

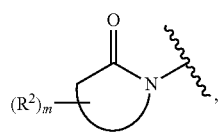
wherein Ring B further comprises one additional group selected from —NH—, —O—, and —NR²—.
Embodiment 44. The compound according to any one of embodiments 1-38, wherein Ring B is selected from
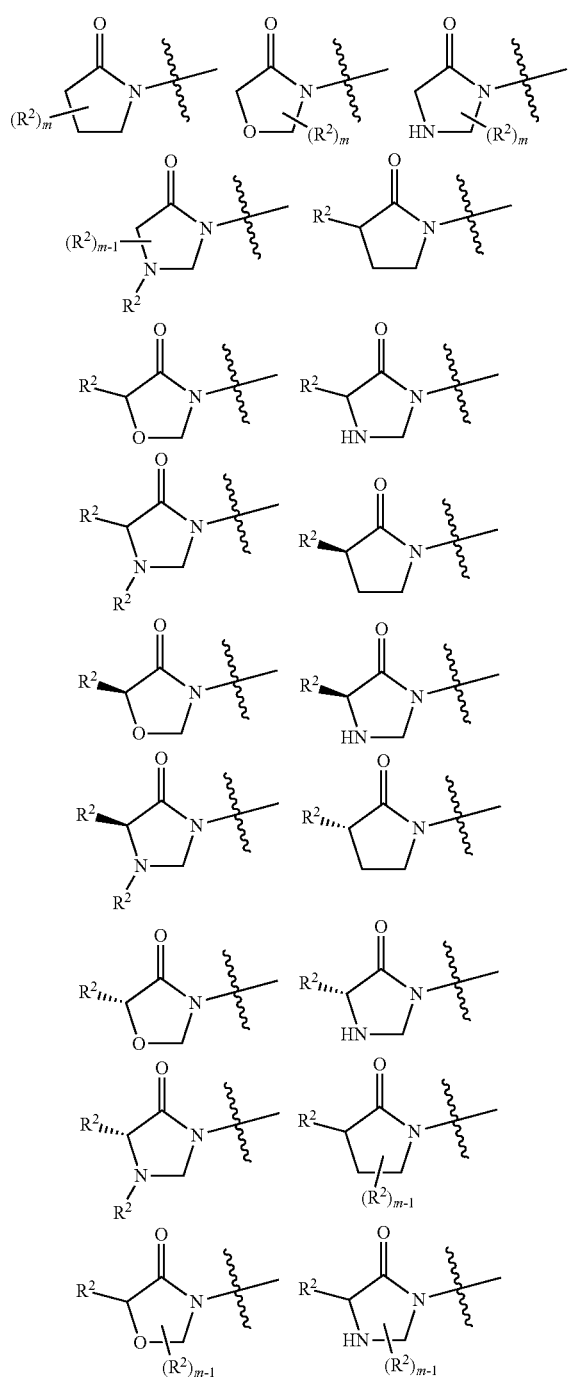
-continued
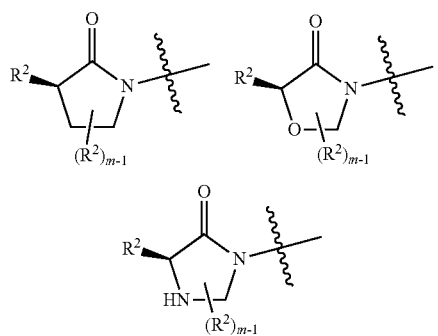
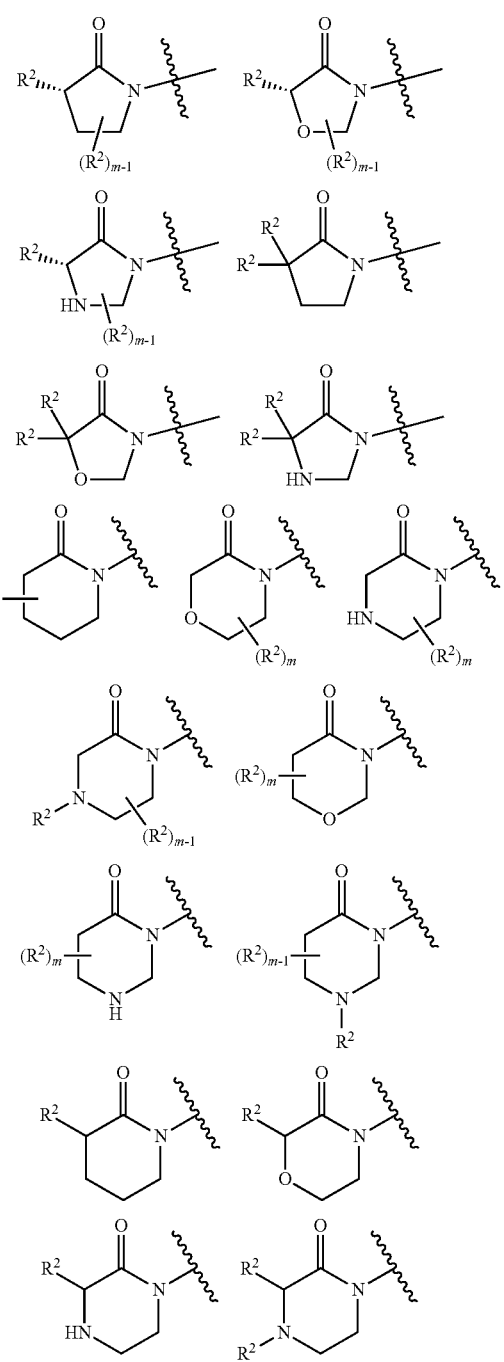

-continued
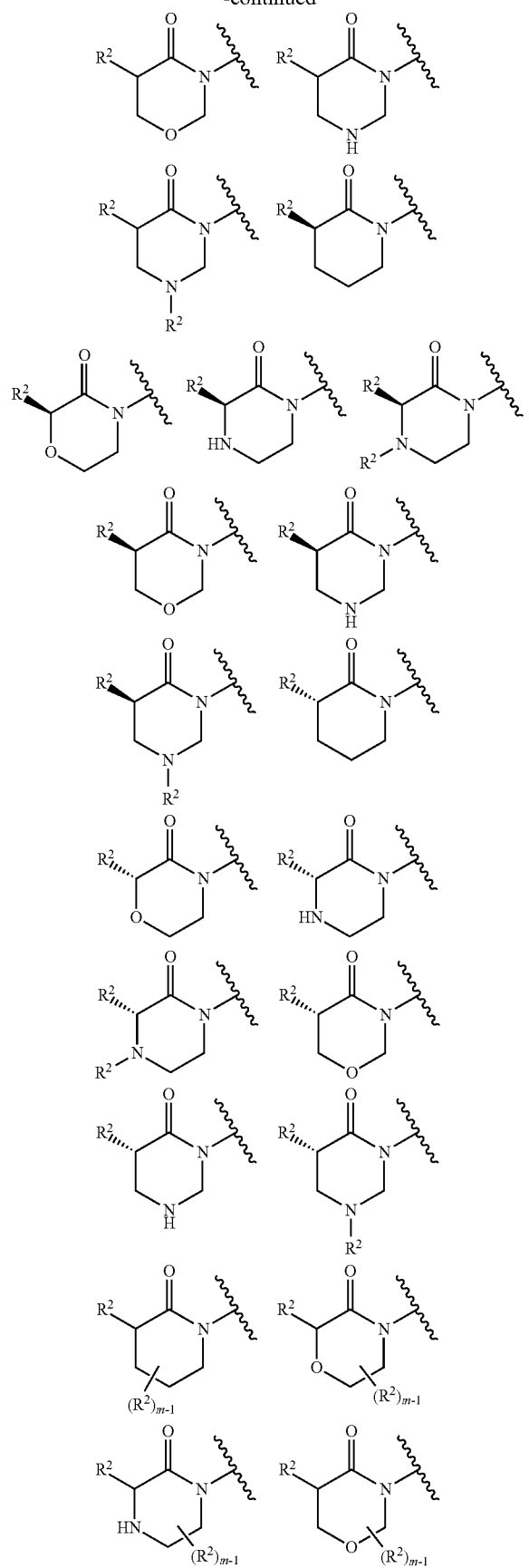
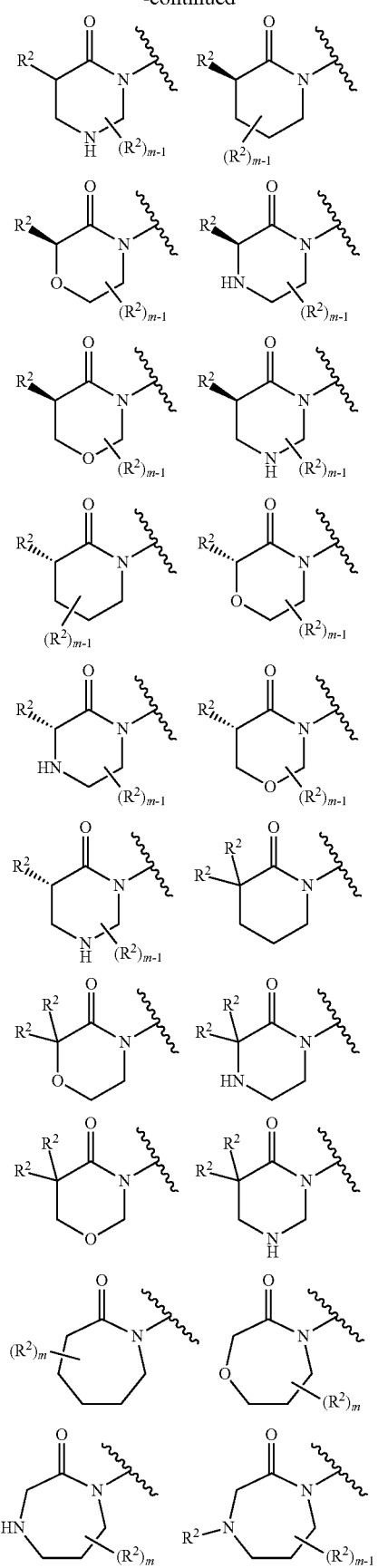

-continued
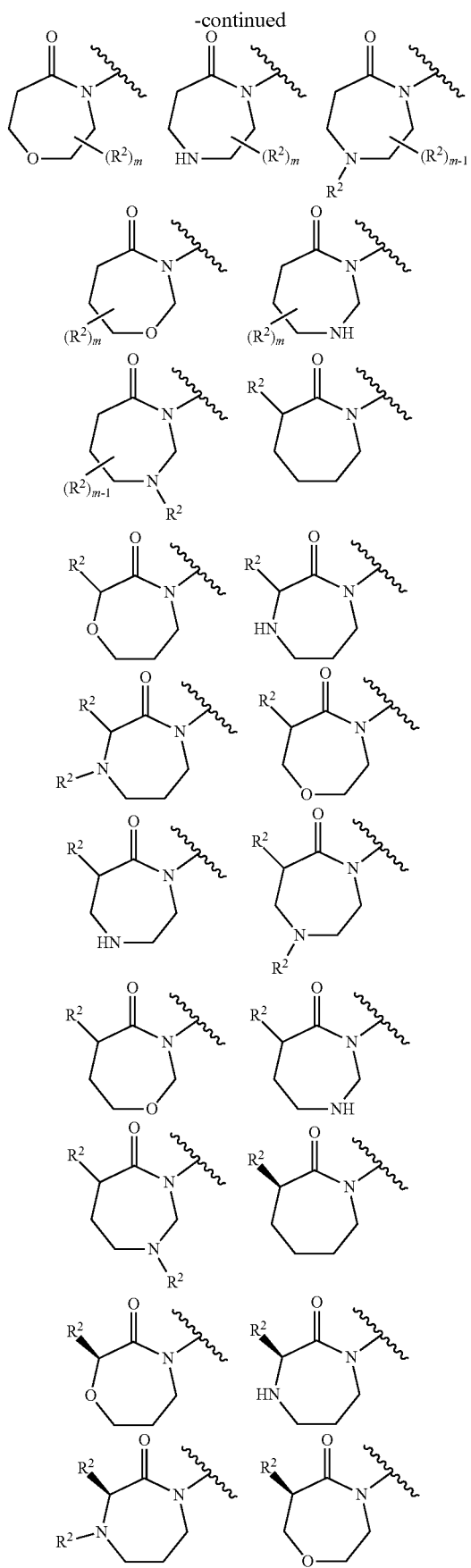
-continued
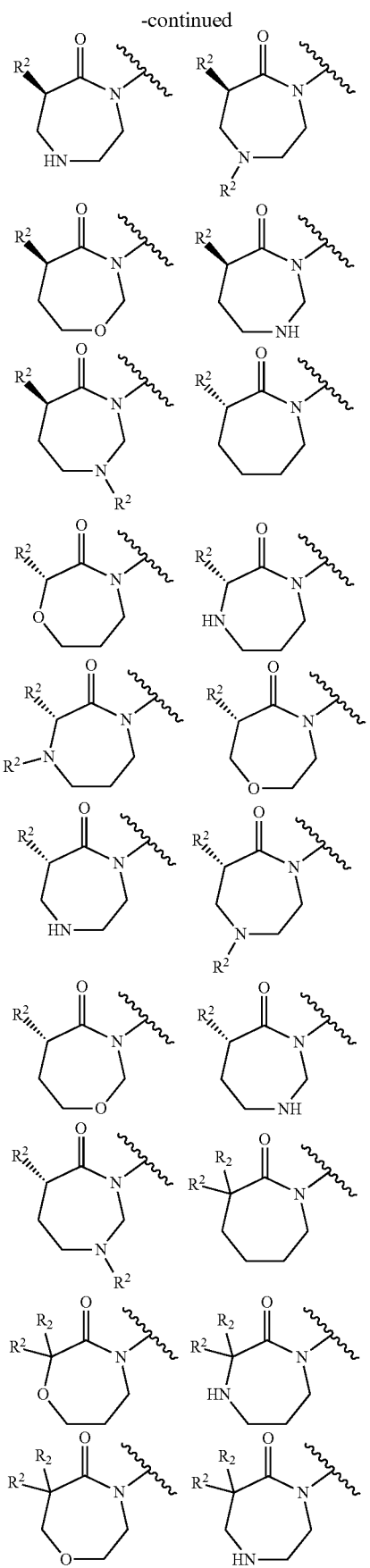

-continued

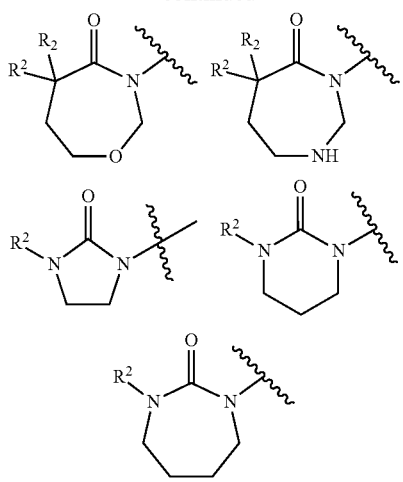

Embodiment 45. The compound according to embodiment 44, wherein Ring B is selected from

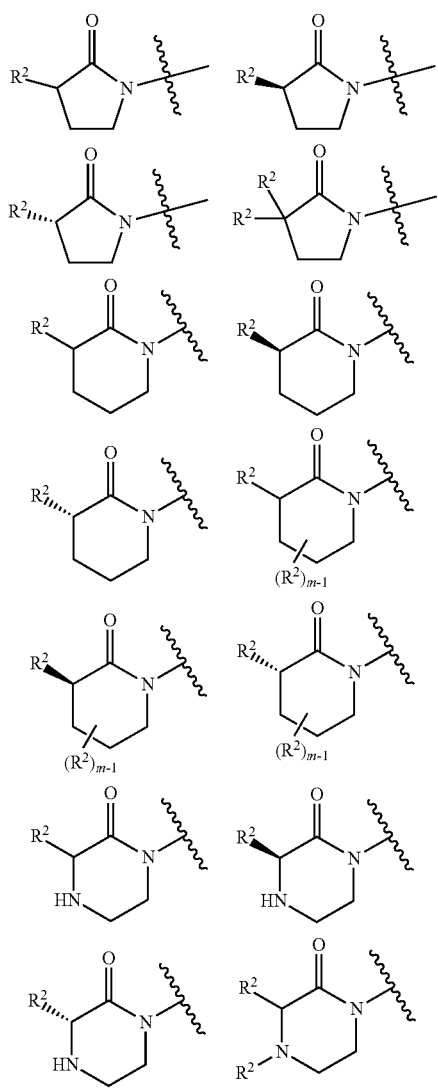

-continued

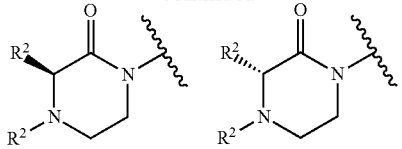

Embodiment 46. The compound according to any one of embodiments 1-45, wherein $R^2$ is —$(C_{1-2}$ aliphatic$)R^3$.

Embodiment 47. The compound according to embodiment 46, wherein $R^2$ is —$CH_2R^3$.

Embodiment 48. The compound according to embodiment 46, wherein $R^2$ is —$CH(CH_3)R^3$.

Embodiment 49. The compound according to embodiment 46, wherein $R^2$ is —$CH_2CH_2R^3$.

Embodiment 50. The compound according to any one of embodiments 1-49, wherein $R^3$ is optionally substituted phenyl.

Embodiment 51. The compound according to any one of embodiments 1-49, wherein $R^3$ is an optionally substituted 5- to 6-membered heteroaryl ring having 1-3 heteroatoms independently selected from oxygen, nitrogen, and sulfur.

Embodiment 52. The compound according to embodiment 51, wherein $R^3$ is an optionally substituted 5-membered heteroaryl ring having 1-2 heteroatoms independently selected from oxygen, nitrogen, and sulfur.

Embodiment 53. The compound according to embodiment 51 or 52, wherein $R^3$ is an optionally substituted group selected from thiophenyl, pyrazolyl, and imidazolyl.

Embodiment 54. The compound according to embodiment 51, wherein $R^3$ is an optionally substituted 6-membered heteroaryl ring having 1-3 nitrogen atoms.

Embodiment 55. The compound according to embodiment 54, wherein $R^3$ is an optionally substituted 6-membered heteroaryl ring having 1-2 nitrogen atoms.

Embodiment 56. The compound according to embodiment 55, wherein $R^3$ is an optionally substituted group selected from pyridinyl or pyrimidinyl.

Embodiment 57. The compound according to any one of embodiments 1-49, wherein $R^3$ is an optionally substituted 8- to 10-membered bicyclic saturated, partially unsaturated or aryl carbocyclic ring.

Embodiment 58. The compound according to embodiment 57, wherein $R^3$ is an optionally substituted 9-membered bicyclic saturated, partially unsaturated or aryl carbocyclic ring.

Embodiment 59. The compound according to embodiment 58, wherein $R^3$ is optionally substituted 2,3-dihydro-1H-indenyl.

Embodiment 60. The compound according to embodiment 57, wherein $R^3$ is an optionally substituted 10-membered bicyclic saturated, partially unsaturated or aryl carbocyclic ring.

Embodiment 61. The compound according to embodiment 60, wherein $R^3$ is optionally substituted group selected from 1,2,3,4-tetrahydronaphthalenyl or naphthalenyl.

Embodiment 62. The compound according to any one of embodiments 1-49, wherein $R^3$ is an optionally substituted 8- to 10-membered bicyclic saturated or partially unsaturated heterocyclic ring having 1-3 heteroatoms independently selected from oxygen, nitrogen, and sulfur.

Embodiment 63. The compound according to embodiment 62, wherein $R^3$ is an optionally substituted 9-membered bicyclic saturated or partially unsaturated heterocyclic ring having 1-3 heteroatoms independently selected from oxygen, nitrogen, and sulfur.

Embodiment 64. The compound according to embodiment 62, wherein $R^3$ is an optionally substituted 10-membered bicyclic saturated or partially unsaturated heterocyclic ring having 1-3 heteroatoms independently selected from oxygen, nitrogen, and sulfur.

Embodiment 65. The compound according to embodiment 64, wherein $R^3$ is an optionally substituted group selected from chromanyl, isochromanyl, 1,2,3,4-tetrahydroquinolinyl, 3,4-dihydro-2H-benzo[b][1,4]oxazinyl, and 2H-benzo[b][1,4]oxazin-3(4H)-onyl.

Embodiment 66. The compound according to any one of embodiments 1-49, wherein $R^3$ is an optionally substituted 8- to 10-membered bicyclic heteroaryl ring having 1-3 heteroatoms independently selected from oxygen, nitrogen, and sulfur.

Embodiment 67. The compound according to embodiment 66, wherein $R^3$ is an optionally substituted 9-membered bicyclic heteroaryl ring having 1-3 heteroatoms independently selected from oxygen, nitrogen, and sulfur.

Embodiment 68. The compound according to embodiment 66 or 67, wherein $R^3$ is an optionally substituted group selected from indolyl, benzopyrazolyl, benzimidazolyl, and imidazo[1,2-a]pyridinyl.

Embodiment 69. The compound according to any one of embodiments 1-49, wherein $R^3$ is selected from the group consisting of

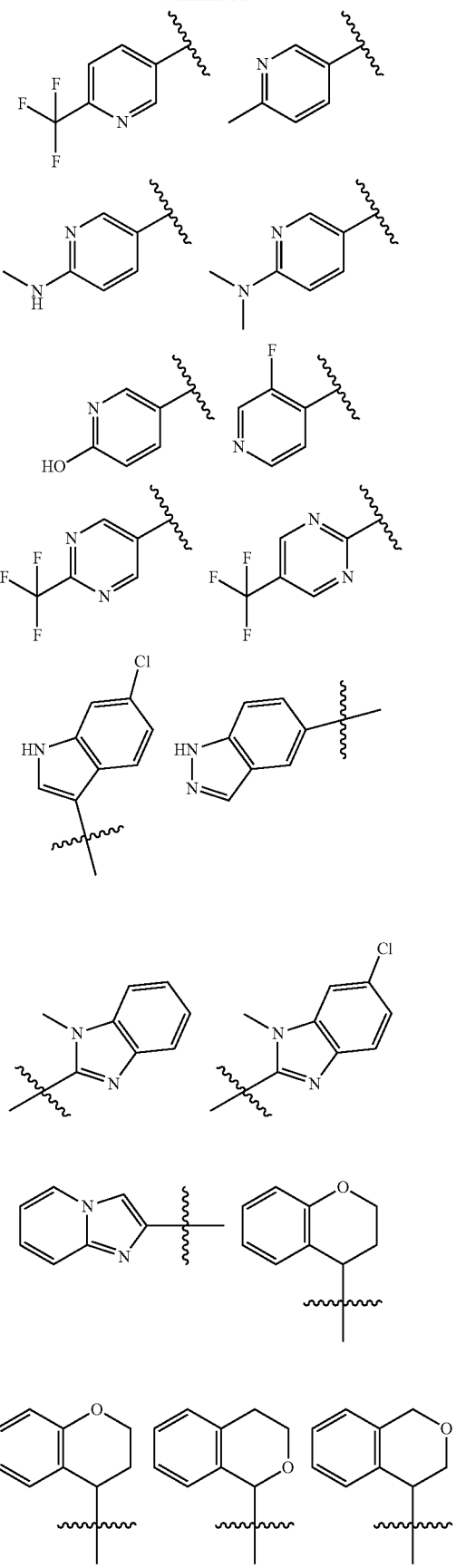

151
-continued
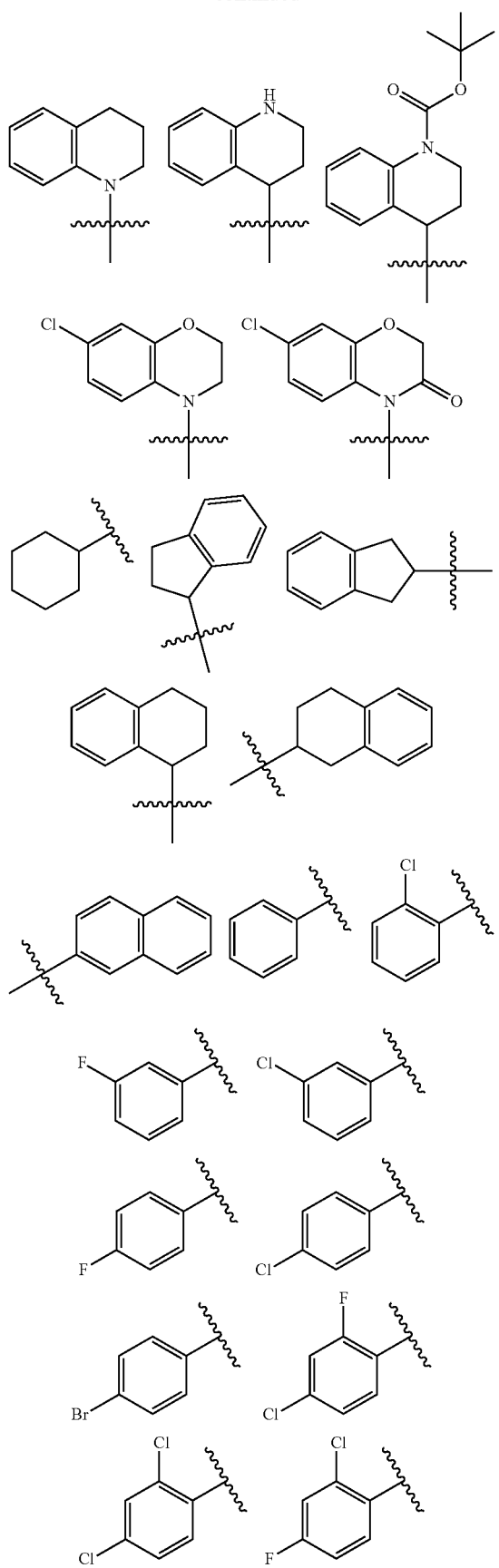
152
-continued
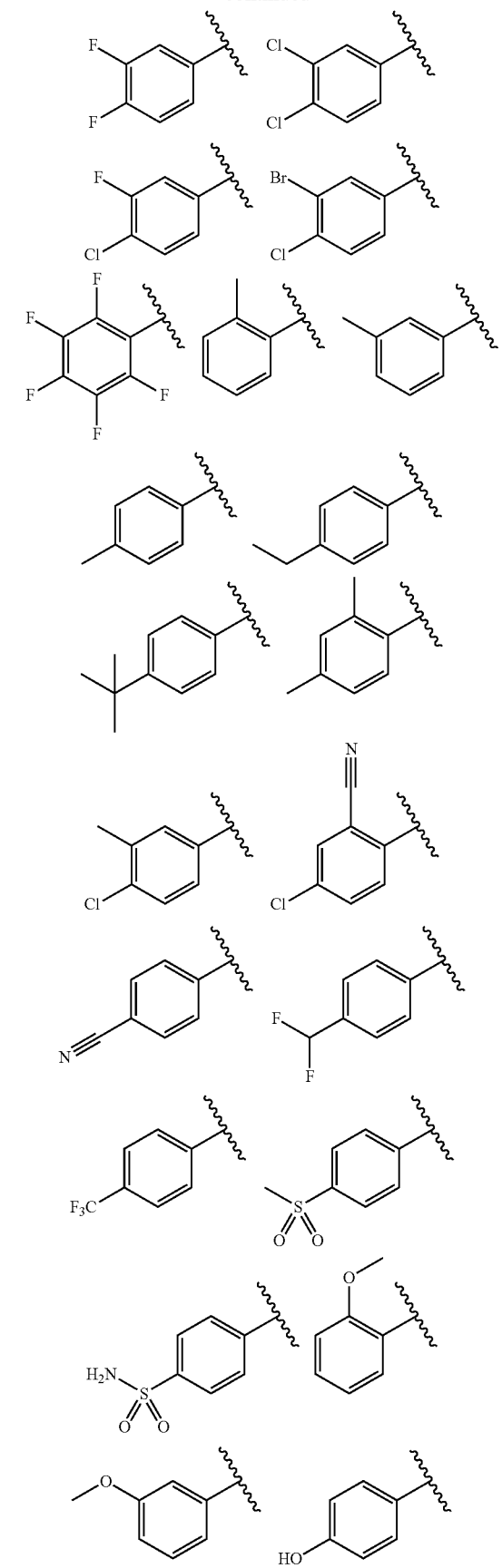

-continued

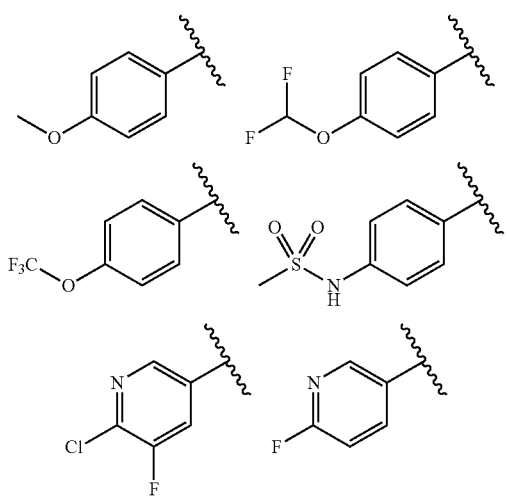

Embodiment 70. The compound according to embodiment 69, wherein R³ is selected from

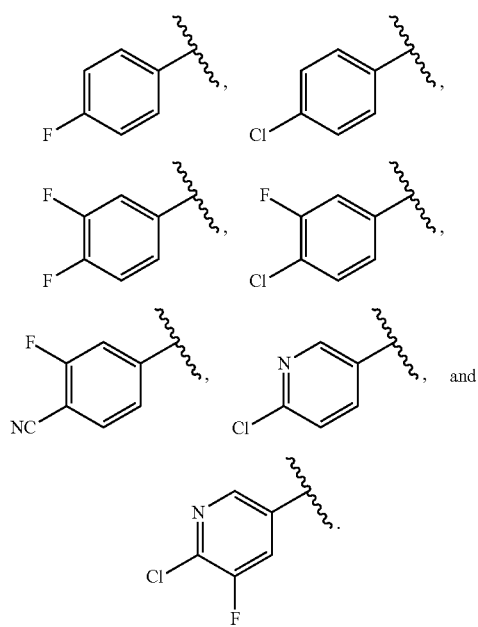

Embodiment 70a. The compound according to embodiment 69, wherein R³ is selected from

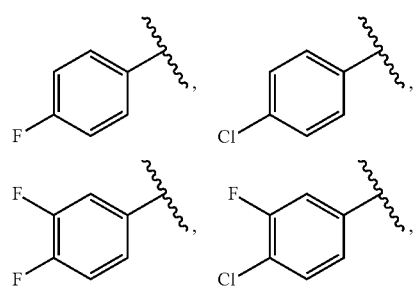

-continued

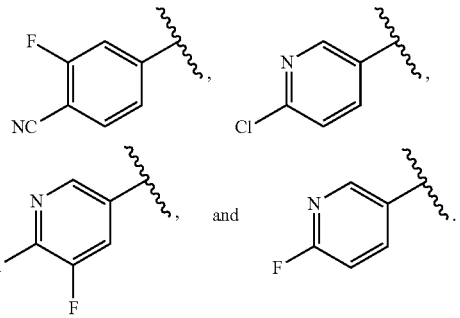

Embodiment 71. The compound according to embodiment 1, wherein the compound is:

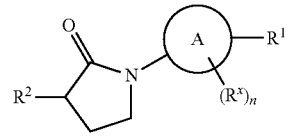

I-a or a pharmaceutically acceptable salt thereof.

Embodiment 72. The compound according to embodiment 1, wherein the compound is:

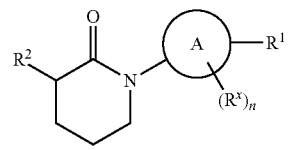

I-b or a pharmaceutically acceptable salt thereof.

Embodiment 73. The compound according to embodiment 1, wherein the compound is:

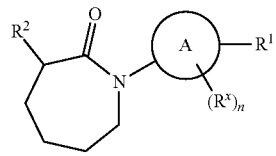

I-c or a pharmaceutically acceptable salt thereof.

Embodiment 74. The compound according to embodiment 1, wherein the compound is:

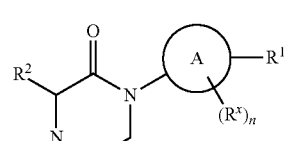

I-d or a pharmaceutically acceptable salt thereof.

Embodiment 75. The compound according to embodiment 1, wherein the compound is:

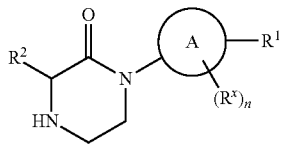

I-e or a pharmaceutically acceptable salt thereof.

Embodiment 76. The compound according to embodiment 1, wherein the compound is selected from:

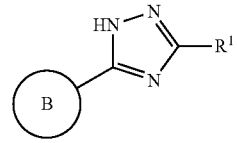

I-f

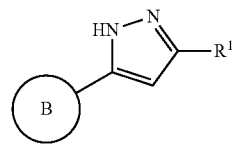

I-g

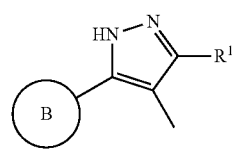

I-h

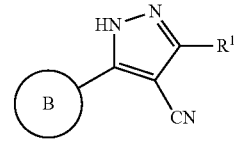

I-i or a pharmaceutically acceptable salt thereof.

Embodiment 77. The compound according to embodiment 1, wherein the compound is selected from:

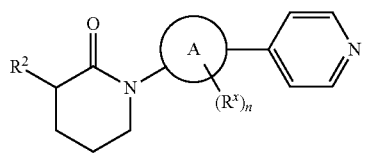

I-a-i

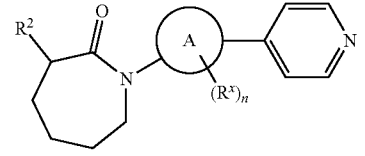

I-b-i

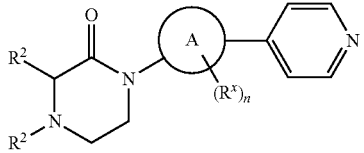

I-c-i

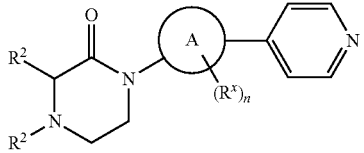

I-d-i

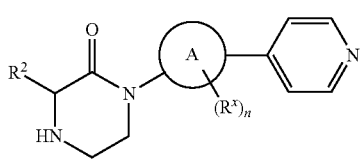

I-e-i

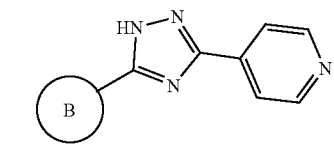

I-f-i

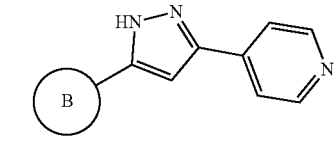

I-g-i

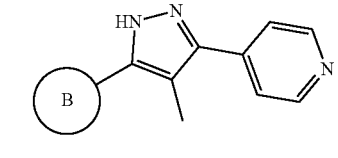

I-h-i

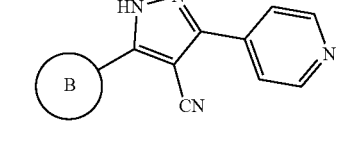

I-i-i or a pharmaceutically acceptable salt thereof.

Embodiment 77a. The compound according to any one of embodiments 1, 3, 5, 6, 7, 8, 32, 35, 36, 37, 38, 40, 44, 45, 46, 47, 51, 54, 55, 56, 69, 70a, and 72, wherein Ring A is

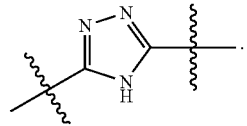 [SMILES: *c1nnc(*)[nH]1]

Embodiment 77b. The compound according to embodiment 77a, wherein the compound is

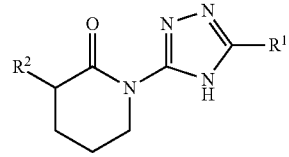

I-b-ii or a pharmaceutically acceptable salt thereof.

Embodiment 77c. The compound according to embodiment 77b, wherein the compound is selected from

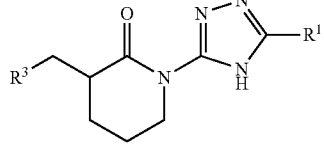
I-j

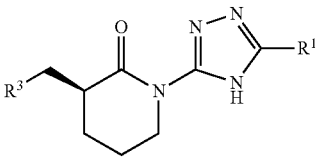
I-j-i

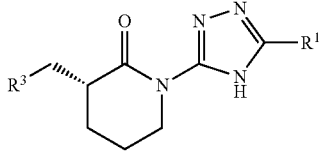
I-j-ii or a pharmaceutically acceptable salt thereof.

Embodiment 77d. The compound according to embodiment 77c, wherein R¹ is

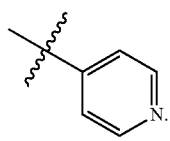 [SMILES: *c1ccncc1]

Embodiment 77e. The compound according to embodiment 77d, wherein R³ is optionally substituted pyridinyl.

Embodiment 77f. The compound according to embodiment 77e, wherein R³ is selected from F and F

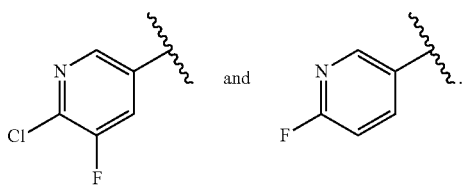 [SMILES: *c1cnc(Cl)c(F)c1 ; *c1ccc(F)nc1]

Embodiment 77g. The compound according to any one of embodiments 1, 77a, 77b, 77c, 77d, 77e, or 77f, wherein the compound is

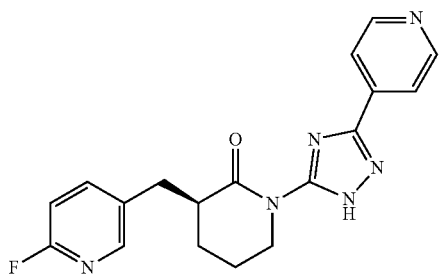
I-23-a or a pharmaceutically acceptable salt thereof.

Embodiment 77h. The compound according to any one of embodiments 1, 77a, 77b, 77c, 77d, 77e, or 77f, wherein the compound is

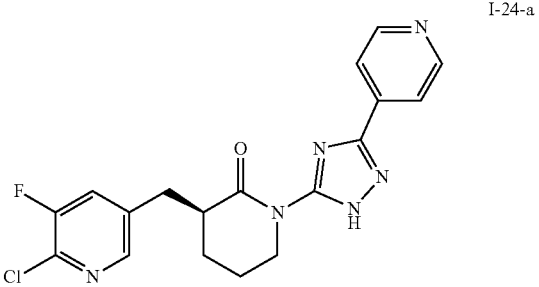 [SMILES: O=C1[C@H](Cc2cnc(Cl)c(F)c2)CCCN1c1nc(-c2ccncc2)n[nH]1]
I-24-a or a pharmaceutically acceptable salt thereof.

Embodiment 78. A pharmaceutical composition comprising a compound according to any one of embodiments 1-77h and a pharmaceutically acceptable carrier.

Embodiment 79. A method comprising a step of:
administering a compound according to any one of embodiments 1-77h to a subject who (i) has a condition characterized by axonal degeneration or (ii) is at risk of developing a condition characterized by axonal degeneration.

Embodiment 80. A method of treating or preventing axonal degeneration comprising administering to a subject in need thereof a compound according to any one of embodiments 1-77h.

Embodiment 81. A method of inhibiting SARM1 comprising contacting a biological sample with a compound according to any one of embodiments 1-77h.

Compositions

In some embodiments, a compound of Formula I may be provided in a composition, e.g., in combination (e.g., admixture) with one or more other components.

In some embodiments, the present disclosure provides compositions that comprise and/or deliver a compound of Formula I, or an active metabolite thereof, e.g., when contacted with or otherwise administered to a system or environment e.g., which system or environment may include SARM1 NADase activity; in some embodiments, administration of such a composition to the system or environment achieves inhibition of SARM1 activity as described herein.

In some embodiments, a provided composition as described herein may be a pharmaceutical composition in that it comprises an active agent and one or more pharmaceutically acceptable excipients; in some such embodiments, a provided pharmaceutical composition comprises and/or delivers a compound of Formula I, or an active metabolite thereof to a relevant system or environment (e.g., to a subject in need thereof) as described herein.

In some embodiments, one or more compounds of Formula I is provided and/or utilized in a pharmaceutically acceptable salt form.

Among other things, the present disclosure provides compositions comprising a compound of Formula I, or a pharmaceutically acceptable salt or derivative thereof, and a pharmaceutically acceptable carrier, adjuvant, or vehicle. The amount of compound in provided compositions is such that is effective to measurably inhibit axonal degeneration in a biological sample or in a patient. In certain embodiments, a provided compound or composition is formulated for administration to a patient in need of such composition. The compounds and compositions, according to the methods of the present disclosure, may be administered using any amount and any route of administration effective for treating or lessening the severity of any disease or disorder described herein. Provided compounds are preferably formulated in dosage unit form for ease of administration and uniformity of dosage. The expression "dosage unit form" as used herein refers to a physically discrete unit of agent appropriate for the patient to be treated. It will be understood, however, that the total daily usage of the provided compounds and compositions will be decided by the attending physician within the scope of sound medical judgment. The specific effective dose level for any particular patient or organism will vary from subject to subject, depending on a variety of factors, including the disorder being treated and the severity of the disorder; the activity of the specific compound employed; the specific composition employed and its route of administration; the species, age, body weight, sex and diet of the patient; the general condition of the subject; the time of administration; the rate of excretion of the specific compound employed; the duration of the treatment; drugs used in combination or coincidental with the specific compound employed, and the like.

Provided compositions may be administered orally, parenterally, by inhalation or nasal spray, topically (e.g., as by powders, ointments, or drops), rectally, buccally, intravaginally, intraperitoneally, intracisternally or via an implanted reservoir, depending on the severity of the condition being treated. Preferably, the compositions are administered orally, intraperitoneally or intravenously. In certain embodiments, provided compounds are administered orally or parenterally at dosage levels of about 0.01 mg/kg to about 50 mg/kg, of subject body weight per day, one or more times a day, to obtain the desired therapeutic effect.

The term "parenteral" as used herein includes subcutaneous, intravenous, intramuscular, intra-articular, intra-synovial, intrasternal, intrathecal, intrahepatic, intralesional and intracranial injection or infusion techniques. Sterile injectable forms of provided compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Pharmaceutically acceptable compositions described herein may be orally administered in any orally acceptable dosage form including, but not limited to, capsules, tablets, aqueous suspensions or solutions. In such solid dosage forms the active compound may be admixed with at least one inert diluent such as sucrose, lactose or starch. Such dosage forms may also comprise, as is normal practice, additional substances other than inert diluents, e.g., lubricants and other tableting aids such a magnesium stearate and microcrystalline cellulose. When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and/or i)

lubricants such as talc, calcium stearate, magnesium stearate, solid polyethylene glycols, sodium lauryl sulfate, and mixtures thereof. In the case of capsules, tablets and pills, the dosage form may also comprise buffering agents. The active compounds can also be in micro-encapsulated form with one or more excipients as noted above.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings (i.e., buffering agents) and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Alternatively, pharmaceutically acceptable compositions described herein may be administered in the form of suppositories for rectal or vaginal administration. These can be prepared by mixing the compounds of the present disclosure with suitable non-irritating excipients or carriers that are solid at room temperature but liquid at body (e.g., rectal or vaginal) temperature and therefore will melt in the rectum or vaginal cavity to release the active compound. Such materials include cocoa butter, a suppository wax (e.g., beeswax) and polyethylene glycols.

Pharmaceutically acceptable compositions described herein may also be administered topically, especially when the target of treatment includes areas or organs readily accessible by topical application, including diseases of the eye, the skin, or the lower intestinal tract. Topical application for the lower intestinal tract can be effected in a rectal suppository formulation (see above) or in a suitable enema formulation.

Dosage forms for topical or transdermal administration of a provided compound include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For topical applications, provided pharmaceutically acceptable compositions may be formulated in a suitable ointment containing the active component suspended or dissolved in one or more carriers. Carriers for topical administration of compounds of this disclosure include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this disclosure are formulated for oral administration.

Identification and/or Characterization of Compounds and/or Compositions

Among other things, the present disclosure provides various technologies for identification and/or characterization of compounds and/or compositions as described herein. For example, the present disclosure provides various assays for assessing SARM1 inhibitory activity, and specifically for assessing SARM1 inhibitory activity.

In some embodiments, performance of one or more compounds or compositions of interest in an assay as described herein is compared with that of an appropriate reference. For example, in some embodiments, a reference may be absence of the relevant compound or composition. Alternatively or additionally, in some embodiments, a reference may be presence of an alternative compound or composition, e.g., which alternative compound or composition has known performance (e.g., as a positive control or a negative control, as is understood in the art) in the relevant assay. In some embodiments, a reference may be an alternative but comparable set of conditions (e.g., temperature, pH, salt concentration, etc.). In some embodiments, a reference may be performance of the compound or composition with respect to a SARM1 variant.

Still further alternatively or additionally, in some embodiments, performance of one or more compounds or compositions of interest in an assay as described herein may be assessed in the presence of an appropriate reference compound or composition, for example, so that ability of the compound or composition to compete with the reference is determined.

In some embodiments, a plurality of compounds or compositions of interest may be subjected to analysis in a particular assay and/or compared with the same reference. In some embodiments, such a plurality of compounds or compositions may be or include a set of compounds or compositions that is considered to be a "library" because multiple members share one or more features (e.g., structural elements, source identity, synthetic similarities, etc.).

Certain exemplary assays that may be useful in the practice of the present disclosure are exemplified in the Examples below. Those skilled in the art, reading the present disclosure, will be aware that useful or relevant systems for identifying and/or characterizing compounds and/or compositions in accordance with the present disclosure are not limited to those included in the Examples, or otherwise discussed below.

In some embodiments, compounds and/or compositions may be identified based on and/or characterized by one or more activities or characteristics such as, for example: promoting axonal integrity, cytoskeletal stability, and/or neuronal survival. In some embodiments, provided SARM1 inhibitors inhibit catabolism of NAD+ to by SARM1. In some embodiments, provided SARM1 inhibitors slow the rate of NAD+ catabolism.

In some embodiments, provided SARM1 inhibitors reduce or inhibit binding of NAD+ by SARM1. In some embodiments, provided SARM1 inhibitors bind to SARM1 within a pocket comprising one or more catalytic residues (e.g., a catalytic cleft of SARM1). Examples of such catalytic residues include the glutamic acid at position 642 (E642).

In some embodiments, provided SARM1 inhibitors disrupt and/or prevent multimerization of the TIR1 domain of SARM1. In some embodiments, provided SARM1 inhibitors disrupt the multimerization of the SAM domains. In some embodiments, provided SARM1 inhibitors disrupt the axonal signaling cascade that leads to depletion of NAD+.

In some embodiments, the present disclosure provides assays useful for identifying and/or characterizing one or more activities and/or characteristics of compound and/or compositions of interest. For example, in some embodiments, the present disclosure provides in vitro, cellular, and/or in vivo systems for assessing one or more such activities and/or characteristics.

SARM1 Activity Assays

In some embodiments, a method of identifying a SARM1 inhibitor comprises: a) providing a mixture comprising i) a mutant or fragment of SARM1, ii) NAD+ and iii) a candidate inhibitor, wherein the mutant or fragment has constitutive activity; b) incubating the mixture; c) quantifying NAD+ in the mixture after the incubating; and d) identifying the candidate inhibitor compound as an inhibitor if the amount of NAD+ is greater than that of a control mixture that does not contain the candidate inhibitor.

In some embodiments, provided are methods of identifying a SARM1 inhibitor, comprising: a) providing a mixture comprising i) a full-length SARM1, ii) NAD+ and iii) a candidate inhibitor, wherein the full-length SARM1 has constitutive activity; b) incubating the mixture; c) quantifying NAD+ and ADPR (or cADPR) in the mixture after the incubating; d) determining the molar ratio of NAD+: ADPR (or cADPR); and e) identifying the candidate inhibitor compound as an inhibitor if the molar ratio is greater than that of a control mixture that does not contain the candidate inhibitor.

In some embodiments, provided are methods of identifying a SARM1 inhibitor, comprising: a) providing a mixture comprising a solid support to which is bound i) a full-length SARM1 and at least one tag, ii) NAD+, and iii) a candidate inhibitor; b) incubating the mixture; c) quantifying the NAD+ after the incubating; and d) identifying the candidate inhibitor compound as a SARM1 inhibitor if the concentration of NAD+ is greater than that of a control.

SARM1 Binding Assays

In some embodiments, the efficacy of provided SARM1 inhibitors can be determined according to, e.g., the assays described in WO 2018/057989, published on Mar. 29, 2018, which is hereby incorporated by reference in its entirety. In some embodiments, the provided SARM1 inhibitors can be applied to a solution containing SARM1 or a fragment thereof. In some embodiments, the provided SARM1 inhibitors can be applied to an in vitro system. In some embodiments, the provided SARM1 inhibitors can be applied to an in vivo. In some embodiments, the provided SARM1 inhibitors can be applied to a patient. In some embodiments, a SARM1 inhibitor can be mixed with SARM1 or fragment thereof that has been labeled with an epitope tag. In some embodiments, the amount of bound SARM1 inhibitor can be compared to the amount of unbound SARM1 inhibitor, yielding the affinity for the SARM1 inhibitor.

In some embodiments, the mutant or fragment of SARM1 is a SAM-TIR fragment having constitutive activity. Fragments of SARM1 having constitutive activity include, for example and without limitation, a SARM1 with the autoinhibitory domain deleted; at least one point mutation of SARM1 that renders the autoinhibitory domain inactive; a fragment of SARM1 containing a TIR domain; or a fragment of SARM1 consisting of SAM and TIR domains. In some embodiments a SARM1 polypeptide can include one or more additional amino acid sequences that can act as tags, such as a His tag, a streptavidin tag, or a combination thereof. In some embodiments a SARM1 polypeptide can include a tag at the amino terminus, at the carboxy terminus, or a combination thereof. In some embodiments, SARM1 or fragment thereof labeled with an epitope tag can be used to measure the binding efficacy of provided SARM1 inhibitors.

Purification of SARM1-TIR domains

In some embodiments, a SARM1-TIR domain can be engineered with various protein, or epitope, tags that can be useful, for example, in purification. In some embodiments, the present disclosure also provides for a NRK1-HEK293T cell line comprising HEK293T cells transformed with a Nicotinamide Riboside Kinase 1 (NRK1). In some embodiments, HEK293T cells transformed or transfected with a DNA sequence encoding Nicotinamide Riboside Kinase 1 (NRK1). In some embodiments, the DNA encoding NRK1 can be genomic or cDNA. In some embodiments, HEK293T cells are stably or transiently transfected with DNA encoding NRK1 from a source exogenous to the host cell. In some embodiments, HEK293T cells are stably or transiently transfected with DNA encoding NRK1 such that the cells express NRK1 at an elevated level compared to control cells. In some embodiments, DNA encoding NRK1 is under the control of one or more exogenous regulatory DNA sequences such as a promoter, an enhancer or a combination thereof. In some embodiments, a combination of a DNA sequences encoding NRK1, and regulatory sequences is a non-naturally occurring combination. In some embodiments, DNA encoding NRK1, either genomic or cDNA, comprises an expression vector such as an FCIV expression vector. In some embodiments, DNA encoding NRK1 is derived from genomic DNA or cDNA from a vertebrate or invertebrate species such as, but not limited to, human, mouse, zebrafish or a *Drosophila*. In some configurations, the NRK1 DNA is a human NRK1 DNA.

Applications and Uses

The present disclosure provides a variety of uses and applications for compounds and/or compositions as described herein, for example in light of their activities and/or characteristics as described herein. In some embodiments, such uses may include therapeutic and/or diagnostic uses. Alternatively, in some embodiments such uses may include research, production, and/or other technological uses.

In one aspect, the present disclosure provides methods comprising administering one or more compounds of Formula I to a subject, e.g., to treat, prevent, or reduce the risk of developing one or more conditions characterized by axonal degeneration. In some such embodiments, the compound of Formula I is a SARM1 inhibitor.

Another embodiment of the present disclosure relates to a method of inhibiting SARM1 activity in a patient comprising steps of administering to said patient a provided compound, or a composition comprising said compound.

Inhibition of enzymes in a biological sample is useful for a variety of purposes that are known to one of skill in the art. Examples of such purposes include, but are not limited to biological assays, gene expression studies, and biological target identification.

In certain embodiments, the present disclosure relates to a method of treating axonal degeneration in a biological sample comprising the step of contacting said biological sample with a compound or composition of Formula I. In some embodiments, one or more compounds and/or compositions as described herein are useful, for example as a method of for inhibiting the degradation of neurons derived from a subject. In some embodiments, one or more compounds and/or compositions as described herein, are useful for inhibiting the degeneration of a neuron, or portion thereof, cultured in vitro. In some embodiments, one or more compounds and/or compositions as described herein, are useful as stabilizing agents to promote in vitro neuronal survival.

In some embodiments, provided compounds and/or compositions inhibit NADase activity of SARM1. Alternatively, or additionally, in some embodiments, provided compounds alleviate one or more attributes of neurodegeneration. In some embodiments, the present disclosure provides methods of treating a neurodegenerative disease or disorder associated with axonal degeneration.

In some embodiments, one or more compounds and/or compositions as described herein are useful, for example, in the practice of medicine. In some embodiments, one or more compounds and/or compositions as described herein are useful, for example, to treat, prevent, or ameliorate axonal degeneration (e.g., one or more features or characteristics thereof). In some embodiments, one or more compounds and/or compositions as described herein are useful, for example to inhibit axonal degeneration, including axonal degeneration that results from reduction or depletion of NAD+. In some embodiments, one or more compounds and/or compositions as described herein are useful, for example to prevent the axon distal to an axonal injury from degenerating.

In some embodiments, one or more compounds and/or compositions as described herein are useful, for example as a method for inhibiting the degradation of a peripheral nervous system neuron or a portion thereof. In some embodiments, one or more compounds and/or compositions as described herein are useful, for example as a method for inhibiting or preventing degeneration of a central nervous system (neuron) or a portion thereof. In some embodiments, one or more compounds or compositions as described herein is characterized that, when administered to a population of subjects, reduces one or more symptoms or features of neurodegeneration. For example, in some embodiments, a relevant symptom or feature may be selected from the group consisting of extent, rate, and/or timing of neuronal disruption.

In certain embodiments, the present disclosure provides compounds that are useful, for example, as analytical tools, as probes in biological assays, or as therapeutic agents in accordance with the present disclosure. Compounds provided by this disclosure are also useful for the study of SARM1 activity in biological and pathological phenomena and the comparative evaluation of new SARM1 activity inhibitors in vitro or in vivo. In certain embodiments, the present disclosure provides assays for identifying and/or characterizing compounds and/or compositions provided herein. In some embodiments, provided assays utilize particular reagents and/or systems (e.g., certain vector constructs and/or polypeptides) useful in assaying SARM1 activity. For example, in some embodiments, provided assays may utilize, for example, a SAM-TIR in which the SARM1 N-terminal auto-inhibitory domain is deleted, and/or one or more tagged versions of a TIR domain.

In some embodiments, one or more compounds and/or compositions as described herein are useful, for example as a method of for inhibiting the degradation of neurons derived from a subject. In some embodiments, one or more compounds and/or compositions as described herein, are useful for inhibiting the degeneration of a neuron, or portion thereof, cultured in vitro. In some embodiments, one or more compounds and/or compositions as described herein, are useful as stabilizing agents to promote in vitro neuronal survival.

In some embodiments, one or more compounds and/or compositions as described herein are useful, for example in affecting biomarkers associated with neurodegeneration. In some embodiments, changes in biomarkers can be detected systemically or with a sample of CSF, plasma, serum, and/or tissue from a subject. In some embodiments, one or more compounds and/or compositions can be used to affect a change in the concentration of NF-L and/or NF-H contained the CSF of a subject. In some embodiments, one or more compounds and/or compositions as described herein can affect constitutive NAD and/or cADPR levels in neurons and/or axons.

In some embodiments, one or more biomarkers of neurodegeneration comprises: concentration of NF-L in one or more of: a CSF sample, a blood sample, and a plasma sample from the subject; concentration of NF-H in one or more of: a CSF sample, a blood sample, and a plasma sample from the subject; concentration of Ubiquitin C-terminal Hydrolase L1 (UCH-L1) in one or more of: a CSF sample, a blood sample, and a plasma sample from the subject; concentration of alpha-synuclein in one or more of: a CSF sample, a blood sample, and a plasma sample from the subject; constitutive NAD+ levels in neurons and/or axons of the subject; constitutive cADPR levels in neurons and/or axons of the subject; levels of albumin, amyloid-P (Aβ)38, Aβ40, Aβ42, GFAβ, hFABP, MCP)-1, neurogranin, NSE, sAPPα, sAPPβ, sTREM 2, phospho-tau, or total-tau in one or more of: a CSF sample, a blood sample, a plasma sample, skin biopsy sample, a nerve biopsy sample, and a brain biopsy sample from the subject; and levels of C-C Motif Chemokine Ligand (CCL)2, CCL7, CCL12, colony stimulating factor (CSF)1, or Interleukin (IL)6 in one or more of: a cerebrospinal fluid (CSF) sample, a blood sample, a plasma sample, skin biopsy sample, a nerve biopsy sample, and a brain biopsy sample from the subject.

In some embodiments, one or more compounds and/or compositions as described herein can affect a detectable change in the levels of one or more neurodegeneration-associated proteins in a subject. Such proteins include, but are not limited to, albumin, amyloid-P (Aβ)38, Aβ40, Aβ42, GFAβ, hFABP, MCP-1, neurogranin, NSE, sAPPα, sAPPβ, sTREM 2, phospho-tau, and/or total-tau. In some embodiments, one or more compounds and/or compositions as described herein can affect a change in cytokines and/or chemokines, including, but not limited to, Ccl2, Ccl7, Ccl12, Csf1, and/or I16.

Diseases, Disorders, and Conditions

In some embodiments, compounds and/or compositions as described herein may be administered to subjects suffering from one or more diseases, disorders, or conditions. In some embodiments, the one or more diseases, disorders, or conditions are mediated by SARM1.

In some embodiments, a neurodegenerative disease or disorder comprises an acute or chronic disease or disorder of the peripheral nervous system (PNS), an acute or chronic disease or disorder of the central nervous system (CNS), or a disease associated with neurodegeneration.

In some embodiments, a neurodegenerative disease or disorder comprises an acute disease or disorder of the PNS. In some embodiments, an acute disease or disorder of the PNS is the result of a mechanical injury, thermal injury, or injury from a chemical agent or chemotherapy. In some embodiments, a mechanical injury comprises a compression or entrapment injury or a pressure injury. In some embodiments, a compression or entrapment injury comprises carpal tunnel syndrome, direct trauma, a penetrating injury, a contusion, a fracture or a dislocated bone. In some embodiments, a pressure injury comprises pressure involving superficial nerves, pressure from a tumor or increased intraocular pressure. In some embodiments, a chemical agent or chemotherapy comprises a cytotoxic anticancer agent, thalidomide, an epothilone, a taxane, a vinca alkaloid, a proteasome inhibitor, a platinum-based drug or an auristatin. In some embodiments, an epothilone is ixabepilone. In some embodiments, a taxane is paclitaxel or docetaxel. In some embodiments, a vinca alkaloid is vinblastine, vinorelbine, vincristine, or vindesine. In some embodiments, a proteasome inhibitor is bortezomib. In some embodiments, a platinum-based drug is cisplatin, oxaliplatin, or carboplatin. In some embodiments, an auristatin is conjugated monomethyl auristatin E.

In some embodiments, a neurodegenerative disease or disorder comprises a chronic disease or disorder of the PNS. In some embodiments, a chronic disease or disorder of the PNS comprises a systemic disorder, a pain disorder, or a metabolic disease or disorder.

In some embodiments, a chronic disease or disorder of the PNS comprises inherited neuropathies, Charcot-Marie-Tooth disease, hereditary sensory and autonomic neuropathy (HSAN), chronic inflammatory demyelinating polyneuropathy (CIDP), idiopathic neuropathies or other peripheral neuropathies.

In some embodiments, a systemic disorder comprises diabetes, uremia, AIDS, leprosy, a nutritional deficiency, atherosclerosis, an enteric neuropathy, an axonopathy, Guillain-Barre syndrome, severe acute motor axonal neuropathy (AMAN), systemic lupus erythematosus, scleroderma, sarcoidosis, rheumatoid arthritis, or polyarteritis nodosa.

In some embodiments, a pain disorder comprises chronic pain, fibromyalgia, spinal pain, carpal tunnel syndrome, pain from cancer, arthritis, sciatica, headaches, pain from surgery, muscle spasms, back pain, visceral pain, pain from injury, dental pain, neurogenic pain, neuropathic pain, nerve inflammation, nerve damage, shingles, herniated disc, torn ligament, or diabetes.

In some embodiments, a metabolic disease or disorder comprises diabetes mellitus, hypoglycemia, uremia, hypothyroidism, hepatic failure, polycythemia, amyloidosis, acromegaly, porphyria, nonalcoholic fatty liver disease (NAFLD), nonalcoholic steatohepatitis (NASH), disorders of lipid/glycolipid metabolism, a nutritional deficiency, a vitamin deficiency, or a mitochondrial disorder.

In some embodiments, a neurodegenerative disease or disorder comprises an acute disease or disorder of the CNS. In some embodiments, an acute disease or disorder of the CNS comprises an ischemia, a traumatic CNS injury, injury from a chemical agent, thermal injury, or viral encephalitis.

In some embodiments, an ischemia comprises cerebral ischemia, hypoxic demyelination, ischemic demyelination, ischemic optic neuropathy, or non-arteritic anterior ischemic optic neuropathy.

In some embodiments, a traumatic CNS injury comprises a spinal cord injury, a TBI, a mechanical injury to the head and/or spine, a traumatic injury to the head and/or spine, blunt force trauma, closed head injury, open head injury, exposure to a concussive and/or explosive force, a penetrating injury to the CNS, increased intraocular pressure, or damage from a force which causes axons to deform, stretch, crush or sheer.

In some embodiments, a viral encephalitis comprises enterovirus encephalitis, arbovirus encephalitis, herpes simplex virus (HSV) encephalitis, West Nile virus encephalitis, La Crosse encephalitis, Bunyavirus encephalitis, pediatric viral encephalitis, or HIV encephalopathy (HIV-associated dementia).

In some embodiments, a neurodegenerative disease or disorder comprises a chronic disease or disorder of the CNS.

In some embodiments, a chronic disease or disorder of the CNS comprises Alzheimer's disease, Parkinson's disease, amyotrophic lateral sclerosis (ALS, Lou Gehrig's disease), multiple sclerosis (MS), Huntington's disease (HD), senile dementia, Pick's disease, Gaucher's disease, Hurler syndrome, progressive multifocal leukoencephalopathy, Alexander's disease, congenital hypomyelination, encephalomyelitis, acute disseminated encephalomyelitis, central pontine myelolysis, osmotic hyponatremia, Tay-Sachs disease, motor neuron disease, ataxia, spinal muscular atrophy (SMA), Niemann-Pick disease, acute hemorrhagic leukoencephalitis, trigeminal neuralgia, Bell's palsy, cerebral ischemia, multiple system atrophy, Pelizaeus Merzbacher disease, periventricular leukomalacia, a hereditary ataxia, noise-induced hearing loss, congenital hearing loss, age-related hearing loss, Creutzfeldt-Jakob disease, transmissible spongiform encephalopathy, Lewy Body Dementia, frontotemporal dementia, amyloidosis, diabetic neuropathy, globoid cell leukodystrophy (Krabbe's disease), Bassen-Kornzweig syndrome, transverse myelitis, motor neuron disease, a spinocerebellar ataxia, pre-eclampsia, hereditary spastic paraplegias, spastic paraparesis, familial spastic paraplegia, French settlement disease, Strumpell-Lorrain disease, nonalcoholic steatohepatitis (NASH), adrenomyeloneuropathy, progressive supra nuclear palsy (PSP), Friedrich's ataxia, or spinal cord injury.

In some embodiments, a chronic disease or disorder of the CNS comprises an optic nerve disorder, a traumatic CNS injury, or a metabolic disease or disorder.

In some embodiments, an optic nerve disorder comprises an acute optic neuropathy (AON), a genetic or idiopathic retinal condition, Leber congenital amaurosis (LCA), Leber hereditary optic neuropathy (LHON), primary open-angle glaucoma (POAG), acute angle-closure glaucoma (AACG), autosomal dominant optic atrophy, retinal ganglion degeneration, retinitis pigmentosa, an outer retinal neuropathy, optic nerve neuritis, optic nerve degeneration associated with multiple sclerosis, Kjer's optic neuropathy, an ischemic optic neuropathy, a deficiency in vitamin B12, a deficiency in folic acid (vitamin B9), isolated vitamin E deficiency syndrome, non-arteritic anterior ischemic optic neuropathy, exposure to ethambutol, or exposure to cyanide.

In some embodiments, a traumatic CNS injury comprises a traumatic brain injury (TBI), a spinal cord injury, traumatic axonal injury or chronic traumatic encephalopathy (CTE).

In some embodiments, a metabolic disease or disorder comprises diabetes mellitus, hypoglycemia, Bassen-Kornzweig syndrome, uremia, hypothyroidism, hepatic failure, polycythemia, amyloidosis, acromegaly, porphyria, disorders of lipid/glycolipid metabolism, nutritional/vitamin deficiencies, and mitochondrial disorders.

In some embodiments, a neurodegenerative disease or disorder comprises a disease associated with neurodegeneration. In some embodiments, a neurodegenerative disease or disorder results from blood clotting issues, inflammation, obesity, aging, stress, cancer, or diabetes.

In some embodiments, the condition is an acute peripheral neuropathy. Chemotherapy-induced peripheral neuropathy (CIPN) is an example of an acute peripheral neuropathy. CIPN can be associated with various drugs, such as, but not limited to, thalidomide, epothilones (e.g., ixabepilone), taxanes (e.g., paclitaxel and docetaxel), vinca alkaloids (e.g., vinblastine, vinorelbine, vincristine, and vindesine), proteasome inhibitors (e.g., bortezomib), platinum-based drugs (e.g., cisplatin, oxaliplatin, and carboplatin).

In some embodiments, one or more compounds and/or compositions as described herein are useful, for example, to treat one or more neurodegenerative diseases, disorders or conditions selected from the group consisting of neuropathies or axonopathies. In some embodiments, one or more compounds and/or compositions as described herein are useful, for example to treat a neuropathy or axonopathy associated with axonal degeneration. In some embodiments, a neuropathy associated with axonal degeneration is a hereditary or congenital neuropathy or axonopathy. In some embodiments, a neuropathy associated with axonal degeneration results from a de novo or somatic mutation. In some embodiments, a neuropathy associated with axonal degeneration is selected from a list contained herein. In some embodiments, a neuropathy or axonopathy is associated with axonal degeneration, including, but not limited to Parkinson's disease, non-Parkinson's disease, Alzheimer's disease, Herpes infection, diabetes, amyotrophic lateral sclerosis, a demyelinating disease, ischemia or stroke, chemical injury, thermal injury, and AIDS.

In some embodiments, one or more compounds or compositions as described herein is characterized that, when administered to a population of subjects, reduces one or more symptoms or features of neurodegeneration. For example, in some embodiments, a relevant symptom or feature may be selected from the group consisting of extent, rate, and/or timing of neuronal disruption. In some embodiments, neuronal disruption may be or comprise axonal degradation, loss of synapses, loss of dendrites, loss of synaptic density, loss of dendritic arborization, loss of axonal branching, loss of neuronal density, loss of myelination, loss of neuronal cell bodies, loss of synaptic potentiation, loss of action-potential potentiation, loss of cytoskeletal stability, loss of axonal transport, loss of ion channel synthesis and turnover, loss of neurotransmitter synthesis, loss of neurotransmitter release and reuptake capabilities, loss of axon-potential propagation, neuronal hyperexitability, and/or neuronal hypoexcitability. In some embodiments, neuronal disruption is characterized by an inability to maintain an appropriate resting neuronal membrane potential. In some embodiments, neuronal disruption is characterized by the appearance of inclusion bodies, plaques, and/or neurofibrillary tangles. In some embodiments, neuronal disruption is characterized by the appearance of stress granules. In some embodiments, neuronal disruption is characterized by the intracellular activation of one or more members of the cysteine-aspartic protease (Caspase) family. In some embodiments, neuronal disruption is characterized by a neuron undergoing programed cell death (e.g., apoptosis, pyroptosis, ferroapoptosis, and/or necrosis) and/or inflammation.

In some embodiments, the neurodegenerative or neurological disease or disorder is associated with axonal degeneration, axonal damage, axonopathy, a demyelinating disease, a central pontine myelinolysis, a nerve injury disease or disorder, a metabolic disease, a mitochondrial disease, metabolic axonal degeneration, axonal damage resulting from a leukoencephalopathy or a leukodystrophy. In some embodiments, the neurodegenerative or neurological disease or disorder is selected from the group consisting of spinal cord injury, stroke, multiple sclerosis, progressive multifocal leukoencephalopathy, congenital hypomyelination, encephalomyelitis, acute disseminated encephalomyelitis, central pontine myelolysis, osmotic hyponatremia, hypoxic demyelination, ischemic demyelination, adrenoleukodystrophy, Alexander's disease, Niemann-Pick disease, Pelizaeus Merzbacher disease, periventricular leukomalacia, globoid cell leukodystrophy (Krabbe's disease), Wallerian degeneration, optic neuritis, transverse myelitis, amyotrophic lateral sclerosis (ALS, Lou Gehrig's disease), Huntington's disease, Alzheimer's disease, Parkinson's disease, Tay-Sacks disease, Gaucher's disease, Hurler Syndrome, traumatic brain injury, post radiation injury, neurologic complications of chemotherapy (chemotherapy induced neuropathy; CIPN), neuropathy, acute ischemic optic neuropathy, vitamin $B_{12}$ deficiency, isolated vitamin E deficiency syndrome, Bassen-Kornzweig syndrome, Glaucoma, Leber's hereditary optic atrophy (neuropathy), Leber congenital amaurosis, neuromyelitis optica, metachromatic leukodystrophy, acute hemorrhagic leukoencephalitis, trigeminal neuralgia, Bell's palsy, cerebral ischemia, multiple system atrophy, traumatic glaucoma, tropical spastic paraparesis human T-lymphotropic virus 1 (HTLV-1) associated myelopathy, west Nile virus encephalopathy, La Crosse virus encephalitis, Bunyavirus encephalitis, pediatric viral encephalitis, essential tremor, Charcot-Marie-Tooth disease, motor neuron disease, SMA, HSAN, adrenomyeloneuropathy, PSP, Friedrich's ataxia, hereditary ataxias, noise induced hearing loss, congenital hearing loss, Lewy Body Dementia, frontotemporal dementia, amyloidosis, diabetic neuropathy, HIV neuropathy, enteric neuropathies and axonopathies, Guillain-Barre syndrome, AMAN, Creutzfeldt-Jakob disease, transmissible spongiform encephalopathy, spinocerebellar ataxias, pre-eclampsia, hereditary spastic paraplegias, spastic paraparesis, familial spastic paraplegia, French settlement disease, Strumpell-Lorrain disease, and NASH.

In some embodiments, the present disclosure provides inhibitors of SARM1 activity for treatment of neurodegenerative or neurological diseases or disorders that involve axon degeneration or axonopathy. The present disclosure also provides methods of using inhibitors of SARM1 activity to treat, prevent or ameliorate axonal degeneration, axonopathies and neurodegenerative or neurological diseases or disorders that involve axonal degeneration.

In some embodiments, the present disclosure provides methods of treating neurodegenerative or neurological diseases or disorders related to axonal degeneration, axonal damage, axonopathies, demyelinating diseases, central pontine myelinolysis, nerve injury diseases or disorders, metabolic diseases, mitochondrial diseases, metabolic axonal degeneration, axonal damage resulting from a leukoencephalopathy or a leukodystrophy.

In some embodiments, neuropathies and axonopathies include any disease or condition involving neurons and/or supporting cells, such as for example, glia, muscle cells or fibroblasts, and, in particular, those diseases or conditions involving axonal damage. Axonal damage can be caused by traumatic injury or by non-mechanical injury due to diseases, conditions, or exposure to toxic molecules or drugs. The result of such damage can be degeneration or dysfunction of the axon and loss of functional neuronal activity. Disease and conditions producing or associated with such axonal damage are among a large number of neuropathic diseases and conditions. Such neuropathies can include peripheral neuropathies, central neuropathies, and combinations thereof. Furthermore, peripheral neuropathic manifestations can be produced by diseases focused primarily in the central nervous systems and central nervous system manifestations can be produced by essentially peripheral or systemic diseases.

In some embodiments, a peripheral neuropathy can involve damage to the peripheral nerves, and/or can be caused by diseases of the nerves or as the result of systemic illnesses. Some such diseases can include diabetes, uremia, infectious diseases such as AIDs or leprosy, nutritional deficiencies, vascular or collagen disorders such as atherosclerosis, and autoimmune diseases such as systemic lupus erythematosus, scleroderma, sarcoidosis, rheumatoid arthritis, and polyarteritis nodosa. In some embodiments, peripheral nerve degeneration results from traumatic (mechanical) damage to nerves as well as chemical or thermal damage to nerves. Such conditions that injure peripheral nerves include compression or entrapment injuries such as glaucoma, carpal tunnel syndrome, direct trauma, penetrating injuries, contusions, fracture or dislocated bones; pressure involving superficial nerves (ulna, radial, or peroneal) which can result from prolonged use of crutches or staying in one position for too long, or from a tumor; intraneural hemorrhage; ischemia; exposure to cold or radiation or certain medicines or toxic substances such as herbicides or pesticides. In particular, the nerve damage can result from chemical injury due to a cytotoxic anticancer agent such as, for example, taxol, cisplatinin, a proteasome inhibitor, or a vinca alkaloid such as vincristine. Typical symptoms of such peripheral neuropathies include weakness, numbness, paresthesia (abnormal sensations such as burning, tickling, pricking or tingling) and pain in the arms, hands, legs and/or feet. In some embodiments, a neuropathy is associated with mitochondrial dysfunction. Such neuropathies can exhibit decreased energy levels, i.e., decreased levels of NAD and ATP.

In some embodiments, peripheral neuropathy is a metabolic and endocrine neuropathy which includes a wide spectrum of peripheral nerve disorders associated with systemic diseases of metabolic origin. These diseases include, for example, diabetes mellitus, hypoglycemia, uremia, hypothyroidism, hepatic failure, polycythemia, amyloidosis, acromegaly, porphyria, disorders of lipid/glycolipid metabolism, nutritional/vitamin deficiencies, and mitochondrial disorders, among others. The common hallmark of these diseases is involvement of peripheral nerves by alteration of the structure or function of myelin and axons due to metabolic pathway dysregulation.

In some embodiments, neuropathies include optic neuropathies such as glaucoma; retinal ganglion degeneration such as those associated with retinitis pigmentosa and outer retinal neuropathies; optic nerve neuritis and/or degeneration including that associated with multiple sclerosis; traumatic injury to the optic nerve which can include, for example, injury during tumor removal; hereditary optic neuropathies such as Kjer's disease and Leber's hereditary optic neuropathy; ischemic optic neuropathies, such as those secondary to giant cell arteritis; metabolic optic neuropathies such as neurodegenerative diseases including Leber's neuropathy mentioned earlier, nutritional deficiencies such as deficiencies in vitamins B12 or folic acid, and toxicities such as due to ethambutol or cyanide; neuropathies caused by adverse drug reactions and neuropathies caused by vitamin deficiency. Ischemic optic neuropathies also include non-arteritic anterior ischemic optic neuropathy.

In some embodiments neurodegenerative diseases that are associated with neuropathy or axonopathy in the central nervous system include a variety of diseases. Such diseases include those involving progressive dementia such as, for example, Alzheimer's disease, senile dementia, Pick's disease, and Huntington's disease; central nervous system diseases affecting muscle function such as, for example, Parkinson's disease, motor neuron diseases and progressive ataxias such as amyotrophic lateral sclerosis; demyelinating diseases such as, for example multiple sclerosis; viral encephalitides such as, for example, those caused by enteroviruses, arboviruses, and herpes simplex virus; and prion diseases. Mechanical injuries such as glaucoma or traumatic injuries to the head and spine can also cause nerve injury and degeneration in the brain and spinal cord. In addition, ischemia and stroke as well as conditions such as nutritional deficiency and chemical toxicity such as with chemotherapeutic agents can cause central nervous system neuropathies.

In some embodiments, the present disclosure provides a method of treating a neuropathy or axonopathy associated with axonal degeneration. In some such embodiments, a neuropathy or axonopathy associated with axonal degeneration can be any of a number of neuropathies or axonopathies such as, for example, those that are hereditary or congenital or associated with Parkinson's disease, Alzheimer's disease, Herpes infection, diabetes, amyotrophic lateral sclerosis, a demyelinating disease, ischemia or stroke, chemical injury, thermal injury, and AIDS. In addition, neurodegenerative diseases not mentioned above as well as a subset of the above-mentioned diseases can also be treated with the methods of the present disclosure. Such subsets of diseases can include Parkinson's disease or non-Parkinson's diseases, or Alzheimer's disease.

Subjects

In some embodiments, compounds and/or compositions as described herein are administered to subjects suffering from or susceptible to a disease, disorder or condition as described herein; in some embodiments, such a disease, disorder or condition is characterized by axonal degeneration, such as one of the conditions mentioned herein.

In some embodiments, a subject to whom a compound or composition is administered as described herein exhibits one or more signs or symptoms associated with axonal degeneration; in some embodiments, the subject does not exhibit any signs or symptoms of neurodegeneration.

In some embodiments, provided methods comprise administering a compound of Formula I to a patient in need thereof. In some such embodiments, the patient is at risk of developing a condition characterized by axonal degeneration. In some embodiments, the patient has a condition characterized by axonal degeneration. In some embodiments, the patient has been diagnosed with a condition characterized by axonal degeneration.

In some embodiments, provided methods comprise administering a composition as described herein to a patient population of in need thereof. In some embodiments, the population is drawn from individuals who engage in activities where the potential for traumatic neuronal injury is high. In some embodiments, the population is drawn from athletes who engage in contact sports or other high-risk activities.

In some embodiments, the subject is at risk of developing a condition characterized by axonal degeneration. In some embodiments, the subject is identified as being at risk of axonal degeneration, e.g., based on the subject's genotype, a diagnosis of a condition associated with axonal degeneration, and/or exposure to an agent and/or a condition that induces axonal degeneration.

In some embodiments, the patient is at risk of developing a neurodegenerative disorder. In some embodiments the patient is elderly. In some embodiments, the patient is known to have a genetic risk factor for neurodegeneration. In some embodiments, the patient has a family history of neurodegenerative disease. In some embodiments, the patient expresses one or more copies of a known genetic risk factor for neurodegeneration. In some embodiments, the patient is drawn from a population with a high incidence of neurodegeneration. In some embodiments, the patient has a hexanucleotide repeat expansion in chromosome 9 open reading frame 72. In some embodiments, the patient has one or more copies of the ApoE4 allele.

In some embodiments, subjects to which a compound or composition as described herein is administered may be or comprise subjects suffering from or susceptible to a neurodegenerative disease, disorder or condition. In some embodiments, a neurodegenerative disease, disorder or condition may be or comprise a traumatic neuronal injury. In some embodiments, a traumatic neuronal injury is blunt force trauma, a closed-head injury, an open head injury, exposure to a concussive and/or explosive force, a penetrating injury into the brain cavity or innervated region of the body. In some embodiments, a traumatic neuronal injury is a force which causes the axons to deform, stretch, crush or sheer.

In some embodiments, the subject engages in an activity identified as a risk factor for neuronal degradation, e.g., a subject that engages in contact sports or occupations with a high chance for traumatic neuronal injury.

For example, the subject may be a patient who is receiving, or is prescribed, a chemotherapy associated with peripheral neuropathy. Examples of chemotherapeutic agents include, but not limited to, thalidomide, epothilones (e.g., ixabepilone), taxanes (e.g., paclitaxel and docetaxel), vinca alkaloids (e.g., vinblastine, vinorelbine, vincristine, and vindesine), proteasome inhibitors (e.g., bortezomib), platinum-based drugs (e.g., cisplatin, oxaliplatin, and carboplatin).

In some embodiments, provided methods comprise administering a composition as described herein to a patient or patient population based on the presence or absence of one or more biomarkers. In some embodiments, provided methods further comprise monitoring the level of a biomarker in a patient or patient population and adjusting the dosing regimen accordingly.

Dosing

Those of skill in the art will appreciate that, in some embodiments, the exact amount of a particular compound included in and/or delivered by administration of a pharmaceutical composition or regimen as described herein may be selected by a medical practitioner and may be different for different subjects, for example, upon consideration of one or more of species, age, and general condition of the subject, and/or identity of the particular compound or composition, its mode of administration, and the like. Alternatively, in some embodiments, the amount of a particular compound included in and/or delivered by administration of a pharmaceutical composition or regimen as described herein may be standardized across a relevant patient population (e.g., all patients, all patients of a particular age or stage of disease or expressing a particular biomarker, etc.).

A provided compound or composition of the present disclosure is preferably formulated in dosage unit form for ease of administration and uniformity of dosage. The expression "dosage unit form" as used herein refers to a physically discrete unit of agent appropriate for the patient to be treated. It will be understood, however, that the total daily usage of a provided compound or composition of the present disclosure will be decided by the attending physician within the scope of sound medical judgment. The specific effective dose level for any particular patient or organism will depend upon a variety of factors including the disorder being treated and the severity of the disorder; the clinical condition of the individual patient; the cause of the disorder; the activity of the specific compound employed; the specific composition employed; the age, body weight, general health, sex and diet of the patient; the time of administration, delivery site of the agent, route of administration, and rate of excretion of the specific compound employed; the duration of the treatment; drugs used in combination or coincidental with the specific compound employed, and like factors well known in the medical arts. The effective amount of the compound to be administered will be governed by such considerations and is the minimum amount necessary to inhibit SARM1 activity as required to prevent or treat the undesired disease or disorder, such as for example, neurodegeneration or traumatic neural injury.

A pharmaceutically acceptable composition of this disclosure can be administered to humans and other animals orally, rectally, intravenously, parenterally, intracisternally, intravaginally, intraperitoneally, topically (as by powders, ointments, or drops), bucally, as an oral or nasal spray, or the like, depending on the severity of the disease, disorder or infection being treated. The daily dose is, in certain embodiments, given as a single daily dose or in divided doses two to six times a day, or in sustained release form. This dosage regimen may be adjusted to provide the optimal therapeutic response. The compounds may be administered on a regimen of 1 to 4 times per day, preferably once or twice per day.

In some embodiments, compositions of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intradermal, intraocular, intralesional and intracranial injection or infusion techniques. Preferably, the compositions are administered orally, intraperitoneally or intravenously.

In some embodiments, pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

Most preferably, pharmaceutically acceptable compositions of this disclosure are formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

Those additional agents may be administered separately from a provided compound or composition thereof, as part of a multiple dosage regimen. Alternatively, those agents may be part of a single dosage form, mixed together with a provided compound in a single composition. If administered as part of a multiple dosage regime, the two active agents may be submitted simultaneously, sequentially or within a period of time from one another, normally within five hours from one another.

It should also be understood that a specific dosage and treatment regimen for any particular patient may depend upon a variety of factors, including the activity of the specific compound employed, the age, body weight, general health, sex, diet, time of administration, rate of excretion, drug combination, and the judgment of the treating physician and the severity of the particular disease being treated. In some embodiments, the amount of a compound of the present disclosure in the composition will also depend upon the particular compound in the composition.

In some embodiments, SARM1 inhibition as described herein may be utilized in combination with one or more other therapies to treat a relevant disease, disorder, or condition. In some embodiments, dosing of a SARM1 inhibitor is altered when utilized in combination therapy as compared with when administered as monotherapy; alternatively, or additionally, in some embodiments, a therapy that is administered in combination with SARM1 inhibition as described herein is administered according to a regimen or protocol that differs from its regimen or protocol when administered alone or in combination with one or more therapies other than SARM1 inhibition. In some embodiments, compositions which comprise an additional therapeutic agent, that additional therapeutic agent and a provided compound may act synergistically. In some embodiments, one or both therapies utilized in a combination regimen is administered at a lower level or less frequently than when it is utilized as monotherapy.

In some embodiments, compounds and/or compositions described herein are administered with a chemotherapeutic agent including, but not limited to, alkylating agents, anthracyclines, taxanes, epothilones, histone deacetylase inhibitors, topoisomerase inhibitors, kinase inhibitors, nucleotide analogs, peptide antibiotics, platinum-based agents, retinoids, vinca alkaloids and derivatives. In some embodiments, compounds and/or compositions described herein are administered in combination with PARP inhibitors.

EXEMPLIFICATION

The present teachings including descriptions provided in the Examples that are not intended to limit the scope of any claim. Unless specifically presented in the past tense, inclusion in the Examples is not intended to imply that the experiments were actually performed. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Methods

Some methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Methods In Molecular Biology, ed. Richard, Humana Press, N J, 1995; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999. Methods of administration of pharmaceuticals and dosage regimes, can be determined according to standard principles of pharmacology, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003.

Example 1: Synthesis of Compounds

General Synthetic Methods

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used.

The general processes for preparing the compounds according to the invention will become apparent to the one skilled in the art studying the following schemes. Starting materials may be prepared by methods that are described in the literature or herein or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Intermediates and products may be purified by chromatography on silica gel, recrystallization and/or reverse phase HPLC (RHPLC). Discrete enantiomers may be obtained by resolution of racemic products using chiral HPLC. RHPLC purification methods used anywhere from 0-100% acetonitrile in water containing 0.1% formic acid, 0.1-0.01% TFA, 10 mM aqueous ammonium bicarbonate or 0.2% aqueous ammonium hydroxide and used one of the following columns:

a) Waters Xbridge C18 10 μm 30×100 mm column
b) Waters Sunfire C18 10 μm 30×100 mm column
c) Waters Xbridge C18 3.5 μm 50×4.6 mm column
d) HALO C18 2.7 μm 30×4.6 mm column
e) Waters Sunfire C18 3.5 μm 50×4.6 mm column Synthesis of Exemplary Compounds Method A: Synthesis of Compound I-1-a

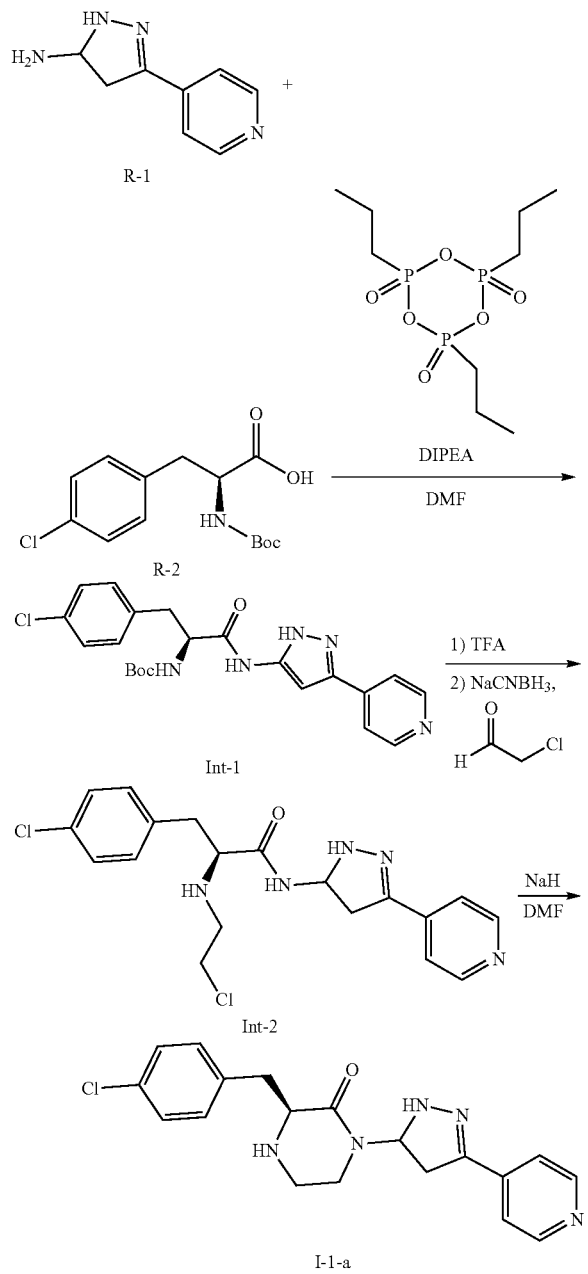

To a solution of R-2 (1.87 g, 6.24 mmol), R-1 (1.00 g, 6.24 mmol), DIPEA (2.2 mL, 12.5 mmol) in anhydrous DMF (10 mL) was added propanephosphonic acid anhydride in EtOAc (50%, 5.6 mL, 9.36 mmol) and the reaction mixture was purged with $N_2$ (g), sealed and stirred at room temperature for 1 hour. Sat. aqueous $NaHCO_3$ (10 mL) and water (10 mL) were added, and the mixture was extracted with $CH_2C_2$ (3×20 mL). The combined organics were dried ($MgSO_4$), filtered and concentrated in vacuo. The product was triturated in $CH_2Cl_2$ (10 mL) and the solid was collected by filtration under vacuum and washed with $CH_2Cl_2$ (2×5 mL) to yield Int-1 (490 mg, 17%).

Int-1 (1.14 g, 1.55 mmol) was dissolved in $CH_2Cl_2$ (5 mL) at room temperature. Trifluoroacetic acid (2.0 mL, 26.1 mmol) was added, and the reaction was stirred for 16 hours. The reaction was concentrated in vacuo and the crude product was dissolved in $CH_2Cl_2$ (20 mL) and sat. aqueous $NaHCO_3$ (10 mL) and water (10 mL) were added. The organic layer was separated, and the aqueous layer was extracted with $CH_2Cl_2$ (2×20 mL). The organics were combined, dried ($MgSO_4$), filtered and concentrated in vacuo to yield crude product. The crude product was purified by preparative HPLC to afford the free amine that was suspended in MeOH (2 mL). To this suspension was added chloroacetaldehyde in water (50% wt, 47 uL, 0.37 mmol) and the mixture was stirred for 4 h then treated with $NaCNBH_3$ (23 mg, 0.37 mmol). The mixture was stirred for 16 h then treated with water (2 mL), extracted with $CH_2Cl_2$ (3×2 mL), dried over $MgSO_4$, filtered and concentrated in vacuo. The crude product was purified by Flash chromatography ($SiO_2$, 0 to 5% MeOH in $CH_2Cl_2$) to afford Int-2 (40 mg, 29%).

To a solution of Int-2 (73%, 40 mg, 0.072 mmol) in anhydrous DMF (2 mL) at room temperature was added sodium hydride (60% dispersion in mineral oil, 5.8 mg, 0.14 mmol) and the reaction was stirred under $N_2$ (g) for 1 hour. The reaction was quenched with water (2 mL) and the mixture was extracted with $CH_2Cl_2$ (3×2 mL). The combined organic layers were dried ($MgSO_4$), filtered and concentrated in vacuo. The crude product was purified by preparative HPLC to afford compound I-1-a (17 mg, 63%).

The following compounds were made in similar fashion from the appropriate amine and acid reagents: I-1-b, I-3-a and I-38.

Method B: Synthesis of Compound I-2-a

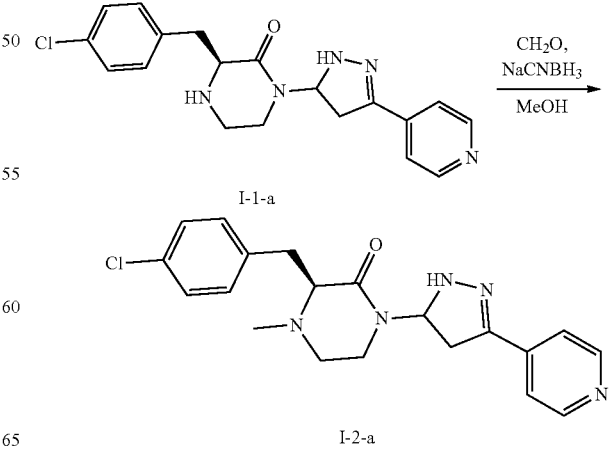

To a solution of compound I-1-a (88%, 86 mg, 0.21 mmol) and formaldehyde (12 mg, 0.41 mmol) in methanol (4 mL) at room temperature was added sodium cyanoborohydride (19 mg, 0.31 mmol) and the reaction mixture stirred for 22 hours. The reaction was quenched with water (4 mL) and the mixture was extracted with v (4×10 mL). The combined organics were dried (MgSO$_4$), filtered and concentrated in vacuo. The crude product was purified by preparative HPLC to afford compound I-2-a (43 mg, 54%).

Method C: Synthesis of Compound I-4

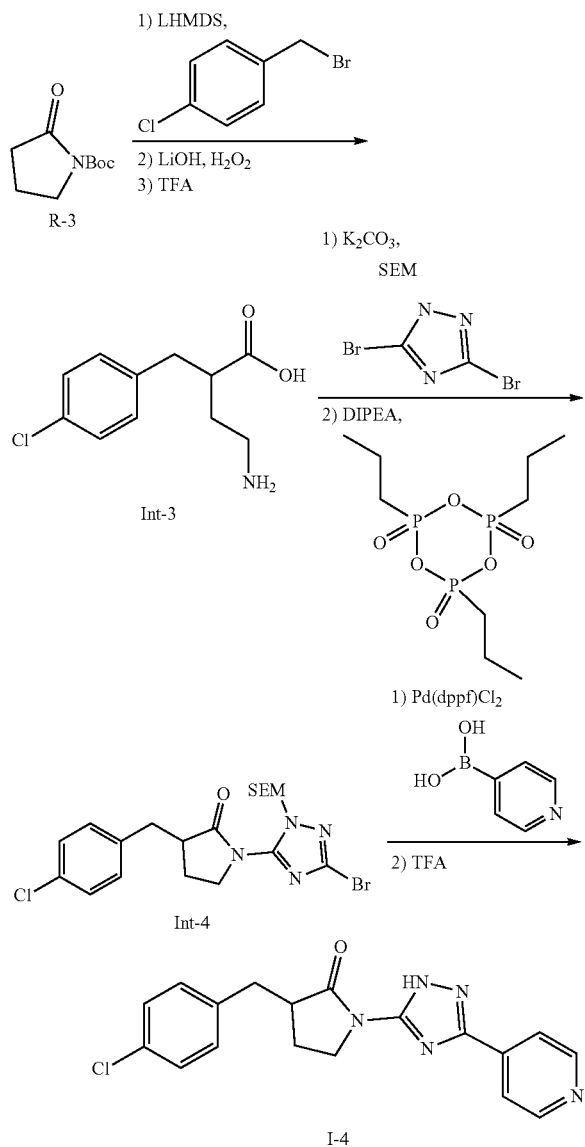

To a mixture of R-3 (15 g, 81 mmol) in THF (100 mL) was added LiHMDS (1 mol/L, 81 mL, 81 mmol) slowly at −60° C. for 1 hours. 1-(bromomethyl)-4-chlorobenzene (16 g, 81 mmol) in THF (100 mL) was added and stirred at −60° C. for 1 hour. The mixture was poured into water (100 mL) and extracted with ethyl acetate (100 mL×2). The combined organics were dried and concentrated in vacuo to give crude product that was purified by column chromatography (SiO$_2$, CH$_2$Cl$_2$: MeOH=100:1) to give the pyrrolidinone (8.0 g, 26 mmol) that was dissolved in THF/H$_2$O (4/1, 80 mL). To the solution was added H$_2$O$_2$ (10 mL) slowly at 0° C. LiOH—H$_2$O (3.3 g, 78 mmol) was added and mixture stirred at room temperature for 2 hours then treated with saturated NaHSO$_3$ (15 mL), extracted with ethyl acetate (100 mL×2), dried and concentrated in vacuo to give the acid (7.8 g, 24.0 mmol) that was treated with TFA (2 mL) in CH$_2$Cl$_2$ (5 mL) and stirred at room temperature for 2 hours. The reaction mixture was concentrated in vacuo to give Int-3 (5.5 g, quant).

A mixture of Int-3 (5.5 g, 24 mmol), 3,5-dibromo-1-((2-(trimethylsilyl)ethoxy) methyl)-1H-1,2,4-triazole (12.8 g, 36 mmol), K$_2$CO$_3$ (9.9 g, 72 mmol) in H2O/1,4-dioxane (1/10, 50 mL) was stirred at 110° C. for 32 hours. To the reaction mixture was added water (50 mL) and extracted with ethyl acetate (200 mL×2). The combined organic was dried and concentrated in vacuo. The residue was purified by flash chromatography (SiO$_2$, DCM:MeOH=20:1) to give the amine (7.0 g, 14 mmol) that was dissolved in DMA (20 mL). To this mixture was added propanephosphonic acid anhydride (13.4 g, 42 mmol) and DIPEA (3.6 g, 28 mmol) and was stirred at 40° C. for 2 hours. Water (60 mL) was added, and the mixture was extracted with ethyl acetate (200 mL×2), dried, and concentrated in vacuo to give crude product that was purified by flash chromatography (SiO$_2$, DCM:MeOH=30:1) to give Int-4 (5.5 g, 81%).

The mixture of Int-4 (5.5 g, 11 mmol), pyridin-4-ylboronic acid (2.1 g, 17 mmol), Pd(dppf)Cl$_2$ (804 mg, 1.1 mmol), K$_2$CO$_3$ (4.6 g, 33 mmol) in H2O/1,4-dioxane (1/10, 50 mL) was stirred at 110° C. for 16 hours. The reaction mixture was treated with water (50 mL) and extracted with ethyl acetate (100 mL×2). The combined organics were dried and concentrated in vacuo to give crude product which was purified by column chromatography (SiO$_2$, DCM: MeOH=20:1) to give the pyridine (4.6 g, 9.5 mmol) that was treated with CH$_2$C$_2$ (5 mL) and TFA (5 mL). The mixture was stirred at 2 h then concentrated in vacuo to give a crude product that was purified by flash chromatography (SiO$_2$, DCM:MeOH=20:1) to give the title compound (3.2 g, 95%).

The following compounds were made in similar fashion from the appropriate amine and acid reagents: I-5 and I-6

Method D: Synthesis of Compound I-7

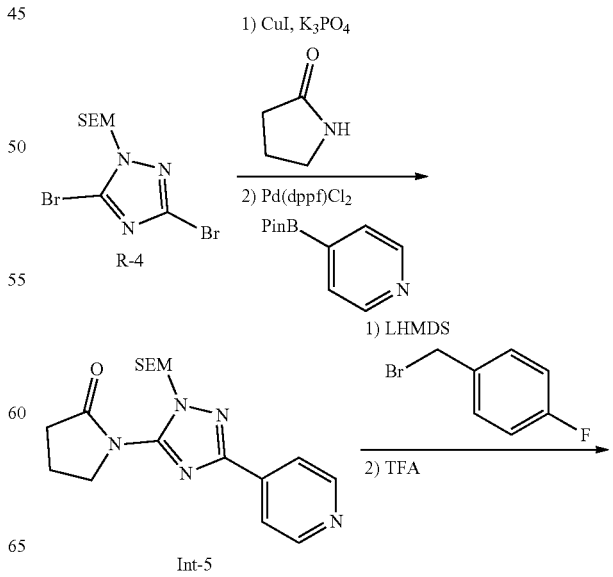

-continued

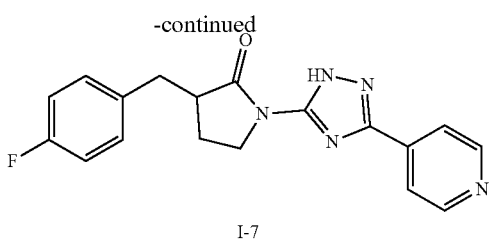

I-7

A suspension of R-4 (5.0 g, 14.0 mmol), pyrrolidin-2-one (3.2 mL, 42.0 mmol), tripotassium phosphate (5.94 g, 28.0 mmol), copper (1+) iodide (0.27 g, 1.40 mmol) and 1,10-phenanthroline (0.76 g, 4.20 mmol) in anhydrous DMF (100 mL) was de-gassed for 5 minutes with a stream of $N_2$ (g). The reaction mixture was stirred at 100° C. under $N_2$ (g) for 5 hours. The reaction mixture was concentrated in vacuo. The product was partitioned between EtOAc and brine, the layers separated and the aqueous re-extracted with EtOAc. The combined organics were dried ($MgSO_4$) and concentrated in vacuo. The crude product was purified by flash column chromatography ($SiO_2$, 0% to 100% EtOAc in heptane) to afford the pyrrolidinone (1.81 g, 5.01 mmol) that was dissolved in 1,4-dioxane (15 mL). 4-(4,4,5,5-tetramethyl-1,3,2-dioxaborolan-2-yl)pyridine (1.34 g, 6.51 mmol) and 2 M aqueous potassium carbonate (7.5 mL, 15.0 mmol) was added and the reaction mixture was degassed with $N_2$ (g) for 5 minutes. 1,1'-bis(diphenylphosphino)ferrocene]dichloropalladium(II) (367 mg, 0.500 mmol) was added and the reaction mixture was stirred at 100° C. under $N_2$ (g) for 5 hours. The reaction mixture was diluted with EtOAc and brine. The layers were separated, and the aqueous layer was further extracted with EtOAc. The combined organics were concentrated in vacuo. The crude product was purified by flash column chromatography using a gradient from 0% to 100% EtOAc in heptane to afford a residue that was suspended in 40° C. warm water (75 mL) and extracted with EtOAc (100 mL), the organic layer washed with warm water (75 mL) then brine (50 mL). The organic layer was dried ($MgSO_4$), filtered and concentrated in vacuo with the water bath set at 60° C., to afford Int-5 (1430 mg, 71%).

Int-5 (90%, 200 mg, 0.501 mmol) was dissolved in anhydrous THF (3 mL). The reaction mixture was cooled to −78° C. under $N_2$ (g) and LiHMDS in THF (1M, 28 uL, 0.25 mmol) was added dropwise. The reaction mixture was stirred for 15 min at −78° C. then a solution of 1-(bromomethyl)-4-fluoro-benzene (69 uL, 0.55 mmol) in anhydrous THF (1 mL) was added dropwise. The reaction mixture was stirred at −78° C. for 1 hour then was quenched with water (5 mL), diluted with brine (30 mL) and extracted with EtOAc (3×40 mL). The combined organics were dried ($MgSO_4$), filtered and concentrated in vacuo. The crude product was purified by flash column chromatography using a gradient from 0% to 100% EtOAc in heptane to afford the benzylated compound (150 mg, 0.23 mmol) that was dissolved in DCM (4 mL). To this mixture was added TFA (0.5 mL) and the mixture stood at room temperature for 20 hours. The reaction mixture was quenched with sat. aqueous $NaHCO_3$ and the resultant solid collected under vacuum filtration. The solid was washed with water then triturated from methanol (2 mL) to afford the title compound (14 mg, 17%).

The following compounds were made in similar fashion from the appropriate lactam and alkylating reagents: I-8, I-9, I-10, I-11, I-12, I-13, I-18, I-26, I-39, I-40, I-42-45, I-54, I-61, I-63, I-95, I-97, I-99, I-101-103, I-111 and I-115.

Method E: Synthesis of Compound I-15

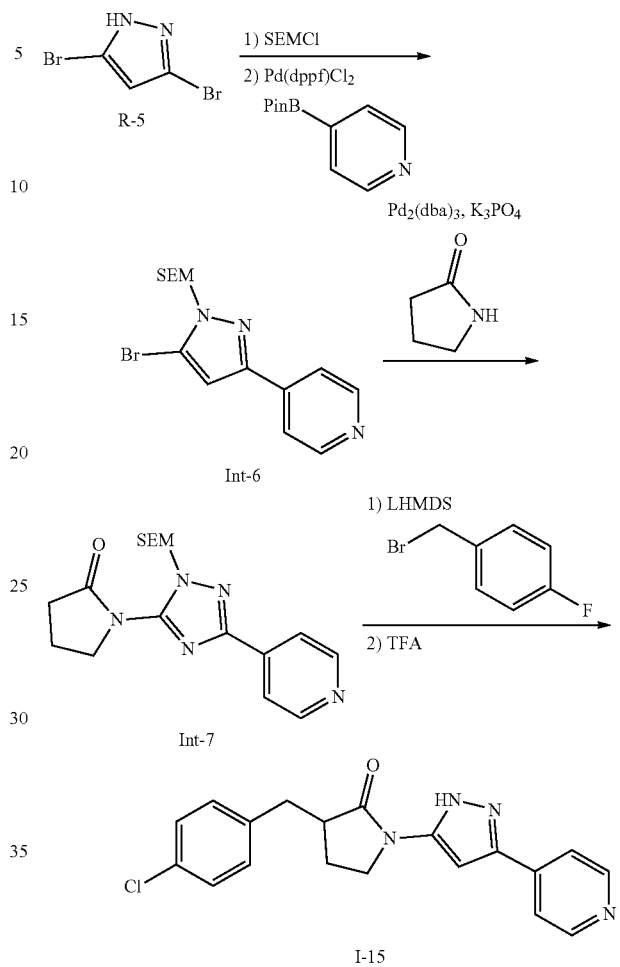

R-5 (7.10 g, 31.4 mmol) was suspended in anhydrous THF (100 mL) and cooled to 0° C. Sodium hydride (60% in mineral oil, 1.26 g, 31.4 mmol) was added portion-wise to the reaction mixture. The reaction mixture was stirred at room temperature under $N_2$ (g) for 10 minutes. [2-(Chloromethoxy)ethyl](trimethyl)silane (6.1 mL, 34.6 mmol) was added and the reaction mixture was stirred under $N_2$ (g) for 18 hours. The reaction was quenched with water and extracted with EtOAc (20 mL). The organics were washed with sat. aqueous $NaHCO_3$ (20 mL) then concentrated in vacuo. The crude product was purified by flash column chromatography with a gradient from 0 to 10% EtOAc in heptane to afford the SEM-protected pyrazole (9.10 g, 80%).

The SEM-protected pyrazole (2.00 g, 5.45 mmol), potassium carbonate (2.26 g, 16.3 mmol), bis(diphenylphosphino)ferrocene]dichloropalladium(II) (400 mg, 0.55 mmol), and 4-(4,4,5,5-tetramethyl-1,3,2-dioxaborolan-2-yl)pyridine (1.12 g, 5.45 mmol) and were placed under a $N_2$ (g) atmosphere. Water (5 mL) and 1,4-dioxane (15 mL) were added to the reaction mixture and purged with $N_2$ (g). The reaction mixture was stirred at 100° C. for 45 min. The reaction mixture was cooled to room temperature and partitioned between EtOAc (150 mL) and brine (100 mL). The layers were separated, and the aqueous layer was further extracted with EtOAc (2×100 mL). The combined organics were dried ($MgSO_4$), filtered and concentrated in vacuo. The crude product was purified by flash column chromatography with a gradient from 0 to 100% EtOAc in heptane to afford Int-6 (3.07 g, 39%).

Int-6 (3.00 g, 8.30 mmol), pyrrolidin-2-one (1.3 mL, 16.6 mmol), tripotassium phosphate (3.57 g, 16.6 mmol), Brett-Phos Pd G1 Methyl-t-Butyl Ether Adduct (128 mg, 0.14 mmol), Brettphos (445 mg, 0.830 mmol) and $Pd_2(dba)_3$ (380 mg, 0.42 mmol) were combined placed under an atmosphere of $N_2$ (g) and dissolved in anhydrous 1,4-dioxane (60 mL). The reaction mixture was stirred for 18 hours at 110° C. The reaction mixture was cooled to room temperature and concentrated in vacuo. The crude product was purified by flash column chromatography with a gradient from 0 to 100% EtOAc in heptane to afford Int-7 (2.31 g, 76%).

Int-7 (400 mg, 1.12 mmol) was dissolved in anhydrous THF (7 mL) and cooled to −78° C. then treated with LiHMDS in THF (1 M, 1.3 mL, 1.34 mmol) and stirred for 10 minutes. 1-(Bromomethyl)-4-chlorobenzene (229 mg, 1.12 mmol) in anhydrous THF (5 ml) was added dropwise and the reaction mixture was stirred for 2 hours at −78° C. The reaction mixture was quenched with water (30 mL) and brine (30 mL) then extracted with EtOAc (3×50 mL). The combined organics were dried ($Na_2SO_4$), filtered and concentrated in vacuo. The crude product was purified by flash column chromatography using a gradient from 0% to 100% EtOAc in heptane to afford the benzylated compound (417 mg, 0.85 mmol) that was dissolved in DCM (6 mL). To the mixture was added trifluoroacetic acid (3.0 mL, 40.4 mmol), and the reaction mixture stirred at room temperature for 2 hours. The reaction mixture was concentrated in vacuo. The crude product was dissolved in a mixture of acetonitrile/water (1:1, 2 mL). Sat. aqueous ammonium hydroxide (1.0 mL) was added and the mixture was sonicated for 2 minutes, resulting in a white precipitate. The volatiles were concentrated in vacuo and the resultant solid collected under vacuum filtration and washed with water. The solid was suspended in boiling acetonitrile, the suspension cooled to room temperature and the resultant solid collected under vacuum filtration to afford compound I-15 (250 mg, 84%).

The following compounds were made in similar fashion from the appropriate lactam and alkylating reagents: I-14, I-16, I-17, I-19, I-20, I-21, I-22, I-37, I-47, I-57, I-58, I-60, I-62, I-65-67, I-70, I-94, I-96, I-98, I-100, I-112, I-114, I-116 and I-118.

Method F: Chiral Separation of Compound I-7 to Provide Compounds I-7-a and I-7-b

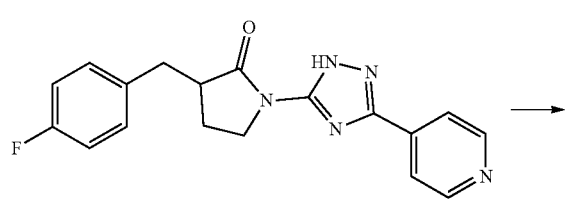

I-7

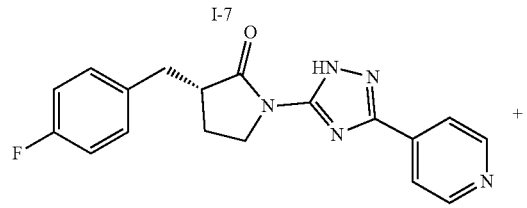

+

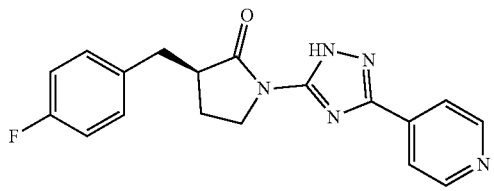

Compound I-7 (63 mg, 0.18 mmol) was dissolved in a mixture of methanol/ethanol and acetonitrile then purified by supercritical fluid chromatography on a Chiralpak AS-H, 20×250 mm, 5 μm column eluting with 30% ethanol in $CO_2$ at a flow rate of 50 mL/min and 100 bar pressure to afford the title compounds.

Peak 1—Chiral LC: Ret time 3.21 min on Chiralpak AS, 4.6×250 mm, 5 μm eluting with 30% ethanol in $CO_2$ at 2.4 mL/min at 100 Bar and detection at 210 nm.

Peak 2—Chiral LC: Ret time 7.34 min on Chiralpak AS, 4.6×250 mm, 5 μm eluting with 30% ethanol in $CO_2$ at 2.4 mL/min at 100 Bar and detection at 210 nm.

Method G: Chiral Separation of Compound I-8 to Provide Compounds I-8-a and I-8-b

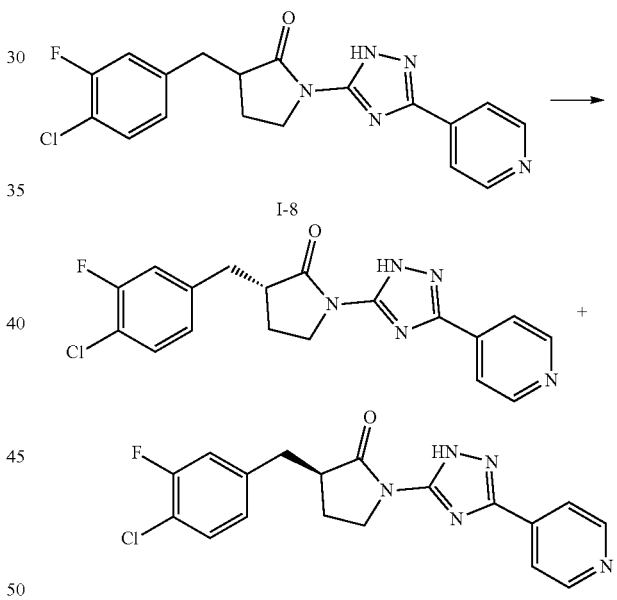

Compound I-8 (96 mg, 0.26 mmol) was dissolved in a mixture of methanol, ethanol, DCM and acetonitrile then purified by supercritical fluid chromatography on a Chiralpak AS-H, 20×250 mm, 5 μm column eluting with 30% ethanol in $CO_2$ at a flow rate of 50 mL/min and 100 bar pressure to afford the title compounds.

Peak 1—Chiral LC: Ret time 4.06 min on Chiralpak AS, 4.6×250 mm, 5 μm eluting with 30% ethanol in $CO_2$ at 2.4 mL/min at 100 Bar and detection at 210 nm.

Peak 2—Chiral LC: Ret time 6.39 min on Chiralpak AS, 4.6×250 mm, 5 μm eluting with 30% ethanol in $CO_2$ at 2.4 mL/min at 100 Bar and detection at 210 nm.

Method H: Chiral Separation of Compound I-9 to Provide Compounds I-9-a and I-9-b

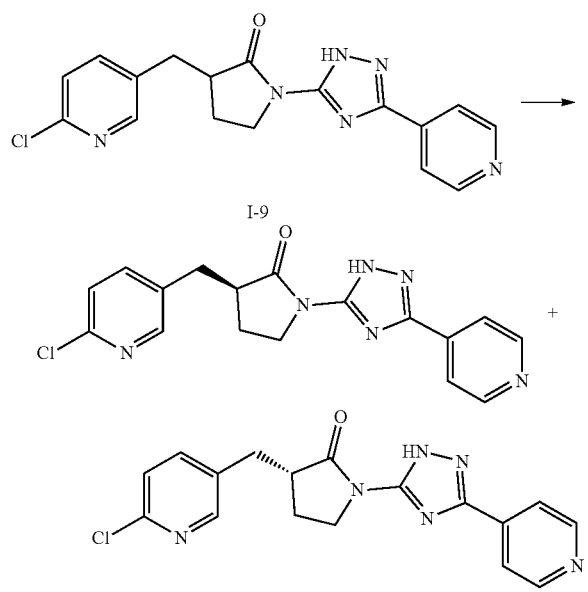

Compound I-9 (24 mg, 0.067 mmol) was dissolved in a mixture of ethanol and acetonitrile then purified by supercritical fluid chromatography on a Chiralpak AS-H, 20×250 mm, 5 μm column eluting with 30% ethanol in $CO_2$ at a flow rate of 50 mL/min and 100 bar pressure to afford the title compounds.

Peak 1—Chiral LC: Ret time 5.72 min on Chiralpak AS, 4.6×250 mm, 5 μm eluting with 30% ethanol in $CO_2$ at 2.4 mL/min at 100 Bar and detection at 210 nm.

Peak 2—Chiral LC: Ret time 11.03 min on Chiralpak AS, 4.6×250 mm, 5 μm eluting with 30% ethanol in $CO_2$ at 2.4 mL/min at 100 Bar and detection at 210 nm.

Method I: Chiral Separation of Compound I-11 to Provide Compounds I-11-a and I-11-b

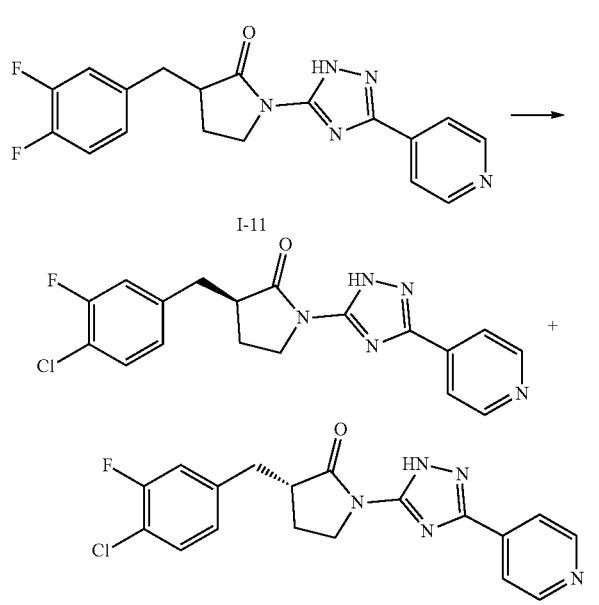

Compound I-11 (30 mg, 0.0844 mmol) was dissolved in a mixture of methanol, acetonitrile, IPA and formic acid then purified by supercritical fluid chromatography on a Chiralpak AD-H, 10×250 mm, 5 μm column eluting with 40% methanol in $CO_2$ at a flow rate of 15 mL/min to afford the title compounds.

Peak 1—Chiral LC: Ret time 11.38 min on Chiralpak AD-H, 4.6×250 mm, 5 μm eluting with 40% methanol in $CO_2$ at 4 mL/min at 100 Bar and detection at 210 nm.

Peak 2—Chiral LC: Ret time 19.13 min on Chiralpak AD-H, 4.6×250 mm, 5 μm eluting with 40% methanol in $CO_2$ at 4 mL/min at 100 Bar and detection at 210 nm.

Method J: Chiral Separation of Compound I-20 to Provide Compounds I-20-a and I-20-b

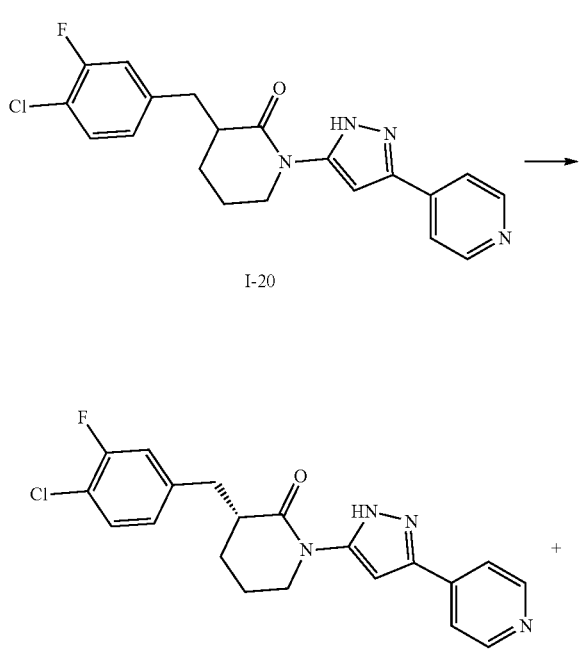

Compound I-20 (124 mg, 0.322 mmol) was dissolved in a mixture of methanol (5 mL), ethanol (15 mL) and acetonitrile (10 mL) then purified by supercritical fluid chromatography on a Chiralpak AS-H, 20×250 mm, 5 μm column eluting with 30% ethanol in $CO_2$ at a flow rate of 50 mL/min at 100 bar pressure to afford the title compounds.

Peak 1—Chiral LC: Ret time 5.69 min on Chiralpak AS-H, 4.6×250 mm, 5 μm eluting with 30% ethanol in $CO_2$ at 2.4 mL/min and 100 bar and detection at 210 nm.

Peak 2—Chiral LC: Ret time 8.88 min on Chiralpak AS-H, 4.6×250 mm, 5 μm eluting with 30% ethanol in $CO_2$ at 2.4 mL/min and 100 bar and detection at 210 nm.

Method K: Chiral Separation of Compound I-19 to Provide Compounds I-19-a and I-19-b

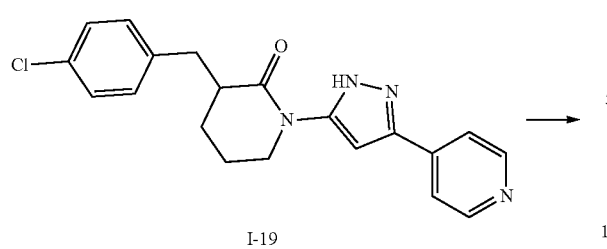

I-19

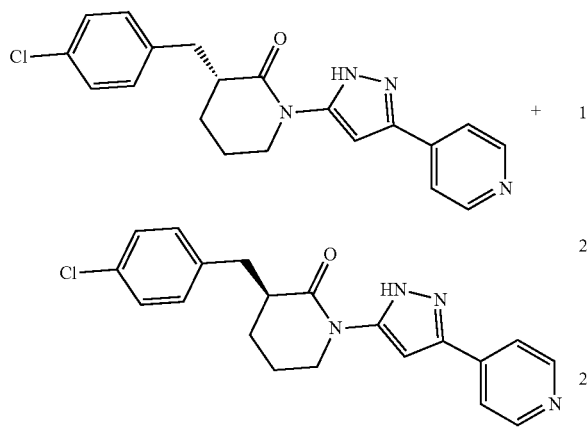

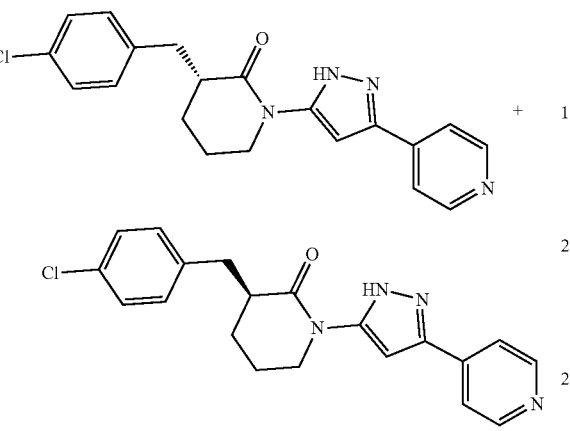

Compound I-19 (20 mg, 0.0545 mmol) was dissolved in a mixture of methanol, acetonitrile and IPA then purified by flash column chromatography on a Chiralcel OJ-H, 20×250 mm, 5 μm column eluting with 15% ethanol in heptane at a flow rate of 18 mL/min to afford the title compounds.

Peak 1—Chiral LC: Ret time 34.09 min on Chiralcel OJ-H, 4.6×250 mm, 5 μm eluting with 15% ethanol in heptane at 1 mL/min and detection at 210 nm.

Peak 2—Chiral LC: Ret time 43.34 min on Chiralcel OJ-H, 4.6×250 mm, 5 μm eluting with 15% ethanol in heptane at 1 mL/min and detection at 210 nm.

Method L: Chiral Separation of Compound I-21 to Provide Compounds I-21-a and I-21-b

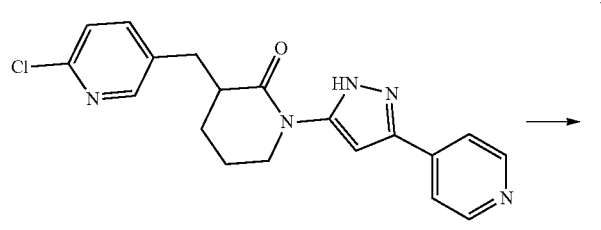

I-21

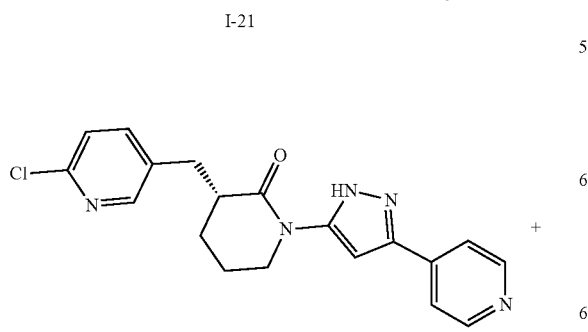

+

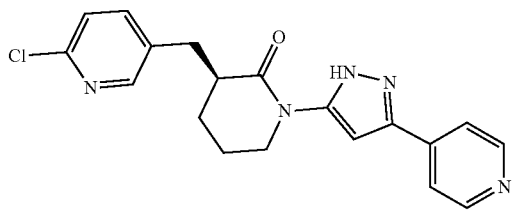

Compound I-21 (112 mg, 0.305 mmol) was dissolved in a mixture of methanol (8 mL) and acetonitrile (2 mL) then purified by supercritical fluid chromatography on a Chiralpak IB, 20×250 mm, 5 μm column eluting with 20% ethanol in $CO_2$ at a flow rate of 50 mL/min at 100 bar pressure to afford the title compounds.

Peak 1—Chiral LC: Ret time 7.55 min on Chiralpak IB, 4.6×250 mm, 5 μm eluting with 30% ethanol in $CO_2$ at 2.4 mL/min and 100 bar detection at 210 nm.

Peak 2—Chiral LC: Ret time 8.53 min on Chiralpak IB, 4.6×250 mm, 5 μm eluting with 30% ethanol in $CO_2$ at 2.4 mL/min and 100 bar detection at 210 nm.

Method M: Chiral Separation of Compound I-16 to Provide Compounds I-16-a and I-16-b

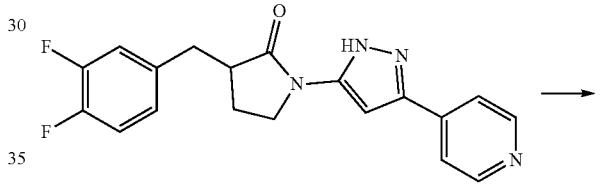

I-16

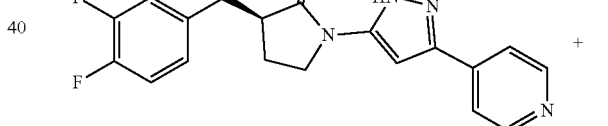

+

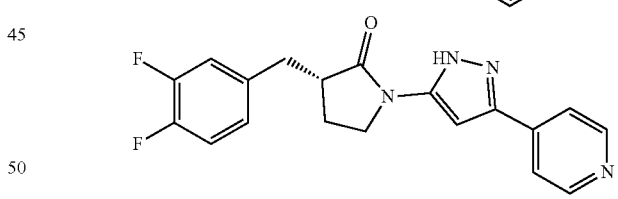

Compound I-16 (172 mg, 0.49 mmol) was dissolved in MeOH:DCM (1:1, 6 mg/mL) and purified by supercritical fluid chromatography on Lux C3 column 20 mm×250 mm×5 μm eluting with 15% MeOH in $CO_2$ with a flow rate of 50 mL/min at 125 bar pressure to afford the title compounds.

Peak 1—Chiral LC: Ret time 1.95 min on Lux C3 (4.6 mm×250 mm×5 μm), eluting with 20% MeOH in $CO_2$ with 0.2% $NH_3$ modifier.

Peak 2—Chiral LC: Ret time 2.24 min on Lux C3 (4.6 mm×250 mm×5 μm), eluting with 20% MeOH in $CO_2$ with 0.2% $NH_3$ modifier.

Method N: Chiral Separation of Compound I-4 to Provide Compounds I-4-a and I-4-b

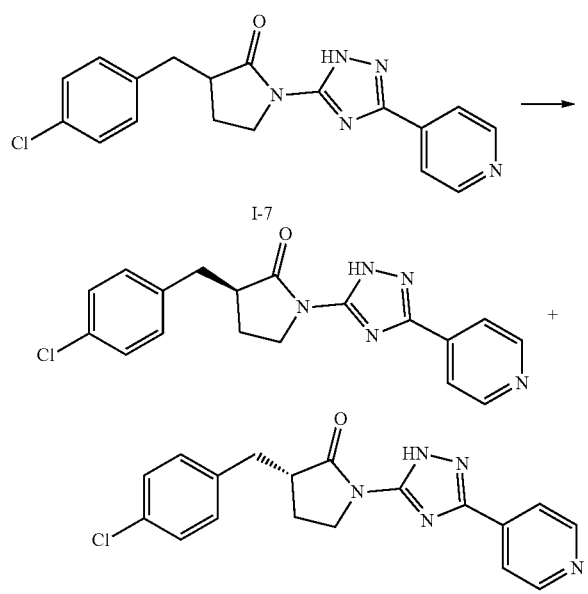

Compound I-4 (2.5 g, 7.0 mmol) was separated by SFC to give compounds I-4-a and I-4-b. Peak 1 (762 mg) and Peak 2 (670 mg).
Chrial Prep Conditions
Instrument: SFC-80 (Thar, Waters)
Column: AS 20*250 mm, 10 μm (Daicel)
Column temperature: 40° C.
Mobile phase: $CO_2$/MeOH (0.2% Methanol Ammonia)=80/65
Flow rate: 80 g/min
Back pressure: 100 bar
Detection wavelength: 220 nm
Cycle time: 9.5 min
Sample solution: 2500 mg dissolved in 250 ml Methanol
Injection volume: 3 ml
Method O: Chiral Separation of Compound I-5 to Provide Compounds I-5-a and I-5-b
Compound I-5 (1.8 g) was separated by SFC to give compounds I-5-a and I-5-b. Peak 1 (486 mg) and Peak 2 (290 mg).
Chiral Prep conditions
Instrument: SFC-80 (Thar, Waters)
Column: OJ 20*250 mm, 10 μm (Daicel)
Column temperature: 35° C.
Mobile phase: $CO_2$/MeOH (0.2% Methanol Ammonia)=60/40
Flow rate: 80 g/min
Back pressure: 100 bar
Detection wavelength: 214 nm
Cycle time: 5.0 min
Sample solution: 1800 mg dissolved in 80 ml Methanol
Injection volume: 1.9 ml
Method P: Chiral Separation of Compound I-6 to Provide Compounds I-6-a and I-6-b
Chiral Prep conditions
Instrument: SFC-80 (Thar, Waters)
Column: (R, R) Whelk-O1 20*250 mm, 10 μm (Daicel)
Column temperature: 40° C.
Mobile phase: CO2/MEOH (1.0% Methanol Ammonia)=60/40
Flow rate: 80 g/min
Back pressure: 100 bar
Detection wavelength: 219 nm
Cycle time: 7 min
Sample solution: 75 mg dissolved in 10 ml Methanol
Injection volume: 1 ml
Method Q: Synthesis of Intermediate Int-8

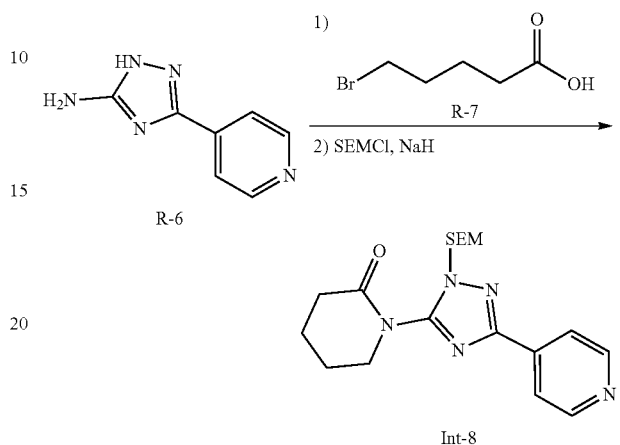

To a solution of R-7 (1.34 g, 7.4 mmol) in DMA (10 ml) was added DIPEA (2.4 g, 18.6 mmol) and propanephosphonic acid anhydride (50% in EtOAc, 5.9 g, 9.3 mmol) at 0° C. The mixture was stirred for 10 min and R-6 (1.0 g, 6.2 mmol) was added. The mixture was stirred for 1 h then quenched with aqueous $NaHCO_3$ and the resulted precipitate was filtered to give 5-bromo-N-(5-(pyridin-4-yl)-2H-1,2,4-triazol-3-yl)pentanamide (0.8 g, 40%).

To a solution of 5-bromo-N-(5-(pyridin-4-yl)-2H-1,2,4-triazol-3-yl)pentanamide (500 mg, 1.55 mmol) in DMF (5 ml) was added NaH (60%, 136 mg, 3.4 mmol) at 0° C. The mixture was stirred for 30 min then SEMCl (258 mg, 1.55 mmol) was added dropwise and stirred for another 30 min. The mixture was quenched with water and extracted with ethyl acetate (100 ml×2). The combined extracts were concentrated in vacuo and purified by reverse phase chromatography (eluting with 0~45% of MeCN in water) to give Int-8 (220 mg, 38%).

Method R: Synthesis of Compound I-23

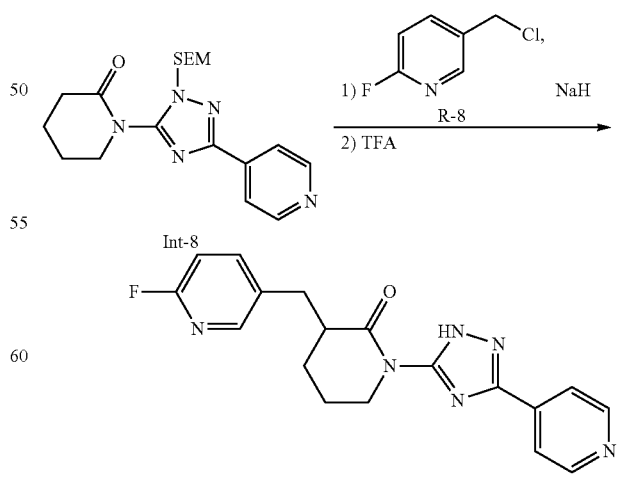

To a mixture of Int-8 (3.0 g, 8.0 mmol) in THF (30 mL) was added a solution of LDA in THF (2 mol/L, 6.0 mL, 12 mmol) slowly at −60° C. for 1.0 hour, followed by R-8 (1.5 g, 8.0 mmol) in THF (30 mL), and the reaction was stirred for 2 hours at −60° C. To the reaction mixture was added water (20 mL) and mixture was extracted with ethyl acetate (100 mL×2). The combined organic was dried and concentrated in vacuo, and the crude product was purified by flash chromatography (SiO₂, DCM:MeOH=20:1). The protected product was collected (2.2 g, 57%), dissolved in DCM (15 mL), and treated with TFA (15 mL) at room temperature for 1 hour. The reaction mixture was concentrated in vacuo to give crude product that was treated with water (15 mL) and saturated NaHCO₃ (80 mL). The solid precipitate was filtered, and the filter cake was concentrated in vacuo to give compound I-23 (1.5 g, 91%).

The following compounds were made in similar fashion using the appropriate intermediate prepared using Method Q: I-25, I-27-34, I-36, I-41, I-48-53, I-55, I-56 and I-68.

Method S: Synthesis of Compound I-24

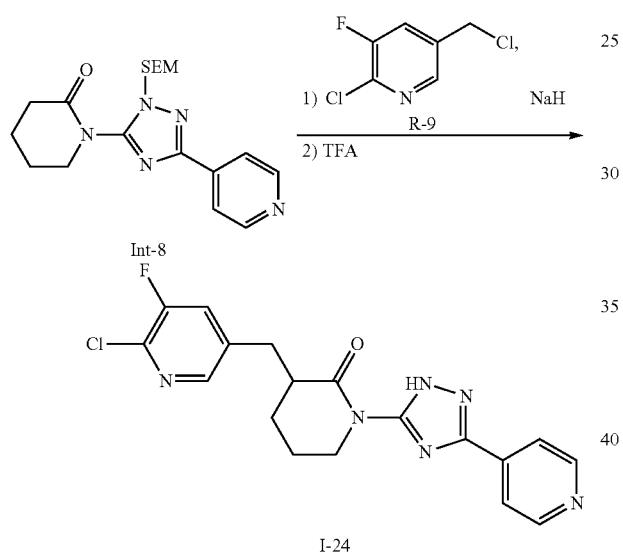

To a solution of Int-8 (2.5 g, 6.7 mmol) in dry THF (30 ml) at −78° C. was added LDA in THF (2.0 M, 5.0 ml, 10 mmol) dropwise over 30 min. The mixture was stirred for 1 h at −78° C., and then a solution of R-9 (2.23 g, 10 mmol) in THF (5 ml) was added dropwise over 30 min. After stirring for 2 h at −78° C., the reaction mixture was quenched with water and extracted with ethyl acetate (100 ml×3). The combined extracts were washed with water and brine and concentrated in vacuo. The residue was purified by reversed phase chromatography (eluting with 0~60% of MeCN in NH₄HCO₃ solution) to give the alkylated product (2.3 g, 67%) that was dissolved in DCM (20 mL) and slowly treated with TFA (10 ml) at 0° C. The mixture was then stirred for 2h at rt, concentrated in vacuo, then partitioned between aqueous NaHCO₃ (20 ml) and ethyl acetate (5 ml). The resultant precipitate was filtered, and the cake was washed with cold ethyl acetate to give compound I-24 (1.2 g, 70%).

Method T: Chiral Separation of Compound I-23 to Provide Compounds I-23-a and I-23-b

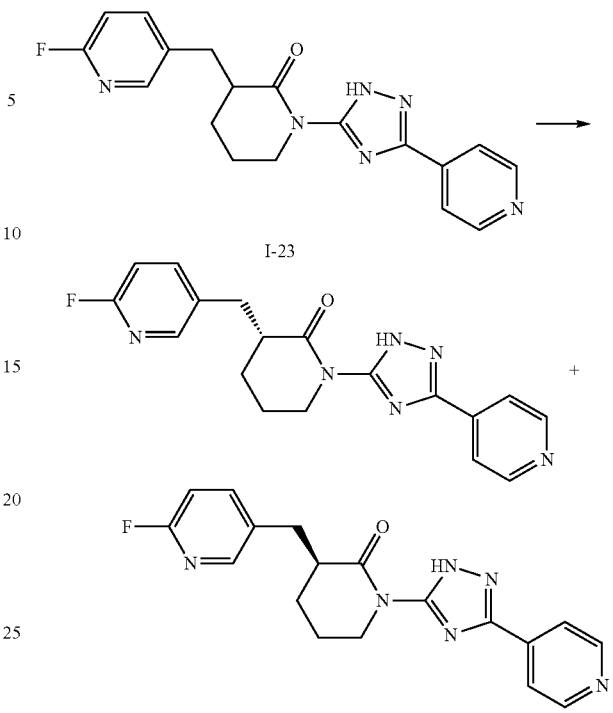

Compound I-23 (2.0 g) was dissolved in 140 mL of MeOH and was separated by SFC on a Daicel OZ, 20×250 mm, 10 μm column eluting with 45% MeOH (1% ammonia) in CO₂ at a flow rate of 80 g/min, 100 bar pressure, and 40° C. to afford the title compounds.

Peak 1—(650 mg) Chiral LC: Ret time 1.93 min on Chiralcel OZ-H, 4.6×100 mm, 5 μm eluting with 45% MeOH (0.2% ammonia) in CO₂ at 4 mL/min.

Peak 2—(680 mg) Chiral LC: Ret time 2.5 min on Chiralcel OZ-H, 4.6×100 mm, 5 μm eluting with 45% MeOH (0.2% ammonia) in CO₂ at 4 mL/min.

Method U: Chiral Separation of Compound I-24 to Provide Compounds I-24-a and I-24-b

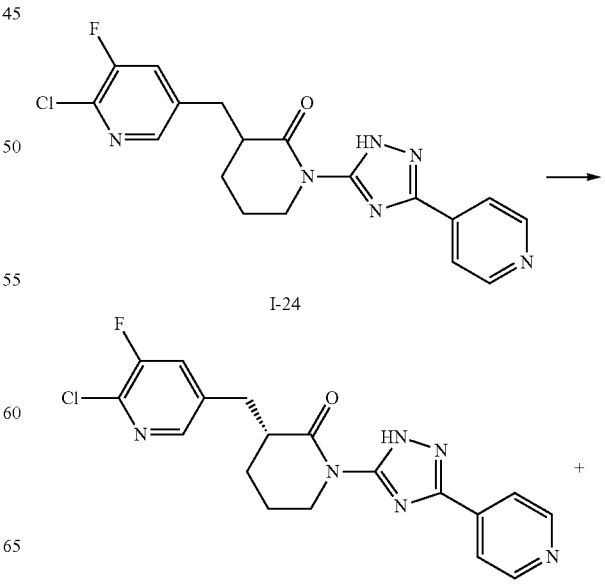

-continued

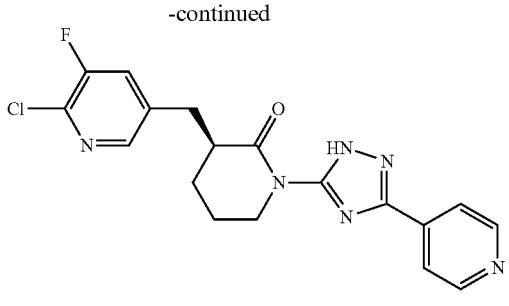

Compound I-24 (1.2 g) was dissolved in 160 mL of MeOH and was separated by SFC on a Daicel AS, 20×250 mm, 10 µm column eluting with 50% MeOH (1% ammonia) in CO₂ at a flow rate of 80 g/min, 100 bar pressure, and 40° C. to afford the title compounds.

Peak 1—(262 mg) Chiral LC: Ret time 1.54 min on Chiralcel AS-H, 4.6×100 mm, 5 µm eluting with 25% MeOH (0.2% ammonia) in CO₂ at 4 mL/min.

Peak 2—(255 mg) Chiral LC: Ret time 2.1 min on Chiralcel AS-H, 4.6×100 mm, 5 µm eluting with 25% MeOH (0.2% ammonia) in CO₂ at 4 mL/min.

Method V: Synthesis of Compound I-59

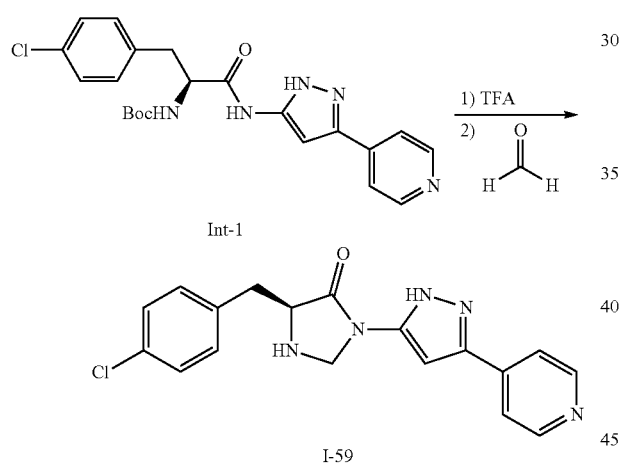

Int-I (1.14 g, 1.55 mmol) was dissolved in CH₂Cl₂ (5 mL) at room temperature. Trifluoroacetic acid (2.0 mL, 26.1 mmol) was added, and the reaction was stirred for 16 hours. The reaction was concentrated in vacuo and the crude product was dissolved in CH₂Cl₂ (20 mL) and sat. aqueous NaHCO₃ (10 mL) and water (10 mL) were added. The organic layer was separated, and the aqueous layer was extracted with CH₂C₂ (2×20 mL). The organics were combined, dried (MgSO₄), filtered and concentrated in vacuo to yield crude product. Formaldehyde (37%, 89 uL, 1.10 mmol) was added to a solution of the crude product (250 mg, 0.73 mmol) in anhydrous ethanol (3 mL) and the reaction mixture was stirred at 37° C. for 20 minutes. The crude product was purified by preparative HPLC to afford the title compound (78 mg, 30%).

The following compounds were made in similar fashion: I-35 and I-64.

Method W: Synthesis of Compound I-76-a

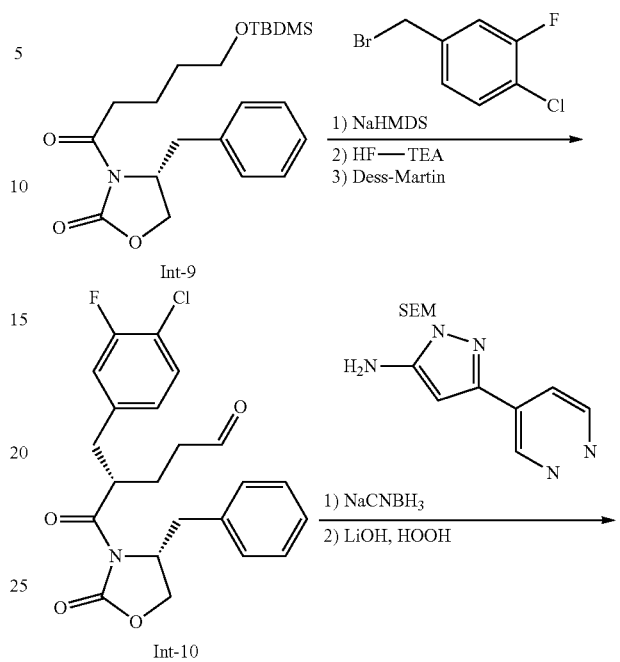

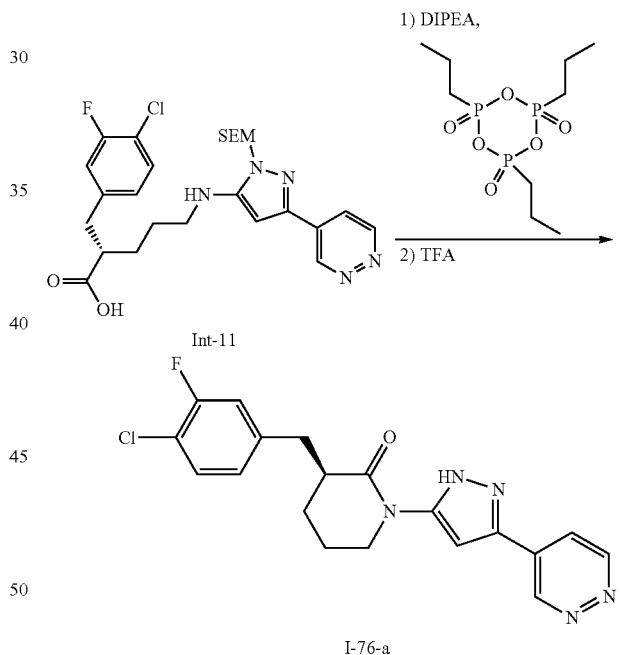

To a solution of Int-9 (3 g, 7.67 mmol) in dry THE (50 mL), cooled to −78° C. under N₂, was added a solution of NaHMDS in THE (2M, 4.2 mL, 8.44 mmol) dropwise while keeping the temperature below −65° C. The mixture was stirred at −78° C. for 2 h, and then the solution of 4-(bromomethyl)-1-chloro-2-fluorobenzene (4.26 g, 19.18 mmol) in dry THE (30 mL) was added. The mixture was stirred at −78° C. to room temperature for 12 h then cooled to −78° C. and quenched with saturated aqueous NaHCO₃ (80 mL). The aqueous phase was extracted with EtOAc (100 ml×5) then combined organic layers were dried over anhydrous Na₂SO₄ and concentrated in vacuo. The residue was purified by column chromatography to obtain the alkylated product (2.5 g, 4.69 mmol) that was dissolved in THF (30 mL) and treated with HF-Pyr (2.32 g, 23.45 mmol) dropwise. The mixture was stirred for 2 h than treated with EtOAc (50 mL), concentrated in vacuo and purified by column chromatography to give the alcohol (1.3 g, 3.1 mmol). The alcohol was dissolved in $CH_2C_2$ (15 mL) and Dess-Martin reagent (1.97 g, 4.65 mmol) and $NaHCO_3$ (0.52 g, 6.21 mmol) was added. The mixture was stirred for 1 h then treated with saturated aqueous $NaS_2O_4$ (30 mL) and saturated aqueous $NaHCO_3$ (20 mL). The aqueous was extracted with EtOAc (5×50 mL), dried over $Na_2SO_4$, and concentrated in vacuo. The residue was purified by column to give Int-10 (1.16 g, 90%).

To a solution of Int-10 (260 mg, 0.62 mmol) in MeOH (5 mL) was added 3-(pyridazin-4-yl)-1-((2-(trimethylsilyl) ethoxy) methyl)-1H-pyrazol-5-amine (183 mg, 0.62 mmol) and AcOH (0.5 mL). After 2 h, $NaBH_3CN$ (79 mg, 1.25 mmol) was added, and the mixture was stirred at room temperature for 12 h. The mixture was quenched with ice water (10 mL) and extracted with EtOAc (5×30 mL). The combined organic layers were dried over anhydrous $Na_2SO_4$ and concentrated in vacuo. The residue was purified by column chromatography to obtain the amine (250 mg, 0.36 mmol) that was dissolved in $THF/H_2O$ (5 mL) and treated with LiOH (25 mg, 1.08 mmol) and $H_2O_2$ (75 mg, 2.17 mmol). The mixture was stirred at room temperature for 30 min then quenched with saturated aqueous $NH_4Cl$ (20 mL) and extracted with EtOAc (5×40 mL). The combined organic layers were dried over anhydrous $Na_2SO_4$ and concentrated in vacuo to give Int-11 (170 mg, 91%).

To a solution of Int-11 (170 mg, 0.32 mmol) in DMA (4 mL) was added DIPEA (82 mg, 0.64 mmol) and propanephosphonic acid anhydride (203 mg, 0.64 mmol). The mixture was stirred at room temperature for 1 h the treated with water (15 ml) and extracted with EtOAc (3×20 mL). The combined organic layers were dried over anhydrous $Na_2SO_4$, concentrated in vacuo and residue was purified by column chromatography to give the lactam (140 mg, 85%). The lactam (30 mg, 0.06 mmol) was dissolved in $CH_2Cl_2$ (2 mL) and treated with TFA (0.5 mL). The mixture was stirred at room temperature for 1 h then concentrated in vacuo. The residue was purified by Prep-HPLC to give I-76-a (19 mg, 85%).

Chiral LC: Ret time 3.73 min on Chiralpak Cellulose-SJ, 4.6*100 mm, 5 μm eluting with 20% Methanol (0.2% methanol ammonia) in $CO_2$ at 3.00 mL/min at 140.1 bar and detection at 214 nm.

The following compounds were made in similar fashion: I-77-a, I-84-a, I-85-a.

Method X: Chiral Separation of Compound I-75 to Provide Compounds 175-a and I-75-b

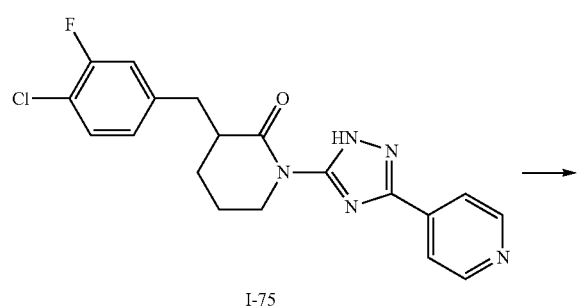

I-75

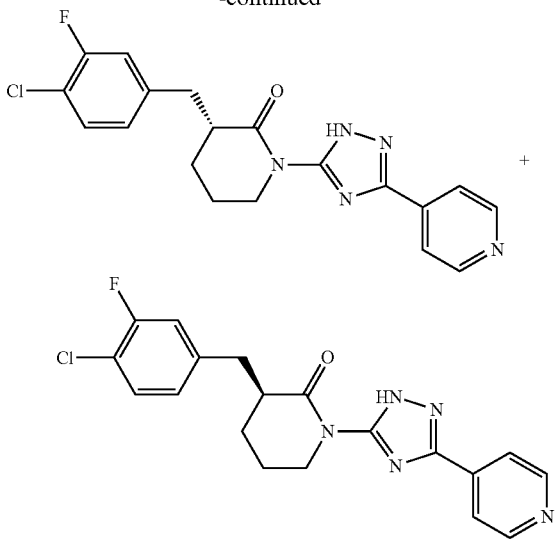

Compound I-75 was dissolved in $CH_2Cl_2$ and methanol and purified by supercritical fluid chromatography on a Chiral ART SA, 21.2×250 mm, 5 μm column eluting with 40% methanol in $CO_2$ at a flow rate of 50 mL/min at 125 bar pressure to afford the title compounds.

Peak 1—Chiral LC: Ret time 3.90 min on a Chiral ART SA, 4.6×250 mm, 5 μm eluting with 40% methanol in $CO_2$ with 0.2% $NH_3$ as a modifier at 4 mL/min and 125 Bar.

Peak 2—Chiral LC: Ret time 6.05 min on a Chiral ART SA, 4.6×250 mm, 5 μm eluting with 40% methanol in $CO_2$ with 0.2% $NH_3$ as a modifier at 4 mL/min and 125 Bar.

Method Y: Chiral Separation of Compound I-74 to Provide Compounds 174-a and I-74-b

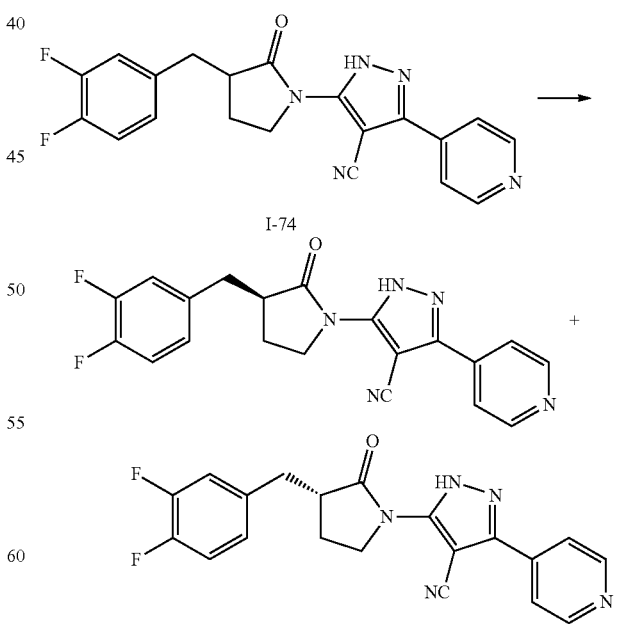

Compound I-74 (300 mg, 0.79 mmol) was dissolved in methanol then purified by supercritical fluid chromatography on a Chiralpak AD 20*250 mm, 10 μm (Daicel) column eluting with 0.2% methanol Ammonia in $CO_2$ at a flow rate of 80 g/min and 100 bar pressure to afford the title compounds.

Peak 1-Chiral LC: Ret time 3.24 min on a Chiralpak AD-H, 4.6*100 mm, 5 μm column eluting with $CO_2$/MeOH (0.2% Methanol Ammonia)=65/35 at 4 ml/min at 156 bar and detection at 214 nm.

Peak 2-Chiral LC: Ret time 4.04 min on a Chiralpak AD-H, 4.6*100 mm, 5 μm column eluting with $CO_2$/MeOH (0.2% Methanol Ammonia)=65/35 at 4 ml/min at 159 bar and detection at 214 nm.

Method Z: Chiral Separation of Compound I-82 to Provide Compounds 182-a and I-82-b

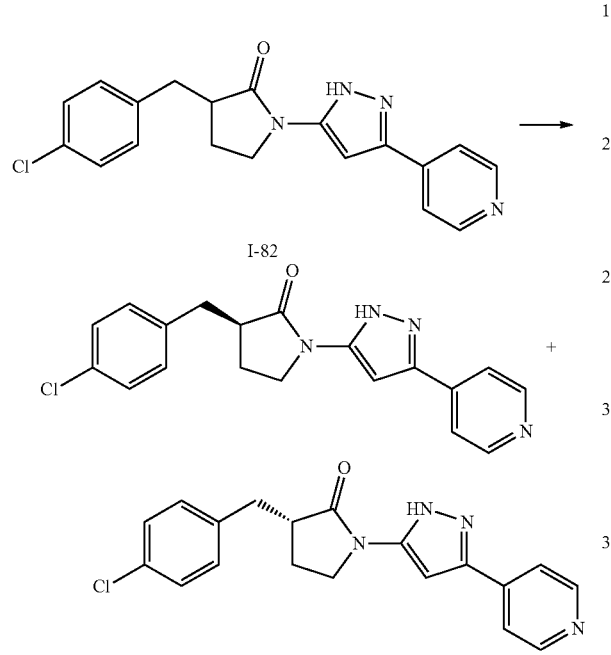

Compound I-82 (250 mg, 0.71 mmol) was dissolved in a mixture of methanol, acetonitrile, ethanol and isopropylamine and purified by supercritical fluid chromatography on a Chiralpak AS-H, 20×250 mm, 5 M, eluting with 20% in ethanol in $CO_2$ at a flow rate of 50 mL/min at 99.5 bar pressure to afford the title compounds.

Peak 1—Chiral LC: Ret time 14.89 mins on Chiralpak AS, 4.6×250 mm, 5 m eluting with 20% in ethanol in $CO_2$ at 2.4 mL/min and 100 Bar with detection at 254 nm.

Peak 2—Chiral LC: Ret time 15.14 mins on Chiralpak AS, 4.6×250 mm, 5 m eluting with 20% in ethanol in $CO_2$ at 2.4 mL/min and 100 Bar with detection at 254 nm.

Method AA: Chiral Separation of Compound I-54 to Provide Compounds I-54-a and I-54-b

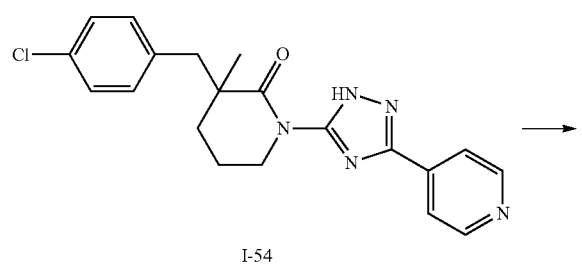

-continued

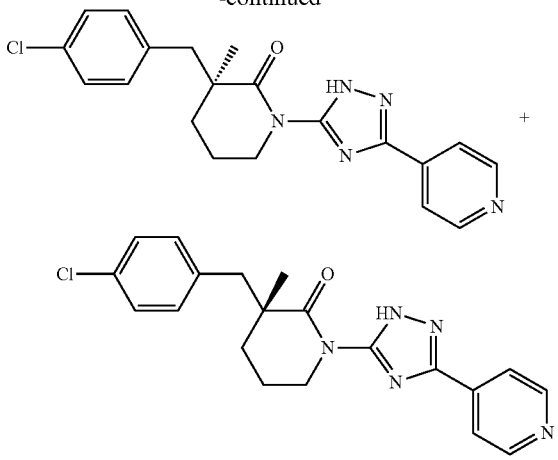

Compound I-54 (90 mg, 0.236 mmol) was dissolved in methanol then purified by supercritical fluid chromatography on an OD 20*250 mm, 10 μm (Daicel), CO2/MEOH (0.2% Methanol Ammonia)=65/35, at a flow rate of 80 g/min and 100 bar pressure to afford the title compounds.

Peak 1-Chiral LC: Ret time 2.33 min on OD-H 4.6*100 mm Sum CO2/MEOH (0.2% Methanol Ammonia)=65/35 at 4 ml/min at 120 bar and detection at 214 nm.

Peak 1-Chiral LC: Ret time 2.62 min on OD-H 4.6*100 mm Sum CO2/MEOH (0.2% Methanol Ammonia)=65/35 at 4 ml/min at 120 bar and detection at 214 nm.

Method AB: Chiral Separation of Compound I-46 to Provide Compounds I-46-a and I-46-b

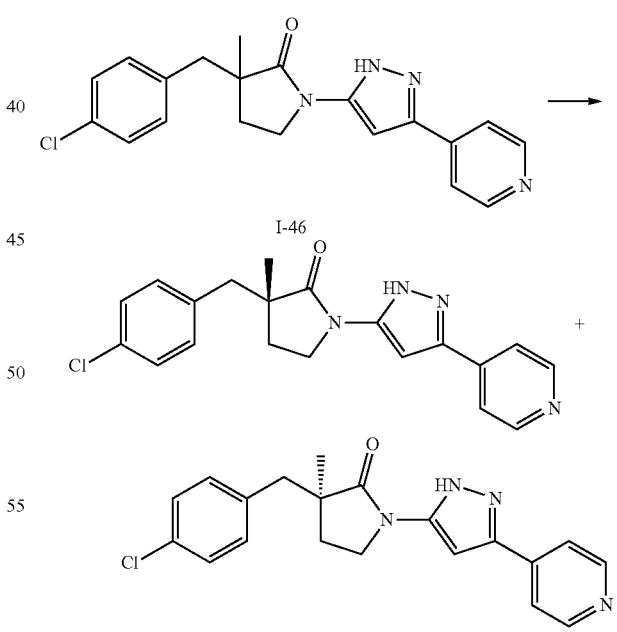

Compound I-46 (100 mg, 0.272 mmol) was dissolved in methanol then purified by supercritical fluid chromatography on a Chiralpak AS 20*250 mm, 10 μm column eluting with 50% methanol with 1.0% methanol ammonia in $CO_2$ at a flow rate of 80 g/min and 100 bar pressure to afford the title compounds.

Peak 1-Chiral LC: Ret time 1.14 min on a Chiralpak AS-3, 4.6*100 mm, 3 μm column eluting with 50% methanol with 1.0% methanol ammonia in CO₂ at 3 ml/min at 100 bar and detection at 214 nm.

Peak 2-Chiral LC: Ret time 2.48 min on a Chiralpak AS-3, 4.6*100 mm, 3 μm column eluting with 50% methanol with 1.0% methanol ammonia in CO₂ at 3 ml/min at 100 bar and detection at 214 nm.

Method AC: Chiral Separation of Compound I-69 to Provide Compounds I-69-a and I-69-b

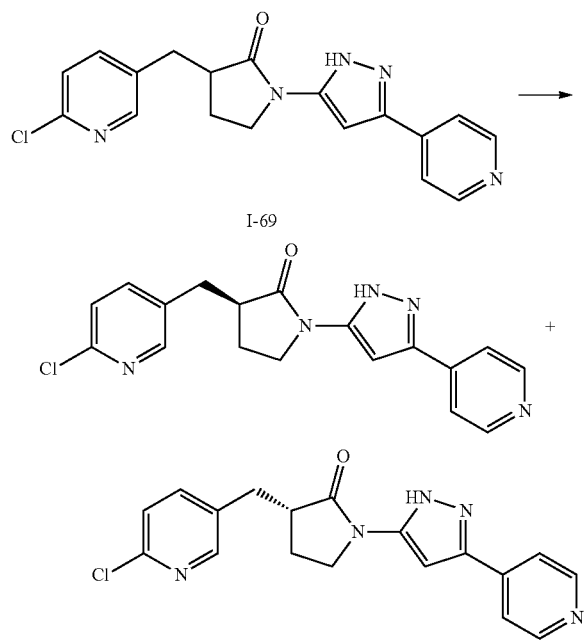

I-69

Compound I-69 (134 mg, 0.38 mmol) was dissolved in ethanol and purified on Chiralpak AS-V, 76.5×300 mm, 20 μm, eluting with 30% ethanol in heptane with 0.5% isopropylamine as a modifier at a flow rate of 275 mL/min to afford the title compounds.

Peak 1—Chiral LC: Ret time—3.02 min on Chirapak AS-H, 4.6×50 mm, 5 μm, eluting with 30% ethanol in CO₂ with 0.5% isopropylamine as a modifier at 0.8 mL/min with detection at 254 nm.

Peak 2—Chiral LC: Ret time—4.44 min on Chirapak AS-H, 4.6×50 mm, 5 μm, eluting with 30% ethanol in CO₂ with 0.5% isopropylamine as a modifier at 0.8 mL/min with detection at 254 nm.

Method AD: Chiral Separation of Compound I-69 to Provide Compounds I-69-a and I-69-b

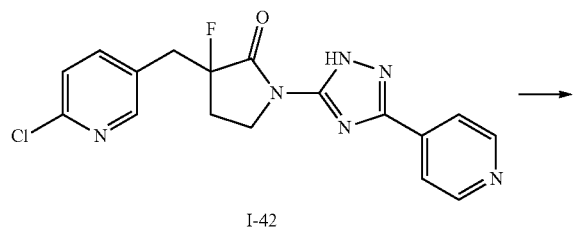

I-42

-continued

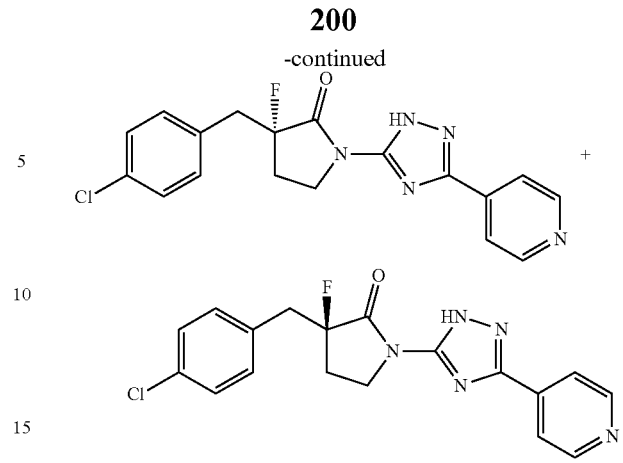

Compound (270 mg, 0.72 mmol) was dissolved in methanol (30 ml) then purified by supercritical fluid chromatography on Chiralpak OJ 20*250 mm, 10 μm (Daicel) column eluting with CO₂/EtOH (1.0% Methanol Ammonia)=65/35 at a flow rate of 100 g/min and 100 bar pressure to afford the title compounds.

Peak 1—Chiral LC: Ret time 4.058 min on Chiralpak OJ-3, 4.6*100 mm, 3 μm column eluting CO₂/EtOH [1% NH3 (7M in MeOH)]=80/20 at a flow rate of 3 ml/min at 2000 psi and detection at 214 nm.

Peak 2—Chiral LC: Ret time 3.447 min on Chiralpak OJ-3, 4.6*100 mm, 3 μm column eluting CO₂/EtOH [1% NH3 (7M in MeOH)]=80/20 at a flow rate of 3 ml/min at 2000 psi and detection at 214 nm.

Method AE: Chiral Separation of Compound I-55 to Provide Compounds I-55-a and I-55-b

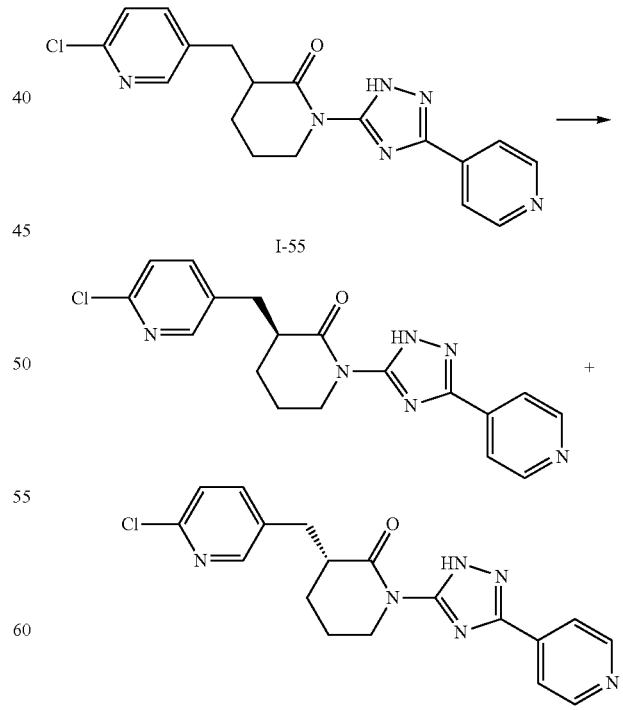

I-55

Compound I-55 (240 mg, 0.65 mmol) was dissolved in a mixture of methanol, acetonitrile and formic acid then purified by supercritical fluid chromatography on a Chiralpak AD-H, 10×250 mm, 5 µm eluting with 30% isopropanol in CO₂ at a flow rate of 15 mL/min to afford the title compounds.

Peak 1—Chiral LC: Ret time 7.05 min on Chiralpak AD-H, 4.6×250 mm, 5 µm eluting with 35% isopropanol in CO₂ at 4 mL/min.

Peak 2—Chiral LC: Ret time 8.36 min on Chiralpak AD-H, 4.6×250 mm, 5 µm eluting with 35% isopropanol in CO₂ at 4 mL/min.

Method AF: Chiral Separation of Compound I-49 to Provide Compounds I-49-a and I-49-b

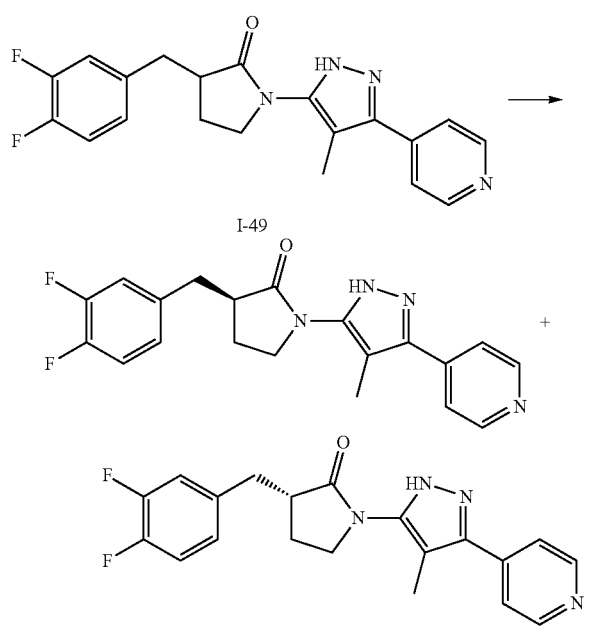

Compound I-49 (134 mg, 0.36 mmol) was dissolved in ethanol and purified by supercritical fluid chromatography on a Lux A2, 21.2 mm×250 mm, 5 µm, eluting with 40% ethanol in CO₂ with 0.2% NH₃ as a modifier at 125 bar pressure and a flow rate of 50 mL/min to afford the title compounds.

Peak 1—Chiral LC: Ret time 1.43 min on Lux A2, 4.6 mm×250 mm, 5 m eluting with 40% ethanol in CO₂ with 0.2% NH3 as a modifier at 4 mL/min and 125 Bar with detection at 210 to 400 nm.

Peak 2—Chiral LC: Ret time 1.69 on Lux A2, 4.6 mm×250 mm, 5 m eluting with 40% ethanol in CO₂ with 0.2% NH3 as a modifier at 4 mL/min and 125 Bar with detection at 210 to 400 nm.

Method AG: Chiral Separation of Compound I-48 to Provide Compounds I-48-a and I-48-b

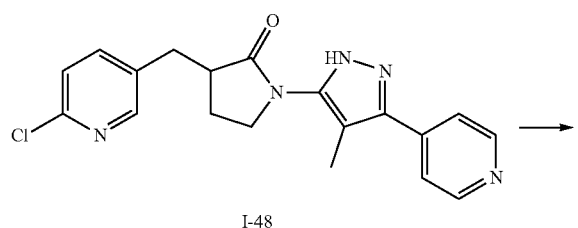

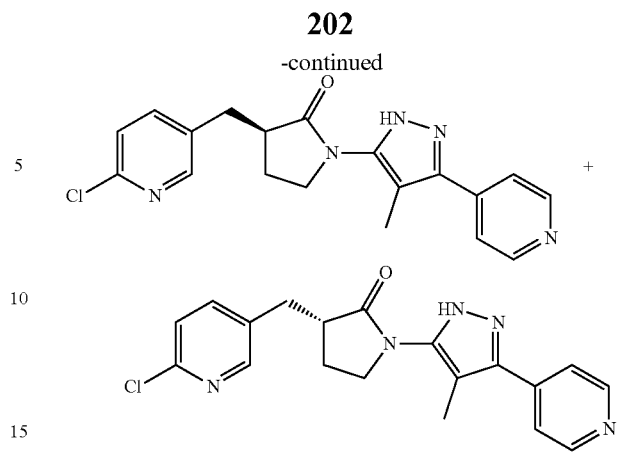

Compound I-48 (100%, 165 mg, 0.449 mmol) was dissolved in ethanol then purified by supercritical fluid chromatography on a Lux A2, 21.2 mm×250 mm, 5 µm, eluting with 30% ethanol in CO₂ with 0.2% NH₃ as a modifier at 125 bar pressure and a flow rate of 50 mL/min to afford the title compounds.

Peak 1—Chiral LC: Ret time 3.25 on Lux A2, 4.6 mm×250 mm, 5 µm, eluting with 40% ethanol in CO₂ with 0.2% NH₃ as a modifier at 4 mL/min with detection at 210 to 400 nm.

Peak 2—Chiral LC: Ret time 3.78 on Lux A2, 4.6 mm×250 mm, 5 µm, eluting with 40% ethanol in CO₂ with 0.2% NH₃ as a modifier at 4 mL/min with detection at 210 to 400 nm.

Method AH: Chiral Separation of Compound I-71 to Provide Compounds I-71-a and I-71-b

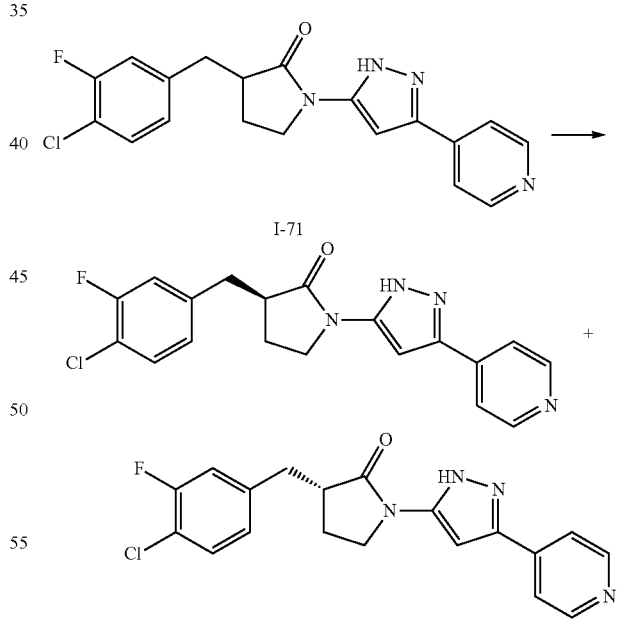

Compound I-71 (256 mg, 0.69 mmol) was dissolved in a mixture of CH₂Cl₂, ethanol, heptane and isopropylamine and purified on a Chiralcel AS-V, 76.5×500 mm, 20 µm, eluting with 15% ethanol in heptane with 0.5% isopropylamine as a modifier at a flow rate of 275 mL/min to afford the title compounds.

Peak 1—Chiral LC: Ret time 3.91 min on Chirapak AS-H, 4.6×50 mm, 5 µm, eluting with 15% ethanol in CO₂ with 0.5% isopropylamine as a modifier at 2.4 mL/min and 100 Bar with detection at 254 nm.

Peak 2—Chiral LC: Ret time 5.11 min on Chirapak AS-H, 4.6×50 mm, 5 μm, eluting with 15% ethanol in CO₂ with 0.5% isopropylamine as a modifier at 2.4 mL/min and 100 Bar with detection at 254 nm.

Method AI: Chiral Separation of Compound I-41 to Provide Compounds I-41-a and I-41-b

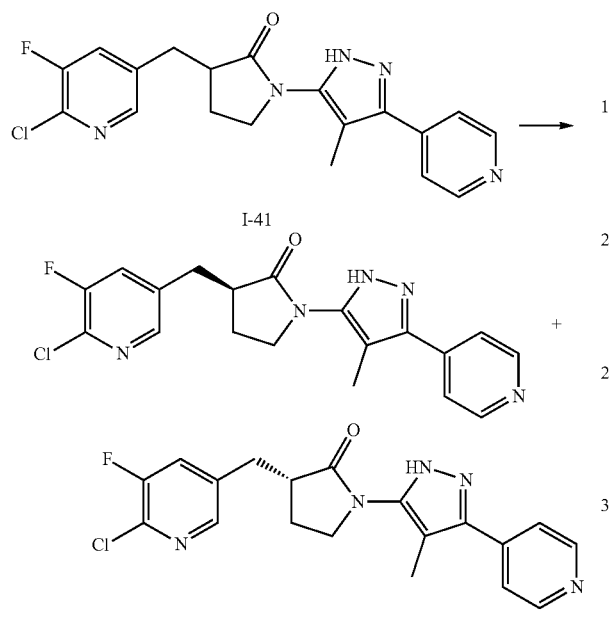

Compound I-41 (181 mg, 0.46 mmol) dissolved in ethanol and purified by chiral supercritical fluid chromatography on a Lux A2 column, 21.2 mm×250 mm, 5 μm, eluting with 45% ethanol in CO₂ with 0.2% NH₃ as a modifier at 100 bar pressure and a flow rate of 50 mL/min to afford the title compounds.

Peak 1—Chiral LC: Ret time 1.80 min on Lux A2, 4.6 mm×250 mm, 5 μm, eluting with 45% ethanol in CO₂ with 0.2% NH₃ as a modifier at 4 mL/min with detection at 210 to 400 nm.

Peak 2—Chiral LC: Ret time 2.14 min on Lux A2, 4.6 mm×250 mm, 5 m), eluting with 45% ethanol in CO₂ with 0.2% NH₃ as a modifier at 4 mL/min with detection at 210 to 400 nm.

Method AJ: Chiral Separation of Compound I-72 to Provide Compounds I-72-a and I-72-b

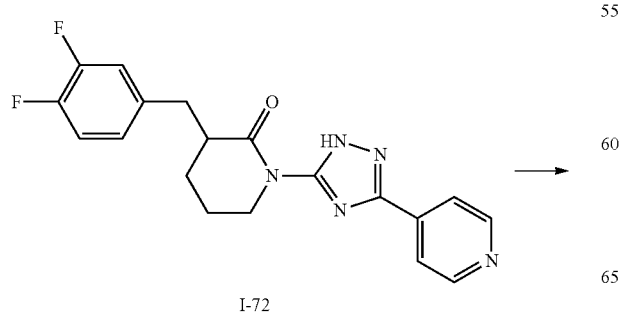

I-72

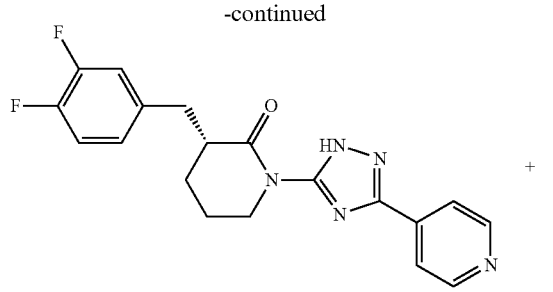

Compound I-72 (152 mg, 0.41 mmol) was dissolved in methanol, acetonitrile and formic acid, then purified by supercritical fluid chromatography on a Chiralpak AD-H, 10×250 mm, 5 μm, eluting with 40% methanol in CO₂ at a flow rate of 15 mL/min to afford the title compounds.

Peak 1—Chiral LC: Ret time 8.47 min on Chiralpak AD-H, 4.6×250 mm, 5 μm eluting with 40% methanol in CO₂ at 4 mL/min.

Peak 2—Chiral LC: Ret time 17.87 min on Chiralpak AD-H, 4.6×250 mm, 5 μm eluting with 40% methanol in CO₂ at 4 mL/min.

Method AK: Chiral Separation of Compound I-47 to Provide Compounds I-47-a and I-47-b Compound I-47 (101 mg, 0.21 mmol) was dissolved CH₂C₂ and methanol and purified by supercritical fluid chromatography on a Lux C3, 21.2×250 mm, 5 µm column eluting with 30% ethanol in CO₂ at a flow rate of 50 mL/min at 100 bar pressure to afford the title compounds.

Peak 1—Chiral LC: Ret time 2.20 min on Lux C3, 4.6×250 mm, 5 µm eluting with 30% ethanol in CO₂ at 4 mL/min and 125 Bar.

Peak 2—Chiral LC: Ret time 2.79 min on Lux C3, 4.6×250 mm, 5 µm eluting with 30% ethanol in CO₂ at 4 mL/min and 125 Bar.

Method AL: Chiral Separation of Int-12 and Deprotection to Provide Compounds I-66-a and I-66-b

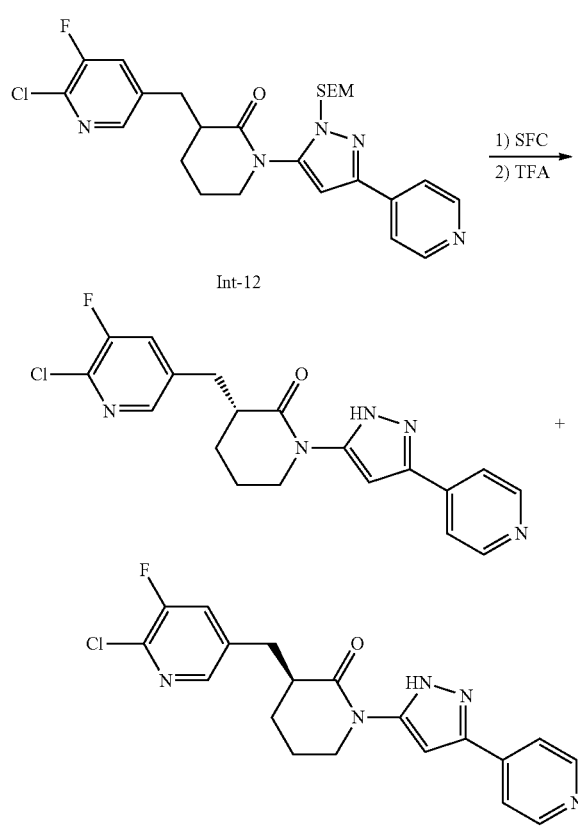

Int-12 (220 mg, 0.43 mmol) was dissolved in acetonitrile and purified by HPLC on a Chiralpak IG, 20 mm×250 mm, 5 µm, eluting with 10% isopropanol in acetonitrile with 0.2% NH₃ at a flow rate of 21 mL/min to afford the title compounds.

Peak 1 was re-purified by supercritical fluid chromatography on a Lux A1, 21.2×250 mm, 5 µm, eluting with 50% methanol in CO₂ with 0.2% NH₃ as a modifier at a flow rate of 50 mL/min at 125 bar to afford the title compounds.

Peak 1—Chiral LC: Ret time 1.53 min on Amy-C, 4.6 mm×250 mm, 5 m eluting with 60% methanol in CO₂ with 0.2% NH3 as a modifier at 4 mL/min and 125 Bar and detection at 254 nm.

Peak 2—Chiral LC: Ret time 2.69 min on Amy-C, 4.6 mm×250 mm, 5 m eluting with 60% methanol in CO₂ with 0.2% NH3 as a modifier at 4 mL/min and 125 Bar and detection at 254 nm.

The discrete enantiomers (30 mg, 0.06 mmol) were dissolved in CH₂C₂ (2 mL) and treated with TFA (0.5 mL). The mixture was stirred at room temperature for 1 h then concentrated in vacuo to provide the title compounds.

Method AM: Chiral Separation of Compound I-51 to Provide Compounds I-51-a and I-51-b

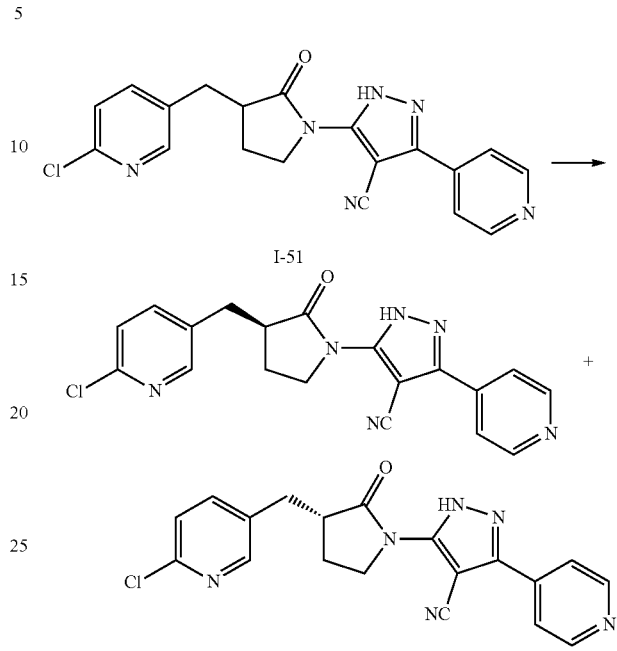

Compound I-51 (200 mg, 0.53 mmol) was dissolved in 30 mL methanol then purified by supercritical fluid chromatography on a Chiralpak AY 20*250 mm, 10 µm (Daicel) column eluting with CO₂/MeOH (0.2% Methanol Ammonia)=40/60 at a flow rate of 100 g/min and 100 bar pressure to afford the title compounds.

Peak 1—Chiral LC: Ret time 2.87 min on Chiralpak OD-H, 4.6*100 mm, 5 µm eluting with 50% ethanol (1% methanol ammonia) in CO₂ at 4.00 mL/min at 153.1 bar and detection at 214 nm.

Peak 2—Chiral LC: Ret time 3.64 min on Chiralpak OD-H, 4.6*100 mm, 5 µm eluting with 50% ethanol (1% methanol ammonia) in CO₂ at 4.00 mL/min at 151.1 bar and detection at 214 nm.

Method AN: Chiral Separation of Compound I-80 to Provide Compounds I-80-a and I-80-b

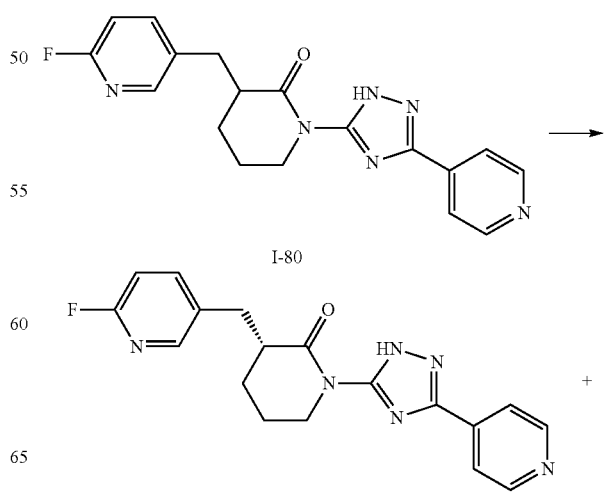

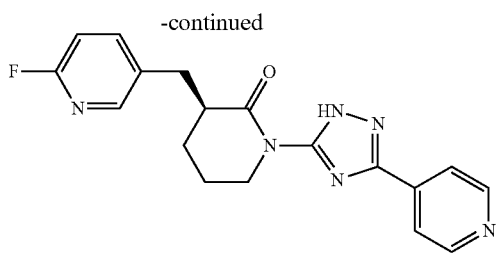

Compound I-80 (2.3 g, 6.5 mmol) was dissolved in methanol then purified by supercritical fluid chromatography on a chiralpak OZ 20*250 mm, 10 μm (Daicel) column eluting with CO$_2$/ETOH (1.0% Methanol Ammonia)=50/50 at a flow rate of 80 g/min and 100 bar pressure to afford the title compounds.

Peak 1-chiral LC: Ret time 2.02 min on chiralpak OZ 4.6*100 mm, 5 μm column eluting with CO2/ETOH (1.0% Methanol Ammonia)=60/40 at a flow rate of 4 mL/min and 155 bar and detection at 260 nm.

Peak 2-chiral LC: Ret time 2.61 min on chiralpak OZ 4.6*100 mm, 5 μm column eluting with CO2/ETOH (1.0% Methanol Ammonia)=60/40 at a flow rate of 4 mL/min and 154.7 bar and detection at 260 nm.

Method AO: Chiral Separation of Int-13 and Deprotection to Provide Compounds I-81-a and I-81-b

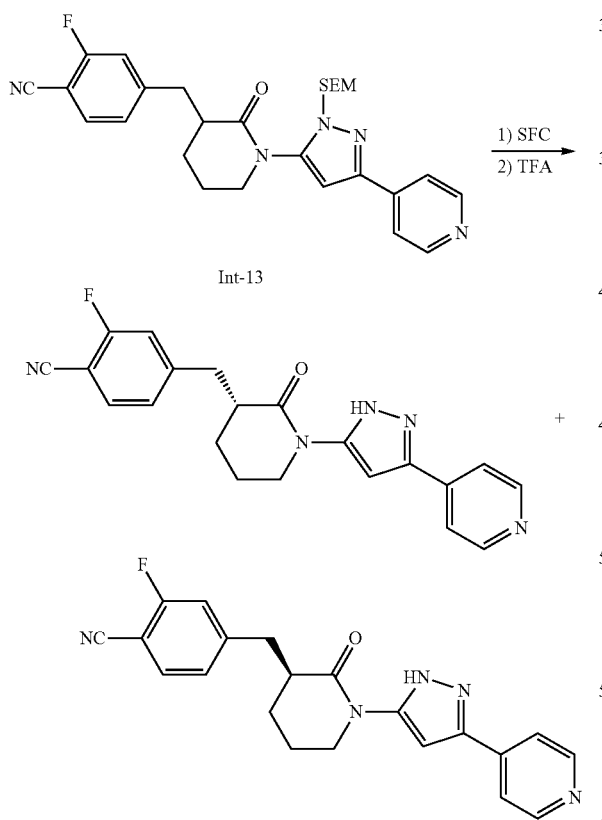

Int-13 (642 mg, 1.27 mmol) was dissolved in ethanol and CH$_2$C$_2$ (3:1) then purified by supercritical fluid chromatography on a Chiralpak IG, 20×250 mm, 5 μm column eluting with 30% ethanol in CO$_2$ with a 0.2% NH3 as a modifier at a flow rate of 50 mL/min and 100 bar pressure to afford the title compounds.

Peak 1—Chiral LC: Ret time 2.6 min on Chiralpak IG, 4.6×250 mm, 5 μm eluting with 35% ethanol in CO$_2$ with a 0.2% NH$_3$ as a modifier at 4 mL/min and 125 Bar pressure.

Peak 2—Chiral LC: Ret time 3.02 min on Chiralpak IG, 4.6×250 mm, 5 μm eluting with 35% ethanol in CO$_2$ with a 0.2% NH$_3$ as a modifier at 4 mL/min and 125 Bar pressure.

The discrete enantiomers (30 mg, 0.06 mmol) were dissolved in CH$_2$C$_2$ (2 mL) and treated with TFA (0.5 mL). The mixture was stirred at room temperature for 1 h then concentrated in vacuo to provide the title compounds.

Method AP: Chiral Separation of Compound I-37 to Provide Compounds I-37-a and I-37-b

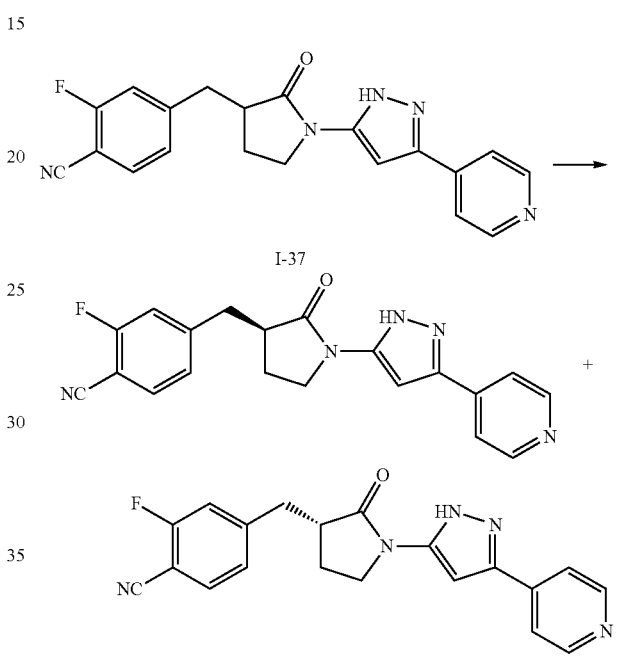

Compound I-37 (285 mg, 0.75 mmol) was dissolved in methanol, acetonitrile and formic acid and purified by supercritical fluid chromatography on a Chiralpak IC, 10×250 mm, 5 μm, eluting with 25% ethanol in CO$_2$ at a flow rate of 15 mL/min and 100 bar pressure to afford the title compounds.

Peak 1—Chiral LC: Ret time 10.99 min on Chiralpak IC, 4.6×250 mm, 5 μm, eluting with 25% ethanol in CO$_2$ at 4 mL/min.

Peak 2—Chiral LC: Ret time 13.35 min on Chiralpak IC, 4.6×250 mm, 5 μm, eluting with 25% ethanol in CO$_2$ at 4 mL/min.

Method AQ: Chiral Separation of Compound I-65 to Provide Compounds I-65-a and I-65-b

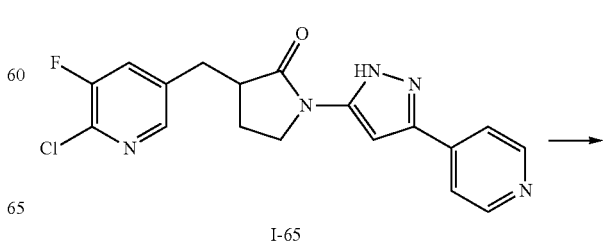

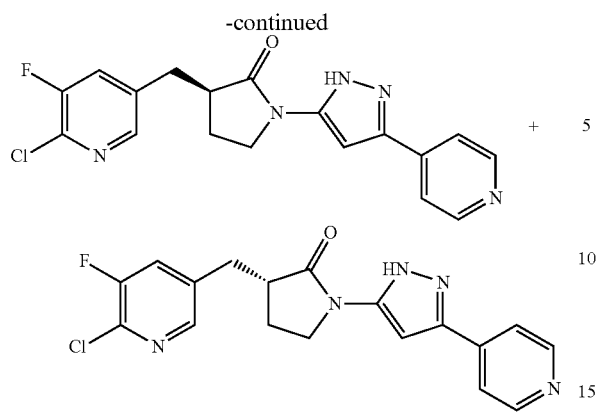

Compound I-65 (1.22 g, 3.28 mmol) was dissolved in methanol (90 ml) then purified by supercritical fluid chromatography on a Chiralpak AS-H, 20*250 mm, 10 μm column eluting with CO₂/EtOH (1.0% Methanol Ammonia)= 65/35 at a flow rate of 80 g/min and 100 bar pressure to afford the title compounds.

Peak 1—Chiral LC: Ret time 3.27 min on Chiralpak AS-H, 4.6×250 mm, Sum column eluting with 20% ethanol in CO₂ at a flow rate of 4 ml/min at 147.3 bar and detection at 260 nm.

Peak 2—Chiral LC: Ret time 4.44 min on Chiralpak AS-H, 4.6×250 mm, Sum column eluting with 20% ethanol in CO₂ at a flow rate of 4 ml/min at 149 bar and detection at 260 nm.

Method AR: Chiral Separation of Compound I-67 to Provide Compounds I-67-a and I-67-b

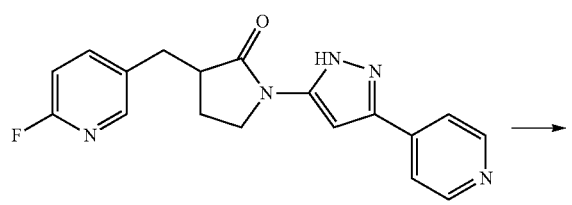

Compound I-67 (1.50 g, 4.45 mmol) was dissolved in methanol (160 ml) then purified by supercritical fluid chromatography on a Chiralpak AS-H, 20*250 mm, 10 μm column eluting with CO2/EtOH (1.0% Methanol Ammonia)= 60/40 at a flow rate of 80 g/min and 100 bar pressure to afford the title compounds.

Peak 1—Chiral LC: Ret time 1.86 min on Chiralpak AS-H, 4.6×100 mm, Sum column eluting with 25% ethanol in CO₂ at a flow rate of 4 ml/min at 149.4 bar and detection at 265 nm.

Peak 2—Chiral LC: Ret time 2.32 min on Chiralpak AS-H, 4.6×100 mm, Sum column eluting with 25% ethanol in CO₂ at a flow rate of 4 ml/min at 149 bar and detection at 265 nm.

Method AS: Chiral Separation of Compound I-39 to Provide Compounds I-39-a and I-39-b

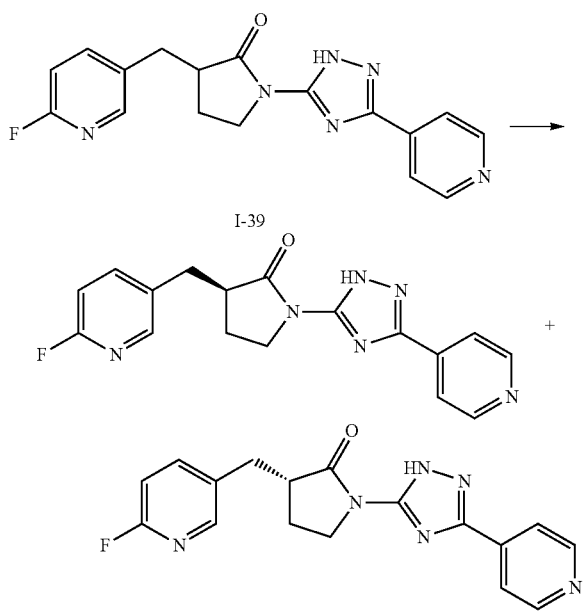

Compound I-39 (690 mg, 2.04 mmol) was dissolved in Methanol (45 mL) purified by supercritical fluid chromatography on a Chiralpak AS-H, 20*250 mm, 10 μm column eluting with CO2/ETOH (1.0% Methanol Ammonia)=80/20 at a flow rate of 80 g/min and 100 bar pressure to afford the title compounds.

Peak 1—Chiral LC: Ret time 1.487 min on Chiralpak AS-H, 4.6*100 mm, 3 μm column eluting with CO₂/MeOH [0.2% NH3(7M in MeOH)]=80/20 at 3 mL/min at 2000 psi and detection at 214 nm.

Peak 2—Chiral LC: Ret time 1.951 min on Chiralpak AS-H, 4.6*100 mm, 3 μm column eluting with CO₂/MeOH [0.2% NH3(7M in MeOH)]=80/20 at 3 mL/min at 2000 psi and detection at 214 nm.

Method AT: Chiral Separation of Compound I-60 to Provide Compounds I-60-a and I-60-b

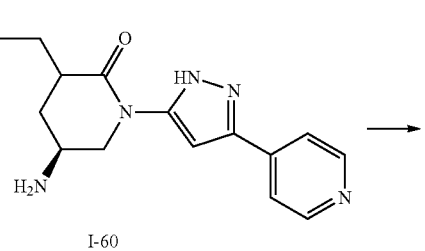

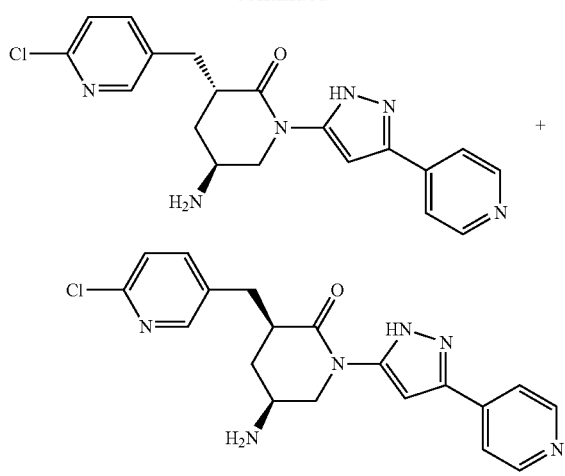

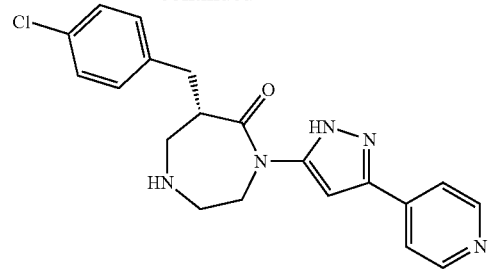

Compound I-60 (40 mg, 0.1 mmol) was dissolved in methanol (3 ml) then purified by supercritical fluid chromatography on 20*250 mm, 10 μm (Daicel) eluting $CO_2$/MEOH (1.0% Methanol Ammonia)=60/40 at a flow rate of 80 g/min and 100 bar pressure to afford the title compounds.

Peak 1—Chiral LC: Ret time 1.71 min on AS 4.6×100 mm, 3 μm column eluting with $CO_2$/MeOH [0.2% NH3(7M in MeOH)]=75/25 at a flow rate of 3 ml/min at 2000 psi and detection at 214 nm.

Peak 2—Chiral LC: Ret time 2.4 min on AS 4.6×100 mm, Sum column eluting with $CO_2$/MeOH [0.2% NH3(7M in MeOH)]=75/25 at a flow rate of 4 ml/min at 152.9 bar and detection at 214 nm.

Method AU: Chiral Separation of Compound I-38 to Provide Compounds I-38-a and I-38-b

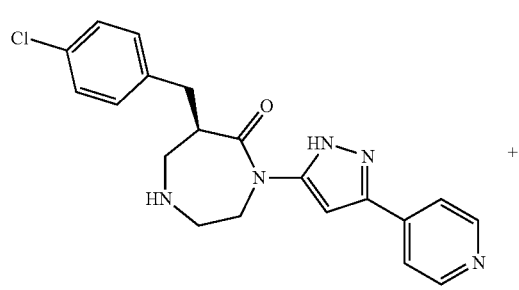

I-38

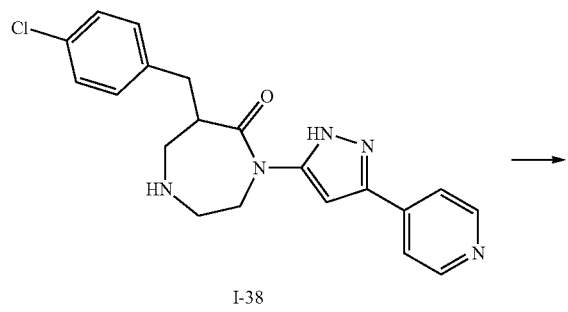

Compound I-38 (115 mg, 0.30 mmol) was dissolved in a mixture of methanol and diethylamine then purified by supercritical fluid chromatography on a Chiralcel OJ-H, 10×250 mm, 5 μm column eluting with 30% methanol in $CO_2$ at a flow rate of 15 mL/min with 0.2% diethylamine as a modifier to afford the title compounds.

Peak 1—Chiral LC: Ret time 3.09 min on Chiralcel OJ-H, 4.6×250 mm, 5 μm eluting with 35% methanol in $CO_2$ with 0.2% diethylamine at 4 mL/min and detection at 220 nm.

Peak 2—Chiral LC: Ret time 4.74 min on Chiralcel OJ-H, 4.6×250 mm, 5 μm eluting with 35% methanol in $CO_2$ with 0.2% diethylamine at 4 mL/min and detection at 220 nm.

Method AV: Chiral Separation of Compound I-73 to Provide Compounds I-73-a and I-73-b

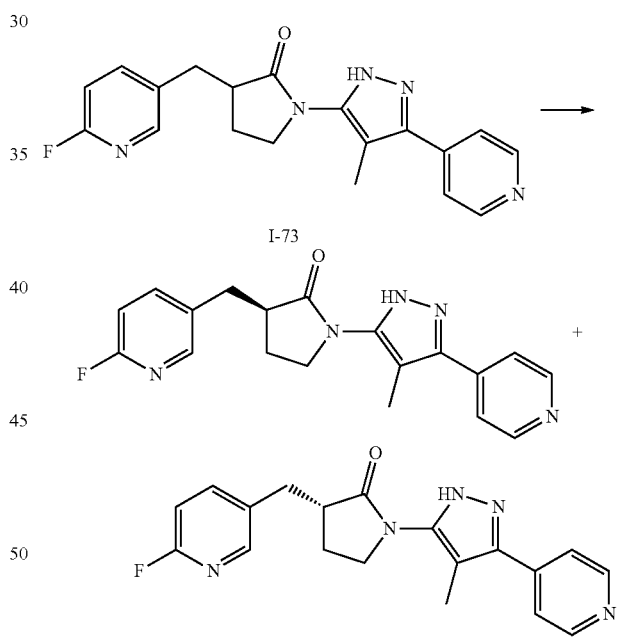

Compound I-73 (1.1 g, 3.13 mmol) was dissolved in a mixture of methanol and dichloromethane, then purified by supercritical fluid chromatography on a chiralpak OZ-H, 20*250 mm, 10 μm (Daicel) column eluting with CO2/MEOH (0.2% Methanol Ammonia)=45/55 at a flow rate of 80 g/min and 100 bar pressure to afford the title compounds.

Peak 1-chiral LC: Ret time 3.93 min on chiralpak OZ-H, 4.6*100 mm, 5 μm eluting with 35% methanol in $CO_2$ at 4.0 mL/min at 152.9 Bar and detection at 265 nm.

Peak 2-chiral LC: Ret time 5.49 min on chiralpak OZ-H, 4.6*100 mm, 5 μm eluting with 35% methanol in $CO_2$ at 4.0 mL/min at 157.3 Bar and detection at 265 nm.

Method AW: Chiral Separation of Compound I-61 to Provide Compounds I-61-a and I-61-b

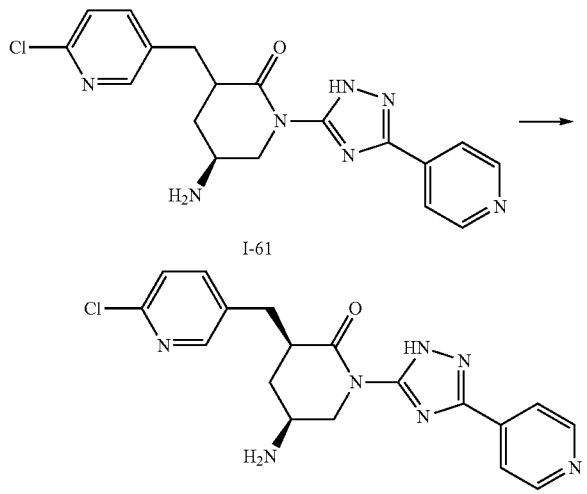

I-61

Compound I-61 (30 mg, 0.08 mmol) was dissolved in methanol (2 ml) then purified by supercritical fluid chromatography on AS 20*250 mm, 10 μm (Daicel) eluting CO2/MEOH (0.2% Methanol Ammonia)=60/40 at a flow rate of 80 g/min and 100 bar pressure to afford the title compounds.

Peak 1—Chiral LC: Ret time 1.61 min on AS 4.6×100 mm, 5um column eluting with CO$_2$/MeOH (0.2% MeOH ammonia)=75/25 at a flow rate of 4 ml/min at 153.2 bar and detection at 214 nm.

Method AX: Chiral Separation of Compound I-40 to Provide Compounds I-40-a and I-40-b

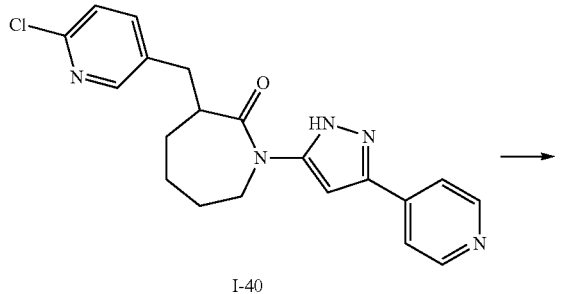

I-40

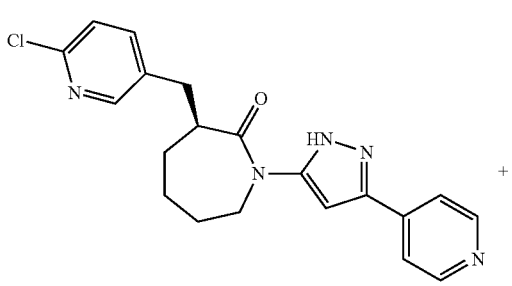

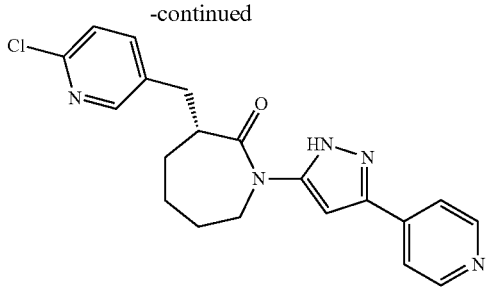

Compound I-40 (25 mg, 0.07 mmol) was dissolved in methanol then purified by supercritical fluid chromatography on a Chiralcel OD-H, 10×250 mm, 5 μm column eluting with 15% methanol in CO$_2$ at a flow rate of 15 mL/min and 100 bar pressure to afford the title compounds.

Peak 1—Chiral LC: Ret time 8.13 min on Chiralcel OD-H, 4.6×250 mm, 5 μm eluting with 20% Methanol in CO$_2$ at 4 mL/min at 100 Bar and detection at 254 nm.

Peak 2—Chiral LC: Ret time 10.60 min on Chiralcel OD-H, 4.6×250 mm, 5 μm eluting with 20% Methanol in CO$_2$ at 4 mL/min at 100 Bar and detection at 254 nm.

Method AY: Chiral Separation of Compound I-34 to Provide Compounds I-34-a and I-34-b

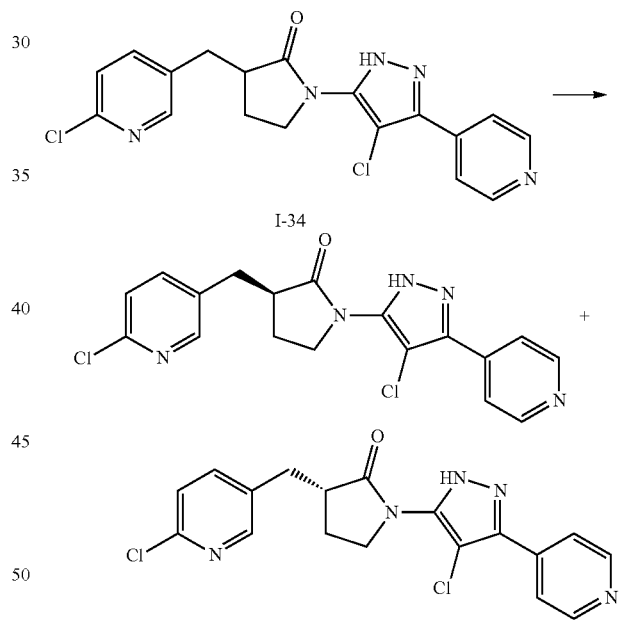

Compound I-34 (1.70 g, 4.38 mmol) was dissolved in methanol (140 ml) then purified by supercritical fluid chromatography on a Chiralpak OX, 20×250 mm, 10 μm column eluting with CO$_2$/MEOH (0.5% Methanol Ammonia)=40/60 at a flow rate of 80 g/min and 100 bar pressure to afford the title compounds.

Peak 1—Chiral LC: Ret time 2.48 min on Chiralpak OX-H, 4.6×100 mm, 5um column eluting with CO$_2$/MEOH (0.2% Methanol Ammonia)=55/45 at a flow rate of 4 ml/min at 160.5 bar and detection at 265 nm.

Peak 2—Chiral LC: Ret time 3.35 min on Chiralpak OX-H, 4.6×100 mm, 5um column eluting with CO$_2$/MEOH (0.2% Methanol Ammonia)=55/45 at a flow rate of 4 ml/min at 162.1 bar and detection at 265 nm.

Method AZ: Chiral Separation of Compound Int-14 and Deprotection to Provide Compounds I-78-a and I-78-b

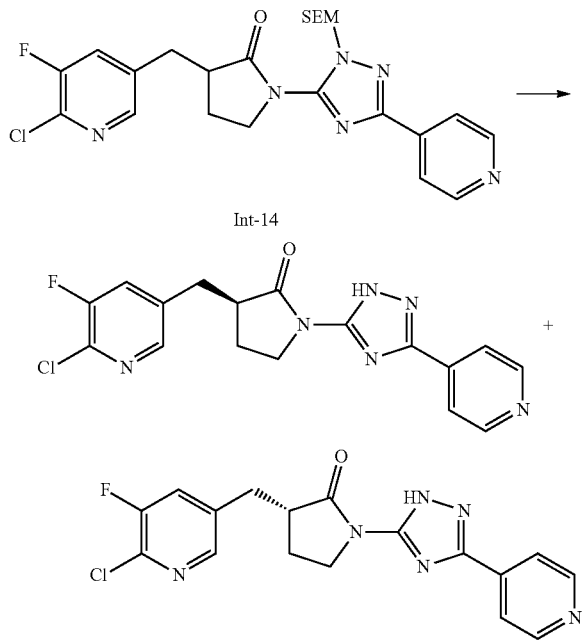

Int-14

Compound Int-14 (1 g, 1.99 mmol) was dissolved in a methanol (25 ml) then purified by supercritical fluid chromatography on a Chiralpak OX, 20*250 mm, 10 μm column eluting with CO₂/MEOH (1.0% Methanol Ammonia)=45/55 at a flow rate of 80 g/min and 100 bar pressure to afford the title compounds.

Peak 1—Chiral LC: Ret time 4.2 min on Chiralpak IG, 4.6×100 mm, Sum column eluting with 60% Methanol in CO₂ at a flow rate of 4 ml/min at 157.3 bar and detection at 260 nm.

Peak 2—Chiral LC: Ret time 2.77 min on Chiralpak IG, 4.6×100 mm, Sum column eluting with 60% Methanol in CO₂ at a flow rate of 4 ml/min at 149 bar and detection at 260 nm.

The discrete enantiomers were dissolved in CH₂Cl₂ and treated with TFA. The mixture was stirred at room temperature for 1 h then concentrated in vacuo to provide the title compounds.

Method BA: Chiral Separation of Compound I-79 to Provide Compounds I-79-a and I-79-b

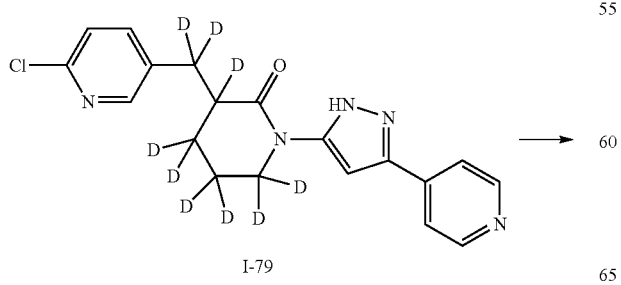

I-79

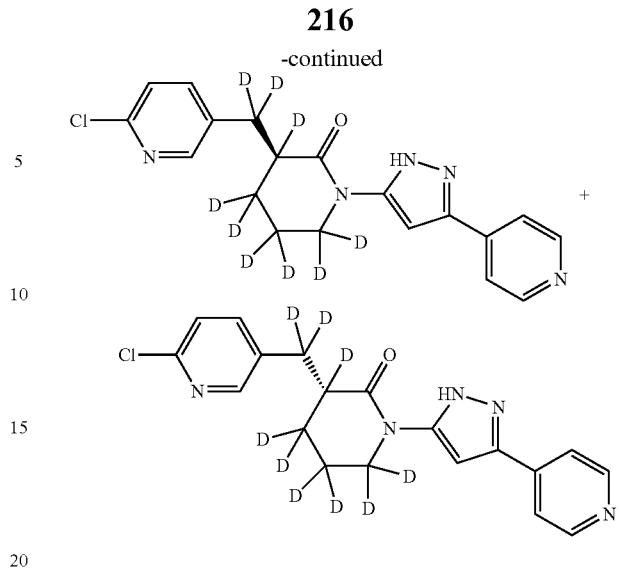

Compound I-79 (700 mg, 1.9 mmol) was dissolved in a mixture of methanol then purified by supercritical fluid chromatography on a chiralpak AS 20*250 mm, 10 μm (Daicel) column eluting with CO₂/MEOH (0.4% Methanol Ammonia)=50/50 at a flow rate of 80 g/min and 100 bar pressure to afford the title compounds.

Peak 1-chiral LC: Ret time 2.17 min on chiralpak AS 4.6*100 mm, 5 μm column eluting with CO₂/MEOH (0.2% Methanol Ammonia)=65/35 at a flow rate of 4 mL/min and 145.5 bar and detection at 260 nm.

Peak 2-chiral LC: Ret time 3.61 min on chiralpak AS 4.6*100 mm, 5 μm column eluting with CO₂/MEOH (0.2% Methanol Ammonia)=65/35 at a flow rate of 4 mL/min and 150.5 bar and detection at 260 nm.

Method BB: Chiral Separation of Compound I-32 to Provide Compounds I-32-a and I-32-b

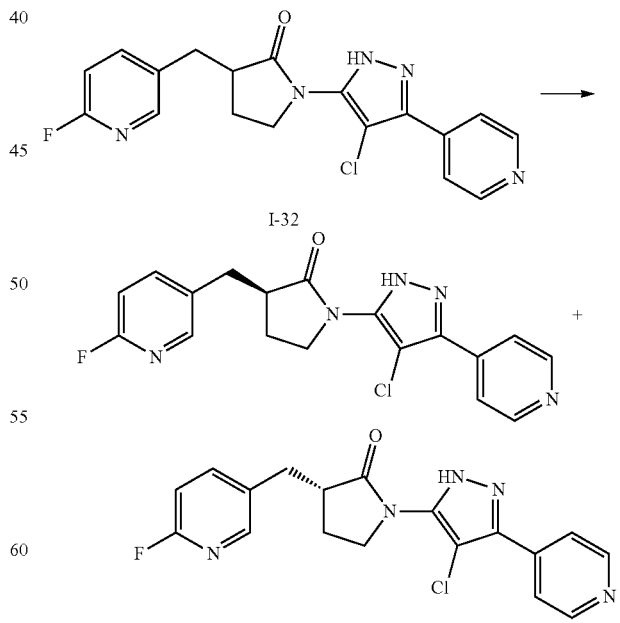

Compound I-32 (1500 mg, 4.04 mmol) was dissolved in methanol (30 ml) then purified by supercritical fluid chromatography on OX, 20*250 mm, 10 μm column eluting with CO2/MEOH (0.2% Methanol Ammonia)=45/55 at a flow rate of 80 g/min and 100 bar pressure to afford the title compounds.

Peak 1—Chiral LC: Ret time 2.22 min on Chiralpak OX-H, 4.6×100 mm, 5 µm column eluting with 0.2% methanol in CO2 at a flow rate of 4 ml/min at 157.3 bar and detection at 260 nm.

Peak 2—Chiral LC: Ret time 2.99 min on Chiralpak OX-H, 4.6×250 mm, 5 µm column eluting with 0.2% methanol in CO2 at a flow rate of 4 ml/min at 158.1 bar and detection at 260 nm.

Method BC: Chiral Separation of Compound I-36 to Provide Compounds I-36-a and I-36-b

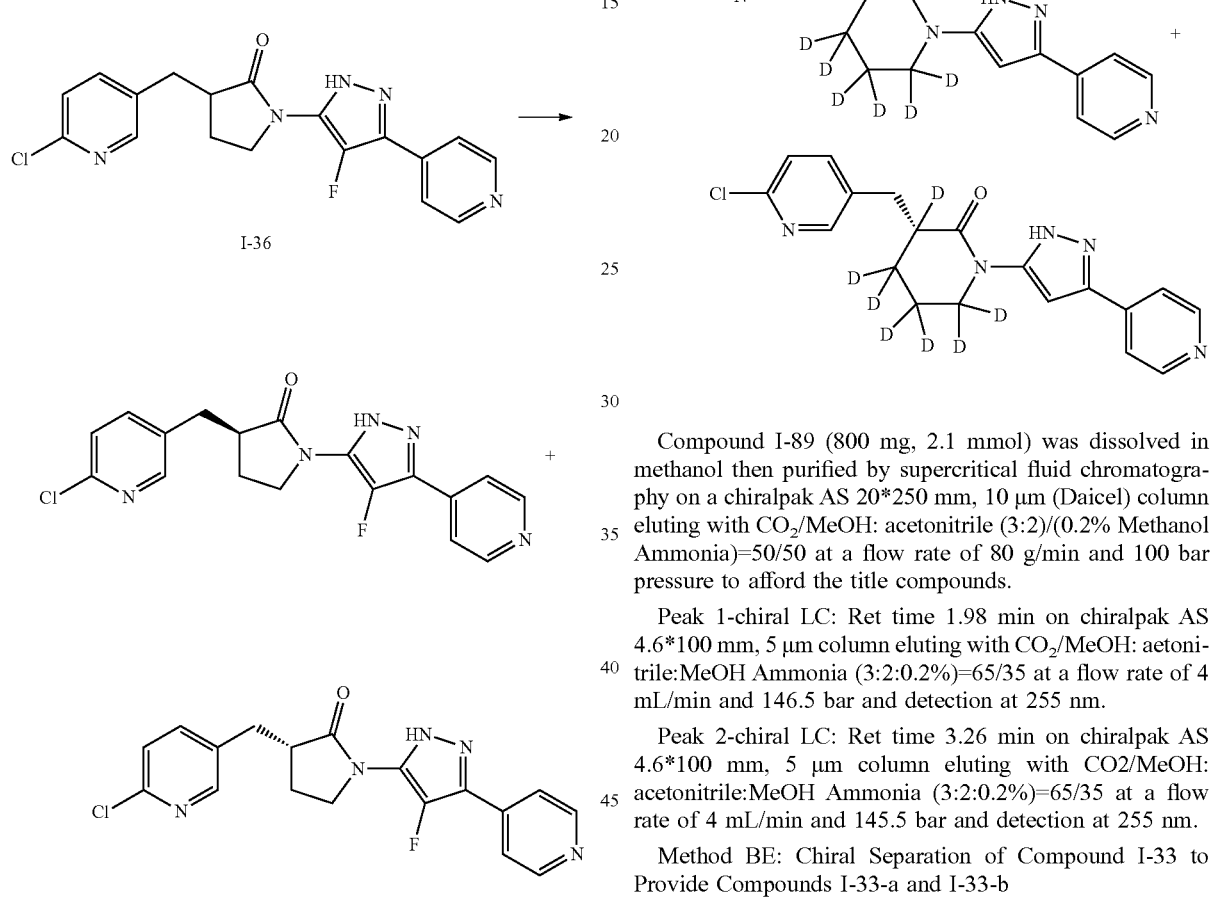

I-36

Compound I-36 (580 mg, 1.56 mmol) was dissolved in a mixture of 80 mL methanol and dichloromethane then purified by supercritical fluid chromatography on a Chiralpak OX 20*250 mm, 10 µm (Daicel) column eluting with CO$_2$/(MeOH/ACN (0.2% Methanol Ammonia)=1:1)=55/45 at a flow rate of 110 g/min and 100 bar pressure to afford the title compounds.

Peak 1—Chiral LC: Ret time 2.29 min on Chiralpak OX-H, 4.6*100 mm, 5 µm eluting with 45% Methanol (0.2% methanol ammonia) in CO$_2$ at 4.00 mL/min at 163.8 bar and detection at 214 nm.

Peak 2—Chiral LC: Ret time 3.02 min on Chiralpak OX-H, 4.6*100 mm, 5 µm eluting with 45% Methanol (0.2% methanol ammonia) in CO$_2$ at 4.00 mL/min at 164.7 bar and detection at 214 nm.

Method BD: Chiral Separation of Compound I-89 to Provide Compounds I-89-a and I-89-b

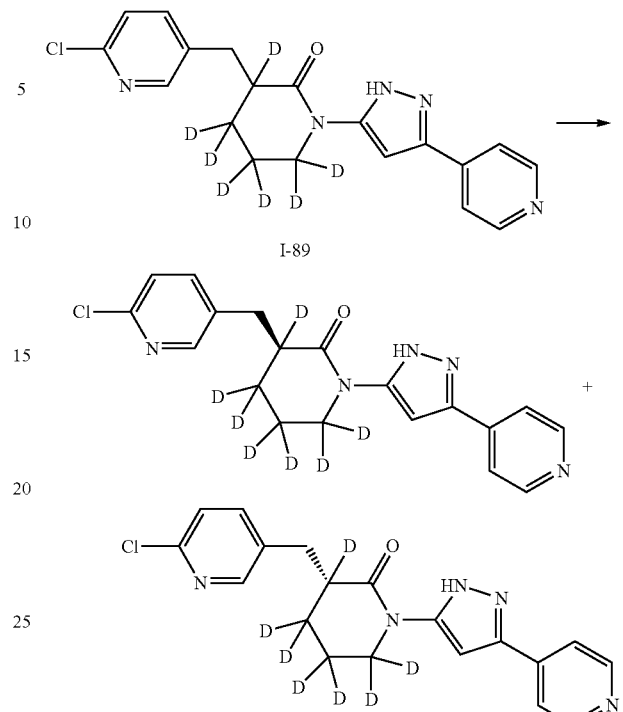

I-89

Compound I-89 (800 mg, 2.1 mmol) was dissolved in methanol then purified by supercritical fluid chromatography on a chiralpak AS 20*250 mm, 10 µm (Daicel) column eluting with CO$_2$/MeOH: acetonitrile (3:2)/(0.2% Methanol Ammonia)=50/50 at a flow rate of 80 g/min and 100 bar pressure to afford the title compounds.

Peak 1-chiral LC: Ret time 1.98 min on chiralpak AS 4.6*100 mm, 5 µm column eluting with CO$_2$/MeOH: aetonitrile:MeOH Ammonia (3:2:0.2%)=65/35 at a flow rate of 4 mL/min and 146.5 bar and detection at 255 nm.

Peak 2-chiral LC: Ret time 3.26 min on chiralpak AS 4.6*100 mm, 5 µm column eluting with CO2/MeOH: acetonitrile:MeOH Ammonia (3:2:0.2%)=65/35 at a flow rate of 4 mL/min and 145.5 bar and detection at 255 nm.

Method BE: Chiral Separation of Compound I-33 to Provide Compounds I-33-a and I-33-b

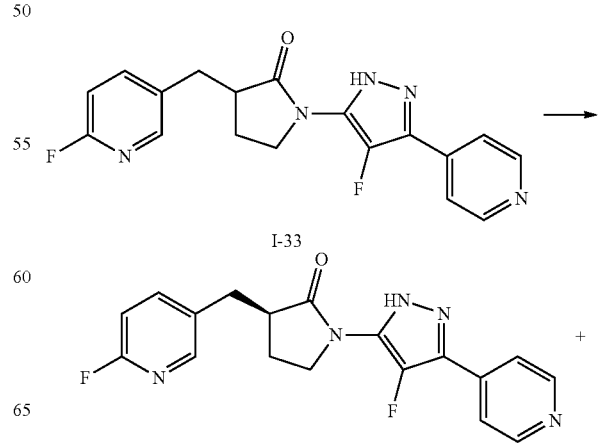

I-33

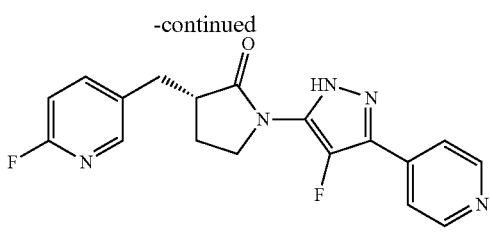

Compound I-33 (800 mg, 2.25 mmol) was dissolved in methanol (25 ml) then purified by supercritical fluid chromatography on OX, 20*250 mm, 10 μm column eluting with CO2/MEOH (0.2% Methanol Ammonia)=50/50 at a flow rate of 80 g/min and 100 bar pressure to afford the title compounds.

Peak 1—Chiral LC: Ret time 1.64 min on Chiralpak OX-H, 4.6×100 mm, 5um column eluting CO$_2$/MEOH (0.2% Methanol Ammonia)=55/45 at a flow rate of 4 ml/min at 163.2 bar and detection at 260 nm.

Peak 2—Chiral LC: Ret time 2.17 min on Chiralpak OX-H, 4.6×250 mm, 5um column eluting CO$_2$/MEOH (0.2% Methanol Ammonia)=55/45 at a flow rate of 4 ml/min at 156.6 bar and detection at 260 nm.

Method BF: Chiral Separation of Compound I-31 to Provide Compounds I-31-a and I-31-b

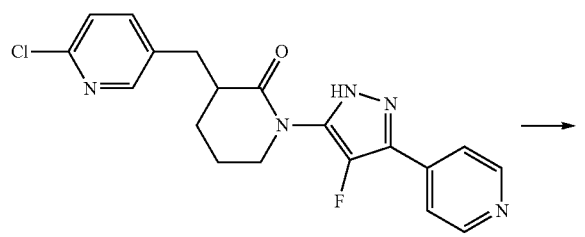

I-31

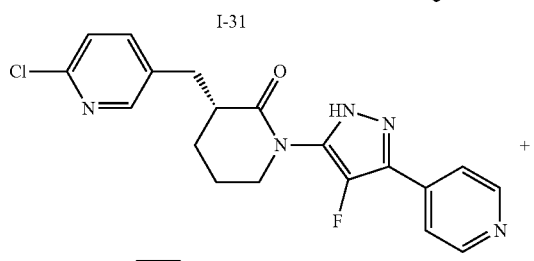

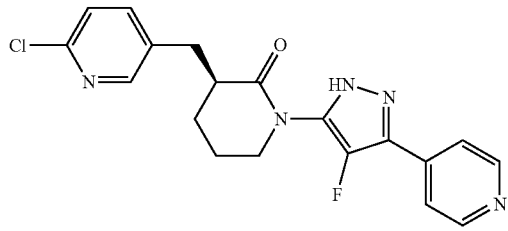

Compound I-31 (480 mg, 1.25 mmol) was dissolved in a mixture of 25 mL methanol and dichloromethane then purified by supercritical fluid chromatography on a Chiralpak OX 20*250 mm, 10 μm (Daicel) column eluting with CO$_2$/(MeOH (0.2% Methanol Ammonia)=50/50 at a flow rate of 100 g/min and 100 bar pressure to afford the title compounds.

Peak 1—Chiral LC: Ret time 1.92 min on Chiralpak OX-H, 4.6*100 mm, 5 μm eluting with 45% Methanol (0.2% methanol ammonia) in CO$_2$ at 3.00 mL/min at 154.4 bar and detection at 214 nm.

Peak 2—Chiral LC: Ret time 2.64 min on Chiralpak OX-H, 4.6*100 mm, 5 μm eluting with 45% Methanol (0.2% methanol ammonia) in CO$_2$ at 3.00 mL/min at 148.7 bar and detection at 214 nm.

Method BG: Chiral Separation of Compound I-29 to Provide Compounds I-29-a and I-29-b

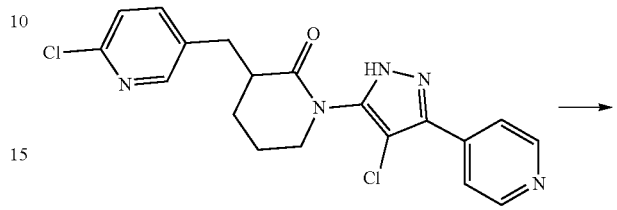

I-29

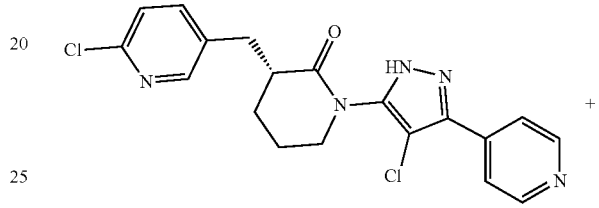

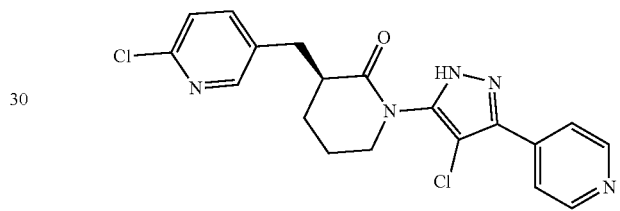

Compound I-29 (1900 mg, 4.74 mmol) was dissolved in methanol and dichloromethane then purified by supercritical fluid chromatography on a Chiralpak OZ 20*250 mm, 10 μm (Daicel) column eluting with CO$_2$/(MeOH/ACN (0.2% Methanol Ammonia)=1:1)=45/55 at a flow rate of 120 g/min and 100 bar pressure to afford the title compounds.

Peak 1—Chiral LC: Ret time 2.76 min on Chiralpak OZ-H, 4.6*100 mm, 5 μm eluting with 55% Methanol (0.2% methanol ammonia) in CO$_2$ at 3.0 mL/min at 155.6 bar and detection at 214 nm.

Peak 2—Chiral LC: Ret time 4.53 min on Chiralpak OZ-H, 4.6*100 mm, 5 μm eluting with 55% Methanol (0.2% methanol ammonia) in CO$_2$ at 3.0 mL/min at 152.9 bar and detection at 214 nm.

Method BH: Chiral Separation of Compound I-28 to Provide Compounds I-28-a and I-28-b

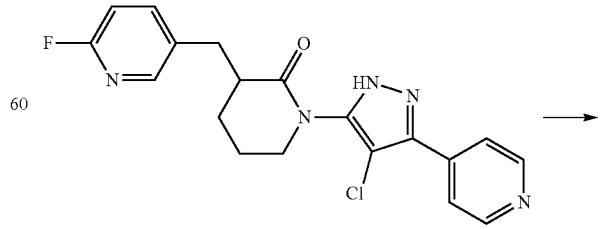

I-28

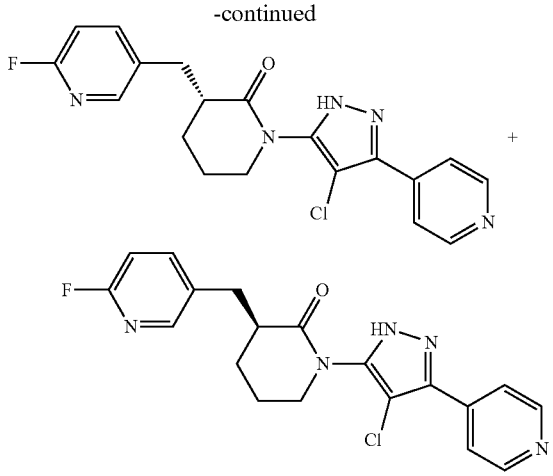

Compound I-28 (1300 mg, 3.38 mmol) was dissolved in methanol then purified by supercritical fluid chromatography on a Chiralpak OX 20*250 mm, 10 μm (Daicel) column eluting with $CO_2$/MeOH (0.2% Methanol Ammonia)=45/55 at a flow rate of 80 g/min and 100 bar pressure to afford the title compounds.

Peak 1—Chiral LC: Ret time 1.92 min on Chiralpak OX-H, 4.6*100 mm, 5 μm eluting with 45% Methanol (0.2% methanol ammonia) in $CO_2$ at 3.00 mL/min at 154.4 bar and detection at 265 nm.

Peak 2—Chiral LC: Ret time 2.64 min on Chiralpak OX-H, 4.6*100 mm, 5 μm eluting with 45% Methanol (0.2% methanol ammonia) in $CO_2$ at 3.00 mL/min at 148.7 bar and detection at 265 nm.

Method BI: Chiral Separation of Compound I-90 to Provide Compounds I-90-a and I-90-b

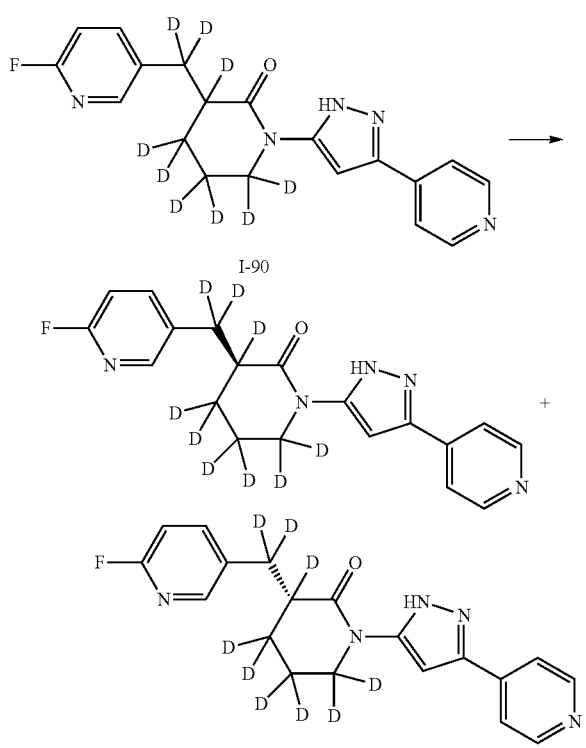

Compound I-90 (940 mg, 2.6 mmol) was dissolved in methanol then purified by supercritical fluid chromatography on a chiralpak AS 20*250 mm, 10 μm (Daicel) column eluting with CO2/MEOH (0.2% Methanol Ammonia)=50/50 at a flow rate of 80 g/min and 100 bar pressure to afford the title compounds.

Peak 1-chiral LC: Ret time 1.36 min on chiralpak AS 4.6*100 mm, 5 μm column eluting with $CO_2$/MEOH (0.2% Methanol Ammonia)=60/40 at a flow rate of 4 mL/min and 147.8 bar and detection at 260 nm.

Peak 2-chiral LC: Ret time 1.89 min on chiralpak AS 4.6*100 mm, 5 μm column eluting with $CO_2$/MEOH (0.2% Methanol Ammonia)=60/40 at a flow rate of 4 mL/min and 147.8 bar and detection at 260 nm.

Method BJ: Chiral Separation of Compound I-91 to Provide Compounds I-91-a and I-91-b

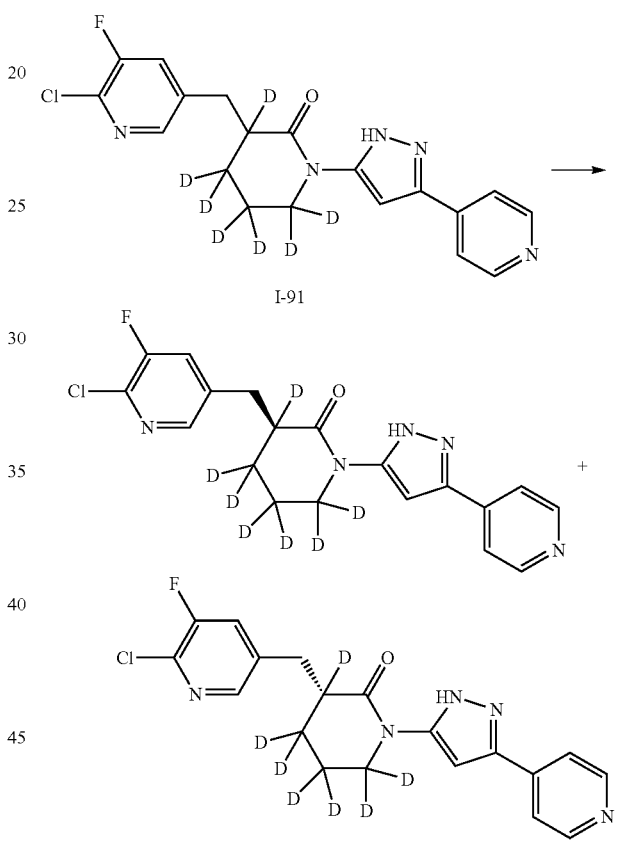

Compound I-91 (1.2 g, 3.1 mmol) was dissolved in methanol then purified by supercritical fluid chromatography on a chiralpak AS 20*250 mm, 10 μm (Daicel) column eluting with CO2/ETOH (1.0% Methanol Ammonia)=50/50 at a flow rate of 80 g/min and 100 bar pressure to afford the title compounds.

Peak 1-chiral LC: Ret time 3.05 min on chiralpak AS 4.6*100 mm, 5 μm column eluting with $CO_2$/ETOH (1.0% Methanol Ammonia)=65/35 at a flow rate of 3 mL/min and 138.9 bar and detection at 265 nm.

Peak 2-chiral LC: Ret time 3.99 min on chiralpak AS 4.6*100 mm, 5 μm column eluting with $CO_2$/ETOH (1.0% Methanol Ammonia)=65/35 at a flow rate of 3 mL/min and 140.6 bar and detection at 265 nm.

Method BK: Chiral Separation of Compound Int-15 Followed by Deprotection to Provide Compounds I-93-a and I-93-b

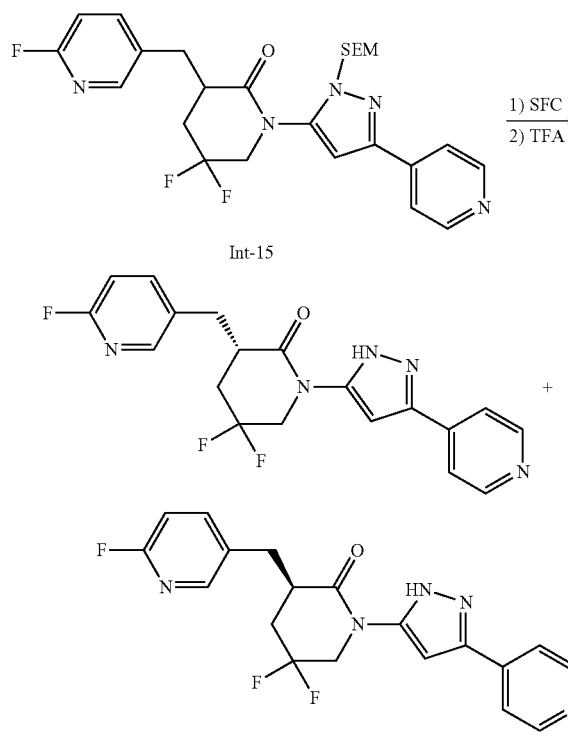

Int-15

Int-15 (220 mg, 0.34 mmol) was dissolved in methanol and isopropanol and purified by supercritical fluid chromatography on a Chiralpak AD-H, 10×250 mm, 5 μm column eluting with 30% isopropanol in $CO_2$ at a flow rate of 15 mL/min to afford the title compounds.

Peak 1—Chiral LC: Ret time 1.78 on Chiralpak AD-H, 10×250 mm, 5 μm, eluting with 30% isopropanol in $CO_2$ at 4 mL/min with detection at 254 nm.

Peak 2—Chiral LC: Ret time 4.10 on Chiralpak AD-H, 10×250 mm, 5 μm, eluting with 30% isopropanol in $CO_2$ at 4 mL/min with detection at 254 nm.

The discrete enantiomers were dissolved in $CH_2C_2$ treated with TFA then concentrated in vacuo to afford the title compounds.

Method BL: Chiral Separation of Compound Int-16 Followed by Deprotection to Provide Compounds I-92-a and I-92-b

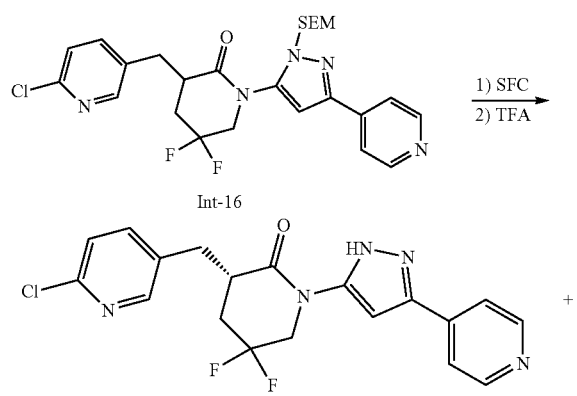

Int-16

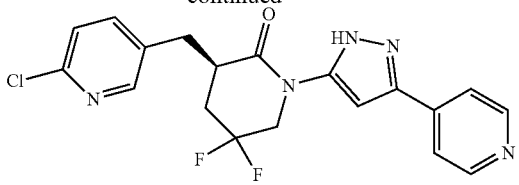

Int-16 (290 mg, 0.54 mmol) was dissolved in ethanol and purified by supercritical fluid chromatography on a Lux A1, 21.2 mm×250 mm, 5 m column eluting with 50% ethanol in $CO_2$ at a flow rate of 50 mL/min and 100 bar pressure to afford the title compounds.

Peak 1—Chiral LC: Ret time 1.20 on Amy-C, 4.6 mm×250 mm, 5 m eluting with 50% ethanol in $CO_2$ with 0.2% $NH_3$ modifier at 4 mL/min at 100 Bar and detection at 210 to 400 nm.

Peak 2—Chiral LC: Ret time 5.65 on Amy-C, 4.6 mm×250 mm, 5 m eluting with 50% ethanol in $CO_2$ with 0.2% NH3 modifier at 4 mL/min and 100 Bar and detection at 210 to 400 nm.

The discrete enantiomers were dissolved in $CH_2C_2$ treated with TFA then concentrated in vacuo to afford the title compounds.

Method BM: Chiral Separation of Compound I-27 to Provide Compounds I-27-a and I-27-b

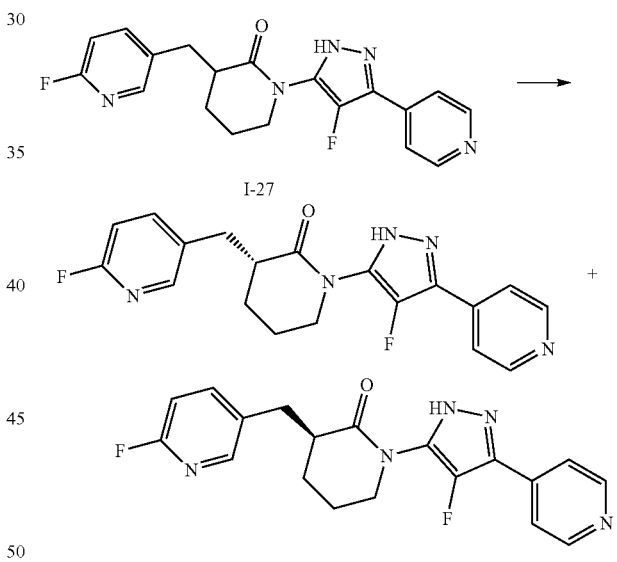

I-27

Compound I-27 (1060 mg, 2.87 mmol) was dissolved in methanol then purified by supercritical fluid chromatography on a Chiralpak OZ 20*250 mm, 10 μm (Daicel) column eluting with $CO_2$/(MeOH (0.2% Methanol Ammonia)=45/55 at a flow rate of 80 g/min and 100 bar pressure to afford the title compounds.

Peak 1—Chiral LC: Ret time 2.463 min on Chiralpak OZ-3, 4.6*100 mm, 3 μm eluting with 35% Methanol (0.2% $NH_3$ (7 M in methanol)) in $CO_2$ at 3.0 mL/min at 137.9 bar and detection at 214 nm.

Peak 2—Chiral LC: Ret time 3.877 min on Chiralpak OZ-3, 4.6*100 mm, 3 μm eluting with 35% Methanol (0.2% $NH_3$ (7 M in methanol)) in $CO_2$ at 3.0 mL/min at 137.9 bar and detection at 214 nm.

Method BN: Chiral Separation of Compound I-88 to Provide Compounds I-88-a and I-88-b

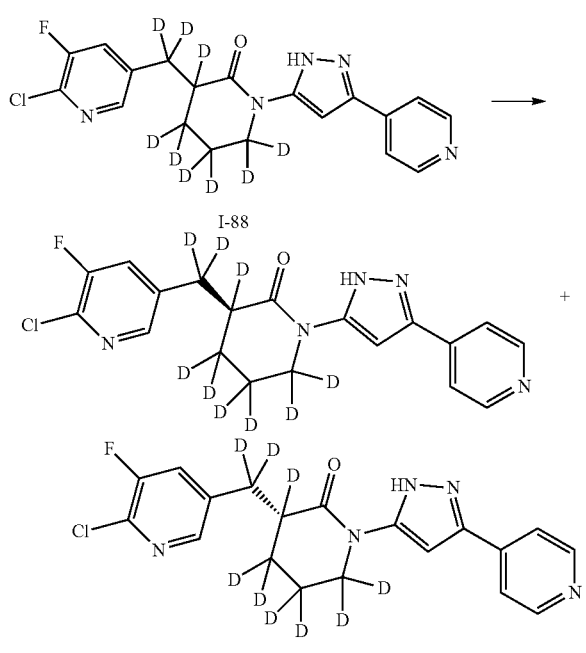

Compound I-88 (1.1 g, 2.8 mmol) was dissolved in a mixture of methanol and dichloromethane then purified by supercritical fluid chromatography on a chiralpak AS 20*250 mm, 10 μm (Daicel) column eluting with CO2/ETOH (0.5% Methanol Ammonia)=55/45 at a flow rate of 80 g/min and 100 bar pressure to afford the title compounds.

Peak 1-chiral LC: Ret time 1.49 min on chiralpak AS 4.6*100 mm, Sum column eluting with $CO_2$/EtOH (1% Methanol Ammonia)=60/40 at a flow rate of 3 mL/min and 147.8 bar and detection at 214 nm.

Peak 2-chiral LC: Ret time 1.86 min on chiralpak AS 4.6*100 mm, Sum column eluting with $CO_2$/EtOH (1% Methanol Ammonia)=60/40 at a flow rate of 3 mL/min and 149.5 bar and detection at 214 nm.

Method BO: Chiral Separation of Compound I-87 to Provide Compounds I-87-a and I-87-b

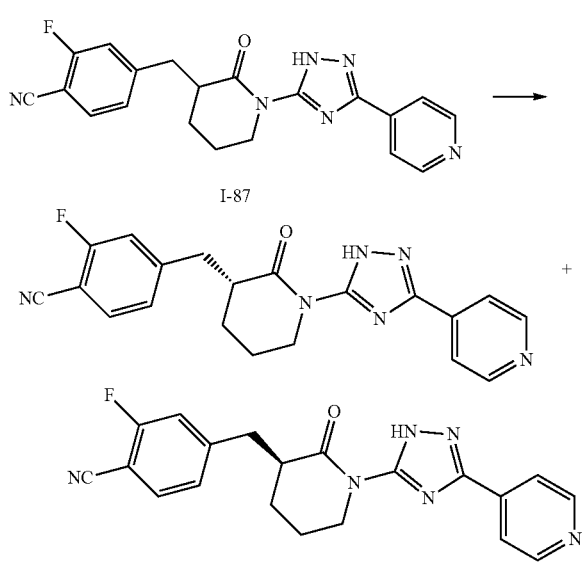

Compound I-87 (1.5 g, 4.0 mmol) was dissolved in a mixture of methanol and dichloromethane, then purified by supercritical fluid chromatography on a chiralpak AS-H, 20*250 mm, 10 μm (Daicel) column eluting with $CO_2$/MEOH (0.2% Methanol Ammonia)=70/30 at a flow rate of 100 g/min and 100 bar pressure to afford the title compounds.

Peak 1-chiral LC: Ret time 2.47 min on chiralpak AS-H, 4.6*100 mm, 5 μm eluting with 25% methanol in $CO_2$ at 3.0 mL/min at 140.1 Bar and detection at 214 nm.

Peak 2-chiral LC: Ret time 2.87 min on chiralpak AS-H, 4.6*100 mm, 5 μm eluting with 25% methanol in $CO_2$ at 3.0 mL/min at 140.4 Bar and detection at 214 nm.

Method BP: Chiral Separation of Compound Int-17 Followed by Deprotection to Provide Compounds I-26-a and I-26-b

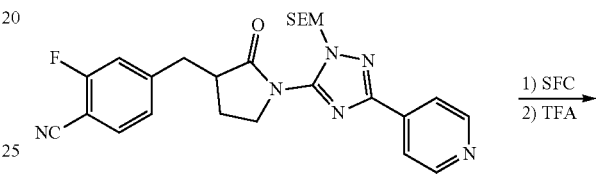

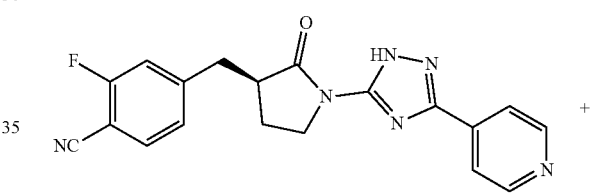

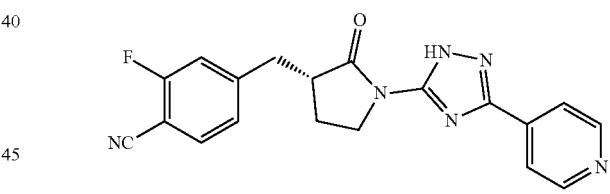

Int-17 (3000 mg, 6.1 mmol) was dissolved in Methanol purified by supercritical fluid chromatography on a chiralpak RR WHELK 20*250 mm, 10 μm column eluting with 25% ethanol in $CO_2$ at a flow rate of 80 g/min and 150.4 bar pressure to afford the title compounds.

Peak 1—Chiral LC: Ret time 2.73 min on Chiralpak R-R-Whelk-O1, 4.6×250 mm, 5 μm eluting with 25.0% ethanol in $CO_2$ at 3 mL/min at 100 Bar and detection at 214 nm.

Peak 2—Chiral LC: Ret time 3.29 min on Chiralpak R-R-Whelk-O1, 4.6×250 mm, 5 μm eluting with 25.0% ethanol in CO2 at 3 mL/min at 100 Bar and detection at 214 nm.

The discrete enantiomers were dissolved in $CH_2C_2$ treated with TFA then concentrated in vacuo to afford the title compounds.

Method BQ: Chiral Separation of Compound I-25 to Provide Compounds I-25-a and I-25-b

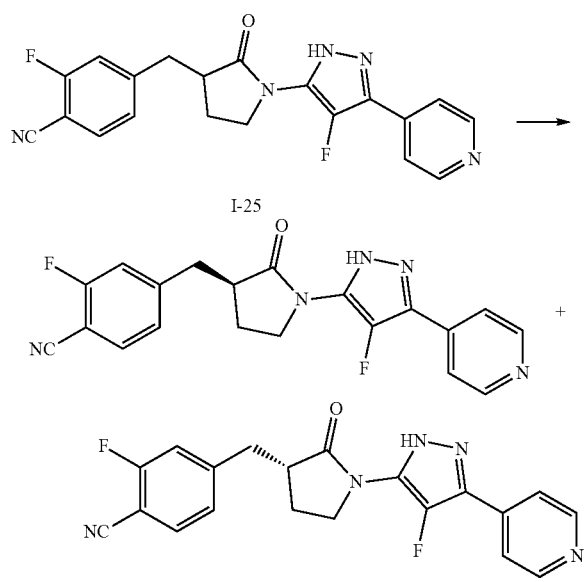

I-25

Compound I-25 (930 mg, 2.45 mmol) was dissolved in Methanol and dichloromethane purified by supercritical fluid chromatography on a chiralpak IC-3 20×250 mm, 10 μm column eluting with 40% ethanol in CO₂ at a flow rate of 100 g/min and 150.4 bar pressure to afford the title compounds.

Peak 1—Chiral LC: Ret time 2.783 min on Chiralpak IC-3 4.5*100 mm, 5 μm eluting with 40.0% ethanol in CO2 at 3 mL/min at 100 Bar and detection at 214 nm.

Peak 2—Chiral LC: Ret time 3.382 min on Chiralpak IC-3 4.6*100 mm, 5 μm eluting with 40.0% ethanol in CO2 at 3 mL/min at 100 Bar and detection at 214 nm.

Method BR: Chiral Separation of Compound Int-18 Followed by Deprotection to Provide Compounds I-86-a and I-86-b

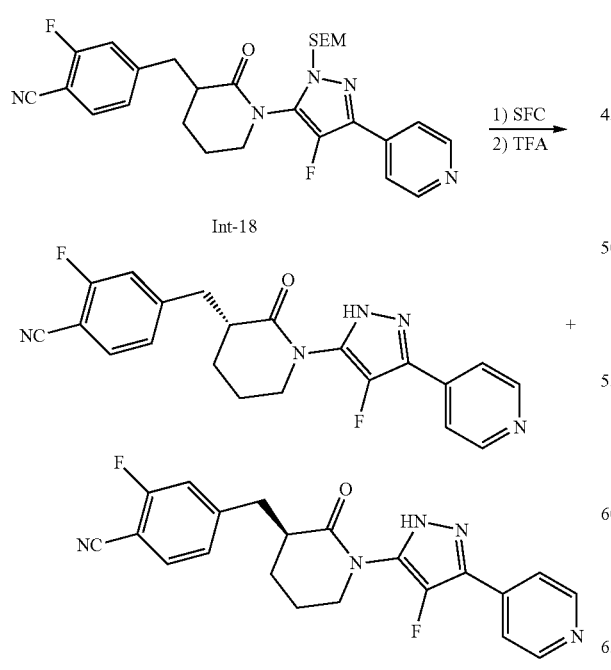

Int-18

Compound Int-18 (2 g, 3.82 mmol) was dissolved in MeOH then purified by supercritical fluid chromatography on a chiralpak OX-H (4.6*100 mm, 5 m column) eluting with 35% methanol in CO₂ at a flow rate of 3 mL/min and 149.7 Bar pressure to afford the title compounds.

Peak 1—Chiral LC: Ret time 1.91 min on Chiralpak OX, 4.6*100 mm, 5 m eluting with 35% methanol in CO₂ at 3 mL/min and 149.7 Bar and detection at 230 nm.

Peak 2—Chiral LC: Ret time 2.26 min on Chiralpak OX, 4.6*100 mm, 5 m eluting with 35% methanol in CO₂ at 3 mL/min and 145.2 Bar and detection at 230 nm.

The discrete enantiomers were dissolved in CH₂C₂ treated with TFA then concentrated in vacuo to afford the title compounds.

Method BS: Chiral Separation of Compound I-104 to Provide Compounds I-104-a and I-104-b

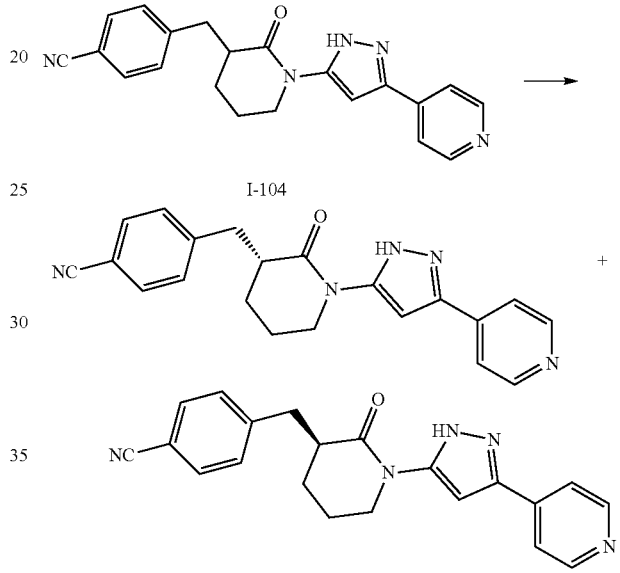

I-104

Compound I-104 (370 mg, 1.0 mmol) was dissolved in a mixture of methanol then purified by supercritical fluid chromatography on a chiralpak OZ 20*250 mm, 10 μm (Daicel) column eluting with CO₂/(MeOH/MeCN (0.2% Methanol Ammonia)=9:1)=50/50 at a flow rate of 120 g/min and 100 bar pressure to afford the title compounds.

Peak 1—Chiral LC: Ret time 2.695 min on Chiralpak OZ, 4.6*100 mm, 5 μm eluting with 45% Methanol (0.2% methanol ammonia) in CO₂ at 3.0 mL/min at 2000 psi and detection at 214 nm.

Peak 2—Chiral LC: Ret time 3.574 min on Chiralpak OZ, 4.6*100 mm, 5 μm eluting with 45% Methanol (0.2% methanol ammonia) in CO₂ at 3.0 mL/min at 2000 psi and detection at 214 nm.

Method BT: Chiral Separation of Compound I-105 to Provide Compounds I-105-a and I-105-b

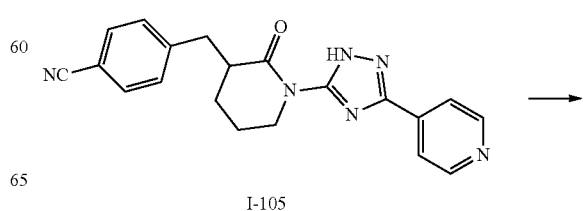

I-105

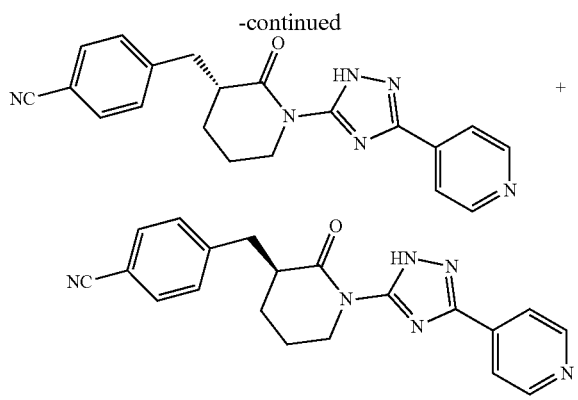

Compound I-105 (330 mg, 0.92 mmol) was dissolved in a mixture of methanol and dichloromethane (80 ml) then purified by supercritical fluid chromatography on a chiralpak AS-H 20*250 mm, 10 μm (Regis) column eluting with $CO_2$/IPA (0.5% Methanol Ammonia)=40/60 at a flow rate of 100 g/min and 100 bar pressure to afford the title compounds.

Peak 1—Chiral LC: Ret time 2.062 min on Chiralpak AS-3 4.6*100 mm, 3 μm eluting with 35% IPA [1% $NH_3$ (7M in MeOH)] in $CO_2$ at 3 mL/min at 2000 psi and detection at 214 nm.

Peak 2-chiral LC: Ret time 2.781 min on chiralpak AS-H 4.6*100 mm, 3 μm eluting with 35% IPA [1% $NH_3$(7M in MeOH)] in $CO_2$ at 3.0 mL/min at 2000 psi and detection at 214 nm.

Method BU: Chiral Separation of Compound I-106 to Provide Compounds I-106-a and I-106-b

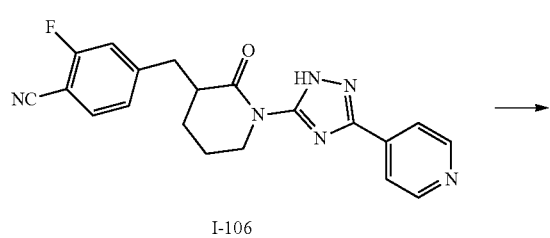

Compound I-106 (450 mg, 1.2 mmol) was dissolved in methanol and dichloromethane (55 mL) then purified by supercritical fluid chromatography on a OZ 20*250 mm, 10 μm (Daicel) column eluting with $CO_2$/(MeOH/CAN (0.2% methanol Ammonia)=1:1)=50/50 at a flow rate of 120 g/min and 100 bar pressure to afford the title compounds.

Peak 1-chiral LC: Ret time 1.984 min on chiralpak OZ 4.6*100 mm, 5 μm column eluting with 45% of MeOH/MeCN=3/2[0.2% $NH_3$(7M in MeOH)] in $CO_2$ at a flow rate of 3 mL/min and 2000 psi and detection at 214 nm.

Peak 2-chiral LC: Ret time 2.682 min on chiralpak OZ 4.6*100 mm, 5 μm column eluting with 45% of MeOH/MeCN=3/2[0.2% $NH_3$(7M in MeOH)] in $CO_2$ at a flow rate of 3 mL/min and 2000 psi and detection at 214 nm.

Method BV: Chiral Separation of Compound I-107 to Provide Compounds I-107-a and I-107-b

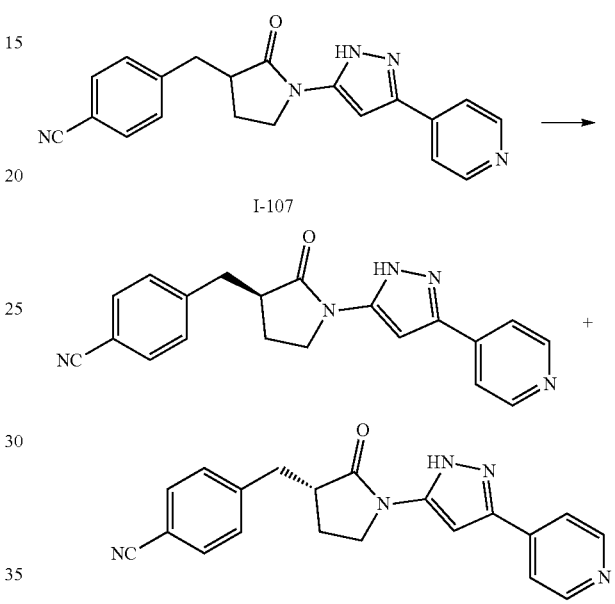

Compound I-107 (550 mg, 1.6 mmol) was dissolved in Methanol and Dichloromethane (80 mL) purified by supercritical fluid chromatography on a chiralpak AS 20*250 mm, 10 μm (Daicel) eluting with CO2/MeOH (0.2% Methanol Ammonia)=60/40 at a flow rate of 100 g/min and 100 bar pressure to afford the title compounds.

Peak 1—Chiral LC: Ret time 2.404 min on Chiralpak AS-3 4.6*100 mm, 3 μm eluting with 20% IPA [1% $NH_3$ (7M in MeOH)] in $CO_2$ at 3 mL/min at 2000 psi and detection at 214 nm.

Peak 2—Chiral LC: Ret time 2.891 min on Chiralpak AS-3 4.6*100 mm, 3 μm eluting with 20.0% IPA [1% $NH_3$(7M in MeOH)] in $CO_2$ at 3 mL/min at 2000 psi and detection at 214 nm.

Method BW: Chiral Separation of Compound I-113 to Provide Compounds I-113-a and I-113-b

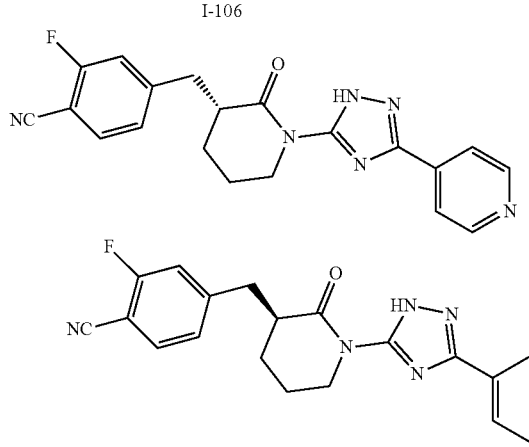

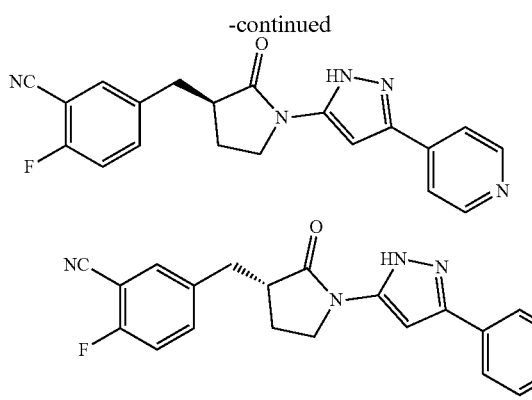

Compound I-113 (800 mg, 2.21 mmol) was dissolved in Methanol (60 mL) purified by supercritical fluid chromatography on AS 20*250 mm, 10 μm (Regis) eluting with $CO_2$/MeOH (0.2% Methanol Ammonia)=60/40 at a flow rate of 100 g/min and 100 bar pressure to afford the title compounds.

Peak 1—Chiral LC: Ret time 1.949 min on Chiralpak OJ-3 4.6*100 mm, 3 μm eluting with 20% IPA [0.2% $NH_3$(7M in MeOH)] in $CO_2$ at 3 mL/min at 2000 psi and detection at 214 nm.

Peak 2—Chiral LC: Ret time 2.369 min on Chiralpak OJ-3 4.6*100 mm, 3 μm eluting with 20% IPA [0.2% $NH_3$(7M in MeOH)] in $CO_2$ at 3 mL/min at 2000 psi and detection at 214 nm.

Method BV: Chiral Separation of Compound I-119 to Provide Compounds I-119-a and I-119-b

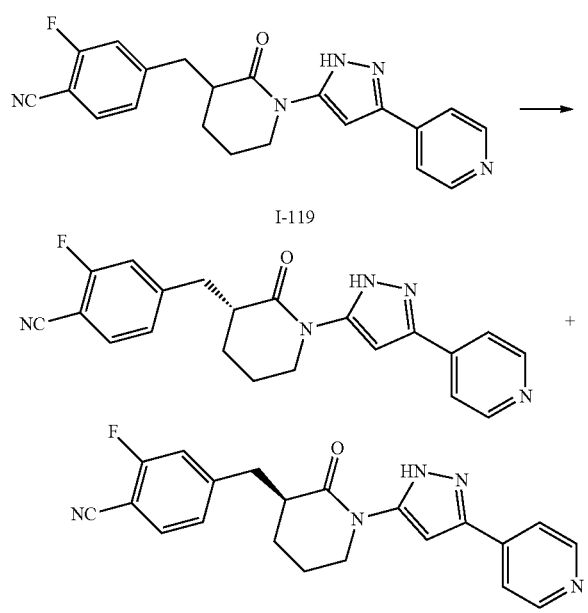

Compound I-119 (450 mg, 1.2 mmol) was dissolved in methanol and dichloromethane (55 mL) then purified by supercritical fluid chromatography on an OZ 20*250 mm, 10 μm (Daicel) column eluting with $CO_2$/(MeOH/CAN (0.2% methanol Ammonia)=1:1)=50/50 at a flow rate of 120 g/min and 100 bar pressure to afford the title compounds.

Peak 1-chiral LC: Ret time 1.984 min on chiralpak OZ 4.6*100 mm, 5 μm column eluting with 45% of MeOH/ MeCN=3/2[0.2% $NH_3$(7M in MeOH)] in $CO_2$ at a flow rate of 3 mL/min and 2000 psi and detection at 214 nm.

Peak 1-chiral LC: Ret time 2.682 min on chiralpak OZ 4.6*100 mm, 5 μm column eluting with 45% of MeOH/ MeCN=3/2[0.2% $NH_3$(7M in MeOH)] in $CO_2$ at a flow rate of 3 mL/min and 2000 psi and detection at 214 nm.

Method BX: Chiral Separation of Compound Int-19 Followed by Deprotection to Provide Compounds I-83-a and I-83-b

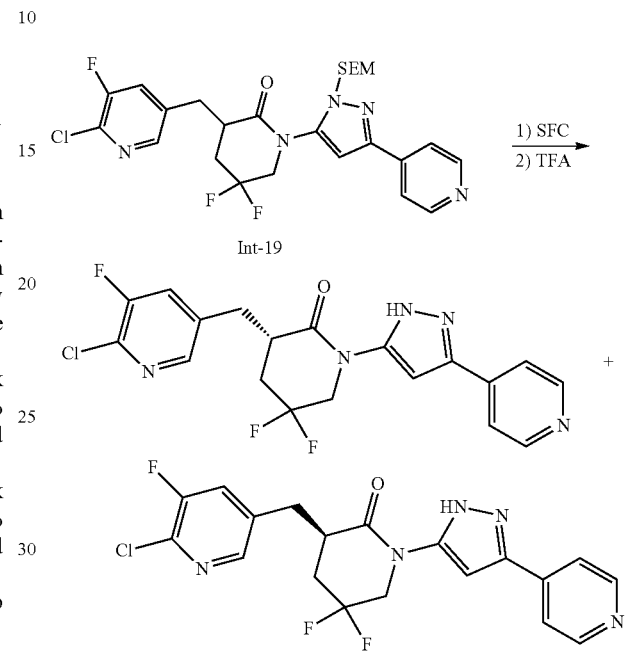

Int-19 (460 mg, 0.70 mmol) was dissolved in ethanol and was purified by supercritical fluid chromatography on a Lux A1, 21.2 mm×250 mm, 5 μm, eluting with 50% ethanol in $CO_2$ at a flow rate of 50 mL/min at 125 bar pressure to afford the title compounds.

Peak 1: Chiral LC: Ret time 1.10 min on Amy-C, 4.6 mm×250 mm, 5 μm, eluting with 50% ethanol in $CO_2$ at 4 mL/min with 0.2% $NH_3$ as a modifier and detection at 210 to 400 nm.

Peak 2: Chiral LC: Ret time 2.84 min on Amy-C, 4.6 mm×250 mm, 5 μm, eluting with 50% ethanol in $CO_2$ at 4 mL/min with 0.2% $NH_3$ as a modifier and detection at 210 to 400 nm.

The discrete enantiomers were dissolved in $CH_2C_2$ treated with TFA then concentrated in vacuo to afford the title compounds.

Example 2. Characterization of Compounds

LCMS Methods:
Analytical LC/MS Analysis Method A:
ESI+/− ion mode 150-850 Da
Column: Phenomenex Kinetix-XB C18, Part No. 00D-4498-AN, 2.1×100 mm, 1.7 μm
Temperature: 40° C.
Gradient:

| Time (min) | 0.1% formic acid in water | acetonitrile | Flow (mL/min) |
| --- | --- | --- | --- |
| 0 | 95% | 5% | 0.6 |
| 5.30 | 0% | 100% | 0.6 |

-continued

| Time (min) | 0.1% formic acid in water | acetonitrile | Flow (mL/min) |
|---|---|---|---|
| 5.80 | 0% | 100% | 0.6 |
| 5.82 | 95% | 5% | 0.6 |
| 7.00 | 95% | 5% | 0.6 |

Analytical LC/MS Analysis Method B:
ESI+/− ion mode 150-850 Da
Column: Phenomenex Gemini-NX C18, Part No. 00D-4453-B0, 2.0×100 mm, 3.0 μm
Temperature: 40° C.
Gradient:

| Time (min) | 2 mM aqueous ammonium bicarbonate | acetonitrile | Flow (mL/min) |
|---|---|---|---|
| 0 | 95% | 5% | 0.6 |
| 5.50 | 0% | 100% | 0.6 |
| 5.90 | 0% | 100% | 0.6 |
| 5.92 | 95% | 5% | 0.6 |
| 7.00 | 95% | 5% | 0.6 |

Analytical LC/MS Analysis Method C:
ESI+/− ion mode 100-1000 Da
Column: Waters UPLC® BEH™ C18, Part No. 186002352, 2.1×100 mm, 1.7 μm
Temperature: 40° C.
Gradient:

| Time (min) | 2 mM aqueous ammonium bicarbonate | acetonitrile | Flow (mL/min) |
|---|---|---|---|
| 0 | 95% | 5% | 0.6 |
| 5.30 | 0% | 100% | 0.6 |
| 5.80 | 0% | 100% | 0.6 |
| 5.82 | 95% | 5% | 0.6 |
| 7.00 | 95% | 5% | 0.6 |

Analytical LC/MS Analysis Method D:
ESI+/− ion mode 100-1000 Da
Column: XBridge C18, 3.5 μm 4.6×50 mm
Temperature: 40° C.
Gradient:

| Time (min) | 10 mM aqueous ammonium bicarbonate | Acetonitrile | Flow (mL/min) |
|---|---|---|---|
| 0.00 | 95% | 5% | 2.0 |
| 1.20 | 5% | 95% | 2.0 |
| 3.00 | 5% | 95% | 2.0 |

Analytical LC/MS Analysis Method E:
ESI+/− ion mode 100-1000 Da
Column: XBridge SB-C18, 3.5 μm 4.6×50 mm
Temperature: 40° C.
Gradient:

| Time (min) | 10 mM aqueous ammonium bicarbonate | Acetonitrile | Flow (mL/min) |
|---|---|---|---|
| 0.00 | 95% | 5% | 2.0 |
| 1.40 | 5% | 95% | 2.0 |
| 4.30 | 5% | 95% | 2.0 |

Analytical LC/MS Analysis Method F:
ESI+/− ion mode 100-1000 Da
Column: Sunfire C18, 3.5 μm 4.6×50 mm
Temperature: 50° C.
Gradient:

| Time (min) | 10 mM aqueous ammonium bicarbonate | Acetonitrile | Flow (mL/min) |
|---|---|---|---|
| 0.00 | 95% | 5% | 2.0 |
| 1.40 | 5% | 95% | 2.0 |
| 3.00 | 5% | 95% | 2.0 |

Analytical LC/MS Analysis Method G:
ESI+/− ion mode 100-1000 Da
Column: Waters UPLC® BEH™ C18, Part No. 186005297, 1.7 μm 2.1×50 mm
Temperature: 40° C.
Gradient:

| Time (min) | 0.1% formic acid in water | 0.1% formic acid in Acetonitrile | Flow (mL/min) |
|---|---|---|---|
| 0.00 | 95% | 5% | 0.9 |
| 1.10 | 0% | 100% | 0.9 |
| 2.45 | 0% | 100% | 0.9 |
| 3.85 | 95% | 5% | 0.9 |
| 5.35 | 95% | 5% | 0.9 |

Analytical LC/MS Method H:
ESI+/− ion mode 100-1000 Da
Column: XBridge C18, 3.5 μm 4.6×50 mm
Temperature: 45° C.
Gradient:

| Time (min) | 0.05% TFA in water | 0.05% TFA in acetonitrile | Flow (mL/min) |
|---|---|---|---|
| 0.00 | 95% | 5% | 2.0 |
| 1.30 | 5% | 95% | 2.0 |
| 3.00 | 5% | 95% | 2.0 |

Analytical LC/MS Method I
ESI+/− ion mode 100-1000 Da
Column: XBridge C18, 3.5 μm 4.6×50 mm
Temperature: 50° C.
Gradient:

| Time (min) | 10 mM aqueous ammonium bicarbonate | Acetonitrile | Flow (mL/min) |
|---|---|---|---|
| 0.00 | 95% | 5% | 2.0 |
| 1.40 | 5% | 95% | 2.0 |
| 3.00 | 5% | 95% | 2.0 |

Analytical LC/MS Method J:
ESI+/− ion mode 100-1000 Da
Column: XBridge C18, 3.5 μm 4.6×50 mm
Temperature: 40° C.

Gradient:

| Time (min) | 10 mM aqueous ammonium bicarbonate | Acetonitrile | Flow (mL/min) |
|---|---|---|---|
| 0.00 | 95% | 5% | 2.0 |
| 1.40 | 5% | 95% | 2.0 |
| 3.10 | 5% | 95% | 2.0 |

Results are presented in Table 1:

TABLE 1

| Compound | LCMS method | RT (min) | Mol ion (m/z) |
|---|---|---|---|
| I-1-a | A | 1.13 | 368.1 |
| I-1-b | A | 1.01 | 368.2 |
| I-2-a | A | 1.44 | 382.2 |
| I-3-a | A | 0.99 | 382.2 |
| I-4 | D | 1.68 | 354 |
| I-4* (peak 1) | D | 1.71 | 354 |
| I-4* (peak 2) | D | 1.71 | 354 |
| I-5 | D | 1.79 | 368 |
| I-5* (peak 1) | A | 1.79 | 368 |
| I-5* (peak 2) | A | 1.79 | 368 |
| I-6 | A | 1.71 | 367 |
| I-6* (peak 1) | A | 1.71 | 367 |
| I-6* (peak 2) | A | 1.71 | 367 |
| I-7 | A | 1.92 | 338.2 |
| I-7* (peak 1) | A | 1.92 | 338.2 |
| I-7* (peak 2) | A | 1.92 | 338.2 |
| I-8 | A | 2.25 | 372.1, 374.1 |
| I-8* (peak 1) | A | 2.25 | 372.2, 374.2 |
| I-8* (peak 2) | A | 2.25 | 372.2, 374.2 |
| I-9 | A | 1.45 | 355.1, 357.1 |
| I-9* (peak 1) | A | 1.49 | 355.2, 357.1 |
| I-9* (peak 2) | A | 1.49 | 355.2, 357.1 |
| I-10 | A | 2.57 | 386.2 |
| I-11 | A | 2.02 | 356.2 |
| I-11* (peak 1) | A | 2.02 | 356.2 |
| I-11* (peak 2) | A | 2.02 | 356.2 |
| I-12 | A | 2.95 | 482.3 |
| I-13 | A | 2.34 | 370.2 |
| I-14 | A | 2.13 | 371.2, 373.2 |
| I-15 | A | 2.06 | 353.2, 355.2 |
| I-16 | A | 1.92 | 355.2 |
| I-16* (peak 1) | A | 1.92 | 355.2 |
| I-16* (peak 2) | A | 1.92 | 355.2 |
| I-17 | A | 1.45 | 354.2, 356.1 |
| I-18 | A | 1.69 | 373.2, 375.2 |
| I-19 | A | 2.19 | 367.2 |
| I-19* (peak 1) | A | 2.20 | 367.2, 369.2 |
| I-19* (peak 2) | A | 2.20 | 367.2, 369.2 |
| I-20 | A | 2.25 | 385.2, 387.2 |
| I-20* (peak 1) | A | 2.25 | 385.2, 387.2 |
| I-20* (peak 2) | A | 2.25 | 385.2, 387.3 |
| I-21 | A | 1.56 | 368.2, 370.2 |
| I-21* (peak 1) | A | 1.57 | 368.2, 370.2 |
| I-21* (peak 2) | A | 1.57 | 368.2, 370.3 |
| I-22 | A | 2.05 | 369.2 |
| I-23 | D | 1.40 | 353.0 |
| I-23* (peak 1) | D | 1.40 | 353.0 |
| I-23* (peak 2) | D | 1.40 | 353.0 |
| I-24 | D | 1.54 | 387.0 |
| I-24* (peak 1) | D | 1.54 | 387.0 |
| I-24* (peak 2) | D | 1.54 | 387.0 |
| I-25 | E | 1.43 | 380.0 |
| I-25* (peak 1) | I | 1.35 | 380.0 |
| I-25* (peak 2) | I | 1.35 | 380.0 |
| I-26 | H | 1.31 | 363.1 |
| I-26* (peak 1) | E | 1.40 | 363.1 |
| I-26* (peak 2) | E | 1.40 | 363.1 |
| I-27 | I | 1.23 | 369.1 |
| I-27* (peak 1) | D | 1.53 | 369.1 |
| I-27* (peak 2) | I | 1.22 | 369.1 |
| I-28 | I | 1.25 | 385.1 |
| I-28* (peak 1) | I | 1.25 | 385.1 |
| I-28* (peak 2) | D | 1.50 | 385.1 |

TABLE 1-continued

| Compound | LCMS method | RT (min) | Mol ion (m/z) |
|---|---|---|---|
| I-29 | I | 1.28 | 401.1 |
| I-29* (peak 1) | D | 1.52 | 401.1 |
| I-29* (peak 2) | I | 1.28 | 401.1 |
| I-30 | A | 1.26 | 355.1 |
| I-31 | D | 1.51 | 385.1 |
| I-31* (peak 1) | I | 1.26 | 385.1 |
| I-31* (peak 2) | I | 1.26 | 385.1 |
| I-32 | I | 1.23 | 371.9 |
| I-32* (peak 1) | I | 1.20 | 371.9 |
| I-32* (peak 2) | I | 1.20 | 371.9 |
| I-33 | D | 1.41 | 356.0 |
| I-33* (peak 1) | D | 1.47 | 356.0 |
| I-33* (peak 2) | D | 1.46 | 356.0 |
| I-34 | I | 1.29 | 387.9 |
| I-34* (peak 1) | I | 1.27 | 387.9 |
| I-34* (peak 2) | I | 1.37 | 387.9 |
| I-35 | A | 1.13 | 355.2 |
| I-36 | E | 1.26 | 371.1 |
| I-36* (peak 1) | H | 1.34 | 371.1 |
| I-36* (peak 2) | E | 1.27 | 371.1 |
| I-37 | A | 1.73 | 362.2 |
| I-37* (peak 1) | A | 1.74 | 362.2 |
| I-37* (peak 2) | A | 1.74 | 362.2 |
| I-38 | A | 1.06 | 383.2, 385.2 |
| I-38* (peak 1) | C | 1.73 | 383.2, 385.2 |
| I-38* (peak 2) | C | 1.74 | 383.2, 385.2 |
| I-39 | H | 1.22 | 339.1 |
| I-39* (peak 1) | I | 1.13 | 339.1 |
| I-39* (peak 2) | I | 1.13 | 339.1 |
| I-40 | A | 1.73 | 382.2 |
| I-40* (peak 1) | A | 1.79 | 382.2 |
| I-40* (peak 2) | A | 1.79 | 382.2 |
| I-41 | A | 1.66 | 386.2, 388.2 |
| I-41* (peak 1) | A | 1.66 | 386.2, 388.2 |
| I-41* (peak 2) | A | 1.67 | 386.2, 388.2 |
| I-42 | D | 1.25 | 373.0 |
| I-42* (peak 1) | D | 1.24 | 373.0 |
| I-42* (peak 2) | D | 1.26 | 373.0 |
| I-43 | D | 1.67 | 370.0 |
| I-44 | A | 2.19 | 370.2 |
| I-45 | D | 1.68 | 368.0 |
| I-46* (peak 1) | E | 1.48 | 368.1 |
| I-46* (peak 2) | E | 1.48 | 368.1 |
| I-47 | A | 1.99 | 369.2, 371.2 |
| I-47* (peak 1) | A | 1.99 | 369.2, 371.2 |
| I-47* (peak 2) | A | 1.99 | 369.2, 371.2 |
| I-48 | A | 1.48 | 368.2, 370.2 |
| I-48* (peak 1) | A | 1.49 | 368.2, 370.2 |
| I-48* (peak 2) | A | 1.49 | 368.2, 370.2 |
| I-49 | A | 1.96 | 369.2 |
| I-49* (peak 1) | A | 1.95 | 369.2 |
| I-49* (peak 2) | A | 1.95 | 369.2 |
| I-50 | A | 2.19 | 381.2, 383.2 |
| I-51 | E | 1.13 | 378.1 |
| I-51* (peak 1) | E | 1.09 | 378.1 |
| I-51* (peak 2) | E | 1.09 | 378.1 |
| I-52 | D | 1.57 | 378.0 |
| I-53 | H | 1.48 | 380.1 |
| I-54 | E | 1.63 | 382.1 |
| I-54* (peak 1) | D | 1.83 | 382.1 |
| I-54* (peak 2) | D | 1.84 | 382.1 |
| I-55 | A | 1.75 | 369.2 |
| I-55* (peak 1) | A | 1.75 | 369.1 |
| I-55* (peak 2) | A | 1.76 | 369.1 |
| I-56 | I | 1.38 | 391.9 |
| I-79 | D | 1.48 | 377.0 |
| I-58 | A | 1.53 | 371.0, 373.0 |
| I-59 | D | 1.58 | 354.1 |
| I-60 | D | 1.24 | 383.0 |
| I-60* (peak 1) | I | 1.14 | 382.9 |
| I-60* (peak 2) | I | 1.11 | 382.9 |
| I-61 | D | 1.20 | 384.0 |
| I-61* | I | 1.03 | 383.9 |
| I-62 | I | 1.27 | 371.9 |
| I-63 | D | 1.58 | 383.0 |
| I-64 | C | 2.00 | 369.3, 371.3 |
| I-65 | I | 1.29 | 371.8 |
| I-65* (peak 1) | I | 1.30 | 371.8 |

TABLE 1-continued

| Compound | LCMS method | RT (min) | Mol ion (m/z) |
|---|---|---|---|
| I-65* (peak 2) | I | 1.30 | 371.9 |
| I-66 | I | 1.36 | 385.9 |
| I-66* (peak 1) | A | 1.75 | 386.3 |
| I-66* (peak 2) | A | 1.75 | 386.2 |
| I-67 | I | 1.17 | 337.9 |
| I-67* (peak 1) | I | 1.18 | 337.9 |
| I-67* (peak 2) | I | 1.18 | 337.9 |
| I-68 | D | 1.37 | 393.0 |
| I-69* (peak 1) | A | 1.45 | 354.1, 356.1 |
| I-69* (peak 2) | A | 1.45 | 354.1, 356.1 |
| I-70 | I | 1.20 | 359.0 |
| I-71* (peak 1) | A | 2.12 | 371.2, 373.3 |
| I-71* (peak 2) | A | 2.12 | 371.2, 373.3 |
| I-72* (peak 1) | A | 2.34 | 370.2 |
| I-72* (peak 2) | A | 2.33 | 370.2 |
| I-73* (peak 1) | D | 1.34 | 351.0 |
| I-73* (peak 2) | D | 1.32 | 351.0 |
| I-74* (peak 1) | E | 1.51 | 380.2 |
| I-74* (peak 2) | E | 1.50 | 380.1 |
| I-75* (peak 1) | A | 2.58 | 386.2 |
| I-75* (peak 2) | A | 2.58 | 386.2 |
| I-76* | H | 1.57 | 385.1 |
| I-77* | I | 1.12 | 368.9 |
| I-78* (peak 1) | I | 1.26 | 372.9 |
| I-78* (peak 2) | I | 1.25 | 372.9 |
| I-79* (peak 1) | D | 1.52 | 377.0 |
| I-79* (peak 2) | D | 1.52 | 377.0 |
| I-80* (peak 1) | D | 1.47 | 352.0 |
| I-80* (peak 2) | D | 1.47 | 352.0 |
| I-81* (peak 1) | A | 1.84 | 376.2 |
| I-81* (peak 2) | A | 1.84 | 376.2 |
| I-82* (peak 1) | A | 2.06 | 353.1, 355.1 |
| I-82* (peak 2) | A | 2.06 | 353.1, 355.1 |
| I-83* (peak 1) | A | 2.08 | 422.2 |
| I-83* (peak 2) | A | 2.08 | 422.2 |
| I-84* | I | 1.15 | 353.0 |
| I-85* | D | 1.61 | 352.0 |
| I-86* (peak 1) | I | 1.37 | 394.0 |
| I-86* (peak 2) | I | 1.36 | 394.0 |
| I-87* (peak 1) | D | 1.58 | 377.0 |
| I-87* (peak 2) | D | 1.57 | 377.0 |
| I-88* | D | 1.58 | 395.0 |
| I-89* | I | 1.24 | 375.0 |
| I-90* | D | 1.44 | 361.0 |
| I-91* | I | 1.36 | 393.0 |
| I-92* (peak 1) | A | 1.85 | 404.2 |
| I-92* (peak 2) | A | 1.85 | 404.2 |
| I-93* (peak 1) | A | 1.70 | 388.2 |
| I-93* (peak 2) | A | 1.70 | 388.2 |
| I-94 | J | 1.40 | 359.0 |
| I-95 | E | 1.21 | 376.0 |
| I-96 | E | 1.38 | 402.0 |
| I-97 | J | 1.64 | 403.0 |
| I-98 | I | 1.35 | 358.0 |
| I-99 | J | 1.62 | 359.1 |
| I-100 | I | 1.36 | 376.0 |
| I-101 | J | 1.67 | 377.0 |
| I-102 | J | 1.71 | 392.0 |
| I-103 | H | 1.45 | 393.1 |
| I-104* (peak 1) | I | 1.32 | 358.0 |
| I-104* (peak 2) | I | 1.32 | 358.0 |
| I-105* | D | 1.56 | 359.2 |
| I-106* (peak 1) | D | 1.58 | 377.2 |
| I-106* (peak 2) | D | 1.58 | 377.1 |
| I-107* (peak 1) | H | 1.30 | 344.2 |
| I-107* (peak 2) | H | 1.30 | 344.1 |
| I-111 | D | 1.26 | 346.0 |
| I-112 | H | 1.35 | 388.2 |
| I-113* (peak 1) | H | 1.34 | 362.1 |
| I-113* (peak 2) | H | 1.35 | 362.1 |
| I-114 | H | 1.31 | 344.1 |
| I-115 | D | 1.41 | 345.1 |
| I-116 | H | 1.35 | 362.1 |
| I-118 | H | 1.40 | 378.0 |
| I-119* (peak 1) | I | 1.36 | 376.0 |
| I-119* (peak 2) | I | 1.37 | 376.0 |

*single enantiomer

Example 3: ARM-SAM-TIR SARM1 IC50 Assay

This Example describes an assay of ARM-SAM-TIR NADase activity and use of this assay to measure the efficacy of compounds of Formula I to block SARM1 mediated NAD+ cleavage. This assay was optimized in such a way as to characterize the efficacy of the compounds in Formula I to inhibit SARM1 activity and to calculate an IC50 value for each compound. This assay makes use of full length SARM1, which encompasses the ARM, SAM and TIR domains. As demonstrated herein, expression of this fragment without the autoinhibitory N− terminal domain generates a constitutively active enzyme that cleaves NAD+.

Preparation of ARM-SAM-TIR lysate (STL)

NRK1-HEK293T cells were seeded onto 150 $cm^2$ plates at 20×106 cells per plate. The next day, the cells were transfected with 15 g ARM-SAM-TIR expression plasmid, SEQ ID NO: 1.

```
                                      (SEQ ID NO: 1)
GCGATCGCGGCTCCCGACATCTTGGACCATTAGCTCCACAGGTATCTTCT

TCCCTCTAGTGGTCATAACAGCAGCTTCAGCTACCTCTCAATTCAAAAAA

CCCCTCAAGACCCGTTTAGAGGCCCCAAGGGGTTATGCTATCAATCGTTG

CGTTACACACACAAAAAACCAACACACATCCATCTTCGATGGATAGCGAT

TTTATTATCTAACTGCTGATCGAGTGTAGCCAGATCTAGTAATCAATTAC

GGGGTCATTAGTTCATAGCCCATATATGGAGTTCCGCGTTACATAACTTA

CGGTAAATGGCCCGCCTGGCTGACCGCCCAACGACCCCCGCCCATTGACG

TCAATAATGACGTATGTTCCCATAGTAACGCCAATAGGGACTTTCCATTG

ACGTCAATGGGTGGAGTATTTACGGTAAACTGCCCACTTGGCAGTACATC

AAGTGTATCATATGCCAAGTACGCCCCCTATTGACGTCAATGACGGTAAA

TGGCCCGCCTGGCATTATGCCCAGTACATGACCTTATGGGACTTTCCTAC

TTGGCAGTACATCTACGTATTAGTCATCGCTATTACCATGCTGATGCGGT

TTTGGCAGTACATCAATGGGCGTGGATAGCGGTTTGACTCACGGGGATTT

CCAAGTCTCCACCCCATTGACGTCAATGGGAGTTTGTTTTGGCACCAAAA

TCAACGGGACTTTCCAAAATGTCGTAACAACTCCGCCCCATTGACGCAAA

TGGGCGGTAGGCGTGTACGGTGGGAGGTCTATATAAGCAGAGCTGGTTTA

GTGAACCGTCAGATCAGATCTTTGTCGATCCTACCATCCACTCGACACAC

CCGCCAGCGGCCGCTGCCAAGCTTCCGAGCTCTCGAATTCAAAGGAGGTA

CCCACCcatgGCCATGCATCACCACCACCATCATAGCTCCGGCGTCGACCT

CGGCACCGAGAATTTATATTTCCAAAGCGGCCTCAATGATATCTTCGAGG

CCCAGAAGATCGAGTGGCACGAGGGCAGCTCCGACCTCGCCGTGCCCGGT

CCCGATGGAGGCGGAGGCACTGGTCCTTGGTGGGCTGCTGGCGGCAGAGG

CCCTAGAGAAGTGAGCCCCGGTGCTGGCACCGAGGTGCAAGACGCTCTGG

AGAGGGCTCTGCCCGAACTGCAGCAAGCTCTGTCCGCTTTAAAGCAAGCT

GGAGGAGCTAGAGCCGTCGGCGCCGGACTGGCCGAAGTGTTCCAGCTCGT

GGAGGAAGCTTGGTTATTACCCGCTGTGGGAAGAGAGGTCGCCCAAGGTC

TGTGTGACGCCATTCGTCTGGACGGAGGTTTAGACTTATTACTGAGGCTG

CTGCAAGCTCCCGAACTGGAGACAAGGGTCCAAGCTGCTCGTCTGCTGGA
```

-continued

GCAGATCCTCGTGGCCGAGAATCGTGACAGAGTGGCTAGAATCGGTTTAG

GCGTCATCCTCAATTTAGCCAAAGAGAGGGAGCCCGTTGAGCTGGCCAGA

AGCGTCGCTGGCATCCTCGAGCACATGTTCAAGCATTCCGAGGAGACTTG

TCAGAGACTGGTCGCCGCCGGAGGACTCGATGCTGTTTTATACTGGTGCA

GAAGGACAGACCCCGCTTTACTGAGGCATTGTGCTCTGGCCCTCGGCAAT

TGCGCTTTACATGGAGGCCAAGCCGTCCAGAGAAGGATGGTGGAGAAAAG

AGCCGCCGAGTGGCTGTTCCCTTTAGCCTTCTCCAAAGAAGACGAACTGT

TACGTCTGCATGCTTGTCTCGCTGTCGCTGTTTTAGCCACCAACAAGGAG

GTGGAAAGGGAAGTGGAAAGAAGCGGAACACTGGCTTTAGTCGAACCTCT

GGTGGCTTCTTTAGATCCCGGAAGGTTTGCCAGATGTCTGGTCGACGCCA

GCGATACCTCCCAAGGAAGAGGCCCCGACGATCTCCAGAGACTGGTGCCT

CTGCTGGACAGCAATCGTCTGGAGGCCCAATGTATTGGCGCCTTCTATCT

CTGCGCCGAAGCCGCCATCAAGTCTTTACAAGGTAAGACCAAGGTGTTCT

CCGACATTGGAGCCATCCAATCTTTAAAGAGGCTGGTGAGCTATTCCACC

AACGGCACAAAAAGCGCTTTAGCCAAAAGAGCTTTAAGACTGCTGGGCGA

AGAGGTGCCTAGGCCCATTTTACCTTCCGTGCCTAGCTGGAAGGAGGCCG

AGGTGCAGACTTGGCTGCAGCAGATCGGCTTTAGCAAATATTGCGAATCC

TTTAGGGAGCAGCAAGTTGACGGCGATTTATTATTAAGGCTGACCGAGGA

AGAGCTCCAGACAGATTTAGGCATGAAAAGCGGCATCACTCGTAAGAGGT

TCTTTCGTGAGCTCACCGAACTGAAGACCTTCGCCAACTACTCCACTTGT

GATCGTAGCAATTTAGCTGATTGGCTCGGATCCCTCGATCCCAGATTTCG

TCAGTACACCTATGGACTCGTCTCTTGTGGACTGGACAGATCTTTACTGC

ATCGTGTGAGCGAGCAACAGCTGCTGGAAGATTGCGGCATCCATTTAGGA

GTGCACAGAGCCAGAATTCTGACCGCCGCTAGAGAGATGCTGCATTCCCC

TCTCCCTTGTACCGGAGGCAAGCCTAGCGGAGACACCCCCGACGTGTTCA

TCAGCTATCGTAGAAACAGCGGAAGCCAGCTGGCCTCTTTACTGAAGGTC

CATTTACAGCTGCACGGATTTAGCGTCTTCATCGACGTGGAGAAACTGGA

GGCTGGCAAGTTCGAGGACAAGCTGATCCAGTCCGTGATGGGCGCTAGGA

ATTTCGTTTTAGTGCTCAGCCCCGGCGCTCTGGATAAATGCATGCAAGAT

CATGACTGTAAGGACTGGGTCCACAAGGAAATCGTGACCGCTCTGTCTTG

TGGCAAGAACATCGTCCCCATCATCGACGGCTTCGAATGGCCCGAGCCTC

AAGTTCTCCCCGAAGATATGCAAGCTGTTTTAACCTTCAATGGAATCAAG

TGGAGCCACGAGTACCAAGAAGCCACAATCGAGAAGATCATTCGTTTTCT

GCAAGGTAGATCCTCCAGAGATTCCTCCGCTGGCAGCGACACATCTTTAG

AGGGCGCCGCCCCTATGGGTCCTACCTAATAATctagAAGTTGTCTCCTC

CTGCACTGACTGACTGATACAATCGATTTCTGGATCCGCAGGCCTCTGCT

AGCTTGACTGACTGAGATACAGCGTACCTTCAGCTCACAGACATGATAAG

ATACATTGATGAGTTTGGACAAACCACAACTAGAATGCAGTGAAAAAAT

GCTTTATTTGTGAAATTTGTGATGCTATTGCTTTATTTGTAACCATTATA

AGCTGCAATAAACAAGTTAACAACAACAATTGCATTCATTTTATGTTTCA

GGTTCAGGGGGAGGTGTGGGAGGTTTTTTAAAGCAAGTAAAACCTCTACA

AATGTGGTATTGGCCCATCTCTATCGGTATCGTAGCATAACCCCTTGGGG

CCTCTAAACGGGTCTTGAGGGGTTTTTTGTGCCCCTCGGGCCGGATTGCT

ATCTACCGGCATTGGCGCAGAAAAAAATGCCTGATGCGACGCTGCGCGTC

TTATACTCCCACATATGCCAGATTCAGCAACGGATACGGCTTCCCCAACT

TGCCCACTTCCATACGTGTCCTCCTTACCAGAAATTTATCCTTAAGGTCG

TCAGCTATCCTGCAGGCGATCTCTCGATTTCGATCAAGACATTCCTTTAA

TGGTCTTTTCTGGACACCACTAGGGGTCAGAAGTAGTTCATCAAACTTTC

TTCCCTCCCTAATCTCATTGGTTACCTTGGGCTATCGAAACTTAATTAAC

CAGTCAAGTCAGCTACTTGGCGAGATCGACTTGTCTGGGTTTCGACTACG

CTCAGAATTGCGTCAGTCAAGTTCGATCTGGTCCTTGCTATTGCACCCGT

TCTCCGATTACGAGTTTCATTTAAATCATGTGAGCAAAAGGCCAGCAAAA

GGCCAGGAACCGTAAAAAGGCCGCGTTGCTGGCGTTTTTCCATAGGCTCC

GCCCCCCTGACGAGCATCACAAAAATCGACGCTCAAGTCAGAGGTGGCGA

AACCCGACAGGACTATAAAGATACCAGGCGTTTCCCCCTGGAAGCTCCCT

CGTGCGCTCTCCTGTTCCGACCCTGCCGCTTACCGGATACCTGTCCGCCT

TTCTCCCTTCGGGAAGCGTGGCGCTTTCTCATAGCTCACGCTGTAGGTAT

CTCAGTTCGGTGTAGGTCGTTCGCTCCAAGCTGGGCTGTGTGCACGAACC

CCCCGTTCAGCCCGACCGCTGCGCCTTATCCGGTAACTATCGTCTTGAGT

CCAACCCGGTAAGACACGACTTATCGCCACTGGCAGCAGCCACTGGTAAC

AGGATTAGCAGAGCGAGGTATGTAGGCGGTGCTACAGAGTTCTTGAAGTG

GTGGCCTAACTACGGCTACACTAGAAGAACAGTATTTGGTATCTGCGCTC

TGCTGAAGCCAGTTACCTTCGGAAAAAGAGTTGGTAGCTCTTGATCCGGC

AAACAAACCACCGCTGGTAGCGGTGGTTTTTTTGTTTGCAAGCAGCAGAT

TACGCGCAGAAAAAAAGGATCTCAAGAAGATCCTTTGATCTTTTCTACGG

GGTCTGACGCTCAGTGGAACGAAAACTCACGTTAAGGGATTTTGGTCATG

AGATTATCAAAAAGGATCTTCACCTAGATCCTTTTAAATTAAAAATGAAG

TTTTAAATCAATCTAAAGTATATATGAGTAAACTTGGTCTGACAGTTACC

AATGCTTAATCAGTGAGGCACCTATCTCAGCGATCTGTCTATTTCGTTCA

TCCATAGTTGCATTTAAATTTCCGAACTCTCCAAGGCCCTCGTCGGAAAA

TCTTCAAACCTTTCGTCCGATCCATCTTGCAGGCTACCTCTCGAACGAAC

TATCGCAAGTCTCTTGGCCGGCCTTGCGCCTTGGCTATTGCTTGGCAGCG

CCTATCGCCAGGTATTACTCCAATCCCGAATATCCGAGATCGGGATCACC

CGAGAGAAGTTCAACCTACATCCTCAATCCCGATCTATCCGAGATCCGAG

GAATATCGAAATCGGGGCGCGCCTGGTGTACCGAGAACGATCCTCTCAGT

GCGAGTCTCGACGATCCATATCGTTGCTTGGCAGTCAGCCAGTCGGAATC

CAGCTTGGGACCCAGGAAGTCCAATCGTCAGATATTGTACTCAAGCCTGG

TCACGGCAGCGTACCGATCTGTTTAAACCTAGATATTGATAGTCTGATCG

GTCAACGTATAATCGAGTCCTAGCTTTTGCAAACATCTATCAAGAGACAG

GATCAGCAGGAGGCTTTCGCATGAGTATTCAACATTTCCGTGTCGCCCTT

ATTCCCTTTTTTGCGGCATTTTGCCTTCCTGTTTTTGCTCACCCAGAAAC

-continued

```
GCTGGTGAAAGTAAAAGATGCTGAAGATCAGTTGGGTGCGCGAGTGGGTT

ACATCGAACTGGATCTCAACAGCGGTAAGATCCTTGAGAGTTTTCGCCCC

GAAGAACGCTTTCCAATGATGAGCACTTTTAAAGTTCTGCTATGTGGCGC

GGTATTATCCCGTATTGACGCCGGGCAAGAGCAACTCGGTCGCCGCATAC

ACTATTCTCAGAATGACTTGGTTGAGTATTCACCAGTCACAGAAAAGCAT

CTTACGGATGGCATGACAGTAAGAGAATTATGCAGTGCTGCCATAACCAT

GAGTGATAACACTGCGGCCAACTTACTTCTGACAACGATTGGAGGACCGA

AGGAGCTAACCGCTTTTTTGCACAACATGGGGGATCATGTAACTCGCCTT

GATCGTTGGGAACCGGAGCTGAATGAAGCCATACCAAACGACGAGCGTGA

CACCACGATGCCTGTAGCAATGGCAACAACCTTGCGTAAACTATTAACTG

GCGAACTACTTACTCTAGCTTCCCGGCAACAGTTGATAGACTGGATGGAG

GCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCA

TTGCAGCACTGGGGCCAGATGGTAAGCCCTCCCGTATCGTAGTTATCTAC

ACGACGGGGAGTCAGGCAACTATGGATGAACGAAATAGACAGATCGCTGA

GATAGGTGCCTCACTGATTAAGCATTGGTAACCGATTCTAGGTGCATTGG

CGCAGAAAAAATGCCTGATGCGACGCTGCGCGTCTTATACTCCCACATA

TGCCAGATTCAGCAACGGATACGGCTTCCCCAACTTGCCCACTTCCATAC

GTGTCCTCCTTACCAGAAATTTATCCTTAAGATCCCGAATCGTTTAAACT

CGACTCTGGCTCTATCGAATCTCCGTCGTTTCGAGCTTACGCGAACAGCC

GTGGCGCTCATTTGCTCGTCGGGCATCGAATCTCGTCAGCTATCGTCAGC

TTACCTTTTTGGCA.
```

The cultures were supplemented with 1 mM NR at time of transfection to minimize toxicity from ARM-SAM-TIR overexpression. Forty-eight hours after transfection, cells were harvested, pelleted by centrifugation at 1,000 rpm (Sorvall ST 16R centrifuge, Thermo Fisher), and washed once with cold PBS (0.01 M phosphate buffered saline NaCl 0.138 M; KCl 0.0027 M; pH 7.4). The cells were resuspended in PBS with protease inhibitors (cOmplete™ protease inhibitor cocktail, Roche product #11873580001) and cell lysates were prepared by sonication (Branson Sonifer 450, output=3, 20 episodes of stroke). The lysates were centrifuged (12,000×g for 10 min at 4° C.) to remove cell debris and the supernatants (containing ARM-SAM-TIR protein) were stored at −80° C. for later use in the in vitro ARM-SAM-TIR NADase assay (see below). Protein concentration was determined by the Bicinchoninic (BCA) method and used to normalize lysate concentrations.

ARM-SAM-TIR IC50 assay of Formula I compounds.

The enzymatic assay was performed in a 384-well polypropylene plate in Dulbecco's PBS buffer in a final assay volume of 20 μL. ARM-SAM-TIR lysate with a final concentration of 5 μg/mL was pre-incubated with the respective compound at 1% DMSO final assay concentration over 2h at room temperature. The reaction was initiated by addition of 5 uM final assay concentration of NAD+ as substrate. After a 2 hr room temperature incubation, the reaction was terminated with 40 μL of stop solution of 7.5% trichloroacetic acid in acetonitrile. The NAD+ and ADPR concentrations were analyzed by a RapidFire High Throughput Mass Spectrometry System (Agilent Technologies, Santa Clara, Calif.) using an API4000 triple quadrupole mass spectrometer (AB Sciex Framingham, Mass.).

Results are presented below in Table 2. Compounds having an activity designated as "A" provided an $IC_{50}$<50 nM; compounds having an activity designated as "B" provided an $IC_{50}$ 51-100 nM; compounds having an activity designated as "C" provided an $IC_{50}$ 101-500 nM; compounds having an activity designated as "D" provided an $IC_{50}$ 501-1000 nM; compounds having an activity designated as "E" provided an $IC_{50}$>1000 nM.

TABLE 2

| Compound | SARM1 $IC_{50}$ (nM) |
|---|---|
| I-1-a | C |
| I-1-b | E |
| I-2-a | E |
| I-3-a | E |
| I-4 | A |
| I-4* (peak 1) | A |
| I-4* (peak 2) | A |
| I-5 | A |
| I-5* (peak 1) | A |
| I-5* (peak 2) | A |
| I-6 | B |
| I-6* (peak 1) | B |
| I-6* (peak 2) | B |
| I-7 | C |
| I-7* (peak 1) | C |
| I-7* (peak 2) | A |
| I-8 | A |
| I-8* (peak 1) | A |
| I-8* (peak 2) | A |
| I-9 | C |
| I-9* (peak 1) | C |
| I-9* (peak 2) | B |
| I-10 | A |
| I-11 | A |
| I-11* (peak 1) | A |
| I-11* (peak 2) | B |
| I-12 | E |
| I-13 | A |
| I-14 | A |
| I-15 | A |
| I-16 | A |
| I-16* (peak 1) | A |
| I-16* (peak 2) | A |
| I-17 | A |
| I-18 | B |
| I-19 | A |
| I-19* (peak 1) | A |
| I-19* (peak 2) | A |
| I-20 | A |
| I-20* (peak 1) | A |
| I-20* (peak 2) | A |
| I-21 | A |
| I-21* (peak 1) | C |
| I-21* (peak 2) | A |
| I-22 | A |
| I-23 | A |
| I-23* (peak 1) | A |
| I-23* (peak 2) | C |
| I-24 | A |
| I-24* (peak 1) | A |
| I-24* (peak 2) | C |
| I-25 | C |
| I-25* (peak 1) | C |
| I-25* (peak 2) | A |
| I-26 | C |
| I-26* (peak 1) | C |
| I-26* (peak 2) | C |
| I-27 | C |
| I-27* (peak 1) | C |
| I-27* (peak 2) | E |
| I-28 | E |
| I-28* (peak 1) | D |
| I-28* (peak 2) | E |
| I-29 | E |
| I-29* (peak 1) | D |
| I-29* (peak 2) | E |

TABLE 2-continued

| Compound | SARM1 IC$_{50}$ (nM) |
|---|---|
| I-30 | E |
| I-31 | C |
| I-31* (peak 1) | C |
| I-31* (peak 2) | E |
| I-32 | A |
| I-32* (peak 1) | B |
| I-32* (peak 2) | A |
| I-33 | A |
| I-33* (peak 1) | B |
| I-33* (peak 2) | A |
| I-34 | A |
| I-34* (peak 1) | A |
| I-34* (peak 2) | A |
| I-35 | D |
| I-36 | A |
| I-36* (peak 1) | A |
| I-36* (peak 2) | A |
| I-37 | B |
| I-37* (peak 1) | B |
| I-37* (peak 2) | B |
| I-38 | D |
| I-38* (peak 1) | D |
| I-38* (peak 2) | E |
| I-39 | C |
| I-39* (peak 1) | C |
| I-39* (peak 2) | C |
| I-40 | C |
| I-40* (peak 1) | E |
| I-40* (peak 2) | C |
| I-41 | C |
| I-41* (peak 1) | C |
| I-41* (peak 2) | C |
| I-42 | E |
| I-42* (peak 1) | E |
| I-42* (peak 2) | E |
| I-43 | E |
| I-44 | A |
| I-45 | D |
| I-46* (peak 1) | C |
| I-46* (peak 2) | E |
| I-47 | B |
| I-47* (peak 1) | B |
| I-47* (peak 2) | E |
| I-48 | C |
| I-48* (peak 1) | C |
| I-48* (peak 2) | C |
| I-49 | B |
| I-49* (peak 1) | C |
| I-49* (peak 2) | B |
| I-50 | E |
| I-51 | B |
| I-51* (peak 1) | B |
| I-51* (peak 2) | C |
| I-52 | A |
| I-53 | B |
| I-54 | C |
| I-54* (peak 1) | D |
| I-54* (peak 2) | C |
| I-55 | B |
| I-55* (peak 1) | B |
| I-55* (peak 2) | B |
| I-56 | C |
| I-79 | A |
| I-58 | C |
| I-59 | C |
| I-60 | D |
| I-60* (peak 1) | E |
| I-60* (peak 2) | C |
| I-61 | E |
| I-61* | E |
| I-62 | D |
| I-63 | D |
| I-64 | E |
| I-65 | A |
| I-65* (peak 1) | A |
| I-65* (peak 2) | A |
| I-66 | A |
| I-66* (peak 1) | A |
| I-66* (peak 2) | C |
| I-67 | A |
| I-67* (peak 1) | B |
| I-67* (peak 2) | A |
| I-68 | C |
| I-69* (peak 1) | A |
| I-69* (peak 2) | A |
| I-70 | B |
| I-71* (peak 1) | A |
| I-71* (peak 2) | A |
| I-72* (peak 1) | C |
| I-72* (peak 2) | A |
| I-73* (peak 1) | D |
| I-73* (peak 2) | D |
| I-74* (peak 1) | E |
| I-74* (peak 2) | E |
| I-75* (peak 1) | A |
| I-75* (peak 2) | A |
| I-76* | A |
| I-77* | A |
| I-78* (peak 1) | C |
| I-78* (peak 2) | B |
| I-79* (peak 1) | A |
| I-79* (peak 2) | C |
| I-80* (peak 1) | A |
| I-80* (peak 2) | C |
| I-81* (peak 1) | A |
| I-81* (peak 2) | C |
| I-82* (peak 1) | A |
| I-82* (peak 2) | A |
| I-83* (peak 1) | C |
| I-83* (peak 2) | C |
| I-84* | A |
| I-85* | A |
| I-86* (peak 1) | C |
| I-86* (peak 2) | E |
| 1-87* (peak 1) | C |
| 1-87* (peak 2) | A |
| 1-88* | A |
| I-89* | A |
| I-90* | C |
| I-91* | B |
| 1-92* (peak 1) | C |
| 1-92* (peak 2) | C |
| 1-93* (peak 1) | D |
| 1-93* (peak 2) | C |
| I-94 | C |
| I-95 | C |
| I-96 | C |
| I-97 | C |
| I-98 | A |
| I-99 | C |
| I-100 | A |
| I-101 | C |
| I-102 | B |
| I-103 | C |
| I-104* (peak 1) | B |
| I-104* (peak 2) | E |
| I-105* | C |
| I-106* (peak 1) | E |
| I-106* (peak 2) | C |
| I-107* (peak 1) | C |
| I-107* (peak 2) | C |
| I-111 | E |
| I-112 | C |
| I-113* (peak 1) | E |
| I-113* (peak 2) | C |
| I-114 | C |
| I-115 | D |
| I-116 | C |
| I-118 | C |
| I-119* (peak 1) | E |
| I-119* (peak 2) | C |

*single enantiomer

Example 4: Axonal Degeneration Index

This Example illustrates an in vitro axon degeneration assay used to characterize compounds of Formula I. This assay was used to test the efficacy of the compounds of Formula I to prevent axonal degeneration in a mouse dorsal root ganglion (DRG) drop culture.

Mouse DRG Drop culture: Mouse dorsal root ganglion neurons (DRGs) are dissected out of E12.5 CD1 mice (50 ganglion per embryo) and incubated with 0.5% Trypsin solution containing 0.02% EDTA (Gibco) at 37° C. for 15 min. The cells are then triturated by gentle pipetting and washed 3 times with DRG growth medium (Neurobasal medium (Gibco) containing 2% B27 (Invitrogen), 100 ng/ml 2.5S NGF (Harland Bioproducts), 1 mM 5-fluoro-2'deoxyuridine (Sigma), penicillin, and streptomycin). Cells are suspended in the DRG growth medium. DRG drop cultures are created by spotting 5000 cells/well into the center of each well of a 96-well tissue culture plate coated with poly-D-Lysine (0.1 mg/ml; Sigma) and laminin (3 mg/ml; Invitrogen). Cells are allowed to adhere to the plates in a humidified tissue culture incubator (5% $CO_2$) for 15 min and then DRG growth medium was gently added (100 ml well).

Axon degeneration assay: Axonal degeneration is stimulated either by manual axonal transection using a scalpel blade, or chemotoxic stimuli. After an appropriate experimental time period, the DRG cultures are fixed in 1% PFA plus sucrose and kept in the fridge prior to imaging. Brightfield images of DRG axons and cell bodies are collected using the 20× water immersion lens of a Phenix automated confocal microscope (PerkinElmer) and quantitation of axonal performed using in-house developed scripts (Acapella, PerkinElmer).

What is claimed is:

1. A compound of the formula:

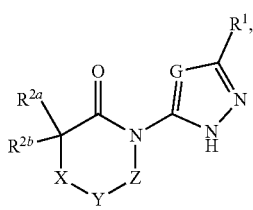

or a pharmaceutically acceptable salt thereof, wherein:
$R^1$ is a 5- to 6-membered heteroaryl ring having 1-3 heteroatoms selected from oxygen, nitrogen and sulfur;
G is CH, $CR^x$ or N;
$R^x$ is $C_1$-$C_3$ alkyl, halogen or cyano;
X is $CH_2$, NH, $N(C_1$-$C_3$ alkyl) or O;
Y is $C(R^P)_2$ or NH;
Z is bond, $CH_2$ or —$CH_2CH_2$—;
$R^{2a}$ is —$(C_1$-$C_3$ alkyl)$R^3$;
$R^{2b}$ is hydrogen, halogen, $C_1$-$C_3$ alkyl or —$(C_1$-$C_3$ alkyl)$R^3$;
$R^P$ is independently hydrogen, halogen or $NH_2$;
$R^3$ is a phenyl ring or a 5- to 6-membered heteroaryl ring having 1-3 heteroatoms selected from oxygen, nitrogen and sulfur, wherein the phenyl ring or 5- to 6-membered heteroaryl ring are optionally substituted with 1 to 2 $R^q$;
$R^q$ is halogen, cyano or —$CF_3$.

2. The compound according to claim 1, wherein $R^{2b}$ is hydrogen, or a pharmaceutically acceptable salt thereof.

3. The compound according to claim 2, wherein $R^1$ is selected from

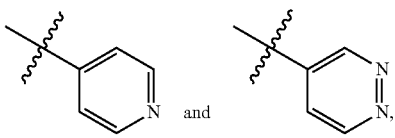 [SMILES: *c1ccncc1 ; "and" ; *c1ccnnc1]

or a pharmaceutically acceptable salt thereof.

4. The compound according to claim 3, wherein G is N, or a pharmaceutically acceptable salt thereof.

5. The compound according to claim 4, wherein X is $CH_2$, Y is $CH_2$, and Z is $CH_2$, or a pharmaceutically acceptable salt thereof.

6. The compound according to claim 5, wherein $R^{2a}$ is —$CH_2$—$R^3$, or a pharmaceutically acceptable salt thereof.

7. The compound according to claim 6, wherein $R^3$ is selected from

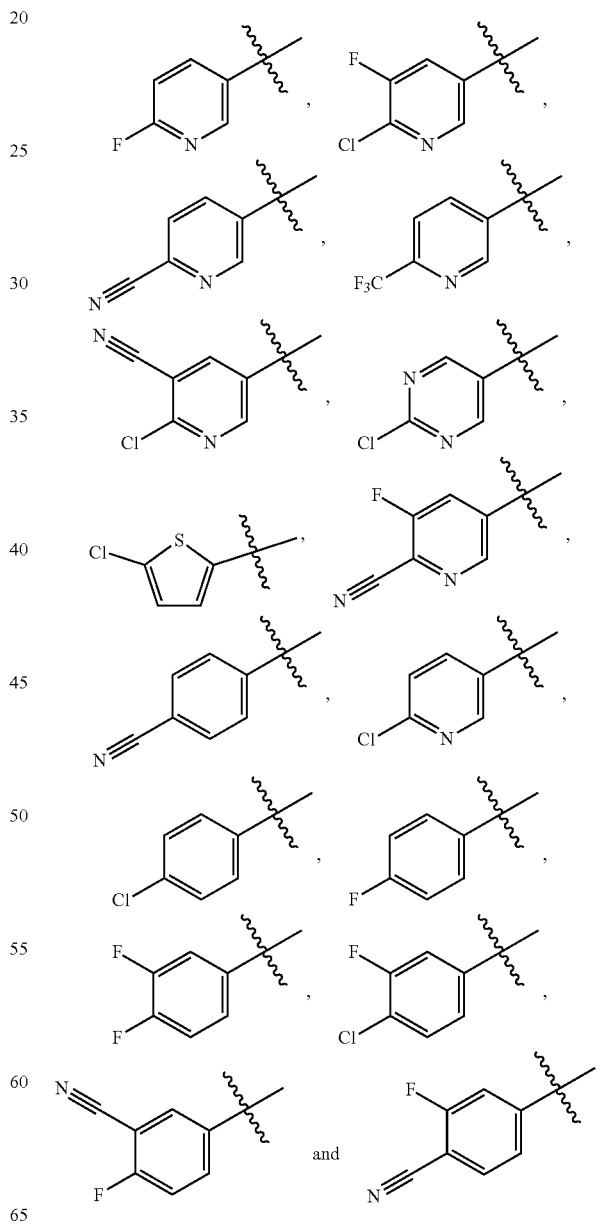

or a pharmaceutically acceptable salt thereof.

8. The compound according to claim 7, wherein R³ is selected from

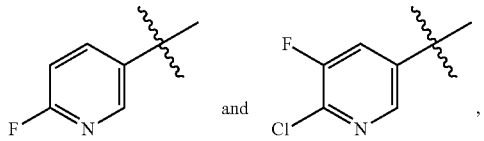 [SMILES: *c1ccc(F)nc1 ; "and" ; *c1cnc(Cl)c(F)c1 ; ","]

and or a pharmaceutically acceptable salt thereof.

9. The compound according to claim 1, which is:

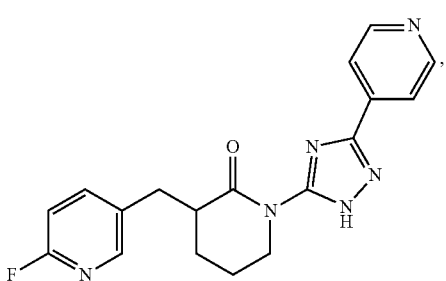 [SMILES: O=C1C(Cc2ccc(F)nc2)CCCN1c1nc(-c2ccncc2)n[nH]1]

or a pharmaceutically acceptable salt thereof.

10. The compound according to claim 9, which is:

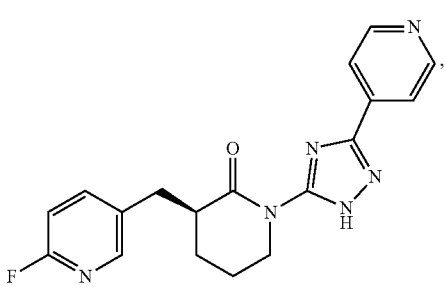 [SMILES: O=C1[C@H](Cc2ccc(F)nc2)CCCN1c1nc(-c2ccncc2)n[nH]1]

or a pharmaceutically acceptable salt thereof.

11. The compound according to claim 1, which is:

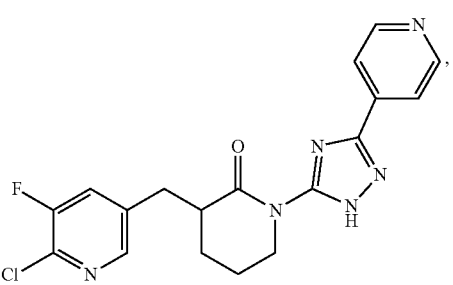

or a pharmaceutically acceptable salt thereof.

12. The compound according to claim 11, which is:

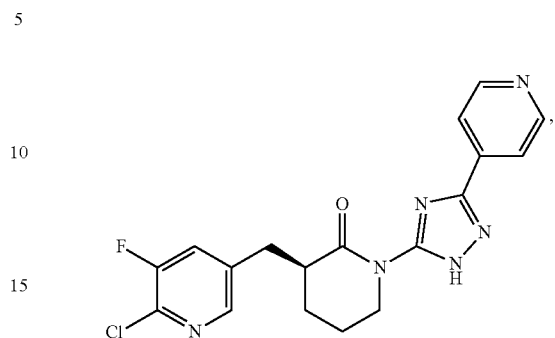

or a pharmaceutically acceptable salt thereof.

13. A pharmaceutical composition comprising a compound or a pharmaceutically acceptable salt thereof according to claim 1 with one or more pharmaceutically acceptable carriers, diluents, or excipients.

14. A method comprising a step of:
administering a compound according to claim 1, or a pharmaceutically acceptable salt thereof, to a patient who (i) has a condition characterized by axonal degeneration or (ii) is at risk of developing a condition characterized by axonal degeneration.

15. A method of treating or preventing axonal degeneration comprising administering to a patient in need thereof a compound according to claim 1, or a pharmaceutically acceptable salt thereof.

16. A method of inhibiting SARM1 comprising contacting a biological sample with a compound according to claim 1, or a pharmaceutically acceptable salt thereof.

17. A method of treating amyotrophic lateral sclerosis in a patient, comprising administering to a patient in need of such treatment and effective amount of a compound according to claim 1, or a pharmaceutically acceptable salt thereof.

18. A method of treating multiple sclerosis in a patient, comprising administering to a patient in need of such treatment and effective amount of a compound according to claim 1, or a pharmaceutically acceptable salt thereof.

19. A method of treating progressive supranuclear palsy in a patient, comprising administering to a patient in need of such treatment and effective amount of a compound according to claim 1, or a pharmaceutically acceptable salt thereof.

* * * * *